(12) United States Patent
Xie et al.

(10) Patent No.: US 11,643,661 B2
(45) Date of Patent: May 9, 2023

(54) DETECTION OF MICROBIAL ENDOTOXINS IN ORAL SAMPLES USING APTAMERS

(71) Applicant: The Procter & Gamble Company, Cincinnati, OH (US)

(72) Inventors: Sancai Xie, Liberty Township, OH (US); Thomas Glenn Huggins, Jr., Mason, OH (US); Cheryl Sue Tansky, Forest Park, OH (US); Ping Hu, Mason, OH (US); Susan Ellen Forest, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/867,587

(22) Filed: May 6, 2020

(65) Prior Publication Data

US 2020/0399639 A1 Dec. 24, 2020

Related U.S. Application Data

(60) Provisional application No. 62/843,619, filed on May 6, 2019.

(51) Int. Cl.
*C12N 15/115* (2010.01)
*G01N 33/53* (2006.01)
*G01N 33/569* (2006.01)

(52) U.S. Cl.
CPC ....... *C12N 15/115* (2013.01); *G01N 33/5308* (2013.01); *G01N 33/56911* (2013.01); *C12N 2310/16* (2013.01); *C12N 2310/317* (2013.01); *C12N 2310/321* (2013.01); *C12N 2310/344* (2013.01); *C12N 2310/351* (2013.01); *G01N 2400/50* (2013.01); *G01N 2800/18* (2013.01)

(58) Field of Classification Search
None
See application file for complete search history.

(56) References Cited

U.S. PATENT DOCUMENTS 10,487,331 B1 * 11/2019 Wu .................. A61B 5/00
2011/0269814 A1 * 11/2011 Manoharan ............ C07H 19/23
530/358

OTHER PUBLICATIONS

Shin et al. Aug. 2013 Conference IADAR Asia/Pacific (APR) Regional Meeting and Co-Annual Scientific Meeting of IADR, DNA aptamers for specific detection of oral bacterial infection, poster session, pp. 1-2 (Year: 2013).*
International Search Report and Written Opinion; Application Ser. No. PCT/US2020/070026; dated Dec. 21, 2020, 18 pages.
Bruno et al., "Fluorescent DNA Aptamer-Magnetic Bead Sandwich Assays and Portable Fluorometer for Sensitive and Rapid Foodborne Pathogen Detection and Epidemiology", J Infect Dis Epidemiol, vol. 2, No. 1, 2016, pp. 1-6.
Ellis et al., "Virulence and Immunomodulatory Roles of Bacterial Outer Membrane Vesicles", Microbiology and Molecular Biology Reviews, vol. 74, No. 1, Mar. 2010, pp. 81-94.
Invitation to Pay Additional Fees; Application No. PCT/US2020/070026; dated Oct. 28, 2020; 14 pages.
Park et al., "Screening and Development of DNA Aptamers Specific to Several Oral Pathogens", J. Microbiol. Biotechnol., vol. 25, No. 3, 2015, pp. 393-398.
Schwechheimer et al., "Outer-membrane vesicles from Gram-negative bacteria: biogenesis and functions", Nature Reviews, Microbiology, vol. 13, Oct. 2015, pp. 605-619.

* cited by examiner

*Primary Examiner* — Brian Whiteman
(74) *Attorney, Agent, or Firm* — James E. Oehlenschlager

(57) ABSTRACT

The present invention is directed to an aptamer composition comprising at least one oligonucleotide consisting of: deoxyribonucleotides, ribonucleotides, derivatives of deoxyribonucleotides, derivatives of ribonucleotides, and mixtures thereof; wherein said aptamer composition has a binding affinity for one or more bacterial species from the genera *Prevotella* and *Porphyromonas*.

18 Claims, 38 Drawing Sheets

Specification includes a Sequence Listing.

| Prevotella pallens | Porphyromonas gingivalis |
|---|---|
| 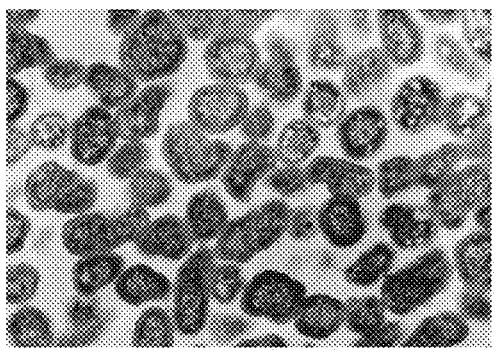 | 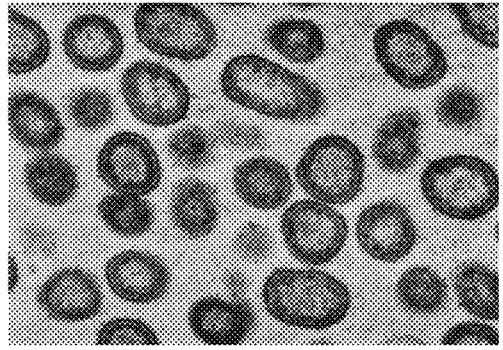 |
| 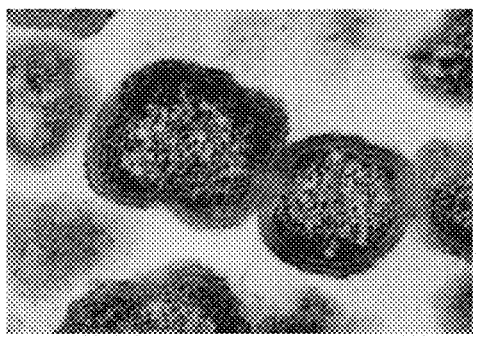 | 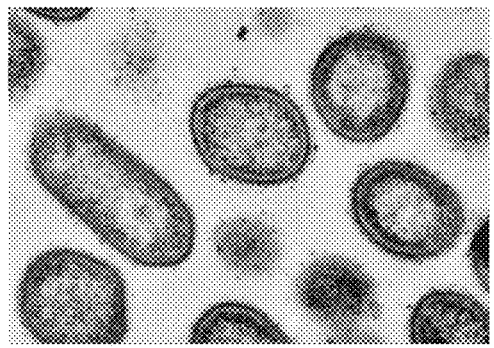 |
| 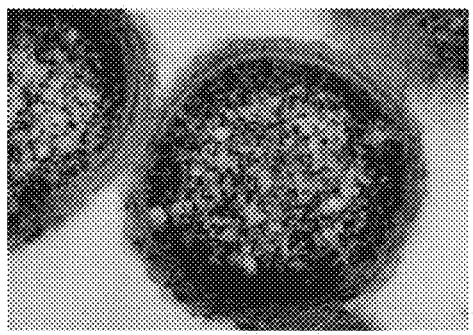 | 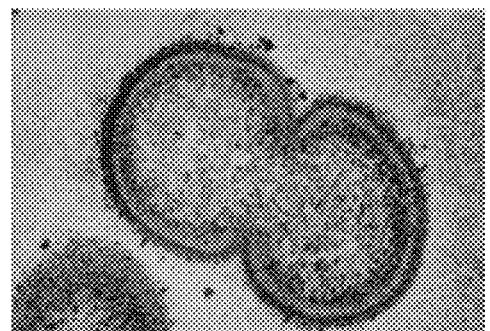 |
Fig. 2B Prevotella pallens | Porphyromonas gingivalis
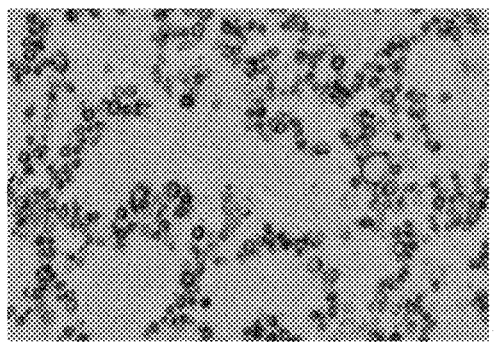 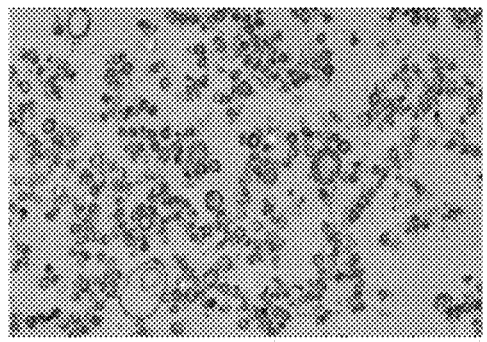
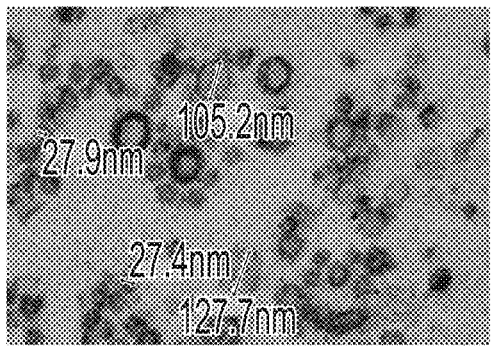 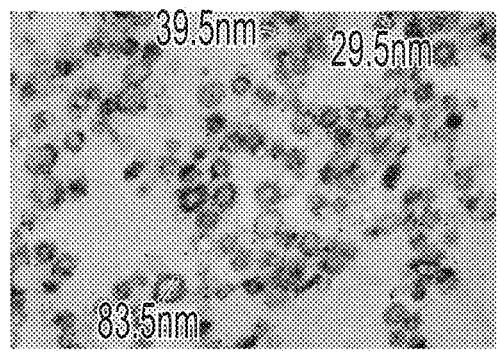
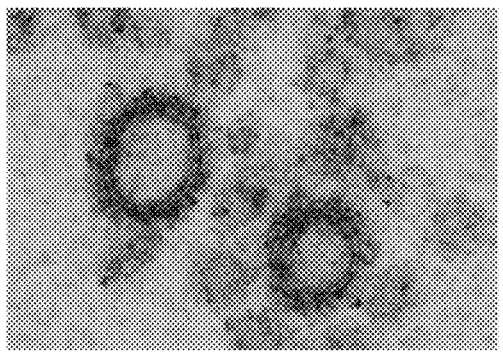 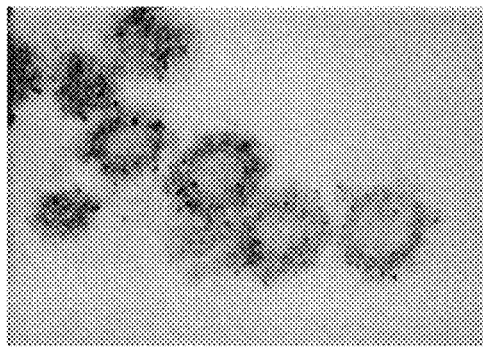
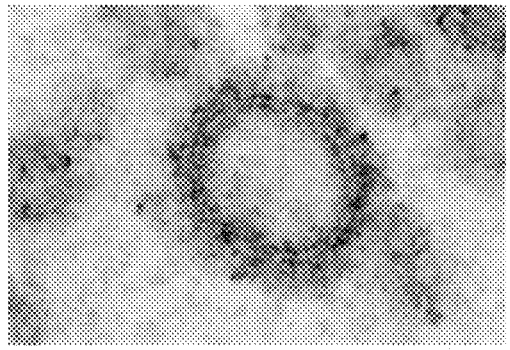 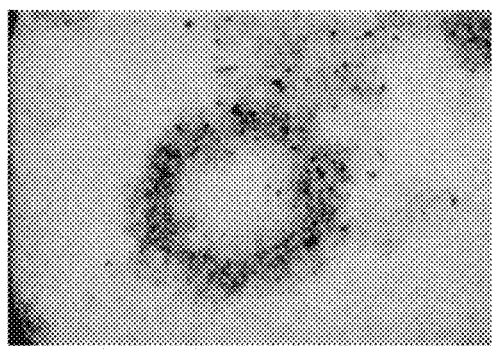
Fig. 2D Before application of a sample
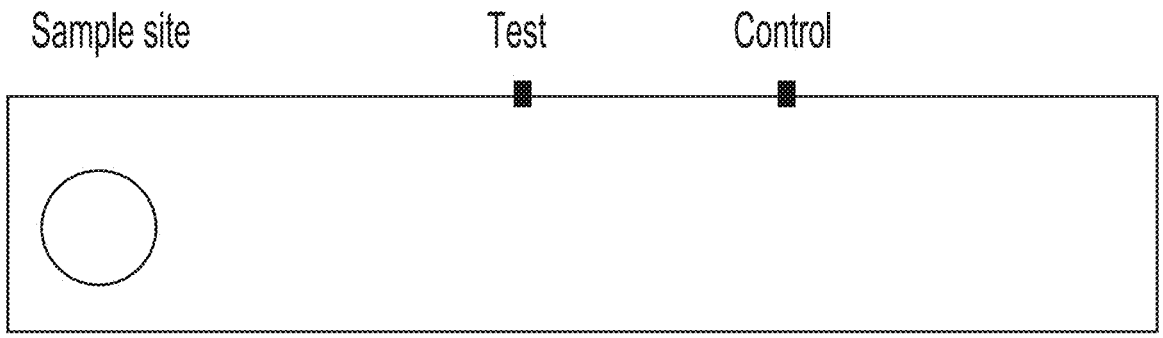
Fig. 7BI
Positive in the test after application of a sample.
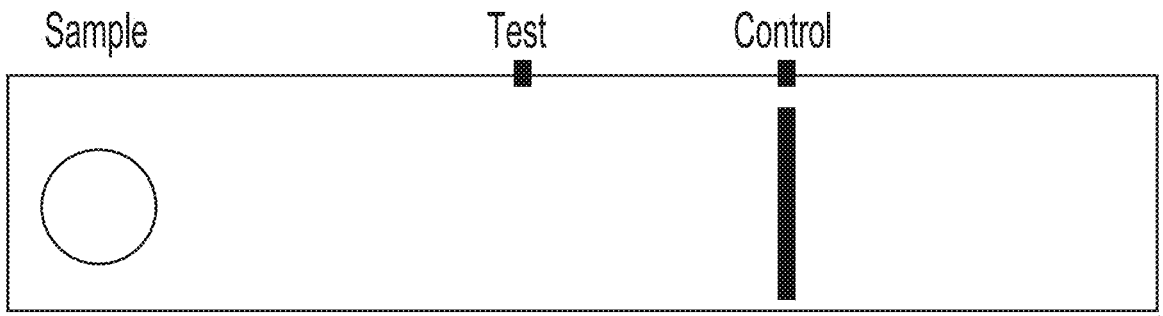
Fig. 7BII
Negative in the test after application of a sample.
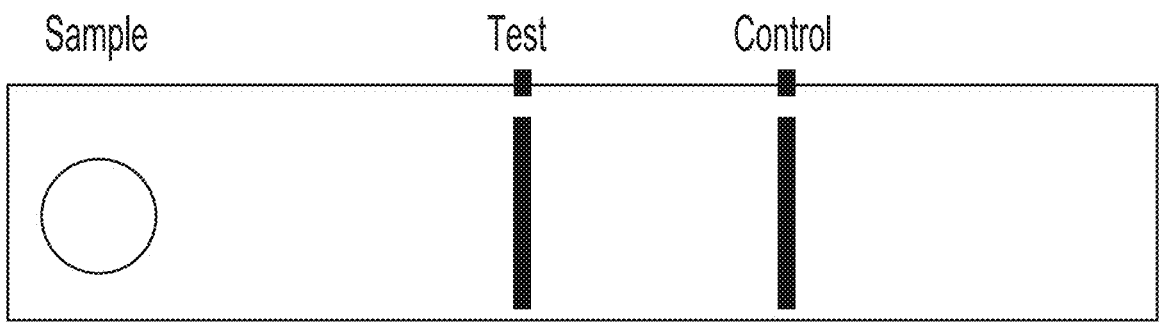
Fig. 7BIII Before application of a sample
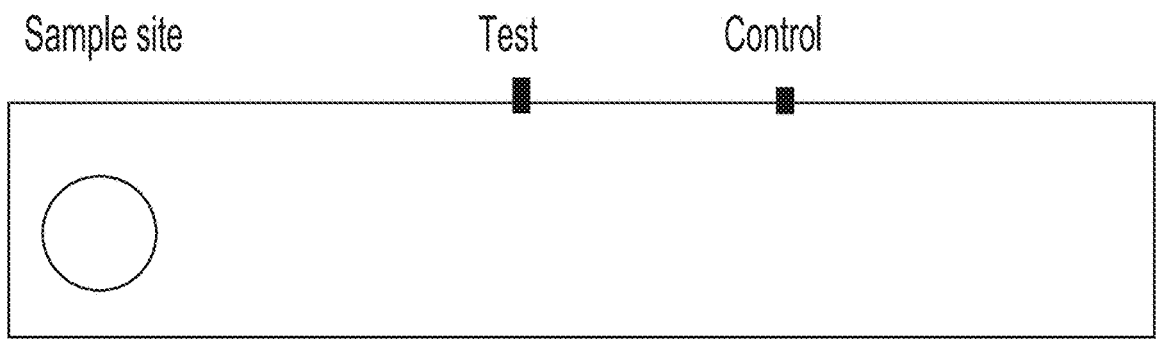
Fig. 7CI
Positive in the test after application of a sample.
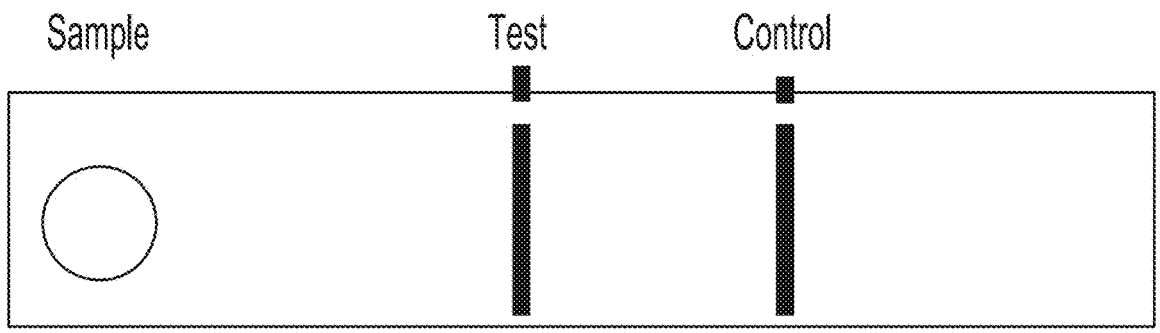
Fig. 7CII
Negative in the test after application of a sample.
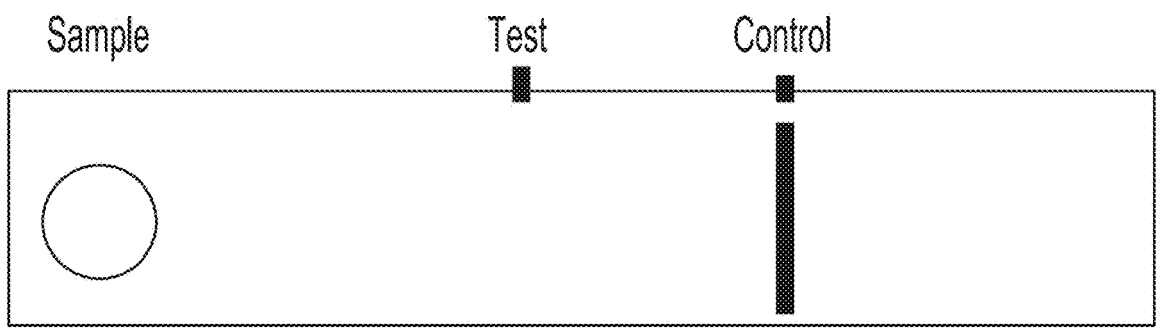
Fig. 7CIII Before application of a sample
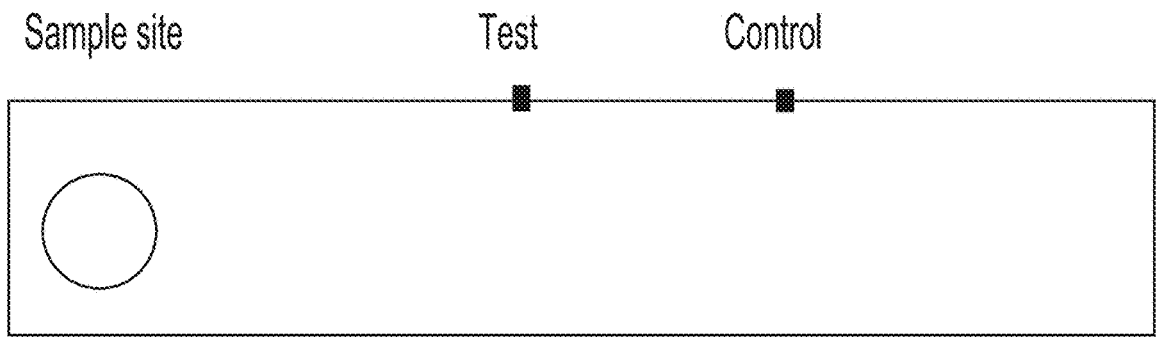
Fig. 7DI
Positive in the test after application of a sample.
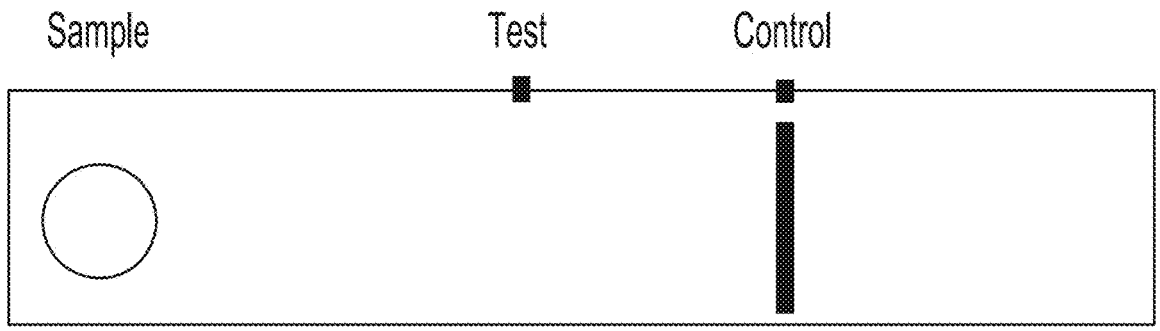
Fig. 7DII
Negative in the test after application of a sample.
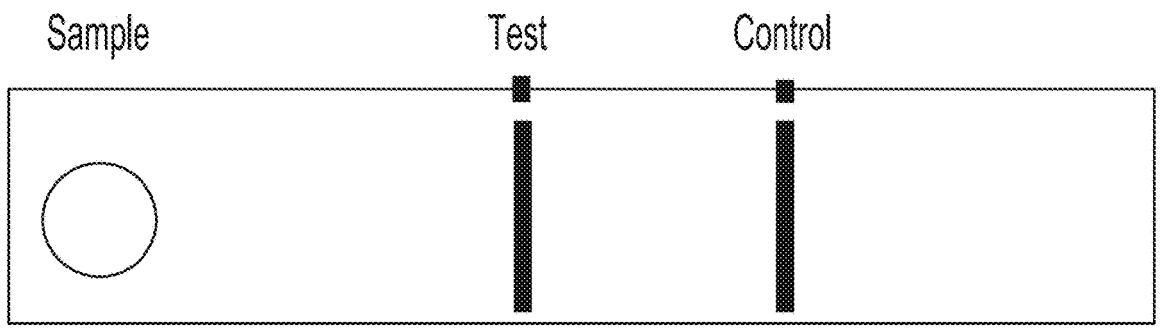
Fig. 7DIII

```
                             SEQUENCE LISTING

<160> NUMBER OF SEQ ID NOS: 466

<210> SEQ ID NO 1
   <211> LENGTH: 76
   <212> TYPE: DNA
   <213> ORGANISM: Artificial Sequence
   <220> FEATURE:
   <223> OTHER INFORMATION: Synthetic Aptamer Sequence

<400> SEQUENCE: 1
tgttgaagtg gtgtaactga gaaagtgaga tacatcactc agttgattgg actaagcaat       60
cctggcacgg gcagtg                                                      76

<210> SEQ ID NO 2
   <211> LENGTH: 76
   <212> TYPE: DNA
   <213> ORGANISM: Artificial Sequence
   <220> FEATURE:
   <223> OTHER INFORMATION: Synthetic Aptamer Sequence

<400> SEQUENCE: 2
aagtgggtgt ttacatggta tccgtcgaga gtaaccttta tcgccatcca gtaatacgta       60
cctggcacgg gcagtg                                                      76

<210> SEQ ID NO 3
   <211> LENGTH: 62
   <212> TYPE: DNA
   <213> ORGANISM: Artificial Sequence
   <220> FEATURE:
   <223> OTHER INFORMATION: Synthetic Aptamer Sequence

<400> SEQUENCE: 3
tgacgtgaag tggctatgct attctctagt tgaaggagga ttgttacctg gcacgggcag       60
tg                                                                     62

<210> SEQ ID NO 4
   <211> LENGTH: 72
   <212> TYPE: DNA
```

```
<213> ORGANISM: Artificial Sequence
<220> FEATURE:
<223> OTHER INFORMATION: Synthetic Apatamer Sequence

<400> SEQUENCE: 4
aagtggaaag gatacagttt gcacatctag gggtaaccga gagttactta atgtcacctg    60
gcacgggcag tg                                                        72

<210> SEQ ID NO 5
<211> LENGTH: 76
<212> TYPE: DNA
<213> ORGANISM: Artificial Sequence
<220> FEATURE:
<223> OTHER INFORMATION: Synthetic Apatamer Sequence

<400> SEQUENCE: 5
tgaagtggct tacactcaca tcctcgttca acacgtgacc ttagtatctt atttgatcaa    60
cctggcacgg gcagtg                                                    76

<210> SEQ ID NO 6
<211> LENGTH: 76
<212> TYPE: DNA
<213> ORGANISM: Artificial Sequence
<220> FEATURE:
<223> OTHER INFORMATION: Synthetic Apatamer Sequence

<400> SEQUENCE: 6
aagtggcgat taactgcaat gtttgtgttt acctggtttt agggtttgat ttcattctca    60
cctggcacgg gcagtg                                                    76

<210> SEQ ID NO 7
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 7
aagtggctat ggatgtagtt cgctttacct ctgtctatct cgttggatgg ttagtaatat    60
cctggcacgg gcagtg                                                    76

<210> SEQ ID NO 8
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 8
tggacagttt ataaccagga cttggatctg ttgtttctac acctttcatg ctccacttct    60
cctggcacgg gcagtg                                                    76

<210> SEQ ID NO 9
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 9
tgggaagtgg cttctttttc actcggcaac aatagcctag gagatatgta tccaaggaaa    60
cctggcacgg gcagtg                                                    76
```

<210> SEQ ID NO 10
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 10
ttaaataata taaccacatt tatttctact tctattatta tactgtagta ttattcaaat    60
cctggcacgg gcagtg                                                    76

<210> SEQ ID NO 11
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 11
atctctaaga atctcagtgc attatgtgat gcattgagaa tgattagaga tgttatggag    60
cctggcacgg gcagtg                                                    76

<210> SEQ ID NO 12
<211> LENGTH: 73
<212> TYPE: DNA
<213> ORGANISM: Artificial Sequence
<220> FEATURE:
<223> OTHER INFORMATION: Synthetic Aptamer Sequence

<400> SEQUENCE: 12
gagacagaca cgataaaatg acgtaattta gacgatataa tctgtaattg aatattgcct    60
ggcacgggca gtg                                                       73

<210> SEQ ID NO 13
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 13
tggttgataa gatcacattc aatgagggtg tagaagagga gatcaagacc ttgaatggag    60
cctggcacgg gcagtg                                                    76

<210> SEQ ID NO 14
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 14
acgtcatatc actttactgt gattatgtaa cgtcagagga atacaatagc ccttaatgca    60
cctggcacgg gcagtg                                                    76

<210> SEQ ID NO 15
<211> LENGTH: 76
<212> TYPE: DNA
<213> ORGANISM: Artificial Sequence
<220> FEATURE:
<223> OTHER INFORMATION: Synthetic Aptamer Sequence

```
<400> SEQUENCE: 15
tgtatacacg tacaagacag ttctgggcta agtattggta cttacccatt atcttatgca        60
cctggcacgg gcagtg                                                        76

<210> SEQ ID NO 16
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 16
ggttgcacaa atatagacag cttcaacgat ttcattctct gtgagagaga tgtaatggag        60
cctggcacgg gcagtg                                                        76

<210> SEQ ID NO 17
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 17 accottgtat gtattgattt accgatatcg atactaggat agtgcacatg gaagatggag        60
cctggcacgg gcagtg                                                        76

<210> SEQ ID NO 18
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 18
tcttacatac ttatacacct ggataaacac gggaagttat tcgtagtatg aggaatggag        60
cctggcacgg gcagtg                                                        76

<210> SEQ ID NO 19
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 19
acacaaaatc cacgctaagt ttcaacaaat cgaattagtt accaatagac tatttcttcg        60
cctggcacgg gcagtg                                                        76

<210> SEQ ID NO 20
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 20
tgagtaaaga ctaacttcca ggatgtatgt gatgcatagt acactaggca acaaaatccg        60
cctggcacgg gcagtg                                                        76

<210> SEQ ID NO 21
<211> LENGTH: 76
```

```
<212> TYPE: DNA
<213> ORGANISM: Artificial Sequence
<220> FEATURE:
<223> OTHER INFORMATION: Synthetic Aptamer Sequence

<400> SEQUENCE: 21
ccattatgtt ggtctggata tttaacattg ggaggaggat agacacggta aaggatcaca      60
cctggcacgg gcagtg                                                     76

<210> SEQ ID NO 22
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 22
gatgttcgtc gaagatcgaa catcatttga cacgatatat tatatcggag gtaaatggag      60
cctggcacgg gcagtg                                                     76

<210> SEQ ID NO 23
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 23
aagatattta cctaagcaca tagacacgtc attctgtcct tgatgaacaa tttgttgcat      60
cctggcacgg gcagtg                                                     76

<210> SEQ ID NO 24
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 24
agatgcacta gatcagttct agatttatgt cggctatgac taatgtaagg tgaatgacat      60
cctggcacgg gcagtg                                                     76

<210> SEQ ID NO 25
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 25
ctgatcttaa gtaggtaggt acaagtacac gcagatcgat tgttctgaat tataatttcg      60
cctggcacgg gcagtg                                                     76

<210> SEQ ID NO 26
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 26
agcatgagac gattccaatg ttcaacgtat tatacgttgc ggcattttc attattggag       60
```
cctggcacgg gcagtg                                                    76

<210> SEQ ID NO 27
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 27
tcctaattat ggcaataggt aagttcatca ttaccgatgt caataatttt aatgatggag    60
cctggcacgg gcagtg                                                    76

<210> SEQ ID NO 28
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 28
gtggtccgat gaatgaaatc gtataccacg attgaaatca tttagcacag agacaattca    60
cctggcacgg gcagtg                                                    76

<210> SEQ ID NO 29
<211> LENGTH: 72
<212> TYPE: DNA
<213> ORGANISM: Artificial Sequence
<220> FEATURE:
<223> OTHER INFORMATION: Synthetic Aptamer Sequence

<400> SEQUENCE: 29
gaaacacaat aacgtcagat ttgagaggta atagtgggga tggtattcag atggagcctg    60
gcacgggcag tg                                                        72

<210> SEQ ID NO 30
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 30
tacaagtaca cgagaattct atgtagagac tcatacaagt atttgttgac actttgacat    60
cctggcacgg gcagtg                                                    76

<210> SEQ ID NO 31
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 31
tgtgcacaag atcaccaaaa tttacaaaat tagacgttct tacgtgtaaa tgtattggag    60
cctggcacgg gcagtg                                                    76

<210> SEQ ID NO 32
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 32
aataatatat ctctagaaca ttaaatatca ttttcatata tttaaagtat atcataataa        60
cctggcacgg gcagtg                                                       76

<210> SEQ ID NO 33
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 33
tactatatat ttctatctga atatcgttat taataaaatt taactatctt aattaaatac        60
ctggcacggg cagtg                                                        75

<210> SEQ ID NO 34
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 34
taataagata gtgaaacata tattattgtc atatacacat ttttattaaa ttttaataat        60
cctggcacgg gcagtg                                                       76

<210> SEQ ID NO 35
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 35
aaataataag gatatttaat aacaatcttt atttaagtag atattaatgt cttaaataat        60
cctggcacgg gcagtg                                                       76

<210> SEQ ID NO 36
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 36
tatatcttct caatatagtt atctttattt cactattatt gaatatattt catatataac        60
ctggcacggg cagtg                                                        75

<210> SEQ ID NO 37
<211> LENGTH: 74
<212> TYPE: DNA
<213> ORGANISM: Artificial Sequence
<220> FEATURE:
<223> OTHER INFORMATION: Synthetic Aptamer Sequence

<400> SEQUENCE: 37
aatatttatc tattaaccaa tatataattg tagattctag atactaatta tatctaatcc        60
tggcacgggc agtg                                                         74

<210> SEQ ID NO 38

<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 38

```
taattttaaa ctaattataa tgaattaaca taaatttcaa ttaaaatgat tttaataatt    60
cctggcacgg gcagtg                                                    76
```

<210> SEQ ID NO 39
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 39

```
aaatctaatt taattgaaat agtatctatc tataatagtt aattagatat ttcaatattt    60
cctggcacgg gcagtg                                                    76
```

<210> SEQ ID NO 40
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 40

```
ttgaatattt catagaatta tttgaaatta tccttaataa ttctaaatttt aaattagatt    60
cctggcacgg gcagtg                                                    76
```

<210> SEQ ID NO 41
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 41

```
tatcataata gaaacaaata aatcagtcaa atattatatt ttcttctaag tatatttatt    60
cctggcacgg gcagtg                                                    76
```

<210> SEQ ID NO 42
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 42

```
ataataacat tctgataaca ttatatcttt aataatgatt acattcataa atttctatat    60
cctggcacgg gcagtg                                                    76
```

<210> SEQ ID NO 43
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 43

```
aattatcaat ataatctttt tttattctaa ttcaattaat aaataaagct aataattatc    60
```

```
ctggcacggg cagtg                                                      75

<210> SEQ ID NO 44
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 44
tatgtgtgtc taacactgtg cgcattcagc ccgacaagtt cccctcattt ggatttcatt      60
cctggcacgg gcagtg                                                     76

<210> SEQ ID NO 45
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 45
tattttatct cataacaaaa tattatgtat atcactttac aataaataat atactctatt      60
cctggcacgg gcagtg                                                     76

<210> SEQ ID NO 46
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 46
ttaaataaag attaataatt atgaaattta ctgttctatt ttaactataa ttttatttca      60
cctggcacgg gcagtg                                                     76

<210> SEQ ID NO 47
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 47
ataaagtata taattaataa tgataactta tgtctcatta atatattcct aaatatcttc      60
ctggcacggg cagtg                                                      75

<210> SEQ ID NO 48
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 48
tattaccaat atatctaata aacacagtta ttctaattat acttttttaa tacattatat      60
cctggcacgg gcagtg                                                     76

<210> SEQ ID NO 49
<211> LENGTH: 76
<212> TYPE: DNA
<213> ORGANISM: Artificial Sequence
<220> FEATURE:
```

<223> OTHER INFORMATION: Synthetic Aptamer Sequence

<400> SEQUENCE: 49
aacatacata attaatttct taagaatata tgttctagat tctttaatta ttatttatct    60
cctggcacgg gcagtg    76

<210> SEQ ID NO 50
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 50
atacttatat gatcctttt atatatgcat tattttatca ttatatatgt cattattatt    60
cctggcacgg gcagtg    76

<210> SEQ ID NO 51
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 51
tataatctta tatccaaata cttcatatat tatacatcat ttcatgttta ataattaaat    60
cctggcacgg gcagtg    76

<210> SEQ ID NO 52
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 52
tctaaatttc ctaaaataat gtatttattg tatacctata taattgttag aaataataaa    60
cctggcacgg gcagtg    76

<210> SEQ ID NO 53
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 53
taataaatta tttcttgtta ttattaatca tgtctaaacc aaatttatta gtatattaat    60
cctggcacgg gcagtg    76

<210> SEQ ID NO 54
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 54
atttttttct attcatatgt ttttcatata cttaagaatt atttttttat atgtttaatt    60
cctggcacgg gcagtg    76

```
<210> SEQ ID NO 55
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 55
aataatatat ctctagaaca ttaaatatca ttttcatata tttaaagtat atcataataa    60
cctggcacgg gcagtg                                                   76

<210> SEQ ID NO 56
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 56
taataagata gtgaaacata tattattgtc atatacacat ttttattaaa ttttaataat    60
cctggcacgg gcagtg                                                   76

<210> SEQ ID NO 57
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 57
aaataataag gatatttaat aacaatcttt atttaagtag atattaatgt cttaaataat    60
cctggcacgg gcagtg                                                   76

<210> SEQ ID NO 58
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 58
tactatatat ttctatctga atatcgttat taataaaatt taactatctt aattaaatac    60
ctggcacggg cagtg                                                    75

<210> SEQ ID NO 59
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 59
tatatcttct caatatagtt atctttattt cactattatt gaatatattt catatataac    60
ctggcacggg cagtg                                                    75

<210> SEQ ID NO 60
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 60
```
taattttaaa ctaattataa tgaattaaca taaatttcaa ttaaaatgat tttaataatt    60
cctggcacgg gcagtg                                                    76

<210> SEQ ID NO 61
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 61
ataaagtata taattaataa tgataactta tgtctcatta atatattcct aaatatcttc    60
ctggcacggg cagtg                                                     75

<210> SEQ ID NO 62
<211> LENGTH: 74
<212> TYPE: DNA
<213> ORGANISM: Artificial Sequence
<220> FEATURE:
<223> OTHER INFORMATION: Synthetic Aptamer Sequence

<400> SEQUENCE: 62
aatatttatc tattaaccaa tatataattg tagattctag atactaatta tatctaatcc    60
tggcacgggc agtg                                                      74

<210> SEQ ID NO 63
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 63
tatgtgtgtc taacactgtg cgcattcagc ccgacaagtt cccctcattt ggatttcatt    60
cctggcacgg gcagtg                                                    76

<210> SEQ ID NO 64
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 64
ataataacat tctgataaca ttatatcttt aataatgatt acattcataa atttctatat    60
cctggcacgg gcagtg                                                    76

<210> SEQ ID NO 65
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 65
tattaccaat atatctaata aacacagtta ttctaattat acttttttaa tacattatat    60
cctggcacgg gcagtg                                                    76

<210> SEQ ID NO 66
<211> LENGTH: 76
<212> TYPE: DNA
<213> ORGANISM: Artificial Sequence

```
<220> FEATURE:
<223> OTHER INFORMATION: Synthetic Aptamer Sequence

<400> SEQUENCE: 66
tatcataata gaaacaaata aatcagtcaa atattatatt ttcttctaag tatatttatt    60
cctggcacgg gcagtg                                                    76

<210> SEQ ID NO 67
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 67
aaatctaatt taattgaaat agtatctatc tataatagtt aattagatat ttcaatattt    60
cctggcacgg gcagtg                                                    76

<210> SEQ ID NO 68
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 68
atacttatat gatccttttt atatatgcat tattttatca ttatatatgt cattattatt    60
cctggcacgg gcagtg                                                    76

<210> SEQ ID NO 69
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 69
tataatctta tatccaaata cttcatatat tatacatcat ttcatgttta ataattaaat    60
cctggcacgg gcagtg                                                    76

<210> SEQ ID NO 70
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 70
tattttatct cataacaaaa tattatgtat atcacttttac aataaataat atactctatt   60
cctggcacgg gcagtg                                                    76

<210> SEQ ID NO 71
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 71
tctaaatttc ctaaaataat gtatttattg tatacctata taattgttag aaataataaa    60
cctggcacgg gcagtg                                                    76
```

<210> SEQ ID NO 72
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 72
ttgaatattt catagaatta tttgaaatta tccttaataa ttctaaattt aaattagatt    60
cctggcacgg gcagtg                                                    76

<210> SEQ ID NO 73
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 73
aacatacata attaatttct taagaatata tgttctagat tctttaatta ttatttatct    60
cctggcacgg gcagtg                                                    76

<210> SEQ ID NO 74
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 74
ataataacaa tattactatt gaatatttag atgattataa aaatcagtat attatataac    60
cctggcacgg gcagtg                                                    76

<210> SEQ ID NO 75
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 75
ttaaataaag attaataatt atgaaattta ctgttctatt ttaactataa ttttatttca    60
cctggcacgg gcagtg                                                    76

<210> SEQ ID NO 76
<211> LENGTH: 77
<212> TYPE: DNA
<213> ORGANISM: Artificial Sequence
<220> FEATURE:
<223> OTHER INFORMATION: Synthetic Aptamer Sequence

<400> SEQUENCE: 76
gagttacgaa gccatggtta actaaagtcg ggacgttttc tcagacgggt ctatattatg    60
gcctggcacg ggcagtg                                                   77

<210> SEQ ID NO 77
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 77
agaaccatag ccctacttct ccatgcgtca cgtgcagtgt ttaattcagt tctttgattt    60
cctggcacgg gcagtg    76

<210> SEQ ID NO 78
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 78
tcttacatac ttatacacct ggataaacac gggaagttat tcgtagtatg aggaatggag    60
cctggcacgg gcagtg    76

<210> SEQ ID NO 79
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 79
tctctgacta gagacgtata gtctcgtgtt ggttggcaca ttgagcccctt cttttggag    60 cctggcacgg gcagtg    76

<210> SEQ ID NO 80
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 80
tggatctcgt cgtaagggtt accttacgta tccgagggcc tagccgcgtc tagaatggag    60
cctggcacgg gcagtg    76

<210> SEQ ID NO 81
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 81
agcatctaga cacgcattag aattagctaa tatagagctg tgtatctgta gagtttgtca    60
cctggcacgg gcagtg    76

<210> SEQ ID NO 82
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 82
gagaagacct gtggagcaac tttaagcatg cttaaatagt ccacgtgaga gaattcagcc    60
cctggcacgg gcagtg    76

<210> SEQ ID NO 83
<211> LENGTH: 76
<212> TYPE: DNA

```
<213> ORGANISM: Artificial Sequence
<220> FEATURE:
<223> OTHER INFORMATION: Synthetic Aptamer Sequence

<400> SEQUENCE: 83
tggtgcattc agcccttcta ttgaatggta tccaaatgca ttctgctgaa atcattctca      60
cctggcacgg gcagtg                                                     76

<210> SEQ ID NO 84
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 84
aagatattta cctaagcaca tagacacgtc attctgtcct tgatgaacaa tttgttgcat      60
cctggcacgg gcagtg                                                     76

<210> SEQ ID NO 85
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 85
cattgctaga ttcactgaga tgcatcggat gcactaagcc cgccccacaa cttgttgtca      60
cctggcacgg gcagtg                                                     76

<210> SEQ ID NO 86
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 86
tgtcaacaca acatgtgtgt tagagatcgc gggggagtat agtcacgaaa gactccacaa      60
cctggcacgg gcagtg                                                     76

<210> SEQ ID NO 87
<211> LENGTH: 73
<212> TYPE: DNA
<213> ORGANISM: Artificial Sequence
<220> FEATURE:
<223> OTHER INFORMATION: Synthetic Aptamer Sequence

<400> SEQUENCE: 87
gagacagaca cgataaaatg acgtaattta gacgatataa tctgtaattg aatattgcct      60
ggcacgggca gtg                                                        73

<210> SEQ ID NO 88
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 88
tgtgatggaa ttcttttcat cagggagtag gtgcagaagg cagggatggg aaatttggcg      60
cctggcacgg gcagtg                                                     76
```

<210> SEQ ID NO 89
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 89
ccagaacatg tgtacgtcag tgagggtaga gttttgctgt gtctgtcgag aatgtgagca      60
cctggcacgg gcagtg                                                     76

<210> SEQ ID NO 90
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 90
aaaaccatgt ctcgaaatat tgggttaaac gttcgtgagc ctagccacga catttggatc      60
ctggcacggg cagtg                                                      75

<210> SEQ ID NO 91
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 91
atcccatcga tggtctacag tacgaagtag gagtacaaat gcccttcagt ttagtaagca      60
cctggcacgg gcagtg                                                     76

<210> SEQ ID NO 92
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 92
agcaattgcc acgttaattg tggaaatggt ttccagcaat ttgttaatgt cacataacaa      60
cctggcacgg gcagtg                                                     76

<210> SEQ ID NO 93
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 93
agcatttgcc acgagttaat atgtgactgg cacgggtaca gttacgtggt tgattagact      60
cctggcacgg gcagtg                                                     76

<210> SEQ ID NO 94
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 94
gatttacaaa gtgagacgat ttgtccaaga caaaactcac tggtaatcca tttggtggag    60
cctggcacgg gcagtg    76

<210> SEQ ID NO 95
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 95
tcattatgca tggacatagc actaagtcac gtcattcaat tatcaaccaa gatttaatca    60
cctggcacgg gcagtg    76

<210> SEQ ID NO 96
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 96
atggtcttat cggtgattga acatcggaca gaacgccacg acattggacg tagatggagc    60
ctggcacggg cagtg    75

<210> SEQ ID NO 97
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 97
ccggattttg atcaaaccaa atttgaatat ggtaacgggg gagcgctagt catttctccg    60
cctggcacgg gcagtg    76

<210> SEQ ID NO 98
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 98
tgttgaagtg gtgtaactga gaaagtgaga tacatcactc agttgattgg actaagcaat    60
cctggcacgg gcagtg    76

<210> SEQ ID NO 99
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 99
aagtgggtgt ttacatggta tccgtcgaga gtaaccttta tcgccatcca gtaatacgta    60
cctggcacgg gcagtg    76

<210> SEQ ID NO 100
<211> LENGTH: 76

```
<212> TYPE: DNA
<213> ORGANISM: Artificial Sequence
<220> FEATURE:
<223> OTHER INFORMATION: Synthetic Aptamer Sequence

<400> SEQUENCE: 100
tggacagttt ataaccagga cttggatctg ttgtttctac acctttcatg ctccacttct      60
cctggcacgg gcagtg                                                     76

<210> SEQ ID NO 101
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 101
aagtggctat ggatgtagtt cgctttacct ctgtctatct cgttggatgg ttagtaatat      60
cctggcacgg gcagtg                                                     76

<210> SEQ ID NO 102
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 102
tgattgaaat ggatctctcg taagatctgt agacgggtaa ctttcaactt tgagtggttt      60
cctggcacgg gcagtg                                                     76

<210> SEQ ID NO 103
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 103
tgaagtggct tacactcaca tcctcgttca acacgtgacc ttagtatctt atttgatcaa      60
cctggcacgg gcagtg                                                     76

<210> SEQ ID NO 104
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 104
aatccaagtt tatcactggg tagacgctcg aattgtgggt ctcttatcca ggagatagtt      60
cctggcacgg gcagtg                                                     76

<210> SEQ ID NO 105
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 105
gatgttcaga ttactgtgct ctcaggaatt atactcttca cagtcaacct agctatgaca      60
```

```
cctggcacgg gcagtg                                                        76

<210> SEQ ID NO 106
<211> LENGTH: 87
<212> TYPE: DNA
<213> ORGANISM: Artificial Sequence
<220> FEATURE:
<223> OTHER INFORMATION: Synthetic Aptamer Sequence

<400> SEQUENCE: 106
gtgctcctcg gtgaagtggc ttgtgctcct cggtgaagtg gcttgtgctc ctcggtgaag       60
tgtttttcaa tcctggcacg ggcagtg                                            87

<210> SEQ ID NO 107
<211> LENGTH: 98
<212> TYPE: DNA
<213> ORGANISM: Artificial Sequence
<220> FEATURE:
<223> OTHER INFORMATION: Synthetic Aptamer Sequence

<400> SEQUENCE: 107
gtgctcctcg aagtggcttg tgctcctcga agtggcttgt gctcctcgaa gtggcttgtg       60
ctcctcgtcg ttctttagta ttcctggcac gggcagtg                                98

<210> SEQ ID NO 108
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 108
gtgctcctcg aagtggcttg tgctcctcga agtggcttgt gctcctcgag caagtttatt       60
taattgacac ctggcacggg cagtg                                              85

<210> SEQ ID NO 109
<211> LENGTH: 68
<212> TYPE: DNA
<213> ORGANISM: Artificial Sequence
<220> FEATURE:
<223> OTHER INFORMATION: Synthetic Aptamer Sequence

<400> SEQUENCE: 109
gtgctcctcg tgaagtggct tgtgctcctc gtggttgata catgaacatt aacctggcac       60
gggcagtg                                                                 68

<210> SEQ ID NO 110
<211> LENGTH: 109
<212> TYPE: DNA
<213> ORGANISM: Artificial Sequence
<220> FEATURE:
<223> OTHER INFORMATION: Synthetic Aptamer Sequence

<400> SEQUENCE: 110
gtgctcctcg gtgaagtggc ttgtgctcct cggtgaagtg gcttgtgctc ctcggtgaag       60
tggcttgtgc tcctcggtga agtgtttttc aatcctggca cgggcagtg                  109

<210> SEQ ID NO 111
<211> LENGTH: 86
<212> TYPE: DNA
<213> ORGANISM: Artificial Sequence
<220> FEATURE:
<223> OTHER INFORMATION: Synthetic Aptamer Sequence
```

<400> SEQUENCE: 111
gtgctcctcg aagtggcttt gcatggctga atgttacaac gaagtgtatg gtctaaacaa    60
tagtttggtt cctggcacgg gcagtg                                          86

<210> SEQ ID NO 112
<211> LENGTH: 74
<212> TYPE: DNA
<213> ORGANISM: Artificial Sequence
<220> FEATURE:
<223> OTHER INFORMATION: Synthetic Aptamer Sequence

<400> SEQUENCE: 112
gtgctcctcg aagtggcttg tgctcctcga tagaagagtg acacgttcta agaaagaacc    60
tggcacgggc agtg                                                       74

<210> SEQ ID NO 113
<211> LENGTH: 98
<212> TYPE: DNA
<213> ORGANISM: Artificial Sequence
<220> FEATURE:
<223> OTHER INFORMATION: Synthetic Aptamer Sequence

<400> SEQUENCE: 113
gtgctcctcg tgacgtgaag tggcttgtgc tcctcgtgac gtgaagtggc tatgctattc    60
tctagttgaa ggaggattgt tacctggcac gggcagtg                             98

<210> SEQ ID NO 114
<211> LENGTH: 70
<212> TYPE: DNA
<213> ORGANISM: Artificial Sequence
<220> FEATURE:
<223> OTHER INFORMATION: Synthetic Aptamer Sequence

<400> SEQUENCE: 114
gtgctcctcg aagtggcttg tgctcctcgg atcaaatacc aatattgttg ttctcctggc    60
acgggcagtg                                                            70

<210> SEQ ID NO 115
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 115
gtgctcctcg aagtggcttg tgctcctcga agtggcataa tgttgttaag tagactggtc    60
ctggcacggg cagtg                                                      75

<210> SEQ ID NO 116
<211> LENGTH: 75
<212> TYPE: DNA
<213> ORGANISM: Artificial Sequence
<220> FEATURE:
<223> OTHER INFORMATION: Synthetic Aptamer Sequence

<400> SEQUENCE: 116
gtgctcctcg aagtggcttg tgctcctcga agtggcataa tgttgttaag tagactggtc    60
ctggcacggg cagtg                                                      75

<210> SEQ ID NO 117

```
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 117
gtgctcctcg tttacattgt tttgaagcac atcataatct ttgcctcgat attttactca    60
tttctcttcc ctggcacggg cagtg                                          85

<210> SEQ ID NO 118
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 118
gtgctcctcg aagtggcttg ttaatttagt gttttacgat gtttgtgtgt tctagtggtg    60
tcacagttgt cctggcacgg gcagtg                                         86

<210> SEQ ID NO 119
<211> LENGTH: 93
<212> TYPE: DNA
<213> ORGANISM: Artificial Sequence
<220> FEATURE:
<223> OTHER INFORMATION: Synthetic Aptamer Sequence

<400> SEQUENCE: 119
gtgctcctcg aagtggcttg tgctcctcga agtggcttgt gctcctcggt gatgtttcta    60
tcagactgtt atgttgtcct ggcacgggca gtg                                 93

<210> SEQ ID NO 120
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 120
gtgctcctcg tttgaagtgg ctttcttcaa ccagtgcgtg ttgtgtttta ttcagtaatg    60
aatcttgttc cctggcacgg gcagtg                                         86

<210> SEQ ID NO 121
<211> LENGTH: 109
<212> TYPE: DNA
<213> ORGANISM: Artificial Sequence
<220> FEATURE:
<223> OTHER INFORMATION: Synthetic Aptamer Sequence

<400> SEQUENCE: 121
gtgctcctcg ctcgaagtgg cttgtgctcc tcgctcgaag tggcttgtgc tcctcgctcg    60
aagtggcttg tgctcctcgt catcgttgat ggacctggca cgggcagtg                109

<210> SEQ ID NO 122
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 122
gtgctcctcg tccaccttga agtgtacctt acactggtgt tctaggagct taccggttgg    60
```

```
gtgcatcata cctggcacgg gcagtg                                            86

<210> SEQ ID NO 123
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 123
gtgctcctcg tttcatgatt ttgtactgtg ttaaagatcc taaatacttc ttggtgcaag      60
gcatgtaaac cctggcacgg gcagtg                                            86

<210> SEQ ID NO 124
<211> LENGTH: 84
<212> TYPE: DNA
<213> ORGANISM: Artificial Sequence
<220> FEATURE:
<223> OTHER INFORMATION: Synthetic Aptamer Sequence

<400> SEQUENCE: 124
gtgctcctcg aagtggcttg tgttcctcgt atatcttctc aatcttctgt acaatgtcat      60
attcttcccc tggcacgggc agtg                                              84

<210> SEQ ID NO 125
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 125
gtgctcctcg tgaagtggct tgtcctagct gttttcactg ttcaccctgt tattctcctt      60
attacacaat cctggcacgg gcagtg                                            86

<210> SEQ ID NO 126
<211> LENGTH: 84
<212> TYPE: DNA
<213> ORGANISM: Artificial Sequence
<220> FEATURE:
<223> OTHER INFORMATION: Synthetic Aptamer Sequence

<400> SEQUENCE: 126
gtgctcctcg tgaagtggct tgtgctcctc gtgaagtggc tgacttatca cttgctccaa      60
ggtataatcc tggcacgggc agtg                                              84

<210> SEQ ID NO 127
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 127
gtgctcctcg tactccctaa ggactaggaa gaacataatg ccatttccac actgtgtgtg      60
atataatcca cctggcacgg gcagtg                                            86

<210> SEQ ID NO 128
<211> LENGTH: 86
<212> TYPE: DNA
<213> ORGANISM: Artificial Sequence
<220> FEATURE:
```

<223> OTHER INFORMATION: Synthetic Aptamer Sequence

<400> SEQUENCE: 128
gtgctcctcg tatggtgtaa gtctctataa cctcgttatg agagattgta ccagaagagg    60
atttaaagca cctggcacgg gcagtg    86

<210> SEQ ID NO 129
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 129
gtgctcctcg tagcacatag acatgtcatt gaactgtccg aatcttcttg tgagtgttag    60
atattctccg cctggcacgg gcagtg    86

<210> SEQ ID NO 130
<211> LENGTH: 87
<212> TYPE: DNA
<213> ORGANISM: Artificial Sequence
<220> FEATURE:
<223> OTHER INFORMATION: Synthetic Aptamer Sequence

<400> SEQUENCE: 130
gtgctcctcg gtgaagtggc ttgtgctcct cggtgaagtg gcttgtgctc ctcggtgaag    60 tgttttcaa tcctggcacg ggcagtg    87

<210> SEQ ID NO 131
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 131
gtgctcctcg acgattgaag gatacaacgt agaactttag aactatcgct aatcgtcggg    60
ataaatggag cctggcacgg gcagtg    86

<210> SEQ ID NO 132
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 132
gtgctcctcg attgaattat gctaatgatt aacaatcgtg gggagaagcc tacgaaagag    60
gaattcagca cctggcacgg gcagtg    86

<210> SEQ ID NO 133
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 133
gtgctcctcg tatatgttta taaatctcta agttataatt aatcatataa atcctaagat    60
tttatttcct cctggcacgg gcagtg    86

```
<210> SEQ ID NO 134
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 134
gtgctcctcg tgatgctctc tagcagtcat atcactgagg ataccaagcc taattagtgt    60
aatatatgcg cctggcacgg gcagtg                                        86

<210> SEQ ID NO 135
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 135
gtgctcctcg ctcaagagga attcacacgt atttatgcgt gttattcctg taccacttat    60
tttttgtcac cctggcacgg gcagtg                                        86

<210> SEQ ID NO 136
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 136
gtgctcctcg gcaagaacat accgttacgg atttccgagt agtcactagt aacacttcag    60
aatatttccg cctggcacgg gcagtg                                        86

<210> SEQ ID NO 137
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 137
gtgctcctcg cagcatctga taggaccaat tcatttttg aacgtgagtt cgttaatgat     60
tttttgctac ctggcacggg cagtg                                         85

<210> SEQ ID NO 138
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 138
gtgctcctcg tcacttgagt ataactgtc cctctgaatg tgtatgagga tgtatcaagt     60
gtatgtggag cctggcacgg gcagtg                                        86

<210> SEQ ID NO 139
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 139
```
gtgctcctcg caacgttctc tatgagatgg agttaagcct ggttttttgat atgatagaaa    60 ttggttggag cctggcacgg gcagtg                                          86

<210> SEQ ID NO 140
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 140
gtgctcctcg tgtagaagaa cagaggagta caaaaacgtt tacgataggc tttaagccga    60
taatttgttg cctggcacgg gcagtg                                          86

<210> SEQ ID NO 141
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 141
gtgctcctcg aaataatac tttcatattt aatcctttat gtatatcatt tgtaatatac    60
tacataaatt cctggcacgg gcagtg                                          86

<210> SEQ ID NO 142
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 142
gtgctcctcg tgcacatgtc caaacttcgt ttattcttac tttccatcgt ggttaacatg    60
gaaatggatc ctggcacggg cagtg                                           85

<210> SEQ ID NO 143
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 143
gtgctcctcg aggtcacatc tatgccagtt ctaaaaatcg atttatgtga tttttacaag    60
taataagtca cctggcacgg gcagtg                                          86

<210> SEQ ID NO 144
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 144
gtgctcctcg tgcaaatcag atgatctatt gactggttat ttcctgattt gtaagaagag    60
tacccacttc cctggcacgg gcagtg                                          86

<210> SEQ ID NO 145
<211> LENGTH: 86
<212> TYPE: DNA
<213> ORGANISM: Artificial Sequence

```
<220> FEATURE:
<223> OTHER INFORMATION: Synthetic Aptamer Sequence

<400> SEQUENCE: 145
gtgctcctcg cacagatcac gtgagtaatt tcaaaggtac ctgacctagg gtattctttg    60
aaatcattcg cctggcacgg gcagtg                                         86

<210> SEQ ID NO 146
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 146
gtgctcctcg tgttaaccat ttacataaca cagagacatt aggcacgttt agaatacaat    60
tcttatggag cctggcacgg gcagtg                                         86

<210> SEQ ID NO 147
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 147
gtgctcctcg tatgaattac taatctatat cagaaaaatt aattctctgt ttaatttaat    60
tttaatgttt cctggcacgg gcagtg                                         86

<210> SEQ ID NO 148
<211> LENGTH: 87
<212> TYPE: DNA
<213> ORGANISM: Artificial Sequence
<220> FEATURE:
<223> OTHER INFORMATION: Synthetic Aptamer Sequence

<400> SEQUENCE: 148
gtgctcctcg cactaataga caattcaata aatccaaccc attggattat cttgaagttt    60
ttcattttcc ccctggcacg ggcagtg                                        87

<210> SEQ ID NO 149
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 149
gtgctcctcg atactccgaa ttctggaact gatttatcgg tgcgtcagag aggaagttaa    60
tattgtggag cctggcacgg gcagtg                                         86

<210> SEQ ID NO 150
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 150
gtgctcctcg gcataagtac acgtagttct gtttcaattg tacttttgag cagaacctag    60
attatttccg cctggcacgg gcagtg                                         86
```

<210> SEQ ID NO 151
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 151
gtgctcctcg taagagtaca aagaccttct cccacagacg tttggatcaa catggtagat    60
aaattgtacg cctggcacgg gcagtg    86

<210> SEQ ID NO 152
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 152
gtgctcctcg tgagacagcc atgacacaaa taatcagtgg atacattgag tatatgagtc    60
ttactttctc cctggcacgg gcagtg    86

<210> SEQ ID NO 153
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 153
gtgctcctcg ctgcaagacc ttacgataca tggatgtaat gtaatgatca tctagaatag    60
gttaatggag cctggcacgg gcagtg    86

<210> SEQ ID NO 154
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 154
gtgctcctcg cagagggaga ataagcctaa gatttttcga atgaaaaact taaacttgtc    60
aggaagaatg cctggcacgg gcagtg    86

<210> SEQ ID NO 155
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 155
gtgctcctcg tattggaata ctaatatatc tataataatg caaattaatc tatatcttac    60
tttttaatat cctggcacgg gcagtg    86

<210> SEQ ID NO 156
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 156
gtgctcctcg aatattaata atatcatgta tgtatcatta agattctatt ttcatttatt    60
acttaataat cctggcacgg gcagtg    86

<210> SEQ ID NO 157
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 157
gtgctcctcg atacatataa ttacatgaaa gtattaaatt atctatgaaa tttatcattt    60
attatttgtt cctggcacgg gcagtg    86

<210> SEQ ID NO 158
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 158
gtgctcctcg taatttacat tttaatcttt accttaaatc tcattataaa tatcatatta    60
gtaaataata cctggcacgg gcagtg    86

<210> SEQ ID NO 159
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 159
gtgctcctcg tacagtttaa atagattata acaatcatta tattacaaat tatgtgtttt    60
aatattaatt cctggcacgg gcagtg    86

<210> SEQ ID NO 160
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 160
gtgctcctcg aactattatt aatgtattat gattctattc tctaatgtaa tattattttt    60
attttaacaa cctggcacgg gcagtg    86

<210> SEQ ID NO 161
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 161
gtgctcctcg tattaataac ttaaatatga tagtttagac tttataatca tttatctact    60
tatttaatat cctggcacgg gcagtg    86

<210> SEQ ID NO 162
<211> LENGTH: 86
<212> TYPE: DNA

```
<213> ORGANISM: Artificial Sequence
<220> FEATURE:
<223> OTHER INFORMATION: Synthetic Aptamer Sequence

<400> SEQUENCE: 162
gtgctcctcg aacaattaaa tctaaatatc tctaaatatt ttttaacatt ttgaatttaa      60
cattaatatt cctggcacgg gcagtg                                          86

<210> SEQ ID NO 163
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 163
gtgctcctcg aattattatt atacattaac acaatctata atcaatttat ttataacaca      60
aataaagtat cctggcacgg gcagtg                                          86

<210> SEQ ID NO 164
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 164
gtgctcctcg tttatattat gataaaatgt tcaagtatta tactataatt gataagtaat      60
aagattacat cctggcacgg gcagtg                                          86

<210> SEQ ID NO 165
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 165
gtgctcctcg tttatcaata ttagcagtaa tattttatag atattttat cccattaata      60 tatctatttc ctggcacggg cagtg                                           85

<210> SEQ ID NO 166
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 166
gtgctcctcg tagtaaaaat ttaatgaaaa tatgaatcaa atattttcac aaataataat      60
tattttaaaa cctggcacgg gcagtg                                          86

<210> SEQ ID NO 167
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 167
gtgctcctcg ctagaataat aatcactatt cttagttgat ttaatattaa tatttatgaa      60
aaatataatt cctggcacgg gcagtg                                          86
```

<210> SEQ ID NO 168
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 168
gtgctcctcg aattttaaat gatatatttt aatgttatat ctatcaactt ctttaaatta    60
attattttct cctggcacgg gcagtg    86

<210> SEQ ID NO 169
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 169
gtgctcctcg caataataat taaaaattat gcaatatatt attaattaat tcatatgcta    60
ttatttattc cctggcacgg gcagtg    86

<210> SEQ ID NO 170
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 170
gtgctcctcg aatattatat attcgttctt ctttagtata gttgttacaa ttaataaaaa    60
aattattatt cctggcacgg gcagtg    86

<210> SEQ ID NO 171
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 171
gtgctcctcg taatacaatt ttattaaatt catagttcta attaataaca ctattcttct    60
tatttaaatt cctggcacgg gcagtg    86

<210> SEQ ID NO 172
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 172
gtgctcctcg ttatagttat ttaattctca tatttatatc acctttaaat caataattaa    60
tgtatattct cctggcacgg gcagtg    86

<210> SEQ ID NO 173
<211> LENGTH: 87
<212> TYPE: DNA
<213> ORGANISM: Artificial Sequence
<220> FEATURE:
<223> OTHER INFORMATION: Synthetic Aptamer Sequence

<400> SEQUENCE: 173
gtgctcctcg taaaaataca ttgatttta ttctaattta ttcttttaaa ttgcttatat    60
agtatttaat tcctggcacg ggcagtg                                       87

<210> SEQ ID NO 174
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 174
gtgctcctcg aaacatattt tagtattcta tatgacatat tttttaagaa tatagatcta   60
ttttatattt cctggcacgg gcagtg                                        86

<210> SEQ ID NO 175
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 175
gtgctcctcg acattaatta ttttctattc aattatctaa tttagttcaa gtattaaaat   60
gattataatt cctggcacgg gcagtg                                        86

<210> SEQ ID NO 176
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 176
gtgctcctcg ttttaaataa cttttttatt cattatccat tttaactaga tttaaaataa   60
aaataattct cctggcacgg gcagtg                                        86

<210> SEQ ID NO 177
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 177
gtgctcctcg aaagaatata attcaatgta gatttatcaa tatttattta tttaattaag   60
tatcattatt cctggcacgg gcagtg                                        86

<210> SEQ ID NO 178
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 178
gtgctcctcg aaagtttaat taataatcta ttcttaagat tacagaaata tatttgtatt   60
taaatattat cctggcacgg gcagtg                                        86

<210> SEQ ID NO 179
<211> LENGTH: 86

```
<212> TYPE: DNA
<213> ORGANISM: Artificial Sequence
<220> FEATURE:
<223> OTHER INFORMATION: Synthetic Aptamer Sequence

<400> SEQUENCE: 179
gtgctcctcg tatttatcat tcttagttaa taatactaac tgtatatata atacacatat      60
atttgatctt cctggcacgg gcagtg                                           86

<210> SEQ ID NO 180
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 180
gtgctcctcg aaatcttcat tgttattaat agatacaata taagtttaaa tagaatatag      60
atgtaataat cctggcacgg gcagtg                                           86

<210> SEQ ID NO 181
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 181
gtgctcctcg tctaaaatat aatcattatg ttagttagat aatcttttg taatattatc       60 aattatattc cctggcacgg gcagtg                                           86

<210> SEQ ID NO 182
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 182
gtgctcctcg aatattaata atatcatgta tgtatcatta agattctatt ttcatttatt      60
acttaataat cctggcacgg gcagtg                                           86

<210> SEQ ID NO 183
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 183
gtgctcctcg tacagtttaa atagattata acaatcatta tattacaaat tatgtgtttt      60
aatattaatt cctggcacgg gcagtg                                           86

<210> SEQ ID NO 184
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 184
gtgctcctcg tattggaata ctaatatatc tataataatg caaattaatc tatatcttac      60
``` ttttttaatat cctggcacgg gcagtg                                              86

<210> SEQ ID NO 185
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 185
gtgctcctcg atacatataa ttacatgaaa gtattaaatt atctatgaaa tttatcattt        60
attatttgtt cctggcacgg gcagtg                                              86

<210> SEQ ID NO 186
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 186
gtgctcctcg tattaataac ttaaatatga tagtttagac tttataatca tttatctact        60
tatttaatat cctggcacgg gcagtg                                              86

<210> SEQ ID NO 187
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 187
gtgctcctcg ttaatattta tattatacta cttgctatat aagtaatata atcaattcat        60
taataagatc ctggcacggg cagtg                                              85

<210> SEQ ID NO 188
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 188
gtgctcctcg caataataat taaaaattat gcaatatatt attaattaat tcatatgcta        60
ttatttattc cctggcacgg gcagtg                                              86

<210> SEQ ID NO 189
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 189
gtgctcctcg tttatattat gataaaatgt tcaagtatta tactataatt gataagtaat        60
aagattacat cctggcacgg gcagtg                                              86

<210> SEQ ID NO 190
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 190
gtgctcctcg tagtatttac atagattaga tatatcgata tattcttctt gtatattttt    60
aacttaatat cctggcacgg gcagtg    86

<210> SEQ ID NO 191
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 191
gtgctcctcg tttatcaata ttagcagtaa tatttttatag atattttttat cccattaata    60 tatctatttc ctggcacggg cagtg    85

<210> SEQ ID NO 192
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 192
gtgctcctcg tatttatcat tcttagttaa taatactaac tgtatatata atacacatat    60
atttgatctt cctggcacgg gcagtg    86

<210> SEQ ID NO 193
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 193
gtgctcctcg taatttacat tttaatcttt accttaaatc tcattataaa tatcatatta    60
gtaaataata cctggcacgg gcagtg    86

<210> SEQ ID NO 194
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 194
gtgctcctcg tagaagataa agataaattt ctagttatta tttgacatca tatttatata    60
aattatcatt cctggcacgg gcagtg    86

<210> SEQ ID NO 195
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 195
gtgctcctcg aaacatattt tagtattcta tatgacatat tttttaagaa tatagatcta    60
ttttatattt cctggcacgg gcagtg    86

<210> SEQ ID NO 196

```
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 196
gtgctcctcg ttgtataaaa tatatctatc taaatcgtaa tgagatatat tctatttgaa    60
ttaattattc ctggcacggg cagtg                                          85

<210> SEQ ID NO 197
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 197
gtgctcctcg ttatagttat ttaattctca tatttatatc acctttaaat caataattaa    60
tgtatattct cctggcacgg gcagtg                                         86

<210> SEQ ID NO 198
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 198
gtgctcctcg aattattatt atacattaac acaatctata atcaatttat ttataacaca    60
aataaagtat cctggcacgg gcagtg                                         86

<210> SEQ ID NO 199
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 199
gtgctcctcg aattttaaat gatatatttt aatgttatat ctatcaactt ctttaaatta    60
attattttct cctggcacgg gcagtg                                         86

<210> SEQ ID NO 200
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 200
gtgctcctcg taaaaaataa tgtgttattc tttatcatgt tattaattta gttaacatgt    60
aaaatatatt cctggcacgg gcagtg                                         86

<210> SEQ ID NO 201
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 201
gtgctcctcg taatgtgatc atattctatg attattatac agatatgttt tctatttata    60
```
taaatgtatt cctggcacgg gcagtg                                          86

<210> SEQ ID NO 202
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 202
gtgctcctcg ctagaataat aatcactatt cttagttgat ttaatattaa tatttatgaa      60
aaatataatt cctggcacgg gcagtg                                          86

<210> SEQ ID NO 203
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 203
gtgctcctcg aactattatt aatgtattat gattctattc tctaatgtaa tattatttt       60 atttaacaa cctggcacgg gcagtg                                           86

<210> SEQ ID NO 204
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 204
gtgctcctcg tcttattaaa tgtattataa ttgaaagatt ctatgataaa tattattggt      60
atattatcct cctggcacgg gcagtg                                          86

<210> SEQ ID NO 205
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 205
gtgctcctcg agtataattt aatagattct tttatataat attactctca tattctgtag      60
atatattaat cctggcacgg gcagtg                                          86

<210> SEQ ID NO 206
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 206
gtgctcctcg ttttatttat tagagttaat aatatatatc attactaagg taattagaat      60
tctatataat cctggcacgg gcagtg                                          86

<210> SEQ ID NO 207
<211> LENGTH: 86
<212> TYPE: DNA
<213> ORGANISM: Artificial Sequence
<220> FEATURE:

<223> OTHER INFORMATION: Synthetic Aptamer Sequence

<400> SEQUENCE: 207

```
gtgctcctcg taatacaatt ttattaaatt catagttcta attaataaca ctattcttct    60
tatttaaatt cctggcacgg gcagtg                                         86
```

<210> SEQ ID NO 208
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 208

```
gtgctcctcg taaaatattt gtttaattgt tattgtataa tactctttag tgttcatact    60
atattatatt cctggcacgg gcagtg                                         86
```

<210> SEQ ID NO 209
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 209

```
gtgctcctcg aacaattaaa tctaaatatc tctaaatatt ttttaacatt ttgaatttaa    60
cattaatatt cctggcacgg gcagtg                                         86
```

<210> SEQ ID NO 210
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 210

```
gtgctcctcg gtaataatta tagagattaa ttgtataaat cgtaatctat aaatatttaa    60
taataaacat cctggcacgg gcagtg                                         86
```

<210> SEQ ID NO 211
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 211

```
gtgctcctcg tactccctaa ggactaggaa gaacataatg ccatttccac actgtgtgtg    60
atataatcca cctggcacgg gcagtg                                         86
```

<210> SEQ ID NO 212
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 212

```
gtgctcctcg gagctggtag acacgataaa cgtacagtta gctggcacga ctgttaaatt    60
ctctcgttcc ctggcacggg cagtg                                          85
```

<210> SEQ ID NO 213
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 213
gtgctcctcg aaatcctaca catacggata aagtctttgg gtgatcacgg gtacagtgta    60
atttcgggag cctggcacgg gcagtg                                        86

<210> SEQ ID NO 214
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 214
gtgctcctcg attgaattat gctaatgatt aacaatcgtg gggagaagcc tacgaaagag    60
gaattcagca cctggcacgg gcagtg                                        86

<210> SEQ ID NO 215
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 215
gtgctcctcg ttgcgaggcc aagacacgac atttagtatg aggtggaggg tggatcaatt    60
gtatgatgtg cctggcacgg gcagtg                                        86

<210> SEQ ID NO 216
<211> LENGTH: 84
<212> TYPE: DNA
<213> ORGANISM: Artificial Sequence
<220> FEATURE:
<223> OTHER INFORMATION: Synthetic Aptamer Sequence

<400> SEQUENCE: 216
gtgctcctcg tgtaacatgc ccgattcaat ttcataccat ctatcactat gatactttaa    60
tttcaacacc tggcacgggc agtg                                          84

<210> SEQ ID NO 217
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 217
gtgctcctcg agagatgaag ccgtacttct gcaggtgacg tagatcccgt aacctggtag    60
aaatttgttc cctggcacgg gcagtg                                        86

<210> SEQ ID NO 218
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 218

```
gtgctcctcg tagattcatt ccgtactagg taatgatact gtgcacattg ccacgctgct    60
ctattgctca cctggcacgg gcagtg                                          86

<210> SEQ ID NO 219
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 219
gtgctcctcg ccacgaaaat tattcgttta cttgtgacta tccacatcag cttagtttca    60
ttatttccca cctggcacgg gcagtg                                          86

<210> SEQ ID NO 220
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 220
gtgctcctcg tcaagcccat gtattaacgt caatcattac taatcattgt ctaatcctct    60
aatttcacca cctggcacgg gcagtg                                          86

<210> SEQ ID NO 221
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 221
gtgctcctcg cattcttcga tgatatcgta gttgtctagt aacgggccaa gcctacatca    60
cttccagcac ctggcacggg cagtg                                           85

<210> SEQ ID NO 222
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 222
gtgctcctcg tatccaagcg gggattccat agatcagcta tacgtacaag ccgcgccacg    60
taaagtattc cctggcacgg gcagtg                                          86

<210> SEQ ID NO 223
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 223
gtgctcctcg cataaccagt tcgtttactt tatatcccat ttcaattcca tagaaatggt    60
aatttctctc cctggcacgg gcagtg                                          86

<210> SEQ ID NO 224
<211> LENGTH: 87
<212> TYPE: DNA
<213> ORGANISM: Artificial Sequence
```

```
<220> FEATURE:
<223> OTHER INFORMATION: Synthetic Aptamer Sequence

<400> SEQUENCE: 224
gtgctcctcg cactaataga caattcaata aatccaaccc attggattat cttgaagttt    60 ttcatttttcc ccctggcacg ggcagtg                                       87

<210> SEQ ID NO 225
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 225
gtgctcctcg tactagacac gacatgcata ttttcgtgat tggataagt tacagtgttt     60 ctgttatgac ctggcacggg cagtg                                          85

<210> SEQ ID NO 226
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 226
gtgctcctcg caaacgagga agcatgccac gctcactgtt tctcggttgc attccagaca    60
cttgttagtt cctggcacgg gcagtg                                         86

<210> SEQ ID NO 227
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 227
gtgctcctcg atacttctgc tacgcagtga gagaaagcac cagggcacgg ataaagtgta    60
aattctgtcc ctggcacggg cagtg                                          85

<210> SEQ ID NO 228
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 228
gtgctcctcg gccaatgtag ccaagacacg actattaggg gggttcaggg tagagtaaga    60
agtaattcag cctggcacgg gcagtg                                         86

<210> SEQ ID NO 229
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 229
gtgctcctcg gggatagagg ttgttggctg caaataacct ctggaaccga ggtatccact    60
tcaattggag cctggcacgg gcagtg                                         86
```

```
<210> SEQ ID NO 230
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 230
gtgctcctcg tacacacagg cacgtcttga ctaggtctcc atacagcaac cattgagatg    60
tatttggtca cctggcacgg gcagtg                                         86

<210> SEQ ID NO 231
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 231
gtgctcctcg acaggagttt acaggagcca cgtacagtca gtttcgccat ttccgtaaag    60
gaattaatca cctggcacgg gcagtg                                         86

<210> SEQ ID NO 232
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 232
gtgctcctcg tatgcactac aagaccttcc tttttcccta tcatacactc aatttgtcaa    60
ttaaatggat cctggcacgg gcagtg                                         86

<210> SEQ ID NO 233
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 233
gtgctcctcg aaatgctatg tacataagta atttatccac aattactacg ttcatagtct    60
tttggagcac ctggcacggg cagtg                                          85

<210> SEQ ID NO 234
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 234
gtgctcctcg caacatttat gttgtgtgga taaagacctt cttcaaagaa taactagttt    60
aatttatgat cctggcacgg gcagtg                                         86

<210> SEQ ID NO 235
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 235
```
gtgctcctcg tatatgttta taaatctcta agttataatt aatcatataa atcctaagat    60
tttatttcct cctggcacgg gcagtg                                         86

<210> SEQ ID NO 236
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 236
gtgctcctcg tggtttaaat accacagggg gaatcagcta cgatttcttc ctattagaga    60
agaaaatcct cctggcacgg gcagtg                                         86

<210> SEQ ID NO 237
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 237
gtgctcctcg tatggtgtaa gtctctataa cctcgttatg agagattgta ccagaagagg    60
atttaaagca cctggcacgg gcagtg                                         86

<210> SEQ ID NO 238
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 238
gtgctcctcg agctctatct tacgttatca agcccttcca ctaaccctga ttttgtgttc    60
ttaatctgca cctggcacgg gcagtg                                         86

<210> SEQ ID NO 239
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 239
gtgctcctcg ctcgaagtgg cttgtgctcc tcgcttgaag tggcttctgc tcctcgtcat    60
cgttgatgga cctggcacgg gcagtg                                         86

<210> SEQ ID NO 240
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 240
gtgctcctcg ttccttttac gccctgaagt ggcttgcact cgttatagct catgttgtga    60
ggtttaactc cctggcacgg gcagtg                                         86

<210> SEQ ID NO 241
<211> LENGTH: 86
<212> TYPE: DNA

```
<213> ORGANISM: Artificial Sequence
<220> FEATURE:
<223> OTHER INFORMATION: Synthetic Aptamer Sequence

<400> SEQUENCE: 241
gtgctcctcg aagtggcttt gcatggctga atgttacaac gaagtgtatg gtctaaacaa    60
tagtttggtt cctggcacgg gcagtg                                         86

<210> SEQ ID NO 242
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 242
gtgctcctcg tttcatgatt ttgtactgtg ttaaagatcc taaatacttc ttggtgcaag    60
gcatgtaaac cctggcacgg gcagtg                                         86

<210> SEQ ID NO 243
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 243
gtgctcctcg aagtgatgac gaccaaaagt caattatcct cactcaacac aacaagtaac    60
ggcagcatcc ctggcacggg cagtg                                          85

<210> SEQ ID NO 244
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 244
gtgctcctcg aagtggcttg ttaatttagt gttttacgat gtttgtgtgt tctagtggtg    60
tcacagttgt cctggcacgg gcagtg                                         86

<210> SEQ ID NO 245
<211> LENGTH: 85
<212> TYPE: DNA
<213> ORGANISM: Artificial Sequence
<220> FEATURE:
<223> OTHER INFORMATION: Synthetic Aptamer Sequence

<400> SEQUENCE: 245
gtgctcctcg tttacattgt tttgaagcac atcataatct ttgcctcgat attttactca    60
tttctcttcc ctggcacggg cagtg                                          85

<210> SEQ ID NO 246
<211> LENGTH: 89
<212> TYPE: DNA
<213> ORGANISM: Artificial Sequence
<220> FEATURE:
<223> OTHER INFORMATION: Synthetic Aptamer Sequence

<400> SEQUENCE: 246
gtgctcctcg tgaagtggct tgtgctcctc gtgaagtggc ttgtgctcct cgtggttgat    60
acatgaacat taacctggca cgggcagtg                                      89
```

<210> SEQ ID NO 247
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 247
gtgctcctcg tccaccttga agtgtacctt acactggtgt tctaggagct taccggttgg    60
gtgcatcata cctggcacgg gcagtg                                         86

<210> SEQ ID NO 248
<211> LENGTH: 102
<212> TYPE: DNA
<213> ORGANISM: Artificial Sequence
<220> FEATURE:
<223> OTHER INFORMATION: Synthetic Aptamer Sequence

<400> SEQUENCE: 248
gtgctcctcg tgaagtggct tgtgctcctc gtgaagtggc ttgtgctcct cgtgaagtgg    60
cttgtgctcc tcgaccctga agtgagcctg gcacgggcag tg                      102

<210> SEQ ID NO 249
<211> LENGTH: 86
<212> TYPE: DNA
<213> ORGANISM: Artificial Sequence
<220> FEATURE:
<223> OTHER INFORMATION: Synthetic Aptamer Sequence

<400> SEQUENCE: 249
gtgctcctcg ttatctagac gcacttgtaa gaatccctgg atacatcagc ttttagtgta    60
taagtgacat cctggcacgg gcagtg                                         86

<210> SEQ ID NO 250
<211> LENGTH: 88
<212> TYPE: DNA
<213> ORGANISM: Artificial Sequence
<220> FEATURE:
<223> OTHER INFORMATION: Synthetic Aptamer Sequence

<400> SEQUENCE: 250
gtgctcctcg aagtggcttg tgctcctcga agtggcttgt gctcctcgaa gtggttgtgc    60
catcatgagc atcctggcac gggcagtg                                       88

<210> SEQ ID NO 251
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 251
taggcgactg agtcgcgcgg cagcgccgat ggagacgccg cggaggggca cgccgagcac    60
cctggcacgg gcagtgtaaa                                                80

<210> SEQ ID NO 252
<211> LENGTH: 76
<212> TYPE: DNA
<213> ORGANISM: Artificial Sequence
<220> FEATURE:
<223> OTHER INFORMATION: Synthetic Aptamer Sequence

```
<400> SEQUENCE: 252
gcggtgggcc ccgcagggggg ctagggggcg tggtggggac gagctgcggg gagggggcaag    60 cctggcacgg gcagtg                                                     76

<210> SEQ ID NO 253
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 253
cggggctggg ggggatgggg tggcaccctc taccgcgtgg gccagtcggg gagccgcgcg    60
cctggcacgg gcagtg                                                     76

<210> SEQ ID NO 254
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 254
cggaaggggg tatgtgggcg gccggcggga gggtggaggg cgcgggcgcg gcgtgtggag    60
cctggcacgg gcagtg                                                     76

<210> SEQ ID NO 255
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 255
ggaggccgtc cgccgatgaa agttcggcgt ggggggggcga ggcgccgggg cacggcagga    60
cctggcacgg gcagtgtaaa                                                 80

<210> SEQ ID NO 256
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 256
actttaagct ttacagtgaa ttatctagca accccctctt cctggcacgg gcagtgtaaa    60

<210> SEQ ID NO 257
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 257
ttgagtctaa ggatttaact cccgatactt ataactagaa cctggcacgg gcagtgtaaa    60

<210> SEQ ID NO 258
<211> LENGTH: 81
<212> TYPE: DNA
<213> ORGANISM: Artificial Sequence
<220> FEATURE:
<223> OTHER INFORMATION: Synthetic Aptamer Sequence
```

-continued

<400> SEQUENCE: 258
ctggtggcgc cgcgacccgc gaccacacgg gccggcggac gaggcgtcgg gtagcagaag    60
acctggcacg ggcagtgtaa a    81

<210> SEQ ID NO 259
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 259
tcacctcggt gtgagggca gggcggaggg gaggcggagg gcacggtgcg gcgtcgcggg    60
cctggcacgg gcagtg    76

<210> SEQ ID NO 260
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 260
tggggtgggc tggcagggag gtgccccggg gacccgcggg tggagggcgg gtcggatgtg    60
cctggcacgg gcagtg    76

<210> SEQ ID NO 261
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 261
ccgtggggcg tgcggatgct gcagctggcc ggaggggcgg ggaggagggc gggggcgcag    60
cctggcacgg gcagtg    76

<210> SEQ ID NO 262
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 262
tgggcgggca gaggagggcc ggaggcgttc gaccgcgggc tgggctgggt tggcgcggtg    60
cctggcacgg gcagtg    76

<210> SEQ ID NO 263
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 263
gcgacgatgt ggcattgcag cgcgcgctgc ggcgggggt gtgacggggg gccggcgagg    60
cctggcacgg gcagtg    76

<210> SEQ ID NO 264

<211> LENGTH: 56
<212> TYPE: DNA
<213> ORGANISM: Artificial Sequence
<220> FEATURE:
<223> OTHER INFORMATION: Synthetic Aptamer Sequence

<400> SEQUENCE: 264
agttgctttg gccttaatgg gataaatgtt agagttgtca cctggcacgg gcagtg    56

<210> SEQ ID NO 265
<211> LENGTH: 56
<212> TYPE: DNA
<213> ORGANISM: Artificial Sequence
<220> FEATURE:
<223> OTHER INFORMATION: Synthetic Aptamer Sequence

<400> SEQUENCE: 265
aacccatcat caaagagagg tgtattgcta ctgtaatgca cctggcacgg gcagtg    56

<210> SEQ ID NO 266
<211> LENGTH: 56
<212> TYPE: DNA
<213> ORGANISM: Artificial Sequence
<220> FEATURE:
<223> OTHER INFORMATION: Synthetic Aptamer Sequence

<400> SEQUENCE: 266
agttatctat gtccacatct accaaaaacg tatccaaccc cctggcacgg gcagtg    56

<210> SEQ ID NO 267
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 267
gaagtggctt gtgttcctcg tcttctgaca atggtcttgt gctcacaggg attacttatg    60
cctggcacgg gcagtgtaaa    80

<210> SEQ ID NO 268
<211> LENGTH: 56
<212> TYPE: DNA
<213> ORGANISM: Artificial Sequence
<220> FEATURE:
<223> OTHER INFORMATION: Synthetic Aptamer Sequence

<400> SEQUENCE: 268
gtttagatgg tacgttctaa tggttgtgag cgaagcaata cctggcacgg gcagtg    56

<210> SEQ ID NO 269
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 269
cgtctttctt cccagcgttt ggaccccaaa tctatccttg cctggcacgg gcagtgtaaa    60

<210> SEQ ID NO 270
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 270
atttttcacc gtctgaaact tttgatgttt tggtctttat cctggcacgg gcagtgtaaa    60

<210> SEQ ID NO 271
<211> LENGTH: 56
<212> TYPE: DNA
<213> ORGANISM: Artificial Sequence
<220> FEATURE:
<223> OTHER INFORMATION: Synthetic Aptamer Sequence

<400> SEQUENCE: 271
cgttctgcct ggcatttttt tgctgatttc tttcttagca cctggcacgg gcagtg    56

<210> SEQ ID NO 272
<211> LENGTH: 56
<212> TYPE: DNA
<213> ORGANISM: Artificial Sequence
<220> FEATURE:
<223> OTHER INFORMATION: Synthetic Aptamer Sequence

<400> SEQUENCE: 272
ccatggcttg attctcgctg gtagggcggg gcgtagatta cctggcacgg gcagtg    56

<210> SEQ ID NO 273
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 273
cgttctgcct ggcatttttt tgctgatttc tttcttagca cctggcacgg gcagtgtaaa    60

<210> SEQ ID NO 274
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 274
tttcaaagtg ggggtagtgc atgtactatg ggtttgtgta cctggcacgg gcagtgtaaa    60

<210> SEQ ID NO 275
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 275
gtttagatgg tacgttctaa tggttgtgag cgaagcaata cctggcacgg gcagtgtaaa    60

<210> SEQ ID NO 276
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 276
ccagaattct cgtaagacgg agaggaatgg atagagtgaa cctggcacgg gcagtgtaaa    60

<210> SEQ ID NO 277

```
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 277
ccagaattct cgtaagacgg agaggaatgg atagagtgaa cctggcacgg gcagtgtaaa      60

<210> SEQ ID NO 278
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 278
cacacgaata tggctctctt tctcccattc acactcctca cctggcacgg gcagtgtaaa      60

<210> SEQ ID NO 279
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 279
gaagtggctt gtgttcctcg aacccatcat caaagagagg tgtattgcta ctgtaatgca      60
cctggcacgg gcagtgtaaa                                                  80

<210> SEQ ID NO 280
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 280
agttatctat gtccacatct accaaaaacg tatccaacca cctggcacgg gcagtgtaaa      60

<210> SEQ ID NO 281
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 281
tcttctgaca atggtcttgt gctcacaggg attacttata cctggcacgg gcagtgtaaa      60

<210> SEQ ID NO 282
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 282
cgtctttctt cccagcgttt ggaccccaaa tctatcctta cctggcacgg gcagtgtaaa      60

<210> SEQ ID NO 283
<211> LENGTH: 60
<212> TYPE: DNA
<213> ORGANISM: Artificial Sequence
<220> FEATURE:
<223> OTHER INFORMATION: Synthetic Aptamer Sequence
```

```
<400> SEQUENCE: 283
cgcacgaata tggctctctt tctcccattc acactcctca cctggcacgg gcagtgtaaa     60

<210> SEQ ID NO 284
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 284
ctgcttgttg acgaaattac gctgcatttg ggtgcttcca cctggcacgg gcagtgtaaa     60

<210> SEQ ID NO 285
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 285
gtgataacga attttagact gcccaacgtc acagcaagtg cctggcacgg gcagtgtaaa     60

<210> SEQ ID NO 286
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 286
ttgatgtttg tctacgaatt gttggcaggt taccgggtaa cctggcacgg gcagtgtaaa     60

<210> SEQ ID NO 287
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 287
tctacgtgga tgtcttcact acggatttat gctggcctta cctggcacgg gcagtgtaaa     60

<210> SEQ ID NO 288
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 288
atgtccacga attttcactc ccataacgtt gccactgcaa cctggcacgg gcagtgtaaa     60

<210> SEQ ID NO 289
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 289
gtgataacga attttagact gcccaacgtc acaacaagtg cctggcacgg gcagtgtaaa     60

<210> SEQ ID NO 290
```

```
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 290
gtgataacga attttagact gcccaacgtc acagtaagtg cctggcacgg gcagtgtaaa     60

<210> SEQ ID NO 291
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 291
tagttactgc tagtacgaat ttagacagtc cgtctctgac cctggcacgg gcagtgtaaa     60

<210> SEQ ID NO 292
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 292
ctgcttgttg acgaaattac gctgcatttg ggtgtttcca cctggcacgg gcagtgtaaa     60

<210> SEQ ID NO 293
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 293
gtgataacga attttagact gcccaacgtc acagcaagta cctggcacgg gcagtgtaaa     60

<210> SEQ ID NO 294
<211> LENGTH: 60
<212> TYPE: DNA
<213> ORGANISM: Artificial Sequence
<220> FEATURE:
<223> OTHER INFORMATION: Synthetic Aptamer Sequence

<400> SEQUENCE: 294
ctactatgta ctgaagcatg aacgagtttt cacgcctgat cctggcacgg gcagtgtaaa     60

<210> SEQ ID NO 295
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 295
ggtggcgcga cggacgtgcg agaggggggcg gagcgcgggg aaggcgagcg gtgtgaggtg     60
cctggcacgg gcagtgtaaa                                                 80

<210> SEQ ID NO 296
<211> LENGTH: 60
<212> TYPE: DNA
<213> ORGANISM: Artificial Sequence
<220> FEATURE:
<223> OTHER INFORMATION: Synthetic Aptamer Sequence
```

```
<400> SEQUENCE: 296
tctacgtgga tgtcttcact acggatttat gctggcctta cctggcacgg gcagtgtaaa     60

<210> SEQ ID NO 297
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 297
aagatattta cctaagcaca tagacacgtc attctgtcct tgatgaacaa tttgttgcat     60
cctggcacgg g                                                         71

<210> SEQ ID NO 298
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 298
aataatatat ctctagaaca ttaaatatca ttttcatata tttaaagtat atcataataa     60
cctggcacgg g                                                         71

<210> SEQ ID NO 299
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 299
tgaagtggct tacactcaca tcctcgttca acacgtgacc ttagtatctt atttgatcaa     60
cctggcacgg g                                                         71

<210> SEQ ID NO 300
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 300
taataagata gtgaaacata tattattgtc atatacacat ttttattaaa ttttaataat     60
cctggcacgg g                                                         71

<210> SEQ ID NO 301
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 301
tatgtgtgtc taaactgtg cgcattcagc ccgacaagtt ccctcatt ggatttcatt       60 cctggcacgg g                                                         71

<210> SEQ ID NO 302
<211> LENGTH: 70
<212> TYPE: DNA
```

```
<213> ORGANISM: Artificial Sequence
<220> FEATURE:
<223> OTHER INFORMATION: Synthetic Aptamer Sequence

<400> SEQUENCE: 302
tatatcttct caatatagtt atctttattt cactattatt gaatatattt catatataac    60
ctggcacggg                                                           70

<210> SEQ ID NO 303
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 303
tggacagttt ataaccagga cttggatctg ttgtttctac acctttcatg ctccacttct    60
cctggcacgg g                                                         71

<210> SEQ ID NO 304
<211> LENGTH: 51
<212> TYPE: DNA
<213> ORGANISM: Artificial Sequence
<220> FEATURE:
<223> OTHER INFORMATION: Synthetic Aptamer Sequence

<400> SEQUENCE: 304
tgcaccgggc gcagggcgag agcatacaag gcacagcgag cctggcacgg g             51

<210> SEQ ID NO 305
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 305
aagatattta cctaagcaca tagacacgtc attctgtcct tgatgaacaa tttgttgcat    60
cctggcacgg gcagtgtaaa                                                80

<210> SEQ ID NO 306
<211> LENGTH: 64
<212> TYPE: DNA
<213> ORGANISM: Artificial Sequence
<220> FEATURE:
<223> OTHER INFORMATION: Synthetic Aptamer Sequence

<400> SEQUENCE: 306
aacattaaat atcattttca tatatttaaa gtatatcata ataacctggc acgggcagtg    60
taaa                                                                 64

<210> SEQ ID NO 307
<211> LENGTH: 59
<212> TYPE: DNA
<213> ORGANISM: Artificial Sequence
<220> FEATURE:
<223> OTHER INFORMATION: Synthetic Aptamer Sequence

<400> SEQUENCE: 307
aataatatat ctctagaaca ttaaatatca ttttcataac ctggcacggg cagtgtaaa    59

<210> SEQ ID NO 308
<211> LENGTH: 47
```

<212> TYPE: DNA
<213> ORGANISM: Artificial Sequence
<220> FEATURE:
<223> OTHER INFORMATION: Synthetic Aptamer Sequence

<400> SEQUENCE: 308
attgacctac gaaagaggaa ttcagcacct ggcacgggca gtgtaaa         47

<210> SEQ ID NO 309
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 309
aataatatat ctctagaaca ttaaatatca ttttcatata tttaaagtat atcataataa      60
cctggcacgg gcagtgtaaa                                                  80

<210> SEQ ID NO 310
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 310
aagatattta cctaagcaca tagacacgtc attctgtcct tgatgaacaa tttgttgcat      60
cctggcacgg gcagtgtaaa                                                  80

<210> SEQ ID NO 311
<211> LENGTH: 57
<212> TYPE: DNA
<213> ORGANISM: Artificial Sequence
<220> FEATURE:
<223> OTHER INFORMATION: Synthetic Aptamer Sequence

<400> SEQUENCE: 311
acacgtcatt ctgtccttga tgaacaattt gttgcatcct ggcacgggca gtgtaaa        57

<210> SEQ ID NO 312
<211> LENGTH: 63
<212> TYPE: DNA
<213> ORGANISM: Artificial Sequence
<220> FEATURE:
<223> OTHER INFORMATION: Synthetic Aptamer Sequence

<400> SEQUENCE: 312
attaacaatc gtggggagaa gcctacgaaa gaggaattca gcacctggca cgggcagtgt     60
aaa                                                                   63

<210> SEQ ID NO 313
<211> LENGTH: 63
<212> TYPE: DNA
<213> ORGANISM: Artificial Sequence
<220> FEATURE:
<223> OTHER INFORMATION: Synthetic Aptamer Sequence

<400> SEQUENCE: 313
aagtggcttg ttaatttagt gttttacgat gtttgtgtgt tgtcctggca cgggcagtgt     60
aaa                                                                   63

<210> SEQ ID NO 314

```
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 314
gtccagtgcc ttgtatggta ggtctattat atcccgactt atattgagtg cagtaagcat      60
cctggcacgg g                                                          71

<210> SEQ ID NO 315
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 315
gtgggggttt agctctggcg catggataga cgatagtgcg atgggataaa gaggaggtag      60
cctggcacgg g                                                          71

<210> SEQ ID NO 316
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 316
tactctttca ctctgtggtt ctgctctcaa actgtcatgc tcttttcatt cacctagttt      60
cctggcacgg g                                                          71

<210> SEQ ID NO 317
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 317
cttgtcgtat gcttatttgt tttcgcctgt ttgtattctt gagtgatatt gcagctcaaa      60
cctggcacgg g                                                          71

<210> SEQ ID NO 318
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 318
tttacgaaca aatcgatacg gtggggaata catgggatgc atctagtcgt tactaagcca      60
cctggcacgg g                                                          71

<210> SEQ ID NO 319
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 319
tagtttttta acgagttcga tcaacatgtg gatgtctcta attcaatccg gcaattgatg      60
```
cctggcacgg g                                                              71

<210> SEQ ID NO 320
<211> LENGTH: 72
<212> TYPE: DNA
<213> ORGANISM: Artificial Sequence
<220> FEATURE:
<223> OTHER INFORMATION: Synthetic Aptamer Sequence

<400> SEQUENCE: 320
accgtgccag agggaacaga ttcgcgggac gcatcggtcg cgacccgaaa catggttggc    60
tcctggcacg gg                                                             72

<210> SEQ ID NO 321
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 321
aaccatcaca aatataatgg atcggacttt gttgttttga aacacacaca cgtgttgtta    60
cctggcacgg g                                                              71

<210> SEQ ID NO 322
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 322
agtcatcgtt cgcgaattag tttattgtgc gcggtaaatt gattatggct aatgtatggt    60
cctggcacgg g                                                              71

<210> SEQ ID NO 323
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 323
caaatggccg tctaaggagc atcccaggtg caacaccacg atattagtat gcggacgtcg    60
cctggcacgg g                                                              71

<210> SEQ ID NO 324
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 324
gaggagttaa tcgtaatggc gctttagcta ttgggtggaa gggaggcggt aggactgcgc    60
cctggcacgg g                                                              71

<210> SEQ ID NO 325
<211> LENGTH: 71
<212> TYPE: DNA
<213> ORGANISM: Artificial Sequence
<220> FEATURE:

<223> OTHER INFORMATION: Synthetic Aptamer Sequence

<400> SEQUENCE: 325

```
cactgtagat gtgagcattc aatccatagg ttatatagtt ccacgtcatg aaattcaccc    60
cctggcacgg g                                                         71
```

<210> SEQ ID NO 326
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 326

```
gcgtttacta ctaccatccc caatgtctaa atttctgtcc tgttttgtta catatggatt    60
cctggcacgg g                                                         71
```

<210> SEQ ID NO 327
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 327

```
agtaatctat cgtggaagtc ggattctact gggcagcatc tcacagtgat ttactgcaca    60
cctggcacgg g                                                         71
```

<210> SEQ ID NO 328
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 328

```
cgacggtgca gacttatatg tctgtcagac ggtgccctgg tacattccgt cagtgacggt    60
cctggcacgg g                                                         71
```

<210> SEQ ID NO 329
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 329

```
tctatgtatt caggtctcct cgatttgcat agagcaattg ggctgatgag atcattgagt    60
cctggcacgg g                                                         71
```

<210> SEQ ID NO 330
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 330

```
gatgcatatt tttacgtctc accgtagact gtcgtagttt ctagggtttc cgaaggtcgg    60
cctggcacgg g                                                         71
```

```
<210> SEQ ID NO 331
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 331
cactacgtgg tgtctacaac ttttcagccg attatccttg ttgtctacgt cgtcgccaac    60
cctggcacgg g                                                         71

<210> SEQ ID NO 332
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 332
cgttaaatgt gagcatcatt ggtgtggagt ccatagcgtg gttgtaggta ttttccttct    60
cctggcacgg g                                                         71

<210> SEQ ID NO 333
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 333
tgccaggtac aataacggtg tttatggtca gttatatcta tcactgggac cctcttgctt    60
cctggcacgg g                                                         71

<210> SEQ ID NO 334
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 334
ttgttcccgc ttttgtgact caggtctaca gtgtctgatg aactcgattt taaagctcca    60
cctggcacgg g                                                         71

<210> SEQ ID NO 335
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 335
gcctttaggc ccagactcct taaatagcct cggccggcca tgttagatta taccttgttt    60
cctggcacgg g                                                         71

<210> SEQ ID NO 336
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 336
```

```
tattactccc gagcacgtag gttaattatt tagaggggaa aaggtgagta gagtagtttt      60
cctggcacgg g                                                          71

<210> SEQ ID NO 337
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 337
tagacatcct accctttaga tttgatctta ttttaccaga ccttctatca ttgattgcag      60
cctggcacgg g                                                          71

<210> SEQ ID NO 338
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 338
tagtgtataa gtcatgcacc ttttagtcg atcttgacca gagtgtttcg tgataagagt       60
cctggcacgg g                                                          71

<210> SEQ ID NO 339
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 339
cctacattgg caatagcaaa tctgttgact gagatgcact ctaaaagcag ttctcctcct      60
cctggcacgg g                                                          71

<210> SEQ ID NO 340
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 340
tgcgcagggc taacattagt catatttttac taaagtatcc tcaccatcgc atttgttagc     60
cctggcacgg g                                                          71

<210> SEQ ID NO 341
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 341
ttcgagggtt gcttactgag atctgtgtca gacgcacagc tcgtagttgg ttagctgtcc      60
cctggcacgg g                                                          71

<210> SEQ ID NO 342
<211> LENGTH: 71
<212> TYPE: DNA
<213> ORGANISM: Artificial Sequence
```

```
<220> FEATURE:
<223> OTHER INFORMATION: Synthetic Aptamer Sequence

<400> SEQUENCE: 342
aacttgttcg aagtttggga attccggaag aattctacgg atggtttgct tatgtcgttt    60
cctggcacgg g                                                         71

<210> SEQ ID NO 343
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 343
ttctccgagt aagttctaaa ttcaatacct cttcctaaag ggttgtgtgg gagtatctaa    60
cctggcacgg g                                                         71

<210> SEQ ID NO 344
<211> LENGTH: 51
<212> TYPE: DNA
<213> ORGANISM: Artificial Sequence
<220> FEATURE:
<223> OTHER INFORMATION: Synthetic Aptamer Sequence

<400> SEQUENCE: 344
taacaccgta cgtattagtc tcagagttgg gcatatctca cctggcacgg g              51

<210> SEQ ID NO 345
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 345
cctttcctgt cgatttggaa actcttagca acaaatcatg ccaactaatg tgctgttgat    60
cctggcacgg g                                                         71

<210> SEQ ID NO 346
<211> LENGTH: 72
<212> TYPE: DNA
<213> ORGANISM: Artificial Sequence
<220> FEATURE:
<223> OTHER INFORMATION: Synthetic Aptamer Sequence

<400> SEQUENCE: 346
aggacggtct tcccggttcg cgggatgtgc agggtatgca ttaaagatct tttaaggatt    60
gcctggcacg gg                                                        72

<210> SEQ ID NO 347
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 347
cgttttctta ctcattcact taatcgttat gtaatgatat catgtaggtg gttattgaaa    60
cctggcacgg g                                                         71

<210> SEQ ID NO 348
```

```
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 348
gttgcttctt taatcttaat tcgtggcata gaagttcaag gtcacaaata tattggacat      60
cctggcacgg g                                                          71

<210> SEQ ID NO 349
<211> LENGTH: 72
<212> TYPE: DNA
<213> ORGANISM: Artificial Sequence
<220> FEATURE:
<223> OTHER INFORMATION: Synthetic Aptamer Sequence

<400> SEQUENCE: 349
tgactcgatt tggatggggt tataacgtag ctacgaaggt taacttctac accttgttag      60
gcctggcacg gg                                                         72

<210> SEQ ID NO 350
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 350
atagtgcgtg ggtgaacggt atacaaaatt aactgcgtgc attcttgggt cttgatccac      60
cctggcacgg g                                                          71

<210> SEQ ID NO 351
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 351
tactagtggt aaggtacctc gcgtgttatg gcggtacgta ctaacgaccg taattgttcg      60
cctggcacgg g                                                          71

<210> SEQ ID NO 352
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 352
tttaacgatt cgtgagagtg tgaatcacct gggataattt tttaatgctt gcagcttatg      60
cctggcacgg g                                                          71

<210> SEQ ID NO 353
<211> LENGTH: 51
<212> TYPE: DNA
<213> ORGANISM: Artificial Sequence
<220> FEATURE:
<223> OTHER INFORMATION: Synthetic Aptamer Sequence

<400> SEQUENCE: 353
atcttctttt taggttttaa tgacccaggt tgtaccctca cctggcacgg g               51
```

<210> SEQ ID NO 354
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 354
gtcgtctaaa atatgttagc agtgtcccga cgtcagtttt tcaagttagt tagcatcgga        60
cctggcacgg g                                                              71

<210> SEQ ID NO 355
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 355
atgggtcatt actcatggct gttatttccg gcagcgatgt taggattcca taaaggtgca        60
cctggcacgg g                                                              71

<210> SEQ ID NO 356
<211> LENGTH: 51
<212> TYPE: DNA
<213> ORGANISM: Artificial Sequence
<220> FEATURE:
<223> OTHER INFORMATION: Synthetic Aptamer Sequence

<400> SEQUENCE: 356
gcccgaacta ccggtctatg gctctcccat gtccctgacg cctggcacgg g                 51

<210> SEQ ID NO 357
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 357
ctactagtgg accttgcacg cacaaatcca cggtatacgg acagtaaata ctacctgtca        60
cctggcacgg g                                                              71

<210> SEQ ID NO 358
<211> LENGTH: 51
<212> TYPE: DNA
<213> ORGANISM: Artificial Sequence
<220> FEATURE:
<223> OTHER INFORMATION: Synthetic Aptamer Sequence

<400> SEQUENCE: 358
cggggtcgag atagtgtctg aagttgaggg aagggctggg cctggcacgg g                 51

<210> SEQ ID NO 359
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 359
gaagtggctt gtgctcctcg aagtggcttg ttaatttagt gttttacgat gtttgtgtgt        60

```
tctagtggtg tcacagttgt cctggcacgg gcagtgtaaa                         100

<210> SEQ ID NO 360
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 360
gaagtggctt gtgctcctcg attgaattat gctaatgatt aacaatcgtg gggagaagcc    60
tacgaaagag gaattcagca cctggcacgg gcagtgtaaa                         100

<210> SEQ ID NO 361
<211> LENGTH: 71
<212> TYPE: DNA
<213> ORGANISM: Artificial Sequence
<220> FEATURE:
<223> OTHER INFORMATION: Synthetic Aptamer Sequence

<400> SEQUENCE: 361
gaagtggctt gtgctcctcg aagtggcttg aagtggcttg tgctcctcgc acctggcacg    60
ggcagtgtaa a                                                        71

<210> SEQ ID NO 362
<211> LENGTH: 82
<212> TYPE: DNA
<213> ORGANISM: Artificial Sequence
<220> FEATURE:
<223> OTHER INFORMATION: Synthetic Aptamer Sequence

<400> SEQUENCE: 362
gaagtggctt gtgctcctcg aagatattta cctaagcaca tagacacgtc attctgttgc    60
atcctggcac gggcagtgta aa                                            82

<210> SEQ ID NO 363
<211> LENGTH: 98
<212> TYPE: DNA
<213> ORGANISM: Artificial Sequence
<220> FEATURE:
<223> OTHER INFORMATION: Synthetic Aptamer Sequence

<400> SEQUENCE: 363
gaagtggctt gtgctcctcg aagtggcttg aagtggcttg tgctcctcga agtggcttga    60
agtggcttgt gctcctcgcc tggcacgggc agtgtaaa                           98

<210> SEQ ID NO 364
<211> LENGTH: 82
<212> TYPE: DNA
<213> ORGANISM: Artificial Sequence
<220> FEATURE:
<223> OTHER INFORMATION: Synthetic Aptamer Sequence

<400> SEQUENCE: 364
gaagtggctt gtgctcctcg attgaattat gctaatgatt aacaatcgtg gggaattcag    60
cacctggcac gggcagtgta aa                                            82

<210> SEQ ID NO 365
<211> LENGTH: 84
<212> TYPE: DNA
<213> ORGANISM: Artificial Sequence
<220> FEATURE:
<223> OTHER INFORMATION: Synthetic Aptamer Sequence
```

<400> SEQUENCE: 365
gaagtggctt gtgctcctcg aagtggctta cgatgtttgt gtgttctagt ggtgtcacag    60
ttgtcctggc acgggcagtg taaa    84

<210> SEQ ID NO 366
<211> LENGTH: 98
<212> TYPE: DNA
<213> ORGANISM: Artificial Sequence
<220> FEATURE:
<223> OTHER INFORMATION: Synthetic Aptamer Sequence

<400> SEQUENCE: 366
gaagtggctt gtgctcctcg aagtggcttg aagtggcttg tgctcctcga agtggcttga    60
agtggcttgt gctcctcgcc tggcacgggc agtgtaaa    98

<210> SEQ ID NO 367
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 367
gaagtggctt gtgctcctcg attgaattat gctaatgatt aacaatcgtg gggagaagcc    60
tacgaaagag gaattcagca cctggcacgg gcagtgtaaa    100

<210> SEQ ID NO 368
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 368
gaagtggctt gtgctcctcg tcggctgcgc ggtccgggct ggctagcagc cgcgtggcac    60
ggggtgacga gagcgcgaca cctggcacgg gcagtgtaaa    100

<210> SEQ ID NO 369
<211> LENGTH: 96
<212> TYPE: DNA
<213> ORGANISM: Artificial Sequence
<220> FEATURE:
<223> OTHER INFORMATION: Synthetic Aptamer Sequence

<400> SEQUENCE: 369
gaagtggctt gtgctcctcg cgggcgaggc tcgcgcgtgg cgcgcggccc cgtgagagga    60
agccggggga gggcagtggg cctggcacgg gcagtg    96

<210> SEQ ID NO 370
<211> LENGTH: 96
<212> TYPE: DNA
<213> ORGANISM: Artificial Sequence
<220> FEATURE:
<223> OTHER INFORMATION: Synthetic Aptamer Sequence

<400> SEQUENCE: 370
gaagtggctt gtgctcctcg gccgcacctg acagtggcga gccggggctc gcgcgaaggg    60
cggcagcacg gggtggacag cctggcacgg gcagtg    96

<210> SEQ ID NO 371

```
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 371
gaagtggctt gtgctcctcg cagagggcgc ggctcagcgc gaccacggca ggatgcggct    60
ggcgcgtcgg gtgggtgcta cctggcacgg gcagtgtaaa                        100

<210> SEQ ID NO 372
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 372
gaagtggctt gtgctcctcg gacccacggc tacgccgtgc ggcgggcgga gagggagcgg    60
ggagccgcgg gccggcggga cctggcacgg gcagtgtaaa                        100

<210> SEQ ID NO 373
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 373
gaagtggctt gtgctcctcg cgacctgtgc gcggcaatgg cgcgcgggac ggggcgtgg    60 cgcttggccg gggagaggtg cctggcacgg gcagtgtaaa                        100

<210> SEQ ID NO 374
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 374
gaagtggctt gtgctcctcg tcgtccggcg gcgccctccc gggtacggag ggcggcagcg    60
cagtcgcggg tgaggaaggc cctggcacgg gcagtgtaaa                        100

<210> SEQ ID NO 375
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 375
gaagtggctt gtgctcctcg tcaagtctaa gcattaagat tatttctcct gcaaccccac    60
cctggcacgg gcagtgtaaa                                               80

<210> SEQ ID NO 376
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 376
gaagtggctt gtgctcctcg actttaagca tacctgttaa tcataagtga cttctaataa    60
```
cctggcacgg gcagtgtaaa                                                80

<210> SEQ ID NO 377
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 377
gaagtggctt gtgctcctcg aacactaagc agttgaatgc taattgattt tgcccctctt    60
cctggcacgg gcagtgtaaa                                                80

<210> SEQ ID NO 378
<211> LENGTH: 93
<212> TYPE: DNA
<213> ORGANISM: Artificial Sequence
<220> FEATURE:
<223> OTHER INFORMATION: Synthetic Aptamer Sequence

<400> SEQUENCE: 378
gaagtggctt gtgctcctcg tccttactct aagcatttac tctgccatta acaagcttag    60
ttctttatgc ttgcctggca cgggcagtgt aaa                                 93

<210> SEQ ID NO 379
<211> LENGTH: 96
<212> TYPE: DNA
<213> ORGANISM: Artificial Sequence
<220> FEATURE:
<223> OTHER INFORMATION: Synthetic Aptamer Sequence

<400> SEQUENCE: 379
gaagtggctt gtgctcctcg agggcaggcc agggaagggg gggcgggggg gcggggctgg    60
gcacggggag aacggcgagc cctggcacgg gcagtg                              96

<210> SEQ ID NO 380
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 380
gaagtggctt gtgctcctca ccagaattct cgtaagacgg agaggaatgg atagagtgaa    60
cctggcacgg gcagtgtaaa                                                80

<210> SEQ ID NO 381
<211> LENGTH: 76
<212> TYPE: DNA
<213> ORGANISM: Artificial Sequence
<220> FEATURE:
<223> OTHER INFORMATION: Synthetic Aptamer Sequence

<400> SEQUENCE: 381
gaagtggctt gtgctcctcg ttgtagtata gcccgatact taccccgtct acccaataac    60
cctggcacgg gcagtg                                                    76

<210> SEQ ID NO 382
<211> LENGTH: 75
<212> TYPE: DNA
<213> ORGANISM: Artificial Sequence
<220> FEATURE:

<223> OTHER INFORMATION: Synthetic Aptamer Sequence

<400> SEQUENCE: 382

```
gaagtggctt gtgctcctcg ctcgactgga agaatagttc ttttagtgtt ggggatgatc      60
ctggcacggg cagtg                                                       75
```

<210> SEQ ID NO 383
<211> LENGTH: 84
<212> TYPE: DNA
<213> ORGANISM: Artificial Sequence
<220> FEATURE:
<223> OTHER INFORMATION: Synthetic Aptamer Sequence

<400> SEQUENCE: 383

```
gtgctcctcg aagtggcttg tgctcctcgc tcgactggaa gaatagttct ttagtgttgg      60
gggatgatcc tggcacgggc agtg                                             84
```

<210> SEQ ID NO 384
<211> LENGTH: 66
<212> TYPE: DNA
<213> ORGANISM: Artificial Sequence
<220> FEATURE:
<223> OTHER INFORMATION: Synthetic Aptamer Sequence

<400> SEQUENCE: 384

```
gtgctcctcg ttgattgttg tttttaagtt acgatattgc aacattgact cctggcacgg      60
gcagtg                                                                 66
```

<210> SEQ ID NO 385
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 385

```
gaagtggctt gtgctcctcg ttggatcgcg acatcttctg atttgctgac tgtttgttta      60
cctggcacgg gcagtgtaaa                                                  80
```

<210> SEQ ID NO 386
<211> LENGTH: 101
<212> TYPE: DNA
<213> ORGANISM: Artificial Sequence
<220> FEATURE:
<223> OTHER INFORMATION: Synthetic Aptamer Sequence

<400> SEQUENCE: 386

```
gaagtggctt gtgctcctcg tccaggacga ggagcacaag ccacttcctg cccgtgccag      60
gaagtggctt gtgctcctcg tcctggcacg ggcagtgtaa a                         101
```

<210> SEQ ID NO 387
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 387

```
gaagtggctt gtactcctcg ttgtagtata gcccgatact taccccgtct acccaataac      60
cctggcacgg gcagtgtaaa                                                  80
```

```
<210> SEQ ID NO 388
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 388
gaagtggctt gtgctcctcg tgtggccaag cctaaggcta gcttgggggc agtacgtgtc    60
cctggcacgg gcagtgtaaa                                                80

<210> SEQ ID NO 389
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 389
gaagtggctt gtgctcctcg tgtggccaag cctaaggcta gcttgggggc agtatgtgtc    60
cctggcacgg gcagtgtaaa                                                80

<210> SEQ ID NO 390
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 390
gaagtggctt gtgctcctcg ctcgactgga agaatagttc ttttagtgtt gggggatgat    60
cctggcacgg gcagtgtaaa                                                80

<210> SEQ ID NO 391
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 391
gaagtggctt gtgctcctcg acctttctta tgttttcttt ttacgatttt acagtgcttt    60
cctggcacgg gcagtgtaaa                                                80

<210> SEQ ID NO 392
<211> LENGTH: 98
<212> TYPE: DNA
<213> ORGANISM: Artificial Sequence
<220> FEATURE:
<223> OTHER INFORMATION: Synthetic Aptamer Sequence

<400> SEQUENCE: 392
gaagtggctt gtgctcctcg atggatattc acgttaatga gtaacgagtt ttcactgctc    60
ctcgtcatcg ttgatggacc tggcacgggc agtgtaaa                            98

<210> SEQ ID NO 393
<211> LENGTH: 79
<212> TYPE: DNA
<213> ORGANISM: Artificial Sequence
<220> FEATURE:
<223> OTHER INFORMATION: Synthetic Aptamer Sequence

<400> SEQUENCE: 393
```

```
gaagtggctt gtgctcctcg atggatattc acgttaatga gtaacgagtt ttcactgctc    60
ctggcacggg cagtgtaaa                                                  79

<210> SEQ ID NO 394
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 394
gaagtggctt gtgctcctcg gtgataacga attttagact gcccaacctc acagcaagtg    60
cctggcacgg gcagtgtaaa                                                 80

<210> SEQ ID NO 395
<211> LENGTH: 100
<212> TYPE: DNA
<213> ORGANISM: Artificial Sequence
<220> FEATURE:
<223> OTHER INFORMATION: Synthetic Aptamer Sequence

<400> SEQUENCE: 395
gaagtggctt gtgctcctcg tacggcgcgg ggggtgcagc gcacgcgtcc gtgtcggcag    60
ggcatgtagg cacgcggggg cctggcacgg gcagtgtaaa                          100

<210> SEQ ID NO 396
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 396
gaagtggctt gtgctcctcg cggaaatata tgtttatttg actacgcatt tatactgcaa    60
cctggcacgg gcagtgtaaa                                                 80

<210> SEQ ID NO 397
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 397
gaagtggctt gtgctcctcg atggatattc acgttaatga gtaacgagtt ttcactgctt    60
cctggcacgg gcagtgtaaa                                                 80

<210> SEQ ID NO 398
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 398
gaagtggctt gtgctcctcg atggatattc acgttaatga gtaacgagtt ttcactgcta    60
cctggcacgg gcagtgtaaa                                                 80

<210> SEQ ID NO 399
<211> LENGTH: 80
<212> TYPE: DNA
<213> ORGANISM: Artificial Sequence
```

```
<220> FEATURE:
<223> OTHER INFORMATION: Synthetic Aptamer Sequence

<400> SEQUENCE: 399
gaagtggctt gtgctcctcg ttcatacagg gagtgtgaga cacgcggtat ttatgggaga    60
cctggcacgg gcagtgtaaa                                                80

<210> SEQ ID NO 400
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 400
gaagtggctt gtgctcctcg tcaatctttt gatacgactt tacgctggct caggtaatta    60
cctggcacgg gcagtgtaaa                                                80

<210> SEQ ID NO 401
<211> LENGTH: 94
<212> TYPE: DNA
<213> ORGANISM: Artificial Sequence
<220> FEATURE:
<223> OTHER INFORMATION: Synthetic Aptamer Sequence

<400> SEQUENCE: 401
gaagtggctt gtgctcctcg tcctgcccgt gccaggacga ggagcacaag ccacttcctg    60
cccgtgctcc tcgtcctggc acgggcagtg taaa                                94

<210> SEQ ID NO 402
<211> LENGTH: 80
<212> TYPE: DNA
<213> ORGANISM: Artificial Sequence
<220> FEATURE:
<223> OTHER INFORMATION: Synthetic Aptamer Sequence

<400> SEQUENCE: 402
gaagtggctt gtgctcctcg acctttctta tgttttcttt ttacgatttt acagtgctct    60
cctggcacgg gcagtgtaaa                                                80

<210> SEQ ID NO 403
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 403
gtgctcctcg aagtggcttg ttaatttagt gttttacgat gtttgtgtgt tctagtggtg    60
tcacagttgt cctggcacgg g                                              81

<210> SEQ ID NO 404
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 404
gtgctcctcg attgaattat gctaatgatt aacaatcgtg gggagaagcc tacgaaagag    60
gaattcagca cctggcacgg g                                              81
```

<210> SEQ ID NO 405
<211> LENGTH: 82
<212> TYPE: DNA
<213> ORGANISM: Artificial Sequence
<220> FEATURE:
<223> OTHER INFORMATION: Synthetic Aptamer Sequence

<400> SEQUENCE: 405
gtgctcctcg cactaataga caattcaata aatccaaccc attggattat cttgaagttt    60
ttcattttcc ccctggcacg gg                                             82

<210> SEQ ID NO 406
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 406
gtgctcctcg tactccctaa ggactaggaa gaacataatg ccatttccac actgtgtgtg    60
atataatcca cctggcacgg g                                              81

<210> SEQ ID NO 407
<211> LENGTH: 82
<212> TYPE: DNA
<213> ORGANISM: Artificial Sequence
<220> FEATURE:
<223> OTHER INFORMATION: Synthetic Aptamer Sequence

<400> SEQUENCE: 407
gtgctcctcg gtgaagtggc ttgtgctcct cggtgaagtg gcttgtgctc ctcggtgaag    60
tgtttttcaa tcctggcacg gg                                             82

<210> SEQ ID NO 408
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 408
gtgctcctcg tagcacatag acatgtcatt gaactgtccg aatcttcttg tgagtgttag    60
atattctccg cctggcacgg g                                              81

<210> SEQ ID NO 409
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 409
gtgctcctcg aagtggcttt gcatggctga atgttacaac gaagtgtatg gtctaaacaa    60
tagtttggtt cctggcacgg g                                              81

<210> SEQ ID NO 410
<211> LENGTH: 61
<212> TYPE: DNA
<213> ORGANISM: Artificial Sequence
<220> FEATURE:
<223> OTHER INFORMATION: Synthetic Aptamer Sequence

<400> SEQUENCE: 410

```
gtgctcctcg cgtgcggcgc agcacaggag aacagaggcg atgcagcaga cctggcacgg    60
g                                                                    61

<210> SEQ ID NO 411
<211> LENGTH: 63
<212> TYPE: DNA
<213> ORGANISM: Artificial Sequence
<220> FEATURE:
<223> OTHER INFORMATION: Synthetic Aptamer Sequence

<400> SEQUENCE: 411
gtgctcctcg tctggcacgg gcagtgtaaa cgaagtggct tgtgctcctc gtcctggcac    60
ggg                                                                  63

<210> SEQ ID NO 412
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 412
gtgctcctcg tacactcata ctcaatctat tttatacggc gatgatatta tttgcgggcg    60
aggtggacgc cctggcacgg g                                              81

<210> SEQ ID NO 413
<211> LENGTH: 41
<212> TYPE: DNA
<213> ORGANISM: Artificial Sequence
<220> FEATURE:
<223> OTHER INFORMATION: Synthetic Aptamer Sequence

<400> SEQUENCE: 413
gtgctcctcg aagtggcttg tgctcctcgt cctggcacgg g                        41

<210> SEQ ID NO 414
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 414
gtgctcctcg ggtagtgatc accaatgatt gtctcttatc agcaattttc ctatggcact    60
ttgctgcggt cctggcacgg g                                              81

<210> SEQ ID NO 415
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 415
gtgctcctcg tcttgtatac tctcagggtt taatcgagtt tgagggtatg attctttgag    60
actgtgggga cctggcacgg g                                              81

<210> SEQ ID NO 416
<211> LENGTH: 81
<212> TYPE: DNA
<213> ORGANISM: Artificial Sequence
<220> FEATURE:
```

<223> OTHER INFORMATION: Synthetic Aptamer Sequence

<400> SEQUENCE: 416
gtgctcctcg gaatttctaa aggctcttcc tgtggttatc gttttcgct tgtataaatt    60 aagtcatgtg cctggcacgg g    81

<210> SEQ ID NO 417
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 417
gtgctcctcg ttatgtcttt gaggtcttgc aagaccatct agcccacact ctggcagcgt    60
tgttgttggc cctggcacgg g    81

<210> SEQ ID NO 418
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 418
gtgctcctcg tctttcagta ggttcatttt ggaaaatgac aagacaagcc ttggtgtttc    60
aatgtgtcgt cctggcacgg g    81

<210> SEQ ID NO 419
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 419
gtgctcctcg gatttctagt ccaactccgt atatgcaatt cttaagtaga ttgtacctga    60
aaggtcagat cctggcacgg g    81

<210> SEQ ID NO 420
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 420
gtgctcctcg tcaatcccat tcttcatcat ggtttggagt aataatctcg acagttttg    60 tcttcagtac cctggcacgg g    81

<210> SEQ ID NO 421
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 421
gtgctcctcg gagcgcgcta aggtcaacca tttcaattct tgcgtttttt gaatatcctt    60
tcccagctct cctggcacgg g    81

```
<210> SEQ ID NO 422
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 422
gtgctcctcg ttagcgacaa tacctacaac tgatgaatag tgtcaaattg gttcttcatt    60
tttcttccta cctggcacgg g                                              81

<210> SEQ ID NO 423
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 423
gtgctcctcg tatgggcatc ttgaaaacag attgttatct gaaatgtttt aaattttggt    60
agaattatgt cctggcacgg g                                              81

<210> SEQ ID NO 424
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 424
gtgctcctcg gttgatcgtt atccagctct caggctatct cattagacgc ttaagtcggg    60
ggggctccgg cctggcacgg g                                              81

<210> SEQ ID NO 425
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 425
gtgctcctcg atcgacactc ctatgtactt gtatttcgat caggtagcca tactcaaatt    60
tttgttgccc cctggcacgg g                                              81

<210> SEQ ID NO 426
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 426
gtgctcctcg acgtatcgtt ggtattaatc agaccaggtg tgtattgtgt gtgggatttt    60
catataaatt cctggcacgg g                                              81

<210> SEQ ID NO 427
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 427
```

```
gtgctcctcg caattgtgct atttttgatt tgtaatctcc caggaggcaa tactaataag    60
agcagttctg cctggcacgg g                                              81
```

<210> SEQ ID NO 428
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 428

```
gtgctcctcg tagatttgtt tgaccagttt gctctctcat gtgagcattc acttcatctc    60
agcaatttgg cctggcacgg g                                              81
```

<210> SEQ ID NO 429
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 429

```
gtgctcctcg actagtcctt cctgattttt atatgcagca cttatgccaa ccctactaat    60
agcacgcttc cctggcacgg g                                              81
```

<210> SEQ ID NO 430
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 430

```
gtgctcctcg atacgaccct cttttttgcgg cttgcaacaa ttatcgcccg tcgtttagag    60
catcctagca cctggcacgg g                                              81
```

<210> SEQ ID NO 431
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 431

```
gtgctcctcg tctcagacgt gaagtggttt gttatgcata ctgatgaatt tccctcataa    60
ttacgggttg cctggcacgg g                                              81
```

<210> SEQ ID NO 432
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 432

```
gtgctcctcg tggttttat ctattcttct tactgaacct catagtgtta tagttgagcg     60
gggatgcgtt cctggcacgg g                                              81
```

<210> SEQ ID NO 433
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 433
gtgctcctcg tgcggactag gaaggacacc agcggtaaga tgcgtggcac cacgtggtaa    60
gcaagatgtg cctggcacgg g    81

<210> SEQ ID NO 434
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 434
gtgctcctcg ttcaaatatc atactctgat aatagttcgt tttaggtggt actttcaatt    60
catttccgta cctggcacgg g    81

<210> SEQ ID NO 435
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 435
gtgctcctcg ttgatgttta gtcatttcat gttttgagtt tgcttggctg tagattatag    60
aagtttgatc cctggcacgg g    81

<210> SEQ ID NO 436
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 436
gtgctcctcg tcctcttgcg cattttgatt gatatgtctt atatagcgat caatcccctc    60
acgatgtttc cctggcacgg g    81

<210> SEQ ID NO 437
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 437
gtgctcctcg tatgggactt agatttgttt gtgctaattg tgcataagcc aacagggtat    60
cctacatgat cctggcacgg g    81

<210> SEQ ID NO 438
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 438
gtgctcctcg tctgattggt gctggacaat gcgcaacaag tttatccaat tcatactgat    60
aatttaatcc cctggcacgg g    81

```
<210> SEQ ID NO 439
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 439
gtgctcctcg tagcatcctc tttggacata tgattcaacg cagtattagg taacattcat    60
cacatcctat cctggcacgg g                                              81

<210> SEQ ID NO 440
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 440
gtgctcctcg gaatcataat tacggagttg gaacggtata gtctggcatc ttctattcta    60
ggcatttctt cctggcacgg g                                              81

<210> SEQ ID NO 441
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 441
gtgctcctcg aatactgact cattctatac atcctctgat gtgaacccac tctctaaagt    60
attttccatc cctggcacgg g                                              81

<210> SEQ ID NO 442
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 442
gtgctcctcg acattagtga acctgtcatt aactgtgcgc tggaagcgcg ggtatttgtc    60
caaattgctc cctggcacgg g                                              81

<210> SEQ ID NO 443
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 443
gtgctcctcg ctcaaagtag atctttcgac tatggcacgc gacggatcag atgctgagga    60
ccagtaggtg cctggcacgg g                                              81

<210> SEQ ID NO 444
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 444
```

-continued

```
gtgctcctcg catgcttggc tattgcaatc gagttttaaa tagtataaat aggaaaccca      60
ggcattttcg cctggcacgg g                                                81
```

<210> SEQ ID NO 445
<211> LENGTH: 61
<212> TYPE: DNA
<213> ORGANISM: Artificial Sequence
<220> FEATURE:
<223> OTHER INFORMATION: Synthetic Aptamer Sequence

<400> SEQUENCE: 445

```
gtgctcctcg cactgcgtag caatgtgcta tttaaaaacc gcacttggag cctggcacgg      60
g                                                                      61
```

<210> SEQ ID NO 446
<211> LENGTH: 61
<212> TYPE: DNA
<213> ORGANISM: Artificial Sequence
<220> FEATURE:
<223> OTHER INFORMATION: Synthetic Aptamer Sequence

<400> SEQUENCE: 446

```
gtgctcctcg ttcattttat tgcggatatc tttcctcccg ttgggggcct cctggcacgg      60
g                                                                      61
```

<210> SEQ ID NO 447
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 447

```
gtgctcctcg attgtctctt ccttttgggg ccataatgag gctttgatgc tgaacgatcg      60
tctcggatgg cctggcacgg g                                                81
```

<210> SEQ ID NO 448
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 448

```
gtgctcctcg gtacattggg tgagagcagt gacttgtggg gcacaacaaa cccagcatct      60
ggatgctaac cctggcacgg g                                                81
```

<210> SEQ ID NO 449
<211> LENGTH: 81
<212> TYPE: DNA
<213> ORGANISM: Artificial Sequence
<220> FEATURE:
<223> OTHER INFORMATION: Synthetic Aptamer Sequence

<400> SEQUENCE: 449

```
gtgctcctcg ccgagttgct tctggaattt cactgggcgt taactgtgtc cttgactttc      60
ttagctgaaa cctggcacgg g                                                81
```

<210> SEQ ID NO 450
<211> LENGTH: 20
<212> TYPE: DNA

```
<213> ORGANISM: Artificial Sequence
<220> FEATURE:
<223> OTHER INFORMATION: Synthetic Primer Sequence

<400> SEQUENCE: 450
gaagtggctt gtgctcctcg                                              20

<210> SEQ ID NO 451
<211> LENGTH: 20
<212> TYPE: DNA
<213> ORGANISM: Artificial Sequence
<220> FEATURE:
<223> OTHER INFORMATION: Synthetic Primer Sequence

<400> SEQUENCE: 451
tttacactgc ccgtgccagg                                              20

<210> SEQ ID NO 452
<211> LENGTH: 20
<212> TYPE: DNA
<213> ORGANISM: Artificial Sequence
<220> FEATURE:
<223> OTHER INFORMATION: Synthetic Primer Sequence

<400> SEQUENCE: 452
tttacactgc ccgtgccagg                                              20

<210> SEQ ID NO 453
<211> LENGTH: 17
<212> TYPE: DNA
<213> ORGANISM: Artificial Sequence
<220> FEATURE:
<223> OTHER INFORMATION: Synthetic Primer Sequence

<400> SEQUENCE: 453
tttacactgc ccgtgcc                                                 17

<210> SEQ ID NO 454
<211> LENGTH: 20
<212> TYPE: DNA
<213> ORGANISM: Artificial Sequence
<220> FEATURE:
<223> OTHER INFORMATION: Synthetic Primer Sequence

<400> SEQUENCE: 454
tttacactgc ccgtgccagg                                              20

<210> SEQ ID NO 455
<211> LENGTH: 25
<212> TYPE: DNA
<213> ORGANISM: Artificial Sequence
<220> FEATURE:
<223> OTHER INFORMATION: Synthetic Primer Sequence

<400> SEQUENCE: 455
acgaatttac actgcccgtg ccagg                                        25

<210> SEQ ID NO 456
<211> LENGTH: 30
<212> TYPE: DNA
<213> ORGANISM: Artificial Sequence
<220> FEATURE:
<223> OTHER INFORMATION: Synthetic Primer Sequence

<400> SEQUENCE: 456
actctaagca tttacactgc ccgtgccagg                                   30
```

<210> SEQ ID NO 457
<211> LENGTH: 20
<212> TYPE: DNA
<213> ORGANISM: Artificial Sequence
<220> FEATURE:
<223> OTHER INFORMATION: Synthetic Primer Sequence

<400> SEQUENCE: 457
tttacactgc ccgtgccagg                                               20

<210> SEQ ID NO 458
<211> LENGTH: 25
<212> TYPE: DNA
<213> ORGANISM: Artificial Sequence
<220> FEATURE:
<223> OTHER INFORMATION: Synthetic Primer Sequence

<400> SEQUENCE: 458
acgaatttac actgcccgtg ccagg                                         25

<210> SEQ ID NO 459
<211> LENGTH: 30
<212> TYPE: DNA
<213> ORGANISM: Artificial Sequence
<220> FEATURE:
<223> OTHER INFORMATION: Synthetic Primer Sequence

<400> SEQUENCE: 459
actctaagca tttacactgc ccgtgccagg                                    30

<210> SEQ ID NO 460
<211> LENGTH: 80
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: misc_feature
<223> OTHER INFORMATION: n is a, t, g or c
<220> FEATURE:
<221> NAME/KEY: misc_feature
<222> LOCATION: (21)..(60)
<223> OTHER INFORMATION: n is a, t, g or c

<400> SEQUENCE: 460
gaagtggctt gtgctcctcg nnnnnnnnnn nnnnnnnnnn nnnnnnnnnn nnnnnnnnnn   60
cctggcacgg gcagtgtaaa                                               80

<210> SEQ ID NO 461
<211> LENGTH: 100
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: misc_feature
<222> LOCATION: (21)..(80)
<223> OTHER INFORMATION: n is a, t, g or c

<400> SEQUENCE: 461
gaagtggctt gtgctcctcg nnnnnnnnnn nnnnnnnnnn nnnnnnnnnn nnnnnnnnnn   60
nnnnnnnnnn nnnnnnnnnn cctggcacgg gcagtgtaaa                        100

<210> SEQ ID NO 462
<211> LENGTH: 10

```
<212> TYPE: DNA
<213> ORGANISM: Artificial Sequence
<220> FEATURE:
<223> OTHER INFORMATION: Synthetic Primer Sequence

<400> SEQUENCE: 462
gtgctcctcg                                                        10

<210> SEQ ID NO 463
<211> LENGTH: 10
<212> TYPE: DNA
<213> ORGANISM: Artificial Sequence
<220> FEATURE:
<223> OTHER INFORMATION: Synthetic Primer Sequence

<400> SEQUENCE: 463
cacgggcagt                                                        10

<210> SEQ ID NO 464
<211> LENGTH: 35
<212> TYPE: DNA
<213> ORGANISM: Artificial Sequence
<220> FEATURE:
<223> OTHER INFORMATION: Synthetic Primer Sequence

<400> SEQUENCE: 464
gaaccactct aagcatttac actgcccgtg ccagg                            35

<210> SEQ ID NO 465
<211> LENGTH: 26
<212> TYPE: DNA
<213> ORGANISM: Artificial Sequence
<220> FEATURE:
<223> OTHER INFORMATION: Synthetic Primer Sequence

<400> SEQUENCE: 465
cgaggagcac aagccacttc tttttt                                      26

<210> SEQ ID NO 466
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 466
cctggcacgg gcagtgtaaa tgcttagagt tttttt                           36
```

DETECTION OF MICROBIAL ENDOTOXINS IN ORAL SAMPLES USING APTAMERS

FIELD OF INVENTION

The contents of the sequence listing text file named "15533M_ST25.txt', which was created on 11 Jul. 2022, and is 122 Kbytes in size, are incorporated herein by reference in its entirety The present invention generally relates to nucleic acid aptamers that have a high binding affinity and specificity for *Porphyromonas gingivalis* and *Prevotella pallens*. This invention also relates to the use of such aptamers as reagents to develop assays and point of care tests for evaluation of microbial toxins and microbial abundance in oral samples.

BACKGROUND OF THE INVENTION

Periodontal diseases, such as gingivitis and periodontitis, involve chronic inflammation in the gingival tissue caused by dysfunctional microbial communities and host immune responses. They are one of the most ubiquitous diseases worldwide and remain the most common cause of tooth loss in the world today and can affect up to 90% of the population worldwide. Gingivitis is defined per the FDA monograph (12 CFR Part 356, Vol. 68, No. 103 (2003)) as "An inflammatory lesion of the gingiva that is most frequently caused by dental plaque. Gingivitis is characterized by tissue swelling and redness, loss of stippling (a normal state in which the surface of healthy gingiva is comprised of small lobes), glossy surface, and increased tissue temperature. The gingiva also may bleed upon gentle provocation, such as tooth brushing or may bleed spontaneously. Gingivitis is usually not painful." In healthy gingiva, the microbial community is in a homeostatic equilibrium with the host, and host immune systems limit bacterial overgrowth and neutralize toxic products, such as lipopolysaccharides (LPS) and lipoteichoic acids (LTA). The intricate balance between host and bacteria is disrupted as bacteria overgrow in the gingival margins or in the subgingival crevice. Recent data from metagenomics studies showed that bacterial species, such as *Prevotella pallens, Prevotella intermedia, Porphyromonas gingivalis*, and *Filifactor alocis*, were increased in supragingival and subgingival plaques. Although the etiology of gingivitis and periodontitis remains elusive, one thing is clear; the composition of the dental plaques is significantly different in healthy sites compared with clinically defined disease sites. This observation, together with advances in characterizing the host and bacterial interactions using the newly developed tools in genomics, proteomics and metabonomics, has led to the notion that gingivitis and periodontitis are the result of disrupted homeostasis between host and polymicrobial communities (Lamont R J and Hajishengallis G. Polymicrobial synergy and dysbiosis in inflammatory disease. G Trends Mol Med. 2015; 21:172-83).

Polymicrobial communities in the dental plaques produce various virulence factors; for example, many bacteria produce digestive enzymes, such as hyaluronidases, to breakdown polysaccharides that glue the host cell together, fibrinolytic enzymes that lyse the fibrins of blood clots, and collagenases that degrade collagens in the connective tissues. Gram negative bacteria secrete endotoxins, also called LPS, while Gram positive bacteria produce LTA and peptidoglycans. Furthermore, one pathogen bacterium can generate multiple virulence factors; for example, *P. gingivalis* has been reported to generate multiple virulence factors that are involved in the inflammatory and destructive events of periodontal tissues. These influence factors include the capsule, outer membrane, its associated LPS, fimbriae, proteinases, and selected enzymes.

LPS is an integral component of all Gram-negative bacteria and is found in the outer membrane layer. *P. gingivalis* LPS possesses significant amounts of heterogeneity containing tetra- and penta-acylated structures. Several of them have been purified. LPS 1690 is highly toxic, while LPS 1435/1449 is relatively mild. Chemically, LPS consists of a hydrophilic polysaccharide and a hydrophobic lipid moiety referred to as lipid A. The latter is the actual toxic moiety of the LPS molecule and contains phosphate groups shown to be essential for its proinflammatory activity. Mechanistically, LPS first binds to LPS-binding protein (LBP), then the LBP-LPS complex is transferred to membrane-bound CD14, thereby enabling interactions with Toll-like receptor (TLR) 4 on cell membranes. Binding of LPS to TLR4 on the cell membrane activates both TIRAP-MyD88-dependent NFkB and TRAM-TRIF-dependent IRF3 or IRF7 signaling pathways, and subsequently stimulate production of proinflammatory cytokines and chemokines, such as interferon (IFN) gamma, tumor necrosis factor-$\alpha$ (TNF$\alpha$), interleukin (IL)-1$\beta$, IL-6, IL-8, and IL-12. Also, induced is production of nitric oxide, prostaglandins, leukotrienes, and proteolytic enzymes. Importantly, LPS has been reported to cause periodontitis in mouse and rats.

*P. gingivalis* also secretes exotoxins and enzymes that exert damage on the host following their release. These enzymes include proteases, coagulases, and fibrinolysins. Noticeably, *P. gingivalis* generates peptidylarginine deiminase that can modify free or peptide-bound arginine to citrulline. The citrullinated proteins are especially harmful since they cause auto-immune responses and are hypothesized to be the culprit of rheumatoid arthritis. In addition, *P. gingivalis* also produces two types of gingipains, lysine specific (Kgp) and arginine specific (Rgps). Gingipains play a major role in stirring up inflammation and tissue destruction in the periodontium.

Assessing the severity of gingivitis and periodontitis in a person is currently achieved with clinical measures such as gum redness, gum bleeding or pocket depth. While the measures are based on professionally developed scales, the actual values can vary due to examiner differences. There exists a need to quantify gingivitis severity and oral hygiene product treatment effectiveness in reducing the inflammatory response. It is desirable to have objective readings from an instrument that is free of human variability and errors.

A variety of point of care tests have been developed, as reviewed recently (Nancy Srivastava, Prathibha Anand Nayak, and Shivendra Rana. J Clin Diagn Res. 2017 August; 11(8): ZE01-ZE06. Point of Care—A Novel Approach to Periodontal Diagnosis-A Review). Both host and microbial biomarkers are used for diagnostics in oral samples, examples of such biomarkers include saliva, oral lavage, subgingival and supragingival plaques, gingival crevicular fluid, buccal brush samples and gingival brush samples. DNA polymerase chain reaction has been used to detect the type and concentration of bacteria present in a salivary sample for pathogenic bacteria, such as *Porphyromonas gingivalis, Prevotella intermedia, Aggregatibacter actinomycetem-comitans, Fusobacterium nucleatum, Eikenella corrodens, Campylobacter rectus, Tannerella forsythia* and *Treponema denticola*). RNA has also been used to detect microorganisms causing periodontitis, such as *A. actinomycetemcomitans, P. gingivalis, T. forsythia* and *T. denticola*.

An alternative approach involves the detection of enzymes produced by periodontal pathogens. Enzymes with a trypsin-like activity are produced by only a few members of the cultivable oral microflora, namely *Porphyromonas gingivalis, Tannerella forsythia, Treponema denticola* and *Capnocytophaga* sp. (Hemmings K W, Griffiths G S, Bulman J S. The presence of this enzyme in a plaque sample can be elicited by the hydrolysis of a synthetic trypsin substrate, N-benzoyl-DL-arginine-2-naphthylamide (BANA). J Clin Periodontol. 1997; 24:110-4). Their enzymes can cleave N-benzoyl-DL-arginine-2-naphthylamide and result in a blue-black product. The BABA test is used to detect *Porphyromonas gingivalis, Bacteroides forsythus, Treponema denticola* and *Capnocytophaga* sp, which are widely believed to be the pathogens for periodontitis.

Periocheck (Advanced Clinical Technologies Inc., Westwood, Mass. 02090, USA) is also a point of care test to detect the presence of neutral proteases, which are implicated in collagen breakdown. Breakdown of collagen is an important feature of periodontal disease. For this test, gingival crevicular fluid is collected on filter paper strips and placed on a collagen dye-labelled gel matrix. The enzymes from gingival crevicular fluid digest the collagen into fragments and the soluble dye-labelled fragments diffuse onto the sample strip paper turning the strip to blue. The quantity and intensity of the color reaction is compared to a standard color chart, and the level of neutral protease activity in the crevicular fluid samples is calculated.

Protease-based point of care tests are convenient and simple to run, but they can't tell the exact bacterial species. DNA and RNA procedures offer species-specificity, but DNA polymerase reaction and RNA measurements are not convenient. As should be apparent from the above, there is a need for a more sensitive, accurate and consistent test.

SUMMARY OF THE INVENTION

An aptamer composition is provided that comprises an oligonucleotide that is at least one of deoxyribonucleotides, ribonucleotides, derivatives of deoxyribonucleotides, derivatives of ribonucleotides, or mixtures thereof; wherein said aptamer composition has a binding affinity for one or more bacterial species from the genus *Prevotella* or the genus *Porphyromonas*.

A method for detecting endotoxins and outer membrane vesicles is provided that comprises obtaining an oral cavity sample; applying an oral cavity sample to an assay kit; and measuring an assay result.

The assay kit may comprise at least one oligonucleotide of SEQ ID NO 1 to SEQ ID NO 105 or SEQ ID NO 251 to SEQ ID NO 358. The assay kit may comprise at least one oligonucleotide with at least 50% nucleotide sequence identity to SEQ ID NO 1 to SEQ ID NO 105 or SEQ ID NO 251 to SEQ ID NO 358. The assay kit may comprise at least one oligonucleotide with the oligonucleotide with natural or non-natural nucleobases of SEQ ID NO 1 to SEQ ID NO 105 or SEQ ID NO 251 to SEQ ID NO 358. The assay kit may comprise an oligonucleotide that is at least one of SEQ ID NO 1 to SEQ ID NO 105 or SEQ ID NO 251 to SEQ ID NO 358.

The method may comprise at least one oligonucleotide that is covalently or non-covalently attached to one or more reporter molecules; wherein said one or more reporter molecules are at least one of gold nanoparticles, fluorescent tags, horse radish peroxidase, alkaline phosphatase, green fluorescence proteins and latex, or mixtures thereof.

BRIEF DESCRIPTION OF THE DRAWINGS

FIG. 2B displays transmission electron microscopic images of bacteria at different magnifications.

FIG. 2D shows transmission electron microscopic images of bacterial outer membrane vesicles.

FIG. 2I shows concentrated retentate was precipitated with ultra-centrifugation and then separated with a discontinuous iodixanol gradient, and a yellow band appeared in the discontinuous iodixanol gradient.

FIG. 7BI-BIII show lateral flow assays are used to detect one or more targets. In FIG. 7B, only one type of endotoxin or outer membrane vesicle from one bacterial species is detected. For Example, one or two aptamers of *P. gingivalis* endotoxins are conjugated to the reporter molecule, such as gold nanoparticles.

FIG. 7CI-CIII show as the sample mix migrates to the test line, the reporter gold nanoparticle-oligonucleotide hybridizes with the capture oligonucleotide which is immobilized in the test line.

FIG. 7DI-DIII show as a gold nanoparticle-aptamer-endotoxin complex migrates to the control line, the biotin in the gold nanoparticle-aptamer-endotoxin complex will bind to the streptavidin in the control line.

DETAILED DESCRIPTION OF THE INVENTION

Figure 1A:
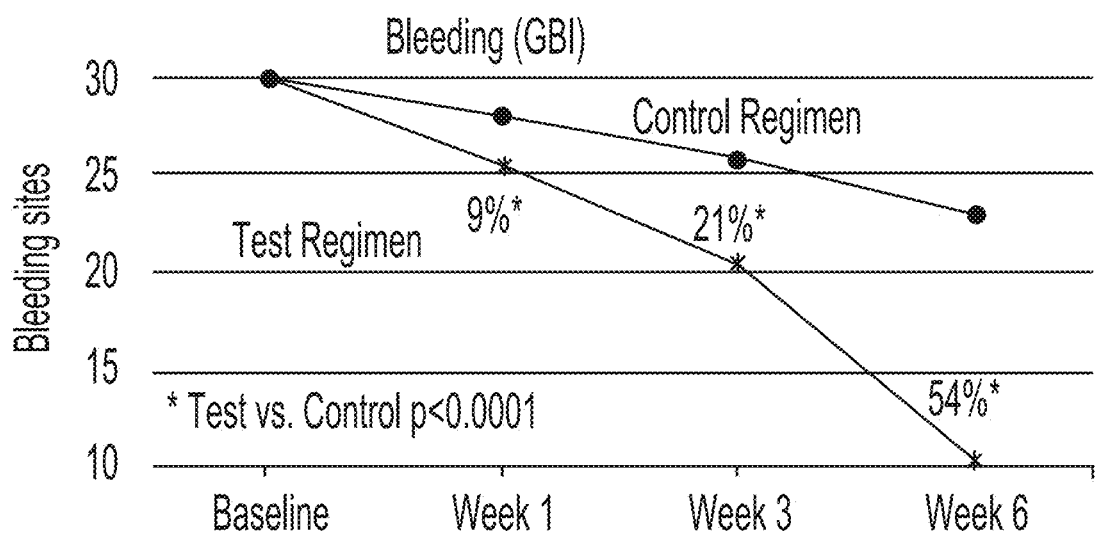
FIG. 1A shows lower mean bleeding (GBI) among a test regimen group relative to a negative control group at Weeks 1, 3 and 6.

The present invention relates to aptamers and their use in determining the presence of specific species of bacteria and endotoxins in the oral cavity.

In embodiments, the present invention includes aptamers, methods and kits for monitoring changes in specific endotoxin levels in oral samples. The method comprises collecting oral samples, applying samples to an assay format and reading the specific binding of endotoxins to relative aptamers. The kits comprise a 96-well assay format and a point of care assay format on the basis of specific aptamers.

In embodiments, the present invention is directed toward methods of developing aptamers; for example, through the use of SELEX for the selection of aptamers against endotoxins and outer membrane vesicles of *Porphyromonas gingivalis, Prevotella pallens* and other Gram-native bacteria and use the aptamers to develop assays to qualitatively and quantitatively measure endotoxins, outer membrane vesicles and bacteria in oral samples.

In embodiments, the present invention provides an aptamer composition. The aptamer composition may comprise at least one oligonucleotide consisting of deoxyribonucleotides, ribonucleotides, derivatives of deoxyribonucleotides, derivatives of ribonucleotides, and mixtures thereof, wherein said aptamer composition has a binding affinity for *Porphyromonas gingivalis, Prevotella pallens* and other Gram-native bacteria.

In embodiments, the present invention is directed toward methods of analyzing endotoxins and outer membrane vesicles of *Porphyromonas gingivalis, Prevotella pallens* and other Gram-native bacteria. The methods comprise at least one oligonucleotide selected from the group consisting of SEQ ID NO 1 to SEQ ID NO 250 and SEQ ID NO 251 to SEQ ID NO 449.

In embodiments, the kits to detect endotoxins and outer membrane vesicles may comprises at least one oligonucleotide comprising one or more motifs selected from the group consisting of SEQ ID NO 1 to SEQ ID NO 250 and SEQ ID NO 251 to SEQ ID NO 449.

In addition, this invention also describes methods and procedures for purification of endotoxins from *P. gingivalis* and *P. pallens*, and for isolation of outer membrane vesicles of *P. gingivalis* and *P. pallens*.

The present invention is directed to methods of selecting high affinity aptamers through capture probes. In the first a few rounds of SELEX, a 17-nucleotide capture probe is used. As selection progresses, the length of the capture probe increases from 17 to 30 nucleotides. Likely, the binding strength is increased with the length of the capture probes. The longer capture probe will help select higher affinity aptamers.

I. Definitions

An "aptamer" may be a peptide or nucleic acid molecule, such as RNA or DNA that is capable of binding to a specific molecule with high affinity and specificity. Exemplary ligands that bind to an aptamer include, without limitation, small molecules, such as drugs, metabolites, intermediates, cofactors, transition state analogs, ions, metals, nucleic acids, and toxins, such as endotoxins. Aptamers may also bind natural and synthetic polymers, including proteins, peptides, nucleic acids, polysaccharides, glycoproteins, hormones, receptors and cell surfaces such as cell walls and cell membranes. The binding of a ligand to an aptamer, causes a conformational change in the effector domain and alters its ability to interact with its target molecule. An aptamer will most typically have been obtained by in vitro selection for binding of a target molecule. However, in vivo selection of an aptamer is also possible. Aptamers have specific binding regions which are capable of forming complexes with an intended target molecule in an environment, wherein other substances in the same environment are not complexed to the nucleic acid. The specificity of the binding is defined in terms of the comparative dissociation constants (Kd) of the aptamer for its ligand as compared to the dissociation constant of the aptamer for other materials in the environment or unrelated molecules in general. A ligand is one which binds to the aptamer with greater affinity than to unrelated material. Typically, the Kd for the aptamer with respect to its ligand will be at least about 10-fold less than the Kd for the aptamer with unrelated material or accompanying material in the environment. Even more preferably, the Kd will be at least about 50-fold less, more preferably at least 50 about 100-fold less, and most preferably at least about 200-fold less. An aptamer will typically be between about 10 and about 300 nucleotides in length. More commonly, an aptamer will be between about 30 and about 100 nucleotides in length.

The terms "nucleic acid molecule" and "nucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (such as, degenerate codon substitutions) and complementary sequences and as well as the sequence explicitly indicated. The nucleic acid may be in any physical form, for example, linear, circular, or supercoiled. The term nucleic acid is used interchangeably with oligonucleotide, gene, cDNA, and mRNA encoded by a gene. As used herein, the term "nucleic acid" refers to a polymer or oligomer of nucleotides. Nucleic acids are also referred as "ribonucleic acids" when the sugar moiety of the nucleotides is D-ribose and as "deoxyribonucleic acids" when the sugar moiety is 2-deoxy-D-ribose.

As used herein, the term "nucleoside" refers to a glycosylamine consisting of a nucleobase, such as a purine or pyrimidine, usually linked to a 5-carbon sugar (e.g. D-ribose or 2-deoxy-D-ribose) via a β-glycosidic linkage. Nucleosides are also referred as "ribonucleosides" when the sugar moiety is D-ribose and as "deoxyribonucleosides" when the sugar moiety is 2-deoxy-D-ribose.

As used herein, the term "nucleobase", refers to a compound containing a nitrogen atom that has the chemical properties of a base. Non-limiting examples of nucleobases are compounds comprising pyridine, purine, or pyrimidine moieties, including, but not limited to adenine, guanine, hypoxanthine, thymine, cytosine, and uracil.

As used herein, the term "oligonucleotide" refers to an oligomer composed of nucleotides.

As used herein, the term "identical" or "sequence identity," in the context of two or more oligonucleotides, nucleic acids, or aptamers, refers to two or more sequences that are the same or have a specified percentage of nucleotides that are the same, when compared and aligned for maximum correspondence, such as when measured using sequence comparison algorithms or by manual sequence listing comparison.

As used herein, the term "substantially homologous" or "substantially identical" in the context of two or more oligonucleotides, nucleic acids, or aptamers, generally refers to two or more sequences or subsequences that have at least 40%, 60%, 80%, 90%, 95%, 96%, 97%, 98% or 99% nucleotide identity, when compared and aligned for maximum correspondence, as measured using sequence comparison algorithms or by visual inspection.

As used herein, the term "epitope" refers to the region of a target that interacts with the aptamer. An epitope can be a contiguous stretch within the target or can be represented by multiple points that are physically proximal in a folded form of the target.

As used herein the term "binding affinity" may be calculated using the following equation: Binding Affinity=Amount of aptamer bound to one or more bacterial species/Total amount of aptamer incubated with the one or more bacterial species.

As used herein, the term "motif" refers to the sequence of contiguous, or series of contiguous, nucleotides occurring in a library of aptamers with binding affinity towards a specific target and that exhibits a statistically significant higher probability of occurrence than would be expected compared to a library of random oligonucleotides. The motif sequence is frequently the result or driver of the aptamer selection process.

As used herein, the term "96-well assays" refer to assays that are routinely run in the lab to analyze more than one samples. The assay is qualitative and quantitative in nature. Usually, a standard curve or a positive or negative control is included in the assay. The assay can be performed in a 6-well plate, a 12-well plate, a 24-well plate, a 48-well plate, or a 96-well plate.

As used herein, the term "point of care tests or assays" include any assays that can be performed in a store, in a dentist office, at consumer's home or anyplace outside a standard laboratory. The point of care assays can be lateral flow assays, can be sandwich assay, can be competitive assays, or can be colorimetric assays, or can be fluorescence assays.

As used herein, the bacterial genus *Porphyromonas* includes any bacteria in this genus in the mouth.

As used herein, the bacterial genus *Prevotella* includes any bacteria in this genus in the mouth.

As used herein, the Gram-negative bacteria include any Gram-negative bacteria in the mouth.

As used herein, the term "outer membrane vesicles" means any structure that is derived from the outer membrane or that contains the outer membrane.

As used herein, the term "endotoxin" means lipopolysaccharides on bacterial outer membrane vesicles or free floating in the environment dissociated from bacteria.

As used herein, the term "oral sample" includes, oral lavage, saliva, gingival brush samples, supragingival plaques, or subgingival plaques.

As used herein, the term "capture probe" means a DNA sequence that can hybridize with another DNA sequence. For example, a capture probe may be anchored to the bottom of a well in a 96-well plate.

This capture probe can hybridize with an aptamer, thus retaining the aptamer in the well.

As used herein, the term "reporter probe" is a DNA sequence that is covalently or non-covalently linked to a molecule or a nanoparticle. The molecule, for example, can be a pigment, a fluorescent dye, an enzyme, or fluorescent protein. The reporter probe may have a DNA sequence that is complementary to another DNA sequence.

As used herein, the word "or" when used as a connector of two or more elements is meant to include the elements individually and in combination; for example X or Y, means X or Y or both.

As used herein, the articles "a" and "an" are understood to mean one or more of the material that is claimed or described, for example, "an aptamer" or "a composition comprising an aptamer."

All measurements referred to herein are made at about 23° C. (i.e. room temperature) unless otherwise specified.

II. Aptamer Compositions

Aptamers are single-stranded oligonucleotides, with a specific and complex three-dimensional shape, that bind to target molecules. The molecular recognition of aptamers is based on structure compatibility and intermolecular interactions, including electrostatic forces, van der Waals interactions, hydrogen bonding, and π-π stacking interactions of aromatic rings with the target material. The targets of aptamers include, but are not limited to, peptides, proteins, nucleotides, amino acids, antibiotics, low molecular weight organic or inorganic compounds, and even whole cells. The dissociation constant of the complexes of aptamers and the corresponding target materials typically varies between micromolar and picomolar levels, which is comparable to the affinity of antibodies to their antigens. Aptamers can also be designed to have high specificity, enabling the discrimination of target molecules from closely related derivatives.

Aptamers are usually designed in vitro from large libraries of random nucleic acids by Systematic Evolution of Ligands by Exponential Enrichment (SELEX). The SELEX method was first introduced in 1990 when single stranded RNAs were selected against low molecular weight dyes (Ellington, A. D., Szostak, J. W., 1990. Nature 346: 818-822). A few years later, single stranded DNA aptamers and aptamers containing chemically modified nucleotides were also described (Ellington, A. D., Szostak, J. W., 1992. Nature 355: 850-852; Green, L. S., et al., 1995. Chem. Biol. 2: 683-695). Since then, aptamers for hundreds of microscopic targets, such as cations, small molecules, proteins, cells, or tissues have been selected. A compilation of examples from the literature is included in the database at the website: http://www.aptagen.com/aptamer-index/aptamer-list.aspx.

Nucleic acid aptamers are single-stranded oligonucleotides with specific secondary and tertiary structures, that can bind to targets with high affinity and specificity. In the present invention, an aptamer composition may comprise at least one oligonucleotide consisting of deoxyribonucleotides, ribonucleotides, derivatives of deoxyribonucleotides, derivatives of ribonucleotides, and mixtures thereof, wherein the aptamer composition has a binding affinity for one or more bacterial species from the genus *Porphyromonas, Prevotella*, and any other Gram-negative bacteria. In the present invention, said one or more genera of *Porphyromonas* and *Prevotella* may be selected from the group consisting of *Porphyromonas asaccharolytica, Porphyromonas catoniae, Porphyromonas endodontalis, Porphyromonas gingivalis, Porphyromonas_sp_oral_taxon_278, Porphyromonas_sp_oral_taxon_279, Porphyromonas_uenonis, Prevotella baroniae, Prevotella bivia, Prevotella, buccae, Prevotella dentalis, Prevotella denticola, Prevotella disiens, Prevotella histicola, Prevotella intermedia, Prevotella loescheii, Prevotella maculosa, Prevotella marshii, Prevotella melaninogenica, Prevotella micans, Prevotella multiformis, Prevotella multisaccharivorax, Prevotella nanceiensis, Prevotella nigrescens, Prevotella oralis, Prevotella oris, Prevotella oulorum, Prevotella pallens, Prevotella pleuritidis, Prevotella saccharolytica, Prevotella salivae, Prevotella_sp_C561, Prevotella_sp_oral_taxon_306, Prevotella_sp_oral_taxon_317, Prevotella_sp_oral_taxon_473, Prevotella timonensis, Prevotella veroralis*, and other Gram-negative bacteria and mixtures thereof.

In the present invention, an aptamer composition may comprise at least one oligonucleotide with at least 85% nucleotide sequence identity to sequences selected from the group consisting of SEQ ID NO 1 to SEQ ID NO 250, and SEQ ID NO 251 to SEQ ID NO 449.

In the present invention, an aptamer composition may comprise at least one oligonucleotide with at least 70% nucleotide sequence identity to sequences selected from the group consisting of SEQ ID NO 1 to SEQ ID NO 250, and SEQ ID NO 251 to SEQ ID NO 449.

In the present invention, an aptamer composition may comprise at least one oligonucleotide with at least 90% nucleotide sequence identity to sequences selected from the group consisting of SEQ ID NO 1 to SEQ ID NO 250, and SEQ ID NO 251 to SEQ ID NO 449.

In the present invention, an aptamer composition may comprise at least one oligonucleotide selected from the group consisting of SEQ ID NO 1 to SEQ ID NO 250, and SEQ ID NO 251 to SEQ ID NO 449.

In the present invention, an aptamer composition may comprise at least one oligonucleotide containing at least 10 contiguous nucleotides from sequences selected from the group consisting of SEQ ID NO 1 to SEQ ID NO 250, and SEQ ID NO 251 to SEQ ID NO 449.

In the present invention, an aptamer composition may comprise at least one oligonucleotide containing at least 20 contiguous nucleotides from sequences selected from the group consisting of SEQ ID NO 1 to SEQ ID NO 250, and SEQ ID NO 251 to SEQ ID NO 449.

In the present invention, an aptamer composition may comprise at least one oligonucleotide containing at least 40 contiguous nucleotides from sequences selected from the group consisting of SEQ ID NO 1 to SEQ ID NO 250, and SEQ ID NO 251 to SEQ ID NO 449.

In the present invention, an aptamer composition may comprise at least one oligonucleotide containing at least 60 contiguous nucleotides from sequences selected from the group consisting of SEQ ID NO 1 to SEQ ID NO 250, and SEQ ID NO 251 to SEQ ID NO 449.

In the present invention, an aptamer composition may comprise at least one oligonucleotide containing at least 70 contiguous nucleotides from sequences selected from the group consisting of SEQ ID NO 1 to SEQ ID NO 250, and SEQ ID NO 251 to SEQ ID NO 449.

In the present invention, an aptamer composition may comprise at least one oligonucleotide containing at least 80 contiguous nucleotides from sequences selected from the group consisting of SEQ ID NO 1 to SEQ ID NO 250, and SEQ ID NO 251 to SEQ ID NO 449.

Chemical modifications can introduce new features into the aptamers, such as different molecular interactions with the target, improved binding capabilities, enhanced stability of oligonucleotide conformations, or increased resistance to nucleases. In the present invention, said at least one oligonucleotide of said aptamer composition may comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, bromouracil, 5-iodouracil, and mixtures thereof.

Modifications of the phosphate backbone of the oligonucleotides can also increase the resistance against nuclease digestion. In the present invention, the nucleosides of said oligonucleotides may be linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In the present invention, the nucleosides of said oligonucleotides may be linked by natural phosphate diesters.

In the present invention, the sugar moiety of the nucleosides of said oligonucleotides may be selected from the group comprising ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, and mixtures thereof.

In the present invention, said derivatives of ribonucleotides or said derivatives of deoxyribonucleotides may be selected from the group comprising: locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

In the present invention, the nucleotides at the 5'- and 3'-ends of said at least one oligonucleotide may be inverted. In the present invention, at least one nucleotide of said at least one oligonucleotide may be fluorinated at the 2' position of the pentose group. In the present invention, the pyrimidine nucleotides of said at least one oligonucleotide may be fluorinated at the 2' position of the pentose group. In the present invention, said aptamer composition may comprise at least one polymeric material, wherein said at least one polymeric material is covalently linked to said at least one oligonucleotide. In the present invention, said at least one polymeric material may be polyethylene glycol.

In the present invention, said at least one oligonucleotide may be between about 10 and about 200 nucleotides in length. In the present invention, said at least one oligonucleotide may be less than about 100 nucleotides in length. In the present invention, said at least one oligonucleotide may be less than about 50 nucleotides in length.

In the present invention, said at least one oligonucleotide may be covalently or non-covalently attached to one or more therapeutic and personal care ingredients. In the present invention, said one or more therapeutic and personal care ingredients can include one or more of anti-fungal agents, anti-micro agents, anti-bacterial agents, cooling agents, natural extracts, peptides, enzymes, and mixtures thereof. Suitable therapeutic and personal care active ingredients can include any material that is generally considered as safe and that provides benefits to the skin, the scalp, the hair, the oral mucosa, the tooth, or the gingiva.

III. Aptamer Assays

In the present invention, assays can include the use of at least one sequence selected from the group consisting of SEQ ID NO 1 to SEQ ID NO 250 and SEQ ID NO 251 to SEQ ID NO 449.

In the present invention, in embodiments said assays may be sandwich assays with two or more sequences selected from the group consisting of SEQ ID NO 1 to SEQ ID NO 250 and SEQ ID NO 251 to SEQ ID NO 449. One sequence functions as the capture aptamer. The other sequence functions as the reporter aptamers.

In one aspect, the capture aptamer may be anchored to a solid surface for example the surface a 96-well plate or nitrocellulose membrane. In embodiments the reporter aptamers may comprise an aptamer and an enzyme, a color molecule, or biological reagent. The said enzyme can be horse radish peroxidase, luciferase, alkaline phosphatase, tyrosinase, or a kinase. The said color molecule can be a pigment, a gold nanoparticle, fluorescence compound or fluorescence protein. The reporter aptamer can also be a combination of an enzyme and a color molecule, such as an enzyme attached to a gold nanoparticle.

This invention also describes an assay in a 96-well plate format. In this assay, two 96-well plates can be used, one is a binding plate, the other is a reading plate. An aptamer capture probe is anchored to the bottom of a well in the binding 96-well plate. This capture probe can hybridize with another the aptamer sequence, thus retaining the aptamer in the bottom of a well through biotin-Streptavidin binding. The bottom surface of a well in 96-well plate is functionalized with Streptavidin. The capture probe is functionalized with a biotin. Biotin has a high affinity for Streptavidin with a dissociation constant on the order of about $10^{14}$ Moles/liter. The reporter molecules, such as horse radish peroxidase or gold nanoparticles, will be linked to another DNA sequence, called reporter probe. The reporter probe is a DNA sequence that is covalently or non-covalently linked to a molecule or a nanoparticle, and that is complementary to the aptamer sequence. The reporter molecule can be a pigment, a fluorescent dye, an enzyme, or fluorescent protein. The reporter probe may have a DNA sequence that is complementary to aptamer sequences. In the 96-well plate, a capture probe holds an aptamer to the 96-well plate at its 5' end through complementary base pairing. The capture probe is tethered to the bottom of a well in the 96-well plate through biotin-Streptavidin binding. A reporter probe is hybridized to the aptamer at its 3' end by complementary base pairing. Then a target molecule is prepared in a binding buffer and added to the well containing the complex of the capture probe-aptamer-reporter probe. This target molecule can be endotoxins, outer membrane vesicles or whole bacteria. As the target molecule binds to the aptamer, the binding will change the 3-D structure of the aptamer, leading to dissociation of the reporter probe from the associated aptamer. The dissociated reporter probe will be free in the binding buffer and transferred to the well of the reading 96-well plate. Another DNA sequence, the reporter-probe-capture probe, or reporter capture probe, is fixed to the bottom of a reading plate through biotin-Streptavidin binding. The reporter capture probe is able to anneal to the reporter probe through complementary base pairing. As the reporter probe contains a pigment, a fluorescent dye, an enzyme, or fluorescent protein, measurement can be made directly by reading absorbance or fluorescence. If the reporter is an enzyme, such as horse radish peroxidase, alkaline phosphatase, or luciferase, the relative substrate is added, and the measurement is taken.

In embodiments this invention also includes a lateral flow assay. Lateral flow assays are the simplest and most common format for point of care assays. A typical lateral flow rapid test cellulose strip consists of a simple pad, a conjugate release pad, a test line, a control line, and absorbent pad. The sample pad is an absorbent pad onto which the test sample is applied. The conjugation release pad is an absorbent pad inside which a target-binding aptamer, reporter probe, and control reporter probe are stored. The reporter probe is hybridized with the target-binding aptamer. When targets in the samples bind to the target-binding aptamer, the reporter probe will be dissociated from the target-binding aptamer, and subsequently be attached to the test line on the test cellulose trip. The control reporter probe will be bound to the control line on the test cellulose strip. The sample will migrate onto a nitrocellulose membrane onto which a capture probe is immobilized in a line that crosses the membrane to act as a capture zone test line for the target molecules in the sample.

As used herein, the term "capture probe" means a DNA sequence, or a protein, or any chemical that can bind to another DNA sequence. For example, a capture probe can hybridize with an aptamer, thus retaining the aptamer in the membrane.

As used herein, the term "reporter probe" is a DNA sequence that is covalently or non-covalently linked to a reporter, such as a molecule or a nanoparticle. The molecule, for example, can be a pigment, a fluorescent dye, an enzyme, or fluorescent protein. The DNA sequence of the reporter probe is complimentary to that of the target-binding aptamer. The reporter probe is usually hybridized with the target-binding aptamer before samples are applied.

As used herein, the term "reporter aptamer" is an oligonucleotide that is covalently or non-covalently linked to a reporter, such as a molecule or a nanoparticle. The molecule, for example, can be a pigment, a fluorescent dye, an enzyme, or fluorescent protein. The DNA sequence of a reporter aptamer is different from a target-binding aptamer. The reporter aptamer can bind to the target, such as endotoxins, in the sample independently.

As used herein, the term "control reporter probe" is a DNA sequence or a protein, or any chemical that is covalently or non-covalently linked to a reporter. The control reporter probe can bind to a protein, an oligonucleotide or any chemical. A reporter is a molecule or a nanoparticle. The molecule, for example, can be a pigment, a fluorescent dye, an enzyme, or fluorescent protein. The control reporter probe may have a DNA sequence or a protein which is linked to a gold nanoparticle.

The lateral flow assays include a capture probe, which will bind to a reporter probe or reporter aptamer, is anchored to the nitrocellulose membrane on a test line (location onto which the reporter probe or reporter aptamer will be held) through biotin-Streptavidin binding. The reporter probe or reporter aptamer will contain a color molecule, such as gold nanoparticle. If the target molecule, such as endotoxins, are present in the sample, the reporter probe or reporter aptamer will be retained by binding to the capture probe on the test line. The test line will display red color, an indicator for presence of target molecule, such as endotoxins, in the sample. The capture probe is an oligonucleotide, or a protein, or any chemical which can bind to the reporter probe or reporter aptamer. An oligonucleotide capture probe can hybridize with a reporter probe or a reporter aptamer sequence. The reporter probe is a DNA sequence that is complementary to a specific aptamer, which can bind to target molecules, such as endotoxins. A capture probe binds to a specific aptamer at its 5' end through complementary base pairing. A reporter probe is hybridized to the aptamer at its 3' end by complementary base pairing. The complex of reporter probe-aptamer is housed on the sample pad, which is an absorbent pad onto which the test sample is applied. Then 100 to 900 µl of sample such as lavage or saliva is applied using a disposable graduated transfer pipet (VWR International LLC, Radnor, Pa. Cat #16001-192) to the sample pad. The sample contains the target molecule. The target molecules can be endotoxins, outer membrane vesicles or whole bacteria. As the target molecule binds to the target-binding aptamer, that has a high affinity to the target molecule, the binding will change the 3-D structure of the target-binding aptamer, leading to dissociation of the reporter probe from the target-binding aptamer. The dissociated reporter probe will be free from the target-binding aptamer and flow to the test line, and bind to the capture probe, which is immobilized to the test line through biotin-Streptavidin binding. The capture probe binds to the reporter probe through complementary base pairing. As described above the reporter probe contains a dye molecule or a nanoparticle, measurement can be made directly using naked eyes or camera in a smart phone. For example, gold nanoparticles appear red in color-a visible red band will appear on the test line.

If the target is not present in the sample, the reporter probe will continue to be associated with the target-binding aptamer and can't bind to the reporter capture probe that is immobilized in the test line onto the nitrocellulose strop—no red line will appear in the test line.

The lateral flow assay strip also contains a control line on the cellulose membrane. A control capture probe is immobilized on the cellulose membrane. The control capture probe is a protein, an oligonucleotide, or any chemical that can bind to a control reporter probe. As used herein, the term "control reporter probe" is a DNA sequence or a protein, or any chemical that is covalently or non-covalently linked to a reporter. The control reporter probe can bind to a protein, an oligonucleotide or any chemical. A reporter is a molecule or a nanoparticle. The molecule, for example, can be a pigment, a fluorescent dye, an enzyme, or fluorescent protein. A nanoparticle can be a gold nanoparticle, which is red in color. The control reporter probe may consist of a DNA sequence that is complementary to another DNA sequence, and a reporter which is a gold nanoparticle. The control reporter probe can bind to the control capture probe at the control line in the cellulose membrane of the lateral flow test strip.

In this assay, a control reporter probe is also embedded in the conjugation release pad, which is an absorbent pad inside which target-binding aptamer, reporter probe, and control reporter are embedded. The control reporter probe with gold nanoparticles will form a red band at the control line as the sample migrates through the lateral flow test strip. The appearance of a red band in the control line indicates that the assays works as designed.

Example 1—Identification of *P. pallens* as a Gingivitis-Associated Bacterium by Metasequencing DNA of Supragingival Plaque Samples To identify bacteria associated with gingivitis, a metasequencing experiment was carried out. A randomized, parallel group clinical study was conducted with 69 subjects (35 in the negative control group and 34 in the test regimen group). Subjects were 39 years old on average, ranging from 20 to 69, and 46% of the subjects were female. Treatment groups were well balanced, since there were no statistically significant ($p \geq 0.395$) differences for demographic characteristics (age, ethnicity, gender) or starting measurements for Gingival Bleeding Index (GBI); mean=29.957 with at least 20 bleeding sites and Modified Gingival Index (MGI); mean=2.086. All sixty-nine subjects attended each visit and completed the research. The following treatment groups were compared over a 6-week period: Test regimen: Crest® Pro-Health Clinical Plaque Control (0.454% stannous fluoride) dentifrice, Oral-B® Professional Care 1000 with Precision Clean brush head and Crest® Pro-Health Refreshing Clean Mint (0.07% CPC) mouth rinse. Control regimen: Crest® Cavity Protection (0.243% sodium fluoride) dentifrice and Oral-B® Indicator Soft Manual toothbrush.

Figure 1B:
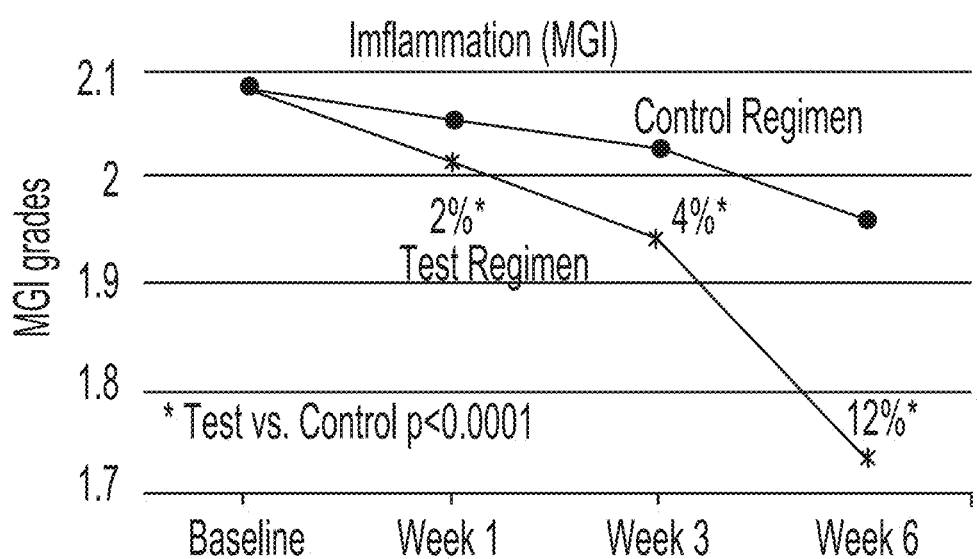
FIG. 1B shows lower mean inflammation (MGI) among a test regimen group relative to a negative control group at Weeks 1, 3 and 6.

The test regimen group demonstrated significantly ($p<0.0001$) lower mean bleeding (GBI) and inflammation (MGI) relative to the negative control group at Weeks 1, 3 and 6 as shown in FIG. 1.

Dental plaques were collected from the same subjects in the test regimen of the clinical study. A supragingival sample was taken from each subject with a sterile curette at the tooth/gum interface, using care to avoid contact with the oral soft tissue. Plaques were sampled from all available natural teeth (upper arch only) until no plaque was visible. Following sampling, plaque was placed into a pre-labeled (subject ID, sample initials, visit, and date) Eppendorf tube with 1 ml of phosphate-buffered saline (Sigma, St. Louis, Mo.) and 5000 sterile 1 mm glass beads (Sigma, St. Louis, Mo.), and stored on ice until all samples were collected. The samples were then transferred to a −70° C. freezer for storage until further processing. Genomic DNA was isolated from supragingival plaque samples using QIAamp® genomic DNA kits (Qiagen, Germany) following the manufacturer's instructions. Metasequencing was carried out at BGI Americas Corporation (Cambridge, Mass.).

The relative abundance of bacteria underwent significant changes during treatment (Table 1). Bacterial species *Prevotella pallens* was abundant, accounting for 2.79% of total microbial sequences at baseline. It decreased with ProHealth treatment regimen at week 1, 3, and 6.

from different bacteria are structurally different and recognized by different antibodies. As a result, either LPS or OMV can be used as biomarkers representing specific bacterial species.

Procedures of OMV isolation: Both *P. pallens* (ATCC catalog #700821 American Type Culture Collection, Manassas, Va.) and *P. gingivalis* (ATCC catalog #33277, American Type Culture Collection, Manassas, Va.) were cultured in 30 ml MTGE media (Anaerobic Enrichment Broth, Anaerobe Systems, 6 ml tubes—catalog #AS-778 & 500 ml bottles—catalog #AS-7785, Anaerobe System, Morgan Hill, Calif.) in a sterile 125 ml Erlenmeyer flask under anaerobic conditions at 37° C. for 48 hours as seeding bacteria. The seeding bacterial culture was inoculated seven liters of fresh MTGE media (Anaerobic Enrichment Broth, Anaerobe Systems, 6 ml tubes—catalog #AS-778 & 500 ml bottles—catalog #AS-7785, Anaerobe System, Morgan Hill, Calif.), and continued to grow for 48 hours under anaerobic conditions at 37° C.

The bacteria were harvested at the end of culture by centrifugation in a JA-10 rotor at 10,000 g, 4° C. for 60 min in Avanti J-26 XPI High-Performance Centrifuge of Beckman Coulter, Indianapolis, Ind. The bacterial pellet was stored at −80° C. for bound lipopolysaccharide isolation. The supernatant was collected and filtered through 0.45 μm pore PVDF membranes to remove cell debris.

TABLE 1

Changes of bacteria in percentage in supragingival plaques during six-week treatment with a ProHealth regimen

| Bacteria | P value compared to baseline | | | Mean percentage in each time point | | | |
|---|---|---|---|---|---|---|---|
| | Wk 1 | Wk 3 | Wk 6 | Baseline | Wk1 | Wk 3 | Wk 6 |
| f_Propionibacteriaceae | 0.0166 | 0.0003 | 0.0173 | 0.01 | 0.12 | 0.15 | 0.19 |
| g_Propionibacterium | 0.0346 | 0.0003 | 0.0173 | 0.01 | 0.12 | 0.15 | 0.19 |
| s_*Propionibacterium_propionicum* | 0.0346 | 0.0003 | 0.0173 | 0.01 | 0.12 | 0.15 | 0.19 |
| t_GCF_000277715 | 0.0346 | 0.0003 | 0.0173 | 0.01 | 0.13 | 0.16 | 0.22 |
| p_Bacteroidetes | 0.0027 | 0.0235 | 0.0215 | 21.50 | 13.46 | 12.88 | 14.36 |
| c_Bacteroidia | 0.0007 | 0.0053 | 0.0135 | 20.85 | 11.02 | 9.40 | 12.70 |
| o_Bacteroidales | 0.0007 | 0.0053 | 0.0135 | 20.85 | 11.02 | 9.40 | 12.70 |
| f_Prevotellaceae | 0.0186 | 0.0235 | 0.0366 | 16.36 | 9.33 | 8.25 | 9.98 |
| g_*Prevotella* | 0.0209 | 0.0105 | 0.0330 | 15.79 | 8.90 | 7.24 | 9.55 |
| s_*Prevotella_pallens* | 0.0020 | 0.0003 | 0.0071 | 2.79 | 0.62 | 0.00 | 0.85 |
| t_GCF_000220255 | 0.0020 | 0.0003 | 0.0071 | 3.09 | 0.67 | 0.00 | 0.92 |
| s_*Prevotella*_sp_C561 | 0.0315 | 0.0168 | 0.0376 | 1.54 | 0.31 | 0.00 | 0.27 |
| t_GCF_000224595 | 0.0315 | 0.0168 | 0.0376 | 1.71 | 0.34 | 0.00 | 0.30 |
| g_Lachnospiraceae_noname | 0.0128 | 0.0009 | 0.0063 | 0.25 | 0.13 | 0.04 | 0.14 |
| s_*Peptostreptococcus*_unclassified | 0.0049 | 0.0045 | 0.0433 | 0.44 | 0.04 | 0.00 | 0.12 |
| g_*Solobacterium* | 0.0099 | 0.0067 | 0.0298 | 0.78 | 0.35 | 0.25 | 0.42 |
| s_*Solobacterium_moorei* | 0.0086 | 0.0067 | 0.0298 | 0.79 | 0.35 | 0.26 | 0.42 |
| t_GCF_000186945 | 0.0113 | 0.0032 | 0.0192 | 0.87 | 0.38 | 0.28 | 0.46 |
| t_*Veillonella_atypica*_unclassified | 0.0037 | 0.0001 | 0.0152 | 1.24 | 0.38 | 0.01 | 0.45 |

Example 2—Isolate Outer Membrane Vesicles from *P. gingivalis* and *P. pallens*

Figure 2A:
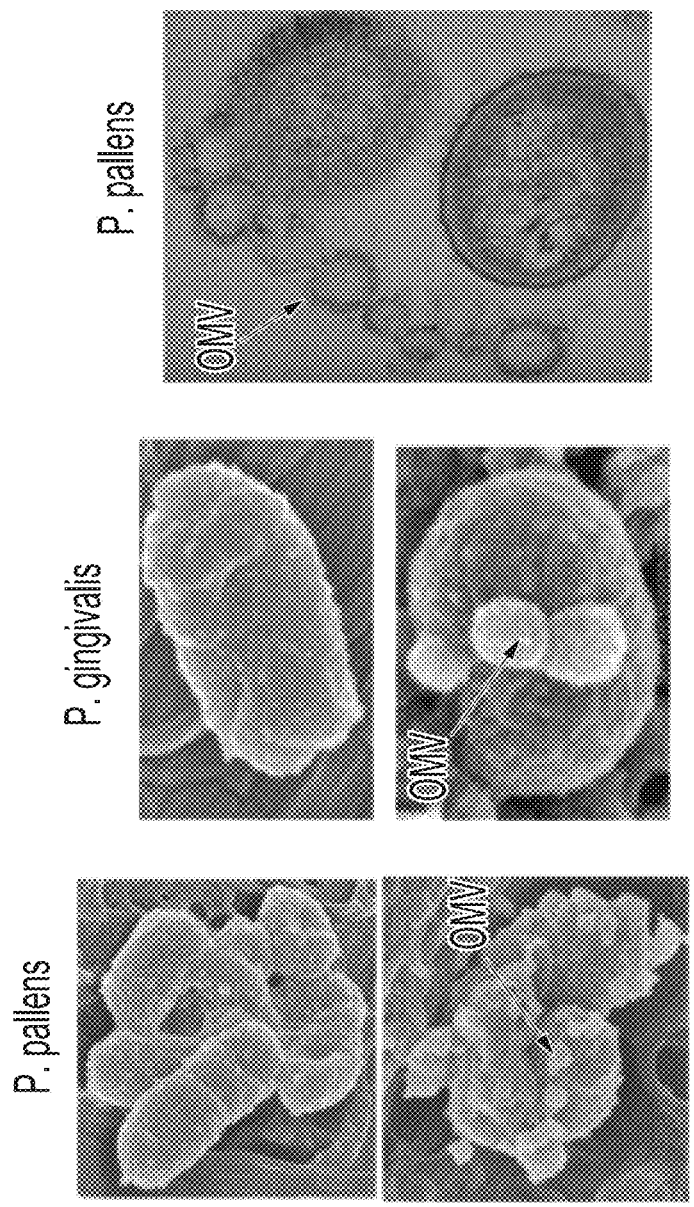
FIG. 2A shows an scanning electron micrograph illustrating bacteria release outer membrane vesicles (OMV) during growth or under stress.

Objectives: *P. gingivalis* has been known as a pathogen for periodontitis and would be a good biomarker for periodontitis. *P. pallens* was identified as being associated with gingivitis, as described in EXAMPLE 1, and would be a good biomarker for gingivitis. Bacteria release outer membrane vesicles (OMV) during growth or under stress as shown FIG. 2A (Roier, S. et al. 2016. A novel mechanism for the biogenesis of outer membrane vesicles in Gram-negative bacteria. Nat. Commun. 7:10515 doi: 10.1038/ncomms10515). OMV carry endotoxins, proteins and other molecules produced by bacteria. OMV are likely to be a good marker for relative bacteria. Lipopolysaccharides (LPS), also known as endotoxins, are highly virulent and toxic to host cells; and when used experimentally can cause gingivitis and periodontitis if administrated to animals. LPS OMV was secreted by the both *P. pallens* and *P. gingivalis* into the MTGE media. To isolate OMV, the conditioned culture medium volume was reduced by filtration using a tangential flow filtration Minimate TFF System (PALL Life Sciences, Port Washington, N.Y.) with an array of filter capsules with molecular weight cutoff from 10 kD to 300 kD, at 40 Psi. The retentate of the tangential flow filtration procedure that contains the OMV, was centrifuged at 140,000×g for 1 hour at 4° C. (using an SW32 swinging bucket rotor on a Beckman XL-100K Ultracentrifuge, Beckman Coulter, Atlanta, Ga.). The pellets were resuspended in dPBS buffer (1× Dulbecco's Phosphate Buffered Saline (dPBS): catalog #14190144; Life Technologies, Grand Island, N.Y.) and centrifuged at 200,000×g for 1 hour at 4° C. (using an SW41 swinging bucket rotor) to yield a standard OMV preparation.

To generate highly pure OMV, the initial OMV from the first ultracentrifugation was then resuspended in 800 μL HEPES buffer (50 mM HEPES, 150 mM NaCl, pH 6.8, Life Technologies, Grand Island, N.Y.), and underwent another round ultracentrifugation using OptiPrep™ (60% w/v iodixanol in water, Sigma-Aldrich, St. Louis, Mo., USA) discontinuous density gradient. The initial OMV preparation was separated into four samples and each resuspended in 3 mL HEPES buffer containing 45% w/v iodixanol and placed in 4 Ultra-Clear™, 14 mL, 14×95 mm tubes (Beckman Coulter, Atlanta, Ga.). A discontinuous iodixanol gradient was achieved in each sample by layering successive 1.5 mL of HEPES buffer containing 45%, then 40%, 35%, 30%, 25% & 20% w/v iodixanol, with 45% at the bottom, in a total of 9.5 ml. Tubes were centrifuged at 173,000×g for 72 hours at 4° C. using a 70.1Ti rotor installed in a Beckman XL-100K Ultracentrifuge (Beckman-Coulter, Atlanta, Ga.). Eight 0.5 mL gradient fractions from each sample (1, 2, 3 & 4) were collected from top to bottom of the density gradient solution and measured at A260 and A280 for DNA/RNA and proteins, respectively, using an 8-channel NanoDrop spectrophotometer according to the manufacturer's instructions (ThermoFisher Scientific, Waltham, Mass., USA). The endotoxin activities were analyzed in the fractions using the Pierce™ LAL Chromogenic Endotoxin Quantitation Kit, per manufacturer's instructions (ThermoFisher Scientific, Waltham, Mass., USA).

Fractions containing the purified OMVs were washed with endotoxin-free water (Sigma, St. Louis, Mo.) and centrifuged twice at 200,000×g for 2 hours at 4° C. using a SW40 Ti rotor installed in a Beckman XL-100K Ultracentrifuge (Beckman-Coulter, Atlanta, Ga.). The highly pure OMV were resuspended in 30 ml of endotoxin-free water, and aliquoted into 0.5 ml Eppendorf tubes and stored at −80° C. for aptamer development.

Figure 2C:
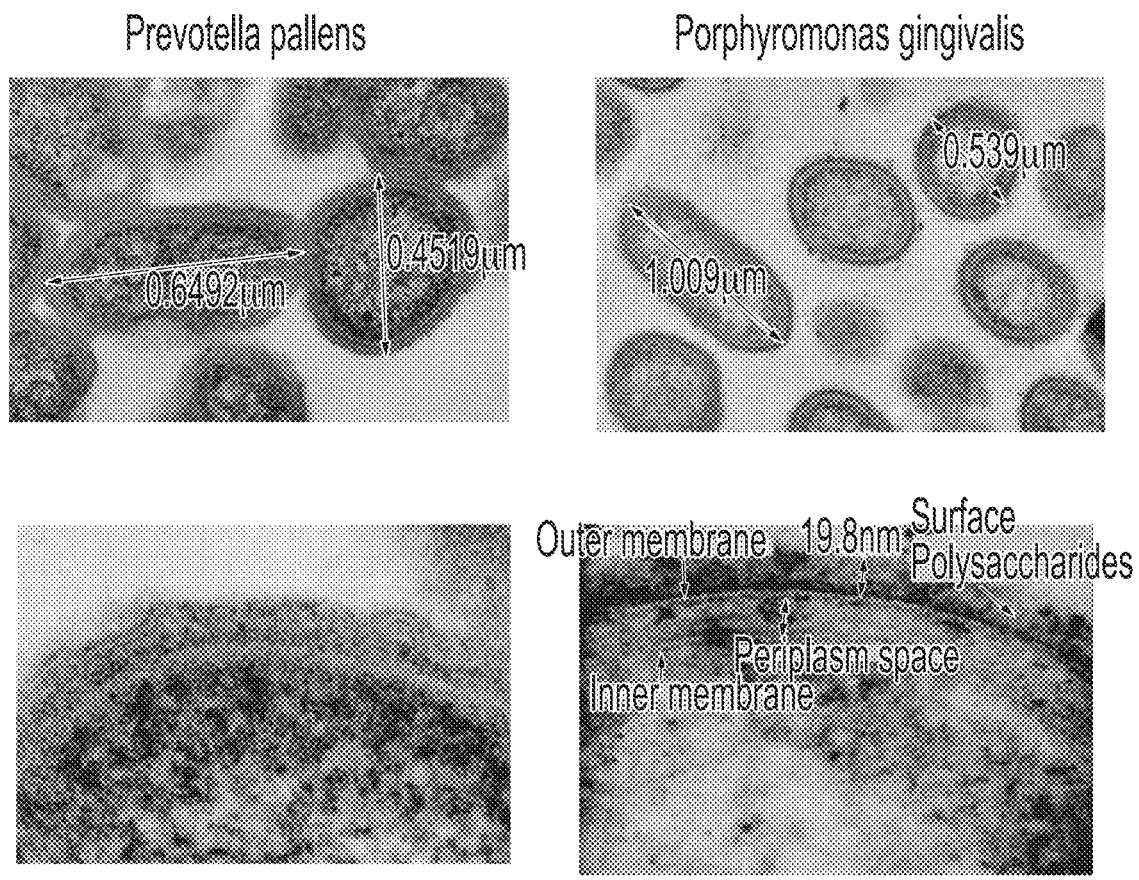
FIG. 2C presents transmission electron microscopic images of bacterial membranes and their measurements.
Figure 2E:
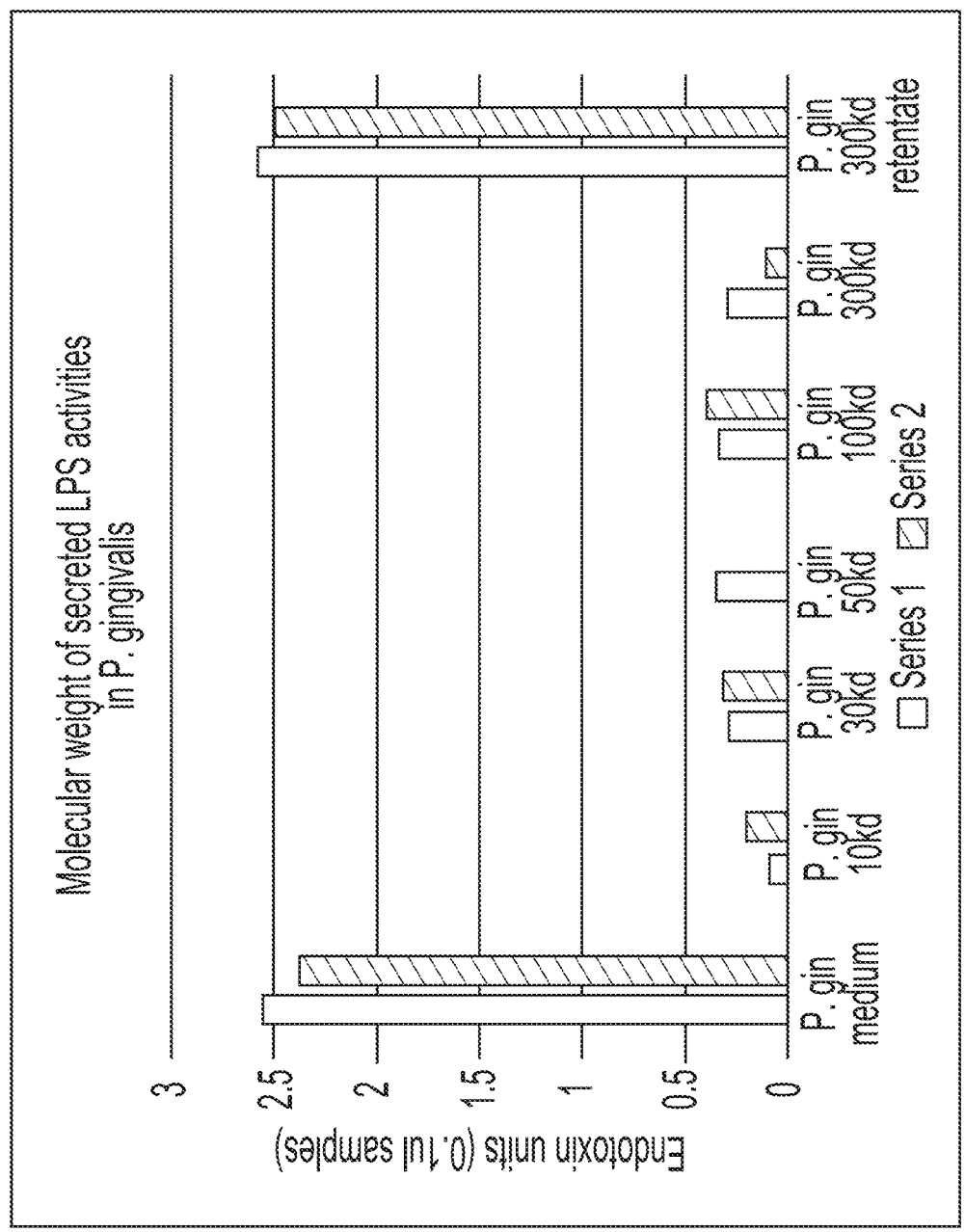
FIG. 2E shows endotoxin activities were low in the filtrates that were filtered through tangential flow filtration of *P. gingivalis* culture medium.
Figure 2F:
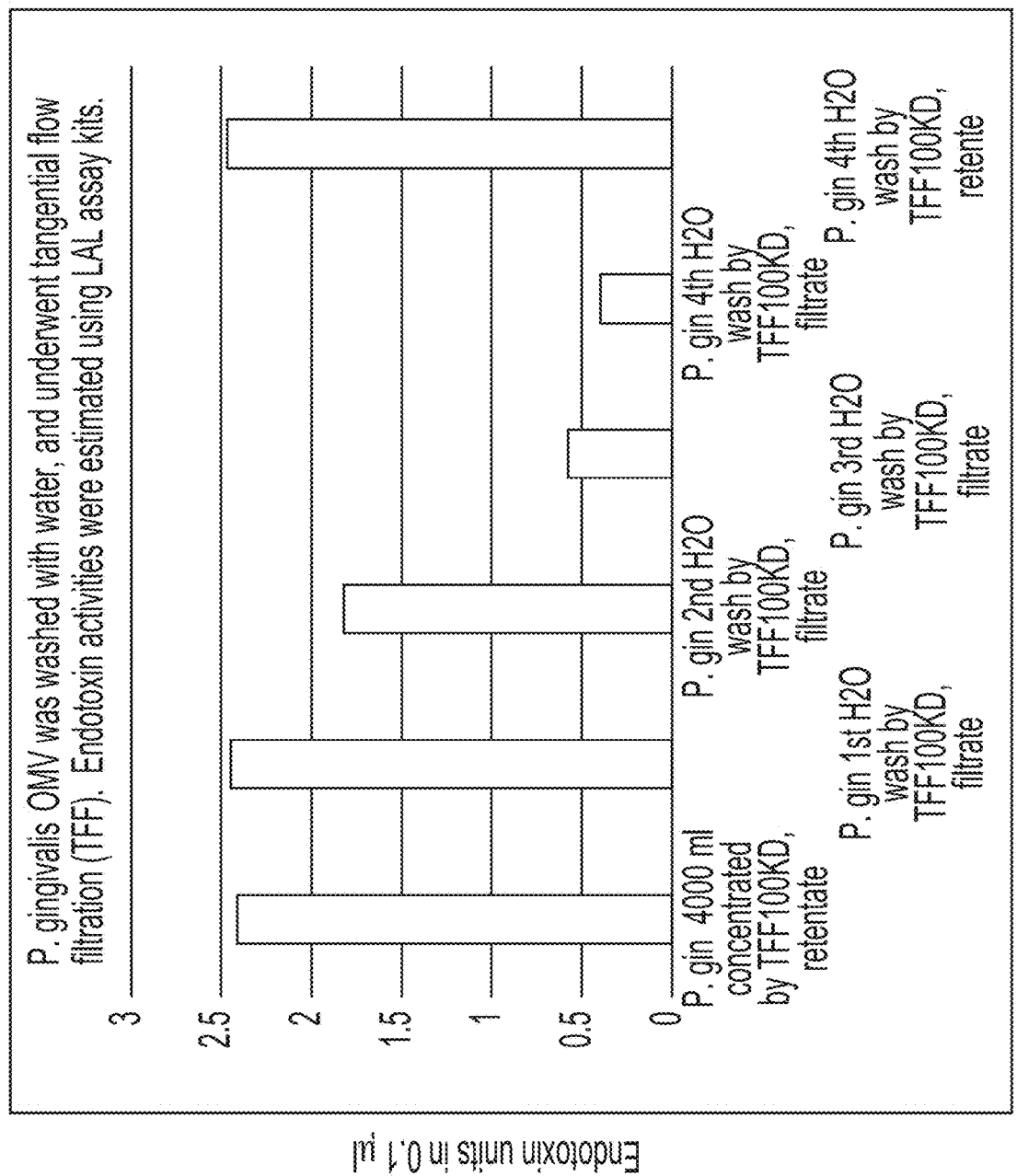
FIG. 2F shows LPS activities were high in the filtrate when the *P. gingivalis* retentate was diluted with water and passed through 100 kD tangential flow filtration processes.
Figure 2G:
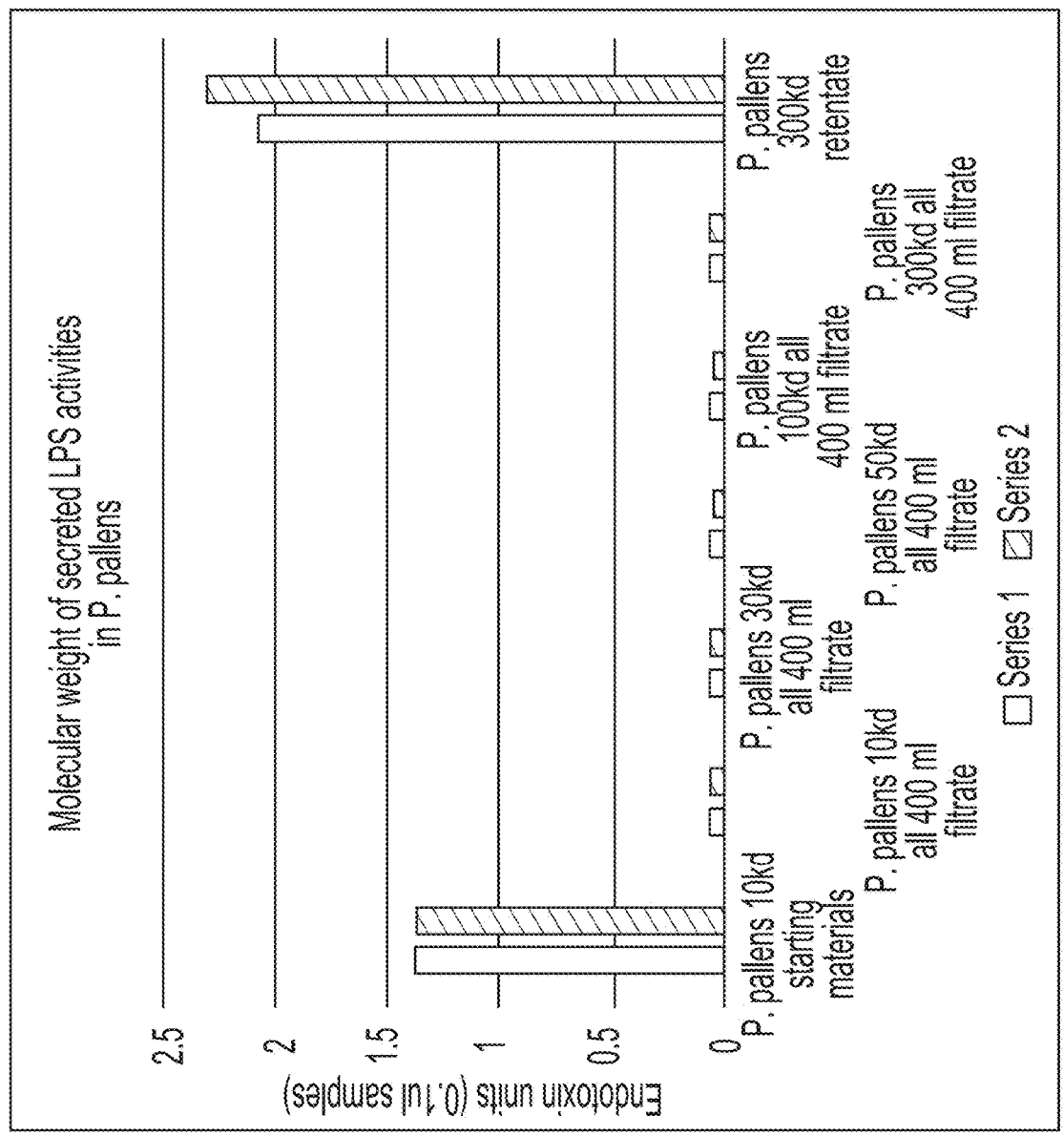
FIG. 2G shows in *P. pallens* almost all endotoxin activities remained in the retentate.
Figure 2H:
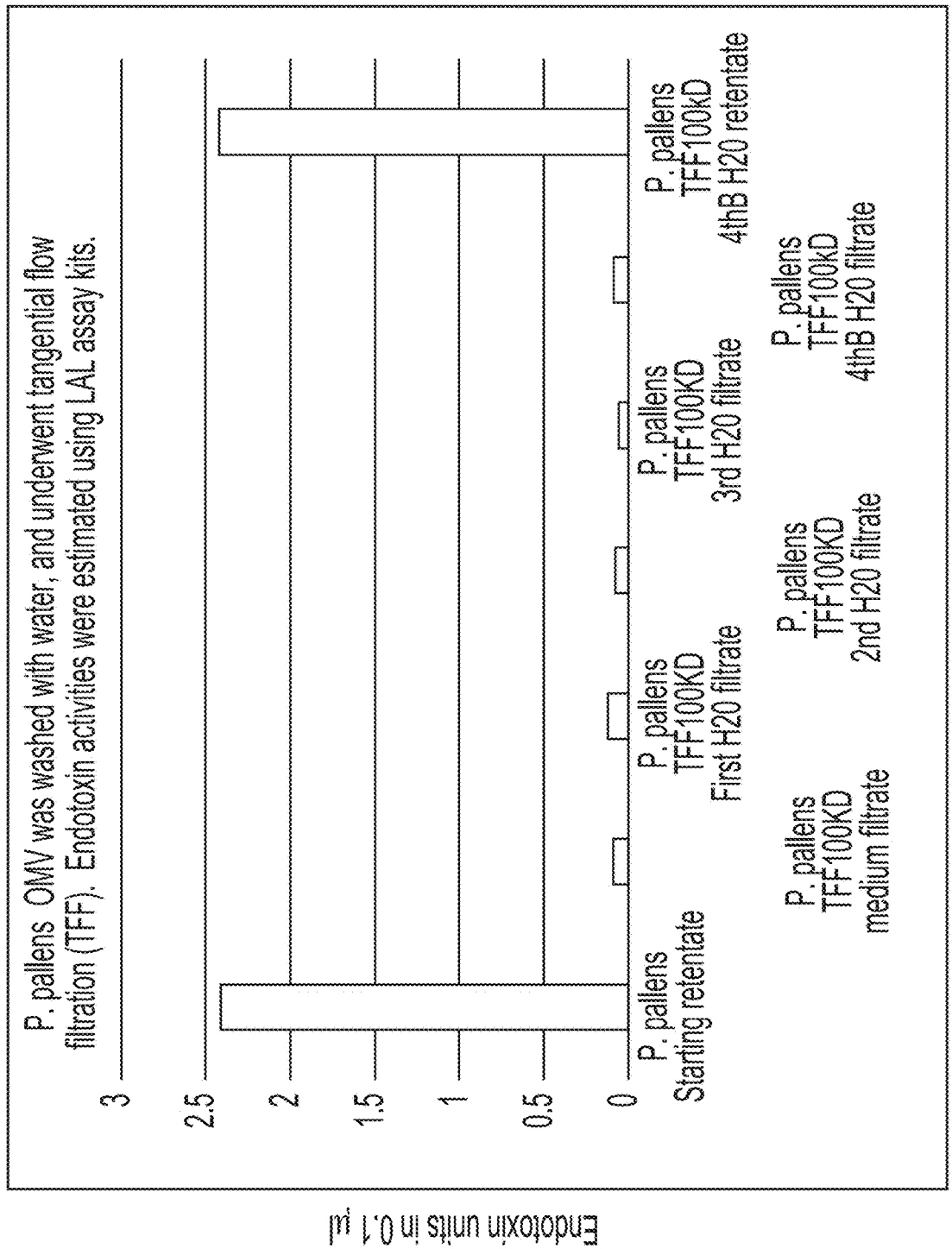
FIG. 2H shows LPS activities were low in the filtrate when the *P. pallens* retentate was diluted with water and passed through 100 kD tangential flow filtration processes.
Figure 21:

Results: Both *P. gingivalis* and *P. pallens* are Gram-negative bacteria in the dental plaques (FIG. 2A to 2C, scanning and transmission electron graphs were prepared using procedure as described by Ronald R Warner 1, Keith J Stone and Ying L Boissy. Hydration Disrupts Human Stratum Corneum Ultrastructure. J Invest Dermatol. 120 (2), 275-84 February 2003, DOI: 10.1046/j.1523-1747.2003.12046.x; R R Warner 1, J R Schwartz, Y Boissy, T L Dawson Jr. Dandruff Has an Altered Stratum Corneum Ultrastructure That Is Improved With Zinc Pyrithione Shampoo. J Am Acad. Dermatol, 45 (6), 897-93 December 2001).

The OMV in the conditioned MTGE medium, in which *P. pallens* had grown for 48 hours, was concentrated using tangential flow filtration with filter capsules ranging from 10 kD to 300 kD molecular weight cutoff. Lipopolysaccharides are reported to have molecular masses between 10-20 kD.

The filtrates and the retentates were analyzed for endotoxin activities. If the OMV or the lipopolysaccharides are in the filtrate, the endotoxin activities would be high in the filtrate. If the OMV or the lipopolysaccharides are not in the filtrate, the endotoxin activities are likely associated with OMV in the retentate. Culture media were filtered with two new units of each molecular weight cutoff capsules, each with 500 ml. As shown in FIG. 2E to 2H, the endotoxin activities were low in the filtrates that were filtered through tangential flow filtration Minimate TFF System (PALL Life Sciences, Port Washington, N.Y.). These results suggest that most of the secreted endotoxins are associated with OMV. In *P. pallens* (FIG. 2G), almost all endotoxin activities remained in the retentate.

The concentrated retentate was precipitated with ultracentrifugation as described above, and then separated with a discontinuous iodixanol gradient as described above. As shown in FIG. 2I, a yellow band appeared in the discontinuous iodixanol gradient.

Figure 2J:
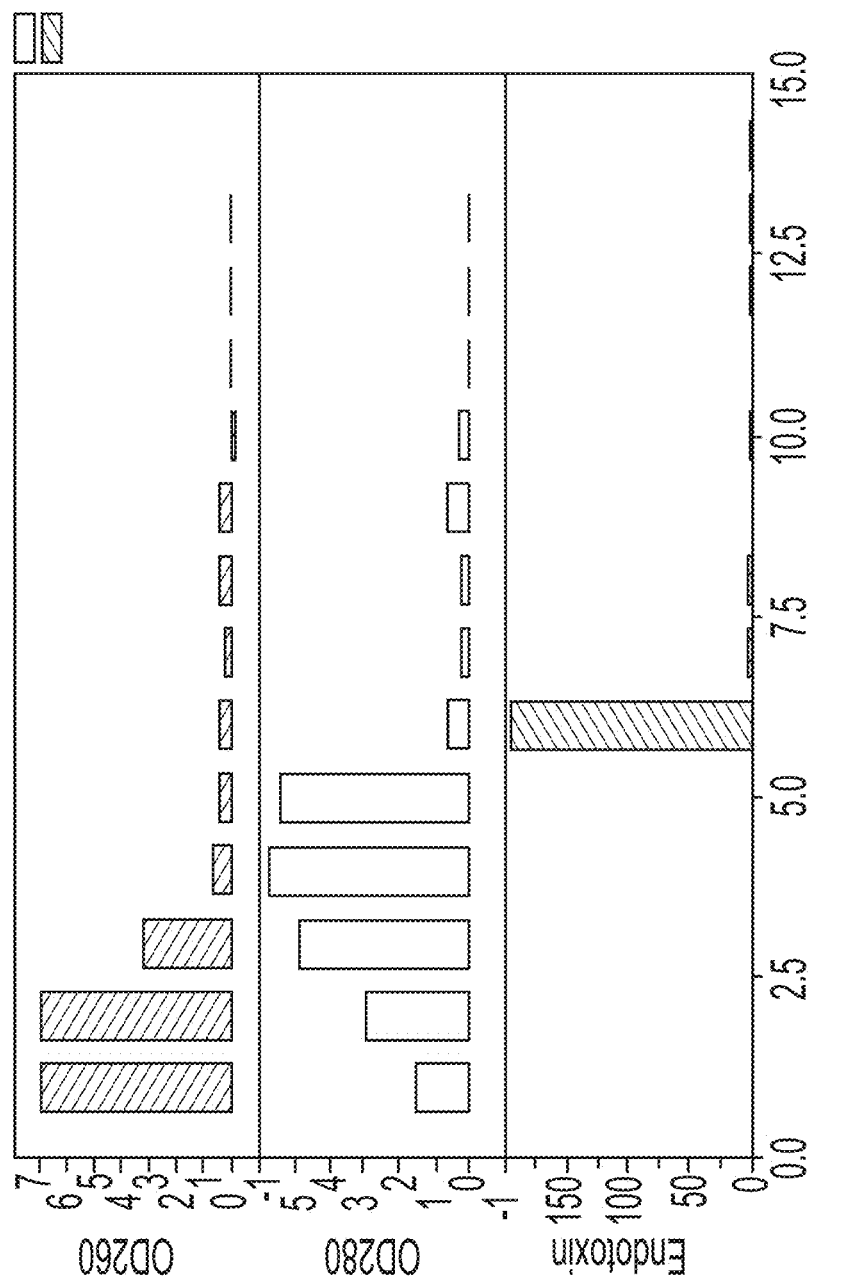
FIG. 2J shows DNA and RNA molecules, measured in OD260, are floated at the top of the gradient. Proteins, estimated by OD280, are located just below DNA and RNA molecules.

To determine whether the endotoxin activities were associated the yellow bands, the gradient solution was fractioned into 0.5 ml by using a pipettor to withdraw 0.5 ml each time from the top to bottom in the ultracentrifuge tube, absorbance was read at 260 and 280 nM in a SpectraMax iD3 spectrometer reader (Molecular Device, Downingtown, Pa.). As shown in FIG. 2J, DNA and RNA molecules, measured in OD260, are floated at the top of the gradient. Proteins, estimated by OD280, are located just below DNA and RNA molecules. Almost all endotoxin activities are associated with the yellow bands, which are the OMV. The sizes of OMV ranges from 27.9 to 127 nanometers and 29.5 to 83.5 nanometers for *P. pallens* and *P. gingivalis*, respectively (FIG. 2D).

Example 3—Isolation of Secreted and Bacterium-Bound Lipopolysaccharides from *P. gingivalis* and *P. pallens*

LPS extraction: Lipopolysaccharides (LPS) from bacterial pellet and standard outer membrane vesicles (OMV) were extracted and purified using the procedures, as described by Westphal and Jann (Bacterial Lipopolysaccharides Extraction with Phenol-Water and Further Applications of the Procedure. 1965; Methods in Carbohydrate Chemistry, 5, 83-91) and Darveau and Hancock (J Bacteriol. 1983 August; 155(2):831-8. Procedure for isolation of bacterial lipopolysaccharides from both smooth and rough *Pseudomonas aeruginosa* and *Salmonella typhimurium* strains). Briefly, bacterial pellets and OMV were dissolved in a 300 ml buffer containing 10 mM Tris-Cl buffer (pH 8), 2% Sodium Dodecyl Sulphate, 2 mM $MgCl_2$ and 40 mg Proteinase K (all chemicals and proteinase K were purchase from Sigma, St. Louis Mo.).

The mixture was vortexed and placed an incubator at 68° C. for 24 hours. Sixty ml of 3M sodium acetate pH 5.2 and 800 ml 100% ethanol were added and kept at −20° C. The crude lipopolysaccharides were precipitated using a JA-10 rotor at 13000 RPM, 4° C. for 60 min in Avanti J-26 XPI High-Performance Centrifuge of Beckman Coulter, Indianapolis, Ind. After the centrifugation, precipitate was suspended in 200 ml of 20 mM Triethylamine (2.8 ml TEA/1000 ml) and 0.5% deoxycholate. Proteinase K (20 mg) was added and the solution was incubated at 65° C. for 24 hours. Phenol −200 ml (BioReagent, equilibrated with 10 mM Tris HCl, pH 8.0, 1 mM EDTA, for molecular biology purchased from Sigma, St. Louis Mo.) was added to crude lipopolysaccharide solution. The phenol and LPS solution was shaken to mix the aqueous and phenol phases and heated at 65° C. for overnight. The mixed solution was then cooled in ice water for 60 min and centrifuged to separate the phenol and aqueous phases using a JA-10 rotor at 13000 RPM, 4° C. for 60 min in Avanti J-26 XPI High-Performance Centrifuge. The aqueous phase was collected. Sixty ml of 3M sodium acetate pH 5.2 and 800 ml 100% ethanol were added and kept at −20° C. The crude lipopolysaccharides were precipitated using a JA-10 rotor at 13,000 RPM, 4° C. for 60 min in Avanti J-26 XPI High-Performance Centrifuge. The pelleted LPS was then resuspended in 400 ml of 100 mM sodium acetate pH 5.2.

Chromatography purification: Both secreted and bacterium-bound LPS were purified using hydrophobic interaction chromatography (Sigma, St. Louis Mo.) following procedures described by Fischer (Eur J Biochem. 1990 Dec. 12; 194(2):655-61. Purification and fractionation of lipopolysaccharide from gram-negative bacteria by hydrophobic interaction chromatography) and Muck et al. (Journal of Chromatography B: Biomedical Sciences and Applications Volume 732, Issue 1, 10 Sep. 1999, Pages 39-46: Biomedical Sciences and Applications Efficient method for preparation of highly purified lipopolysaccharides by hydrophobic interaction chromatography), and affinity chromatography (M. Sakata, M. Todokoro, C. Hirayama, American Biotechnol. 2002; Lab., 20: 36. M. Todokoro, M. Sakata, S. Matama, M. Kunitake, J. Ohkuma, C. Hirayama, 2002; J. Liq. Chrom. & Rel. Technol., 25: 601). The endotoxin activities were also analyzed in the fractions using the Pierce™ LAL Chromogenic Endotoxin Quantitation Kit, per manufacturer's instructions (ThermoFisher Scientific, Waltham, Mass., USA).

Results: Intact bacterial lipopolysaccharides are heterogeneous with a molecular mass ranging from 10 kDa to 20 kDa, composed of three structural components: A) a hydrophobic lipid section, lipid A, which is responsible for the toxic properties of the molecule; B) a hydrophilic core polysaccharide chain; and C) a repeating hydrophilic O-antigenic oligosaccharide side chain that is specific to the bacterial serotype. Purified lipopolysaccharides of *P. gingivalis* were separated using spectrometry methods as described by Haught, Xie, Circello, Tansky, Khambe, Sun, Lin, Sreekrishna, Klukowska, Huggins, and White (Am J Dent. 2016 December; 29(6):328-332.

Figure 3A:
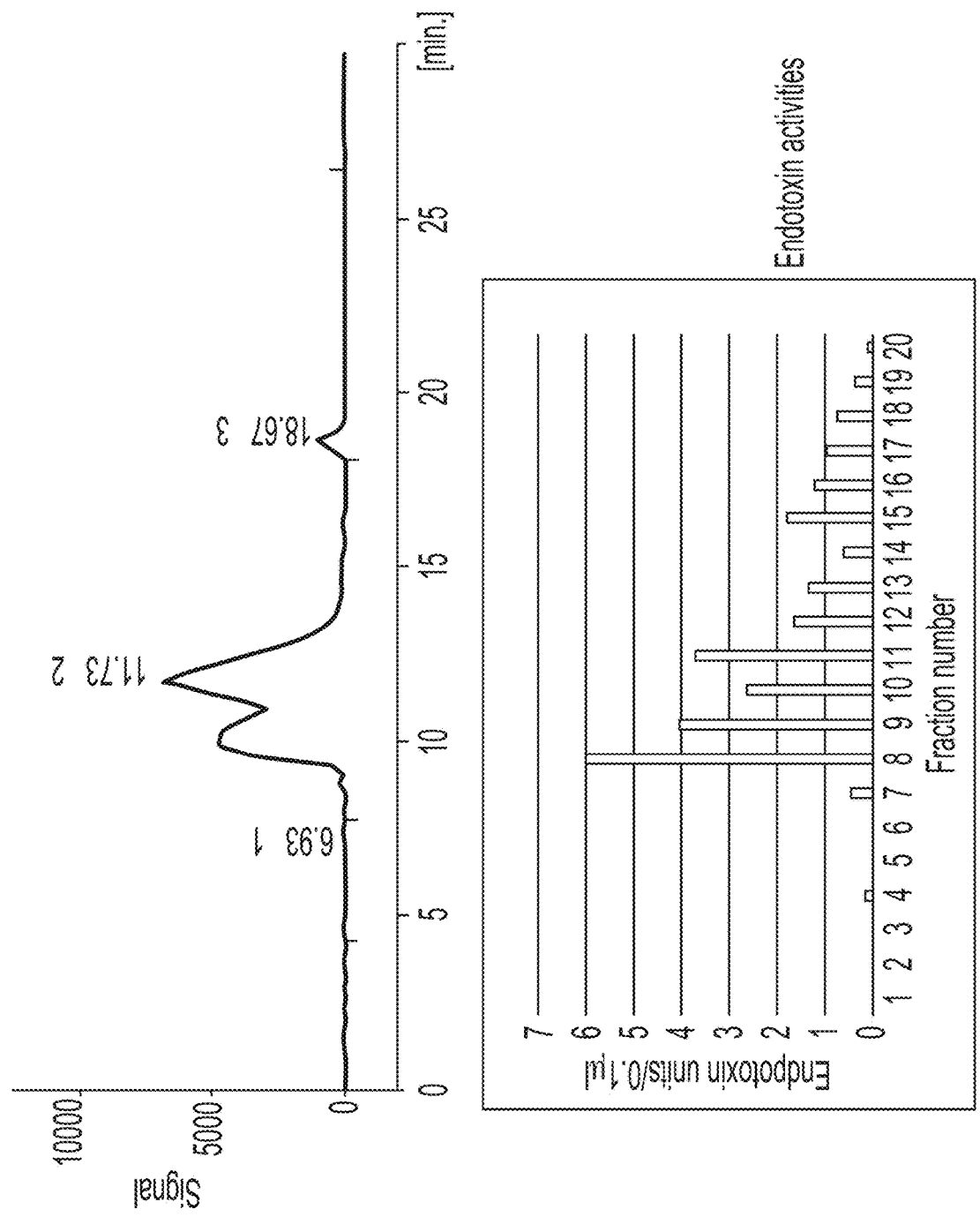
FIG. 3A shows the ultrapure LPS preparation of *P. gingivalis* had two peaks. The elution was collected at one-minute intervals, starting 10 minutes after injection of the samples to account for the flow time from the detector to the sample collection outlet. Endotoxin activities were measured in each fraction, and the majority of endotoxin activity was in fractions 8 to 11.
Figure 3B:
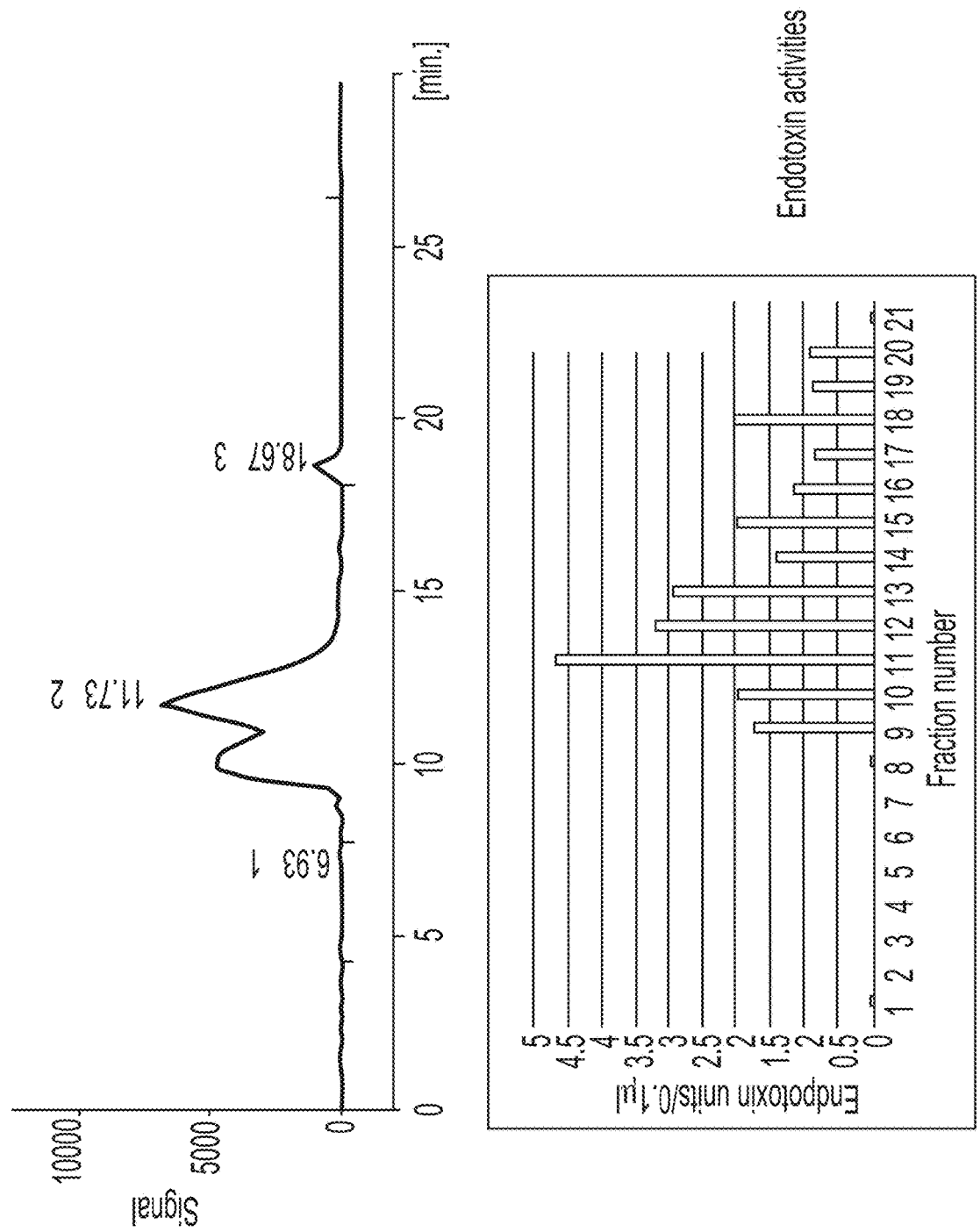
FIG. 3B shows lab purified bacterium bound LPS of *P. gingivalis* had a very similar pattern on spectrometry profiles as the ultrapure LPS preparation of *P. gingivalis*. The main endotoxin activities were in fractions 9 to 13.

Lipopolysaccharide and lipoteichoic acid binding by antimicrobials used in oral care formulations: As shown FIG. 3A, the ultrapure LPS preparation of *P. gingivalis* (Invivogen Cat. Code tlrl-ppglps, San Diego, Calif.), showed two peaks. The LPS preparations also contained a small peak at 18.67 min elution, which is likely some inorganic salts. The elution was collected at one-minute intervals, starting 10 minutes after injection of the samples to account for the flow time from the detector to the sample collection outlet. Endotoxin activities were measured in each fraction. The majority of endotoxin activity was in fractions 8 to 11, as show in FIG. 3A. The bacterium bound LPS of *P. gingivalis* purified in our lab showed a very similar pattern on spectrometry profiles (FIGS. 3B and 3D). The main endotoxin activities were in fractions 9 to 13. These results suggest that *P. gingivalis* lipopolysaccharides are highly heterogeneous.

Figure 3C:
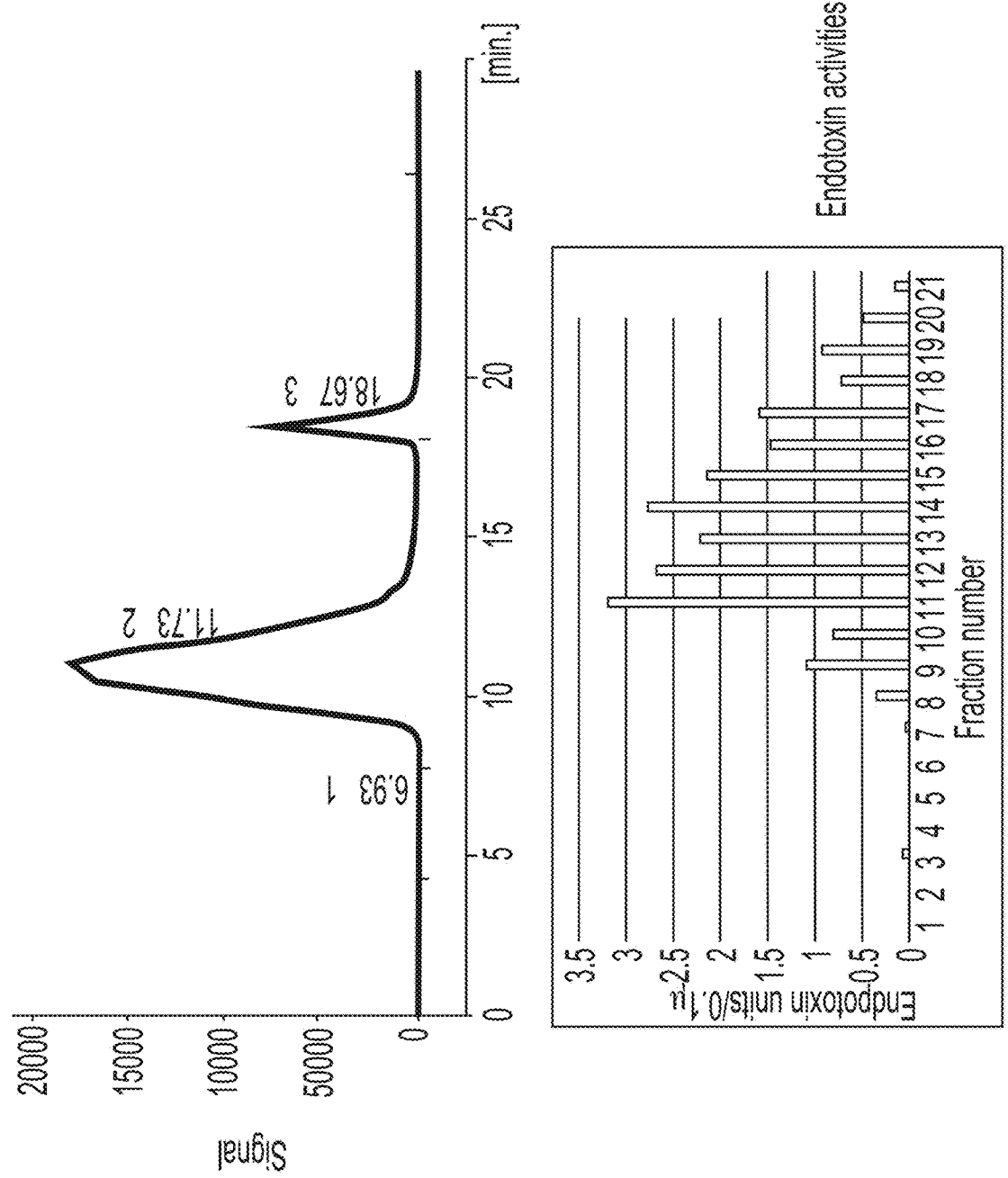
FIG. 3C shows the LPS isolated from the culture medium is somewhat different from the bacterium-bound LPS, as the LPS isolated from the culture medium showed a broad one peak.
Figure 3D:
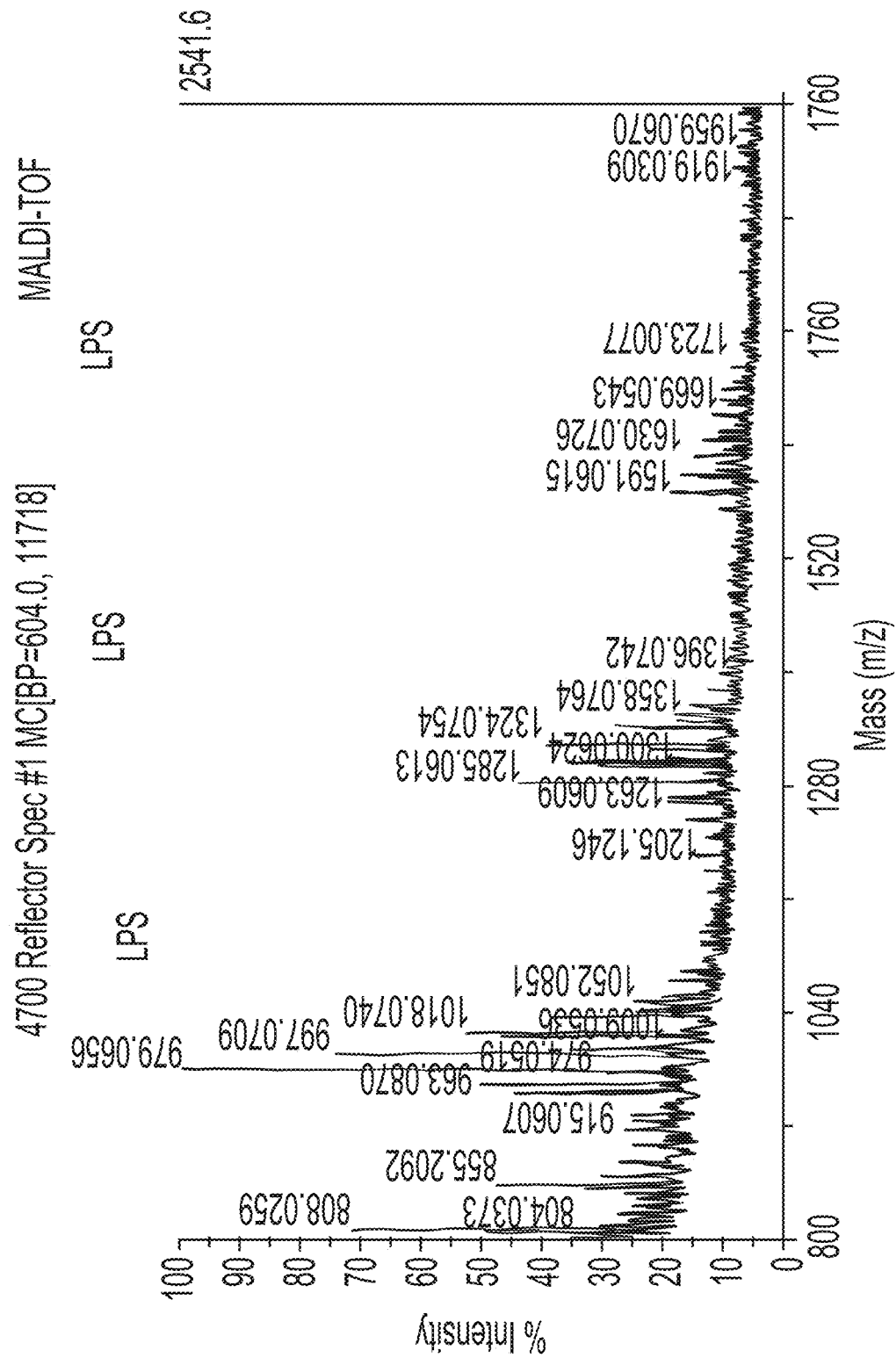
FIG. 3D shows multiple species of purified *P. gingivalis* bacterial cell lipopolysaccharides in mass spectrometry.
Figure 3E:
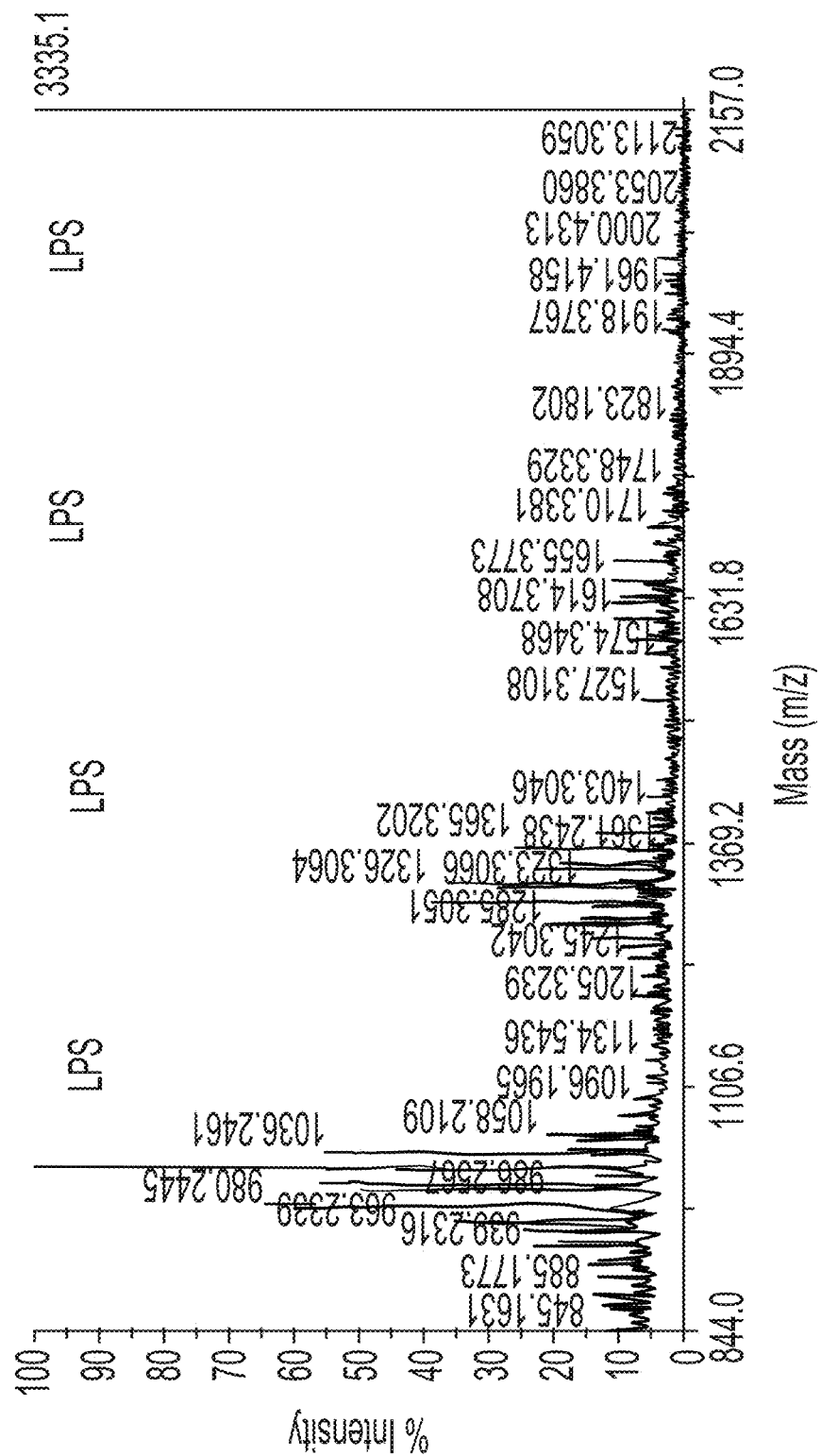
FIG. 3E shows multiple species of purified secreted *P. gingivalis* lipopolysaccharides in mass spectrometry.
Figure 3F:
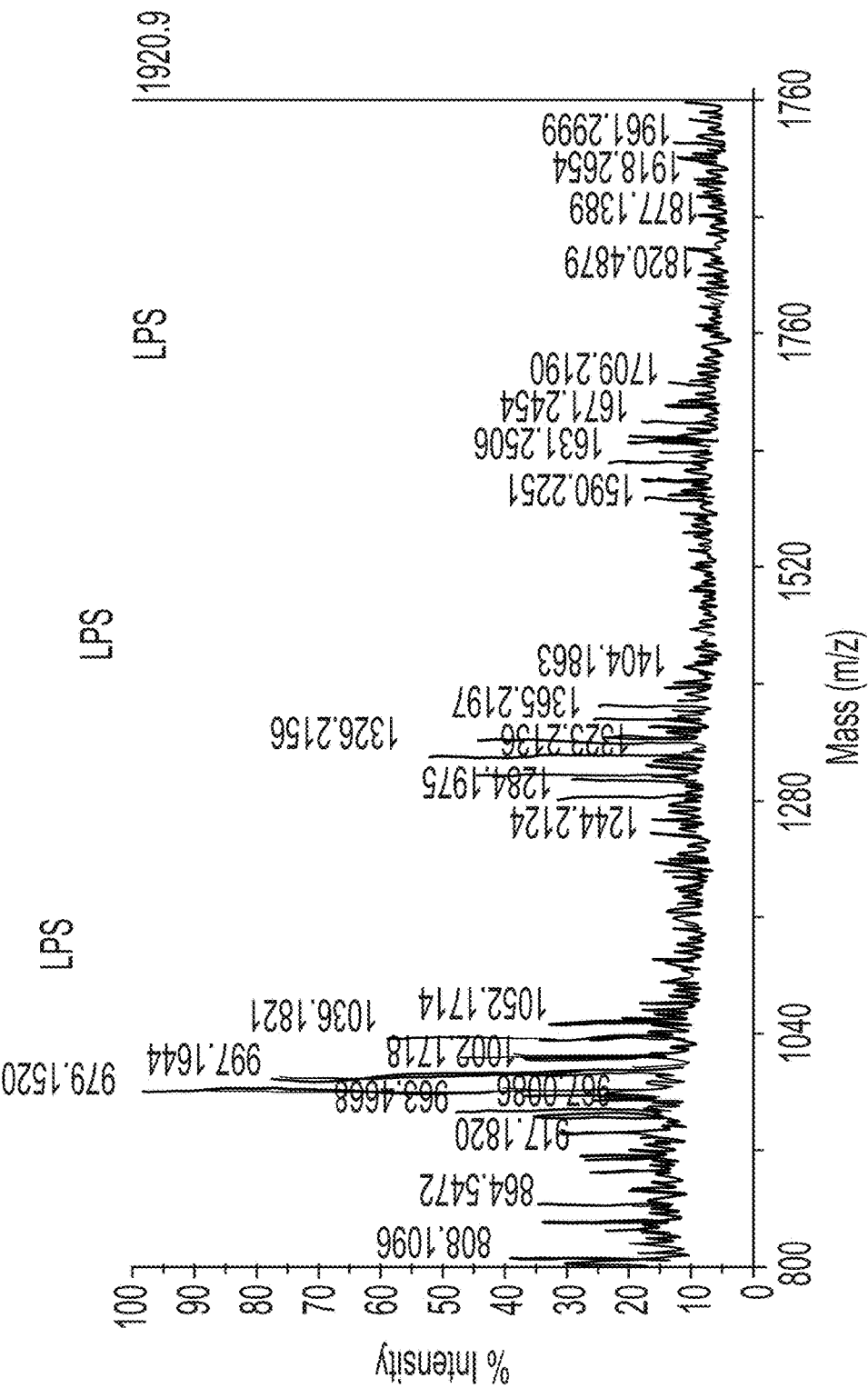
FIG. 3F shows multiple species of purified *P. pallens* bacterial cell lipopolysaccharides in mass spectrometry.
Figure 3G:
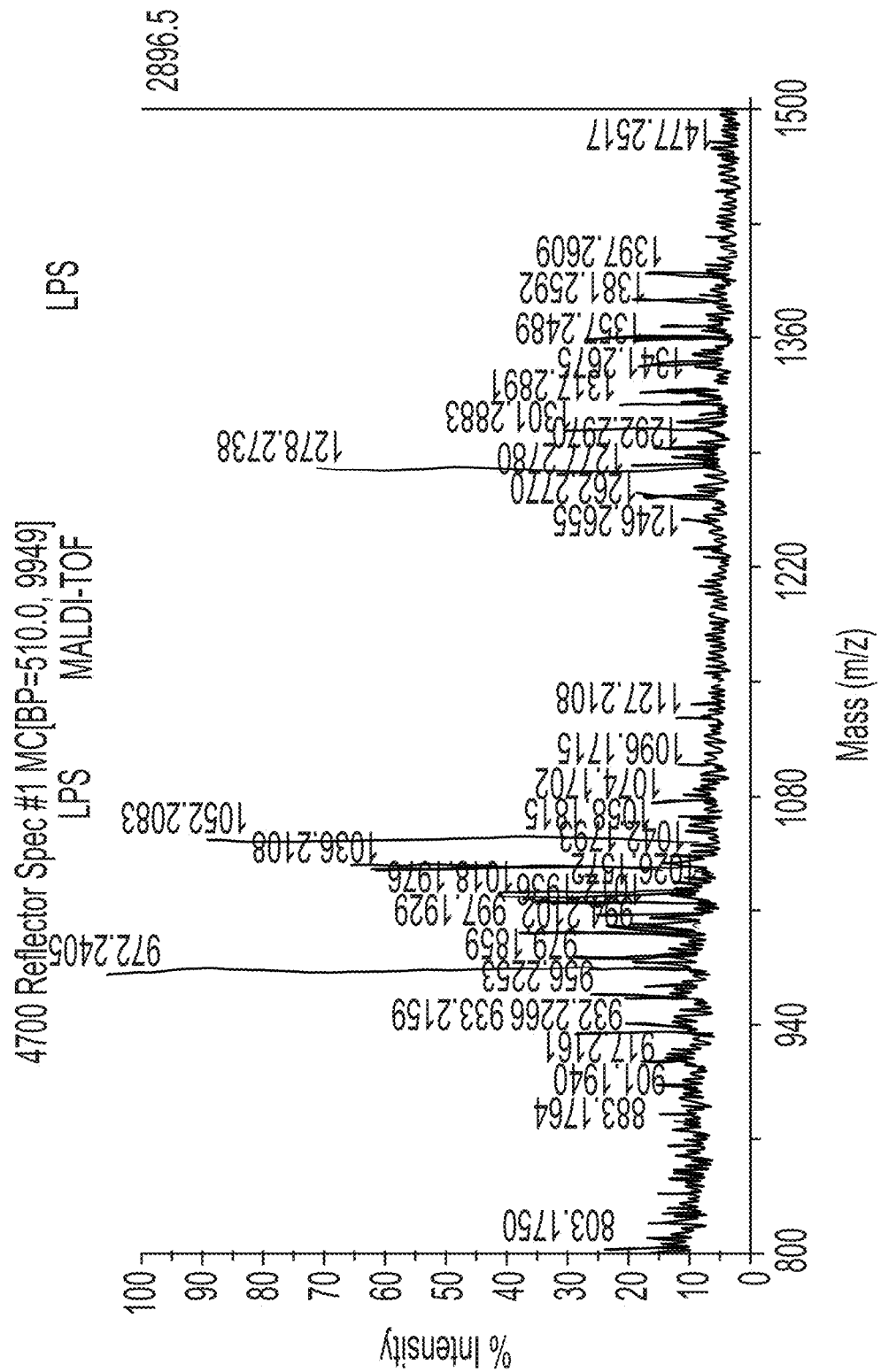
FIG. 3G shows multiple species of ultrapure *E. coli* bacterial cell lipopolysaccharides of Invivogen (Ultrapure LPS from *E. coli* 055:B5) in mass spectrometry.

The LPS isolated from the culture medium, here called secreted LPS from *P. gingivalis*, is somewhat different from the bacterium-bound LPS, as the LPS isolated from the culture medium showed a broad one peak (FIGS. 3C and 3E). Purified *P. pallens* LPS (FIG. 3F) and UltraPure *E. coli* LPS (FIG. 3G) (*E. coli* O55:B5, Invivogen Company, San Diego, Calif.) also contained multiple species.

Example 4—Develop Aptamers to Outer Membrane Vesicles and Lipopolysaccharides of *P. gingivalis* and *P. pallens*

Aptamers were developed following procedures described by Tuerk and Gold (Science. 1990 Aug. 3; 249 (4968):505-10. Systematic evolution of ligands by exponential enrichment: RNA ligands to bacteriophage T4 DNA polymerase), Martin et al. (Anal. Bioanal. Chem. 2014 July; 406(19):4637-47. doi: 10.1007/s00216-014-7883-8. Epub 2014 Jun. 1. Tunable stringency aptamer selection and gold nanoparticle assay for detection of cortisol), and Bharat N. Gawande at al. (Selection of DNA aptamers with two modified bases, PNAS Mar. 14, 2017 114 (11) 2898-2903; first published Mar. 6, 2017 https://doi.org/10.1073/pnas.1615475114).

Library and Primer Design and Synthesis: All primer and nucleotide oligos (shown below) were synthesized by Integrated DNA Technologies, Inc. Skokie, Ill.

```
LPS forward primer:
                                        (SEQ ID NO 450)
GAAGTGGCTTGTGCTCCTCG LPS reverse primer:
                                        (SEQ ID NO 451)
TTTACACTGCCCGTGCCAGG phosphorylated reverse primer,
                                        (SEQ ID NO 452)
5'-(phosphate)-TTTACACTGCCCGTGCCAGG-3'

Capture probe 17:
                                        (SEQ ID NO 453)
5'-biotin-TTTACACTGCCCGTGCC-3'

Capture probe 20:
                                        (SEQ ID NO 454)
5'-biotin-TTTACACTGCCCGTGCCAGG-3'

Capture probe 25:
                                        (SEQ ID NO 455)
5'-biotin-ACGAATTTACACTGCCCGTGCCAGG-3'

Capture probe 30:
                                        (SEQ ID NO 456)
5'-biotin-ACTCTAAGCATTTACACTGCCCGTGCCAGG-3' phosphorylated reverse primer 20:
                                        (SEQ ID NO 457)
5'-(phosphate)-TTTACACTGCCCGTGCCAGG-3' phosphorylated reverse primer 25:
                                        (SEQ ID NO 458)
5'-(phosphate)-ACGAATTTACACTGCCCGTGCCAGG-3' phosphorylated reverse primer 30:
                                        (SEQ ID NO 459)
5'-(phosphate)-ACTCTAAGCATTTACACTGCCCGTGCCAGG-3' ssDNA library with 40 random nucleotides
                                        (SEQ ID NO 460)
GAAGTGGCTTGTGCTCCTCG-N40-CCTGGCACGGGCAGTG TAAA.

ssDNA library with 60 random nucleotides:
                                        (SEQ ID NO 461)
GAAGTGGCTTGTGCTCCTCG-N60-CCTGGCACGGGCAGTG TAAA-3'.
```

Selection of aptamers from random oligonucleotide libraries: All procedures were carried out at room temperature. Commonly used chemicals and reagents were purchased from Sigma, St. Louis Mo.

1. Hybridization of capture probe and ssDNA library: The ssDNA library was mixed with the capture probe 17 mer in a mole ratio of 1:1.5 (25 nmol ssDNA library: 35.5 nmol capture probe) in binding buffer (30 mM Tris at pH 7.5 with 150 mM NaCl, 1 mM MgCl$_2$, 1 mM CaCl$_2$)), denatured under 95° C. for 5 min and then cooled down slowly to room temperature (RT).
2. Bead preparation: Beads (high-performance streptavidin magnetic Sepharose, which has a binding capacity for biotin>300 nmol/mL-Sigma, St. Louis Mo.) were soaked and washed in binding buffer three times, 5 min each.

3. Immobilization of the ssDNA library to the beads: The hybridized ssDNA library and capture probe were transferred to the beads of 50 nmol binding capacity (120 µl) (in 620 µL of binding buffer for 60 min. The ratio of the beads to the ssDNA library was 1:2 (molar ratio of ssDNA library:binding capacity of the beads=1:2).
4. Removed the supernatant, and then washed 5 times with 1 mL of binding buffer (30 mM Tris at pH 7.5 with 150 mM NaCl, 1 mM $MgCl_2$, 1 mM $CaCl_2$)).
5. LPS was dissolved in 1× binding buffer.
6. 1:10 (library:LPS) LPS was added into the aptamer library and then incubated in binding buffer (300 µL) for 30-60 min with gentle shaking.
7. Magnetic Sepharose beads were removed using a magnetic plate.
8. The remaining solution was used as a template for PCR amplification using Taq polymerase system (2×PCR master mix, 1st Base) for DNA aptamer [95° C. 5 min, 10 to 15 cycles (94° C. 30 s, 55° C. 30 s, 72° C. 30 s)] using LPS forward and phosphorylated reverse primers.
9. Lambda exonuclease digestion was performed to generate single stranded DNA using 10 units of enzyme lambda exonuclease following manufacturer's instruction (ThermoFisher).
10. The single-stranded DNA aptamer pool was used for the next round of DNA SELEX.

Figure 4A:
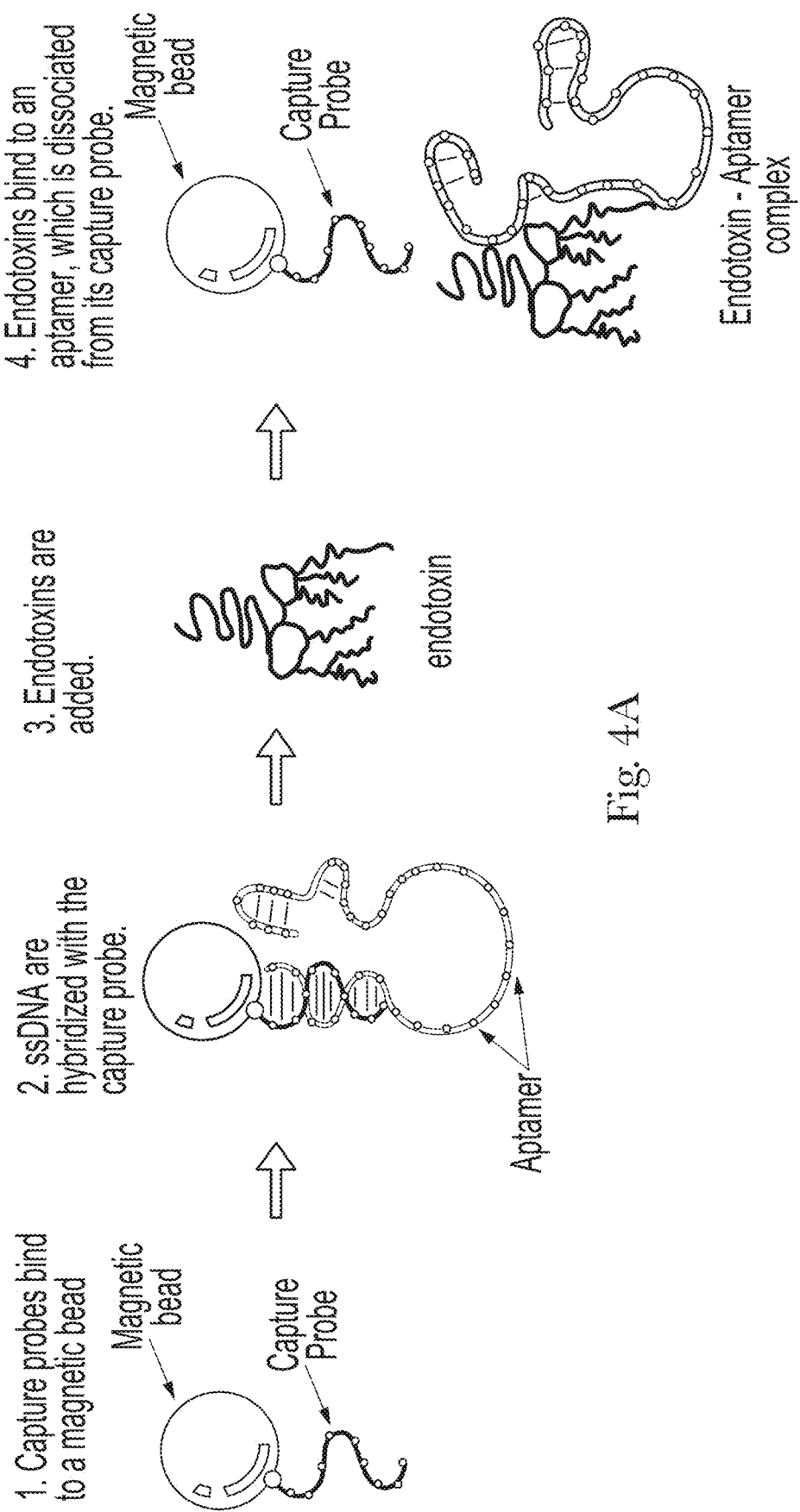
FIG. 4A shows ssDNA hybridized to a capture probe through base pair complementary interactions. ssDNA undergoes conformational changes when a target molecule is bound, which unwinds the base pairings between the capture probe and the ssDNA, leading to dissociation of the ssDNA from the capture probe.

Selection of ssDNA that undergoes conformational change upon binding to target molecules: ssDNA was hybridized to the capture probe through base pair complementary interactions. The strength of the interaction is proportional to the number of base pairs. ssDNA undergoes conformational changes when a target molecule is bound, which unwinds the base pairings between the capture probe and the ssDNA, leading to dissociation of the ssDNA from the capture probe as outlined in FIG. 4A.

Figure 4B:
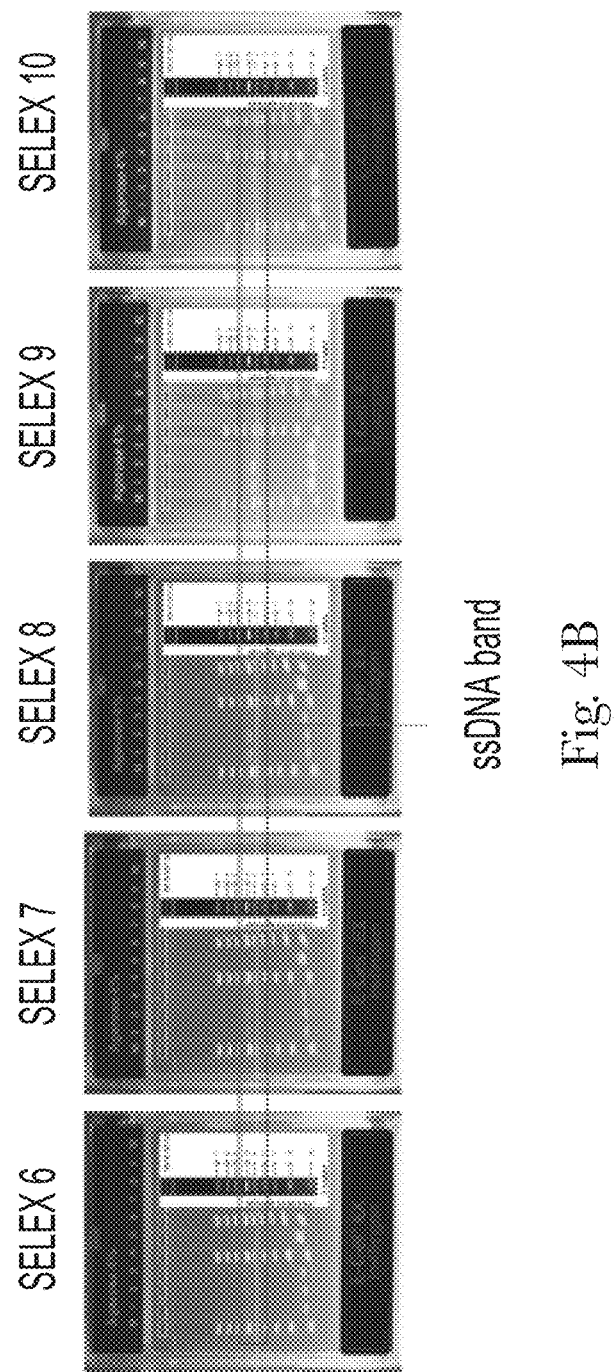
FIG. 4B shows the ssDNA band was gradually enriched. In each round of SELEX, the selected ssDNA was amplified using PCR procedures, and part of the PCR products were visualized on an agarose gel.

The ssDNA was first selected with the target molecule alone, called positive selection. As shown in FIG. 4B, the ssDNA band was gradually enriched. In each round of SELEX, the selected ssDNA was amplified using PCR procedures, and part of the PCR products were visualized on an agarose gel. The band of ssDNA was faint at SELEX 6, but gradually increased over four rounds of SELEX, and by SELEX 10 the bands became clearly visible.

Figure 4C:
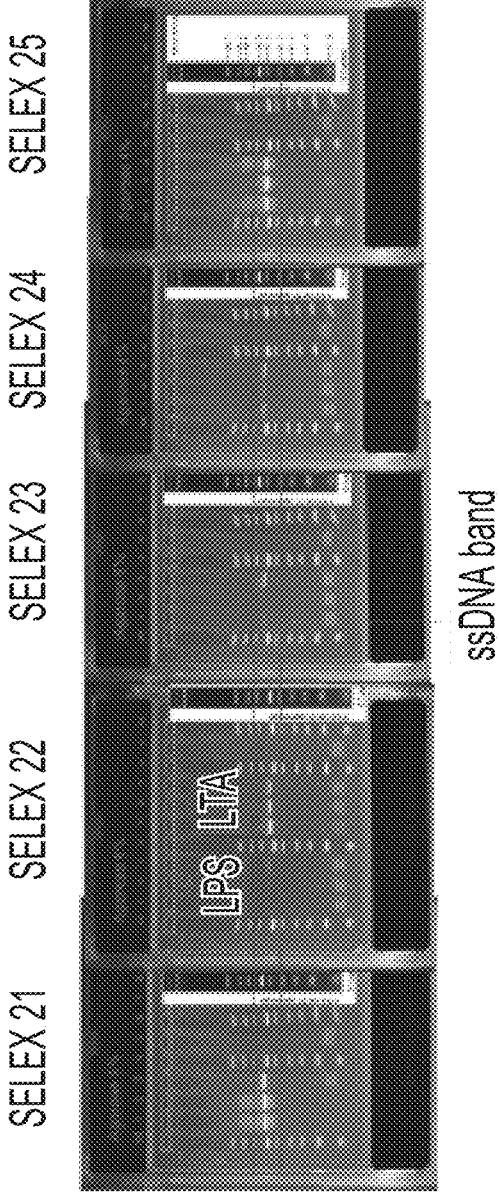
FIG. 4C shows negative selection was carried out using bacterial materials from different species.
Figure 5A:
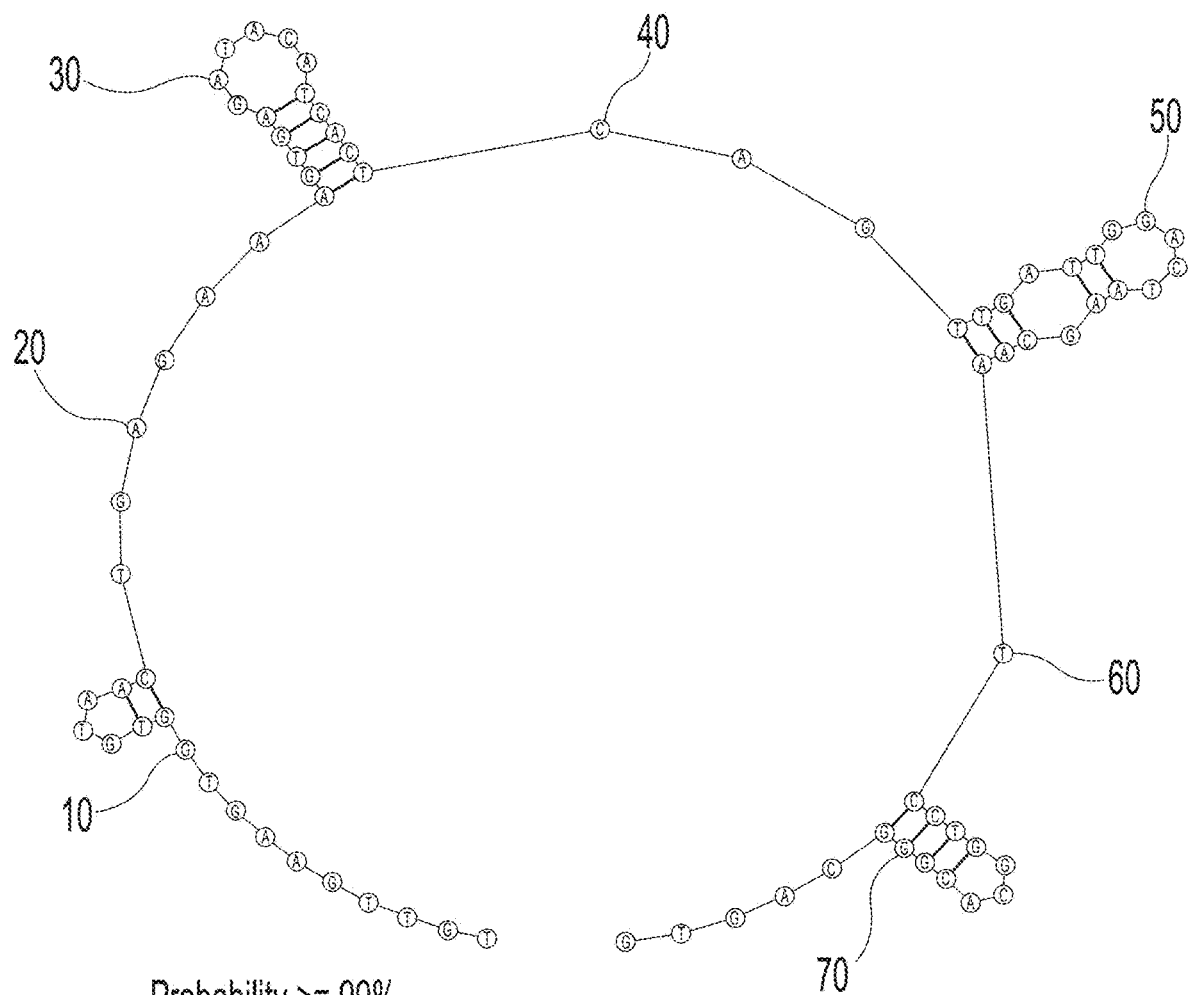
FIG. 5A shows predicted aptamer secondary structure for SEQ ID NO 1.
Figure 5B:
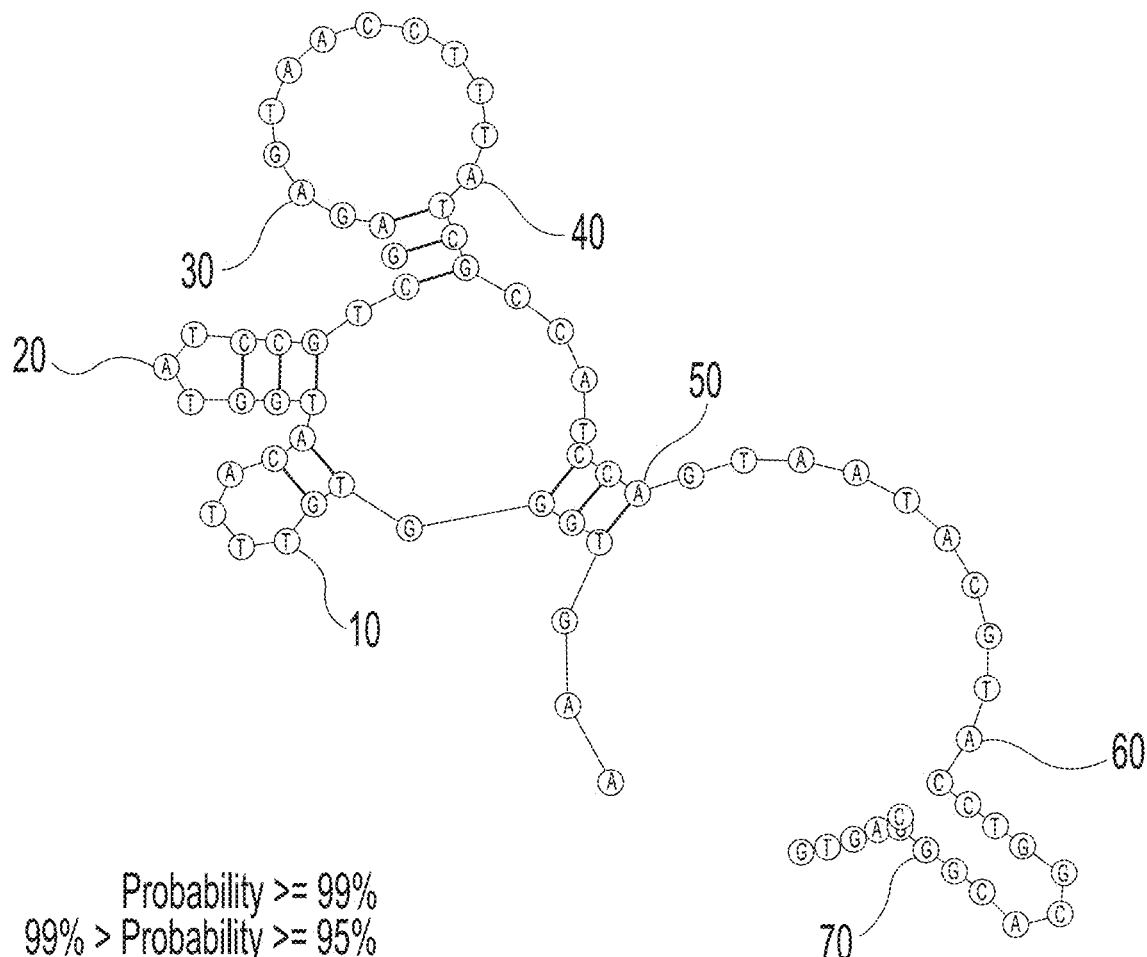
FIG. 5B shows predicted aptamer secondary structure for SEQ ID NO 2.
Figure 5C:
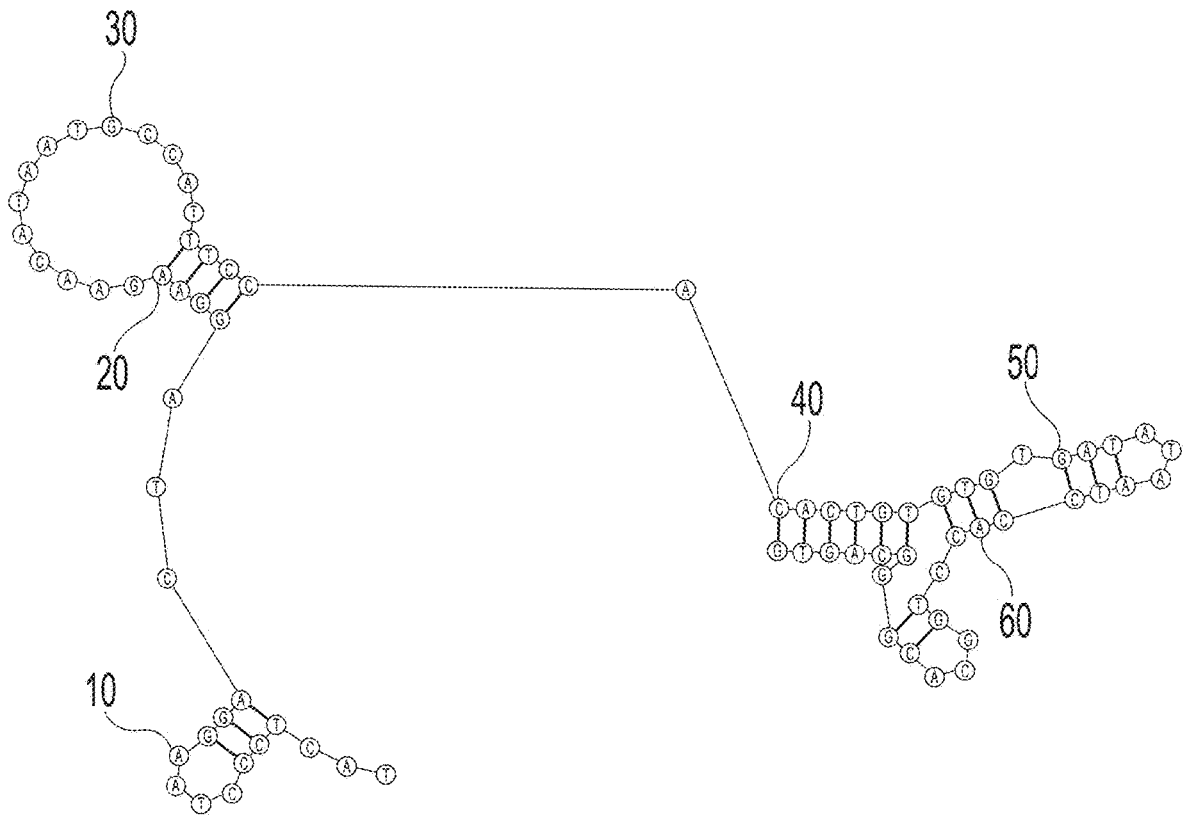
FIG. 5C shows predicted aptamer secondary structure for SEQ ID NO 127.
Figure 5D:
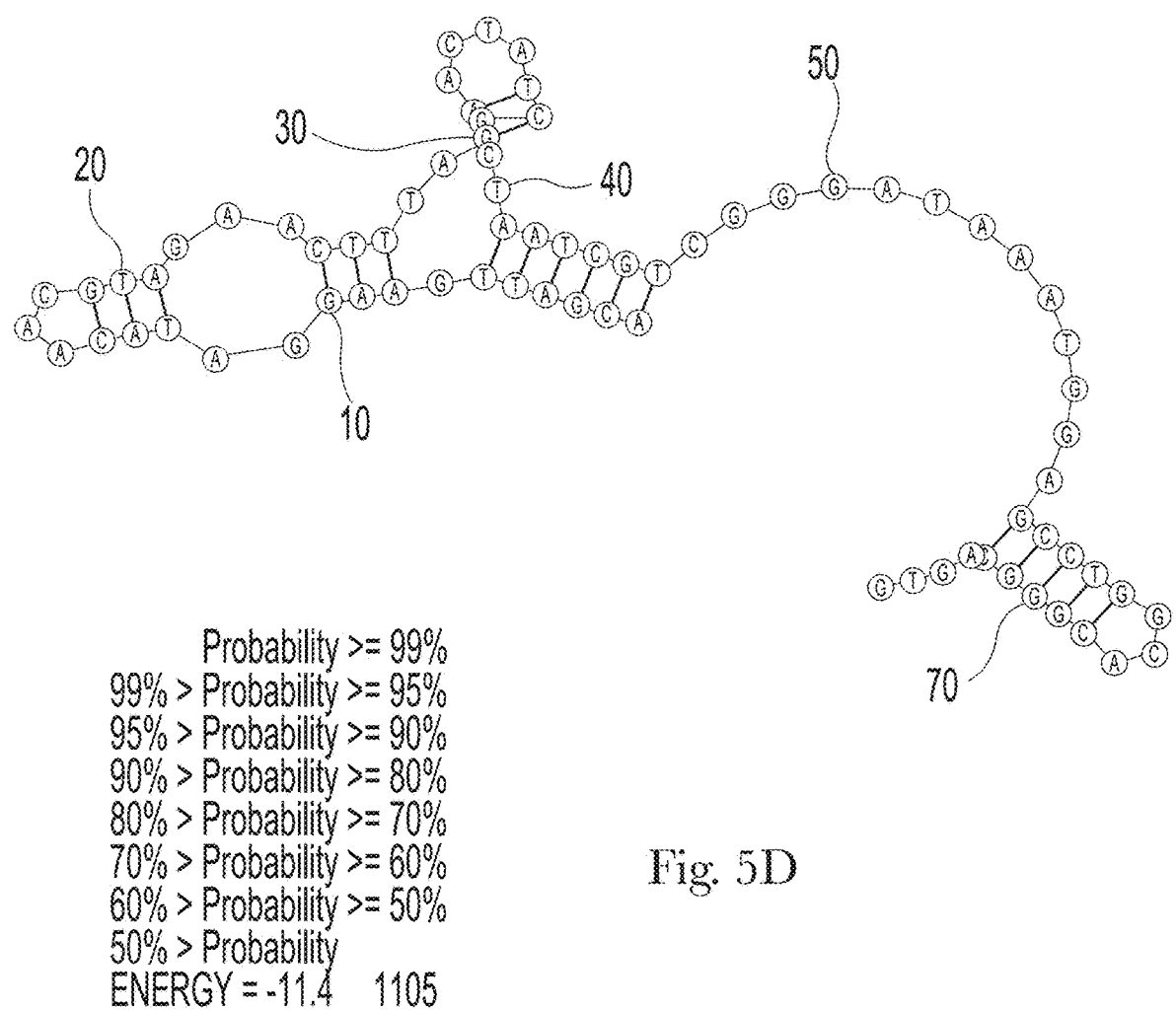
FIG. 5D shows predicted aptamer secondary structure for SEQ ID NO 131.
Figure 5E:
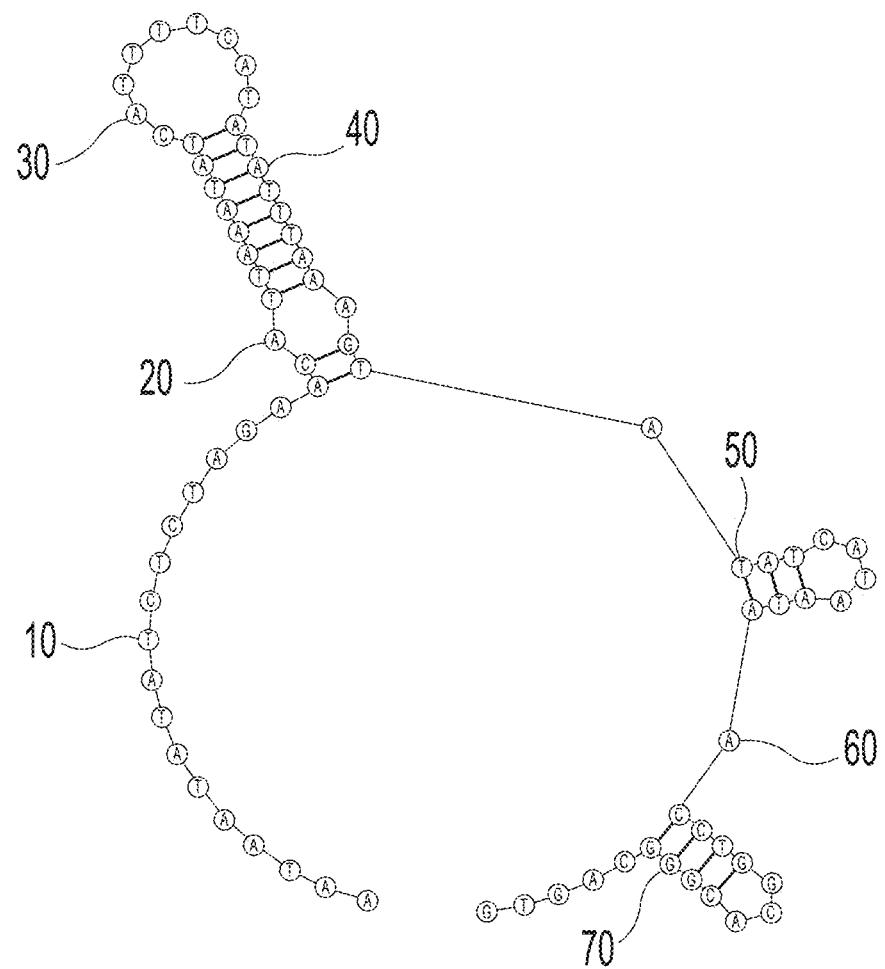
FIG. 5E shows predicted aptamer secondary structure for SEQ ID NO 32.
Figure 5F:
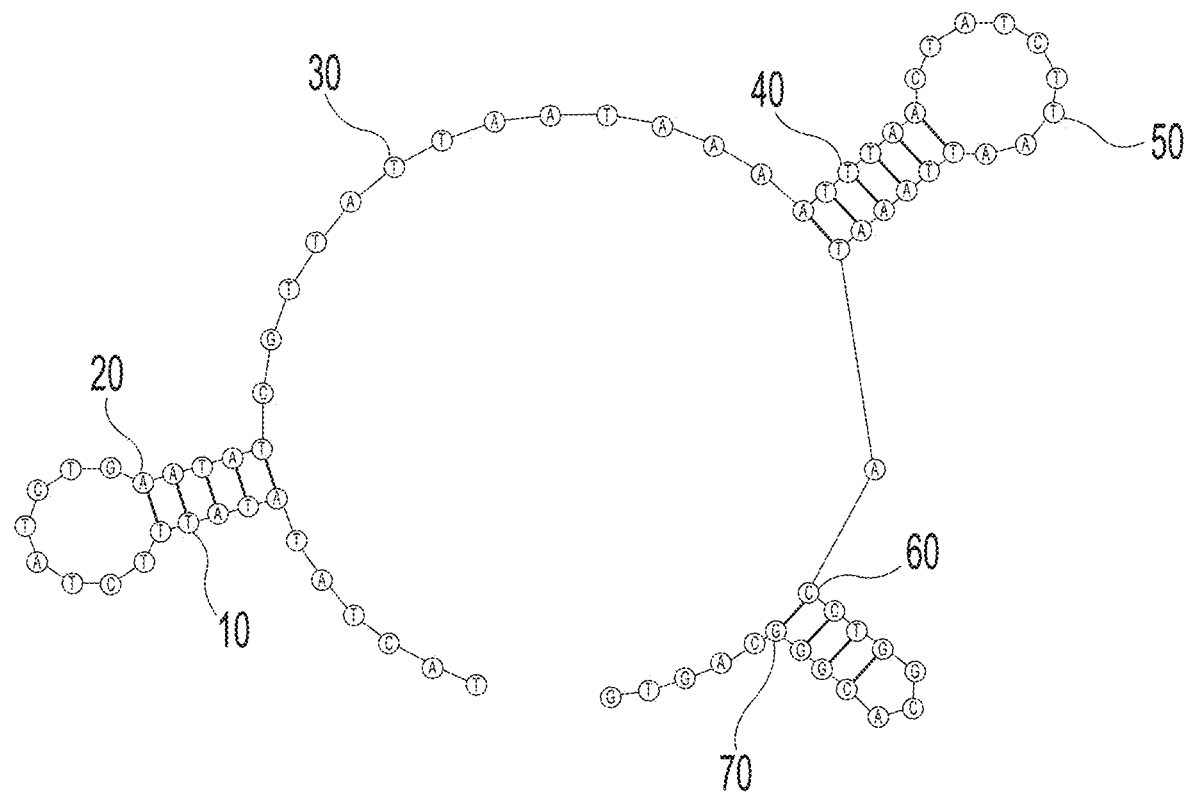
FIG. 5F shows predicted aptamer secondary structure for SEQ ID NO 33.
Figure 5G:
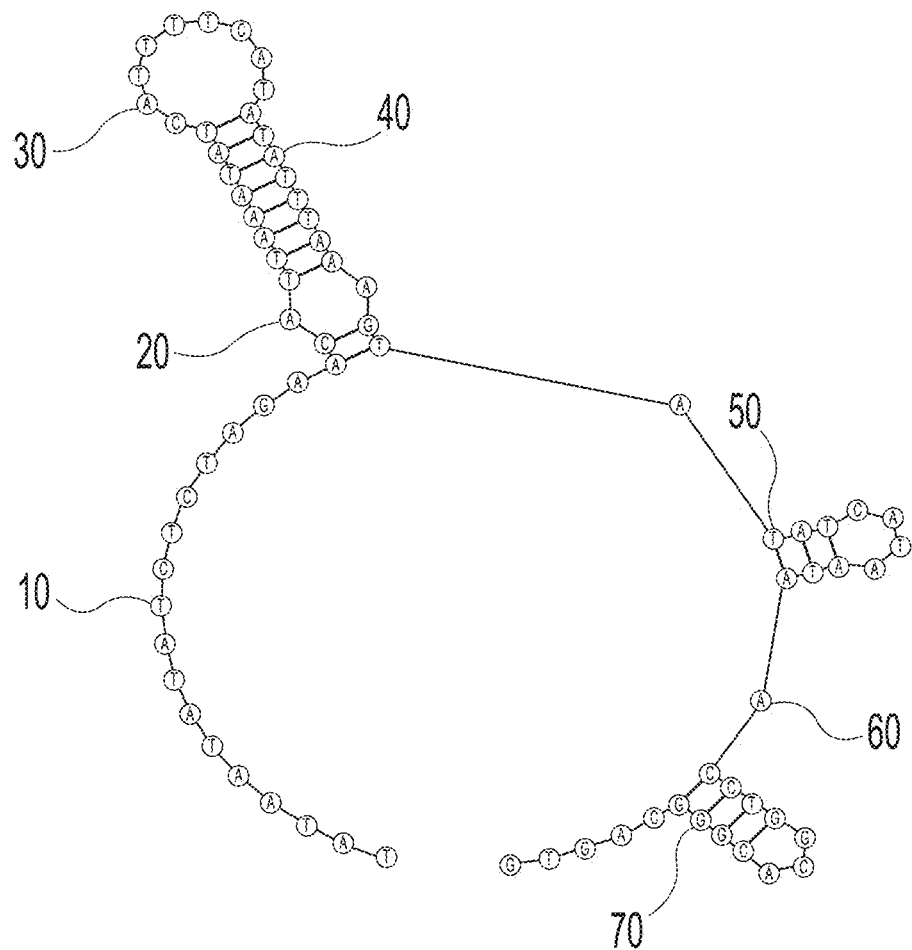
FIG. 5G shows predicted aptamer secondary structure for SEQ ID NO 55.
Figure 5H:
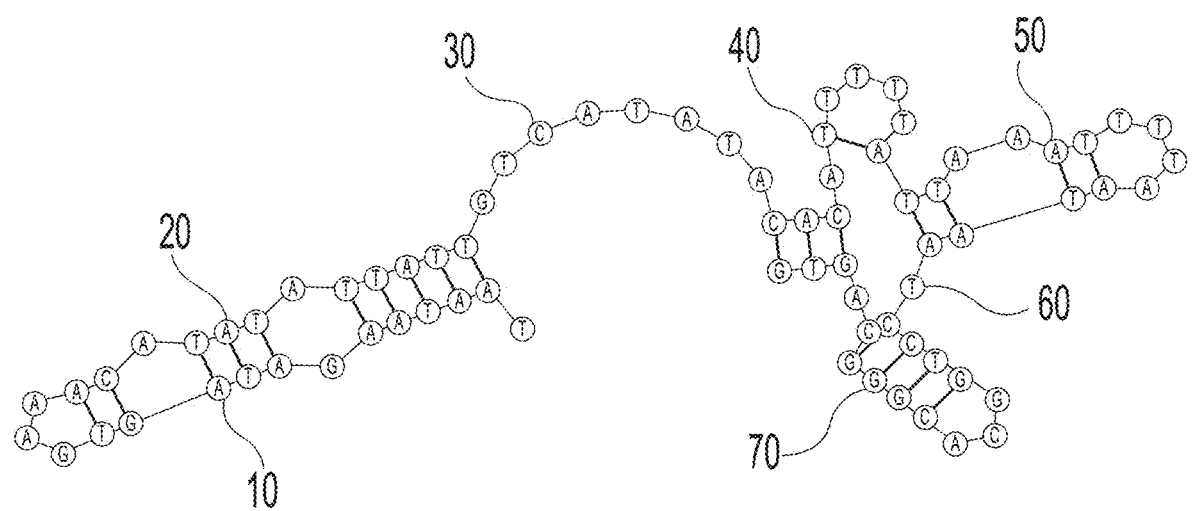
FIG. 5H shows predicted aptamer secondary structure for SEQ ID NO 34.
Figure 5I:
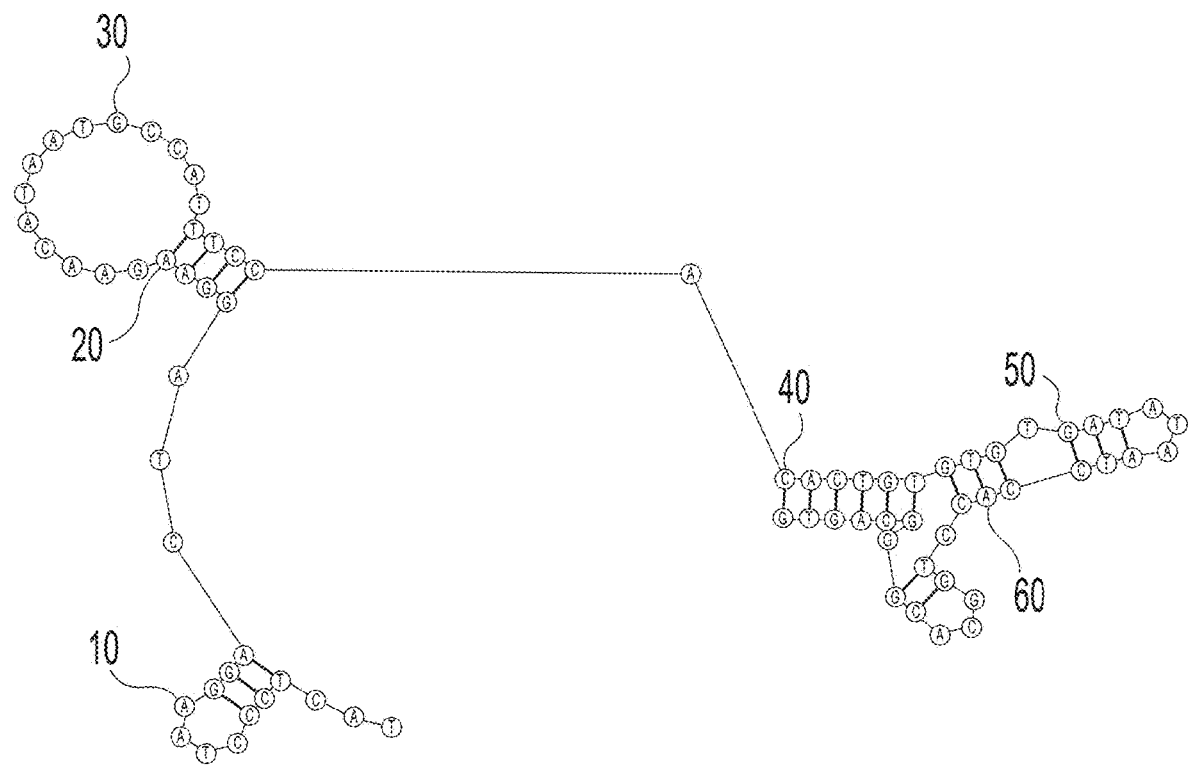
FIG. 5I shows predicted aptamer secondary structure for SEQ ID NO 221.
Figure 5J:
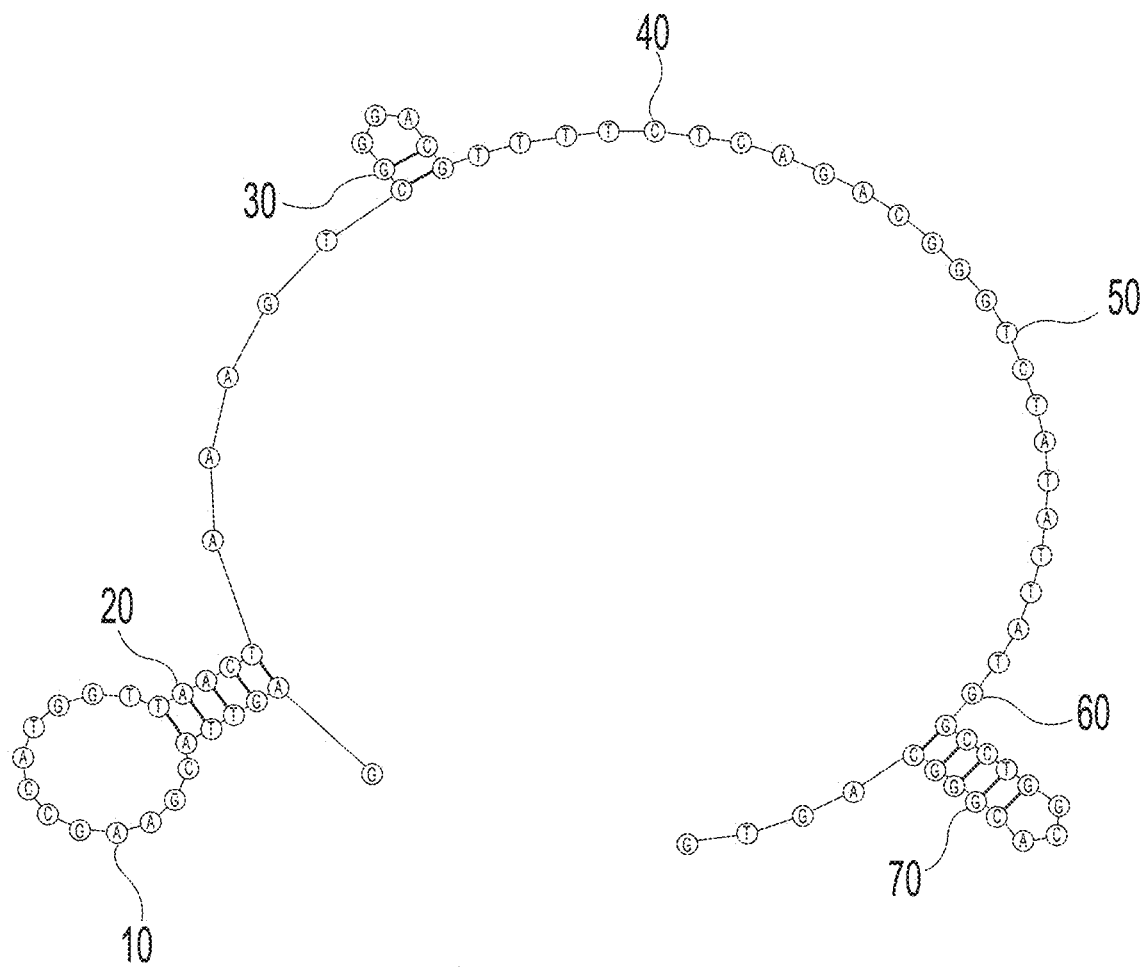
FIG. 5J shows predicted aptamer secondary structure for SEQ ID NO 76.

Negative selection was carried out using bacterial materials from different species. As shown in FIG. 4C, the ssDNA bands were strong. At SELEX 22, Lipoteichoic acids (LTA) from *B. subtilis*, and LPS from different bacterial species were first reacted with the pool of ssDNA. If they are reacted with LTA LPS, ssDNA would be dissociated from the capture probe which is anchored to the magnetic beads through biotin-Streptavidin binding. The capture probe can bind to ssDNA through nucleotide complementation. The magnetic beads, which bind to the ssDNA through a capture probe, were then washed with binding buffers to remove ssDNA that might have high affinities to both lipopolysaccharides from different bacterial species and lipoteichoic acids. Then the remaining pool of ssDNA was incubated with 1 to 100 ng of specific lipopolysaccharides again. At SELEX 22 in FIG. 4C, the ssDNA bands were strong, where the LPS bands were relatively weak. These results suggest that many ssDNA binds to both LPS and LTA. After four rounds of negative selections, the LPS specific ssDNA were enriched at SELEX 25.

A total of 36 rounds of SELEX were carried out (Table 2). At SELEX 32, OMV were used as the targets to react with the ssDNA. ssDNA were incubated with *P. gingivalis* and *P. pallens* OMV. If the ssDNA have a high affinity to the OMV, they would be dissociated from the capture probe which is anchored to the magnetic beads through biotin-Streptavidin binding. Cross-reactive LPS aptamers pulled out from SELEX 17 and 18 were used as a source for aptamers that might bind to LPS from *P. gingivalis, P. pallens* and *E. coli*. For example, ssDNA from *E. coli* LPS selection was incubated with *P. gingivalis* LPS. If ssDNA from *E. coli* LPS selection bind to *P. gingivalis* LPS, they will be dissociated from the capture probe which is anchored to the magnetic beads through biotin-Streptavidin binding. The Pool of SELEX 17 and 18 cross-reactive aptamers were further selected through four more rounds of SELEX to obtain aptamers that bind to endotoxins of *P. gingivalis, P. pallens* and *E. coli*.

TABLE 2

SELEX conditions and parameters.

| | LPS: Target | | | CAPTURE PROBE | | SELEX CONDITIONS | |
| --- | --- | --- | --- | --- | --- | --- | --- |
| Round | Target Volume (µl) | [Target] ng/µL | Amount ng | Name | Amount Probe nmol | Time | Negative Selection | PCR Cycles |
| 1 | 50 | 100 | 5,000.00 | CAP 17 Biotin | 37,500.00 | 60 | — | 20 |
| 2 | 50 | 100 | 5,000.00 | CAP 17 Biotin | 37,500.00 | 60 | — | 20 |
| 3 | 37.21 | 10 | 372.1 | CAP 17 Biotin | 1.12 | 60 | — | 20 |
| 4 | 38.02 | 10 | 380.19 | CAP 17 Biotin | 1.14 | 60 | — | 20 |
| 5 | 34.78 | 10 | 347.83 | CAP 17 Biotin | 1.04 | 60 | — | 15 |
| 6 | 20 | 10 | 200 | CAP 17 Biotin | 1.09 | 60 | — | 10 |
| 7 | 10 | 10 | 100 | CAP 17 Biotin | 1.04 | 60 | — | 10 |
| 8 | 50 | 1 | 50 | CAP 17 Biotin | 1.04 | 60 | — | 10 |
| 9 | 25 | 1 | 25 | CAP 17 Biotin | 1.07 | 60 | — | 10 |
| 10 | 25 | 1 | 25 | CAP 17 Biotin | 1.02 | 60 | — | 10 |

TABLE 2-continued

SELEX conditions and parameters.

| | LPS: Target | | | CAPTURE PROBE | | SELEX CONDITIONS | | |
|---|---|---|---|---|---|---|---|---|
| Round | Target Volume (μl) | [Target] ng/μL | Amount ng | Name | Amount Probe nmol | Time | Negative Selection | PCR Cycles |
| 11 | 25 | 1 | 25 | CAP 17 Biotin | 1.02 | 60 | — | 10 |
| 12 | 25 | 1 | 25 | CAP 17 Biotin | 1.03 | 60 | — | 10 |
| 13 | 25 | 10 | 250 | CAP 17 Biotin | 1.04 | 60 | — | 10 |
| 14 | 25 | 10 | 250 | CAP 17 Biotin | 1.09 | 60 | — | 10 |
| 15 | 25 | 10 | 250 | CAP 17 Biotin | 1.12 | 60 | — | 10 |
| 16 | 25 | 10 | 250 | CAP 25 Biotin | 1.12 | 60 | — | 10 |
| 17 | 25 | 10 | 250 | CAP 25 Biotin | 1.02 | 60 | Cross-reactive LPS | 10 |
| 18 | 25 | 10 | 250 | CAP 25 Biotin | 1.07 | 60 | Cross-reactive LPS | 10 |
| 19 | 25 | 10 | 250 | CAP 25 Biotin | 1.04 | 60 | LTA Mix | 10 |
| 20 | 25 | 10 | 250 | CAP 25 Biotin | 1.02 | 60 | LTA Mix | 10 |
| 21 | 25 | 10 | 250 | CAP 25 Biotin | 1.07 | 60 | — | 10 |
| 22 | 25 | 10 | 250 | CAP 25 Biotin | 1.07 | 60 | LPS/LTA Mix | 10 |
| 23 | 25 | 10 | 250 | CAP 25 Biotin | 1.02 | 60 | — | 10 |
| 24 | 25 | 10 | 250 | CAP 25 Biotin | 1.04 | 60 | — | 10 |
| 25 | 25 | 10 | 250 | CAP 25 Biotin | 1.04 | 60 | — | 10 |
| 26 | 25 | 10 | 250 | CAP 30 Biotin | 1.09 | 60 | — | 10 |
| 27 | 25 | 10 | 250 | CAP 30 Biotin | 1.02 | 60 | — | 10 |
| 28 | 25 | 10 | 250 | CAP 30 Biotin | 1.02 | 60 | LPS/LTA Mix | 10 |
| 29 | 25 | 10 | 250 | CAP 30 Biotin | 1.04 | 60 | — | 10 |
| 30 | 25 | 10 | 250 | CAP 30 Biotin | 1.02 | 60 | OMV Fractions | 10 |
| 31 | 25 | 10 | 250 | CAP 30 Biotin | 1.04 | 60 | — | 10 |
| 32 | 25 | 10 (OMV) | 250 | CAP 30 Biotin | 1.02 | 60 | — | 10 |
| 33 | 25 | 10 | 250 | | 1.02 | 60 | — | 10 |
| 34 | 25 | 10 | 250 | CAP 30 Biotin | 1.04 | 60 | — | 10 |
| 35 | 25 | 10 | 250 | CAP 30 Biotin | 1.04 | 60 | — | 10 |
| 36 | 100 | 10 | 1,000.00 | CAP 25 Biotin | 0.97 | 60 | — | 15 |

Example 5—Sequence and Cluster Aptamers of Outer Membrane Vesicles and Lipopolysaccharides of *P. gingivalis* and *P. pallens*

Aptamer samples were sent to BGI sequence service (Cambridge, Mass.). Sequences were analyzed internally. Pair end reads sequences were merged with FLASH (v1.2.11; FLASH: Fast length adjustment of short reads to improve genome assemblies. T. Magoc and S. Salzberg. Bioinformatics 27:21 (2011), 2957-63). Merged sequences were filtered to remove sequences with any base of a quality score less than 30 using FASTX_Toolkit (v0.0.13; FASTX_Toolkit: http://hannonlab.cshl.edu/fastx_toolkit/index.html), followed up by removing any sequences longer than 125 bases or shorter than 85 bases using Cutadapt (v 1.16; Marcel Martin. Cutadapt removes adapter sequences from high-throughput sequencing reads. EMBnet. Journal, 17(1):10-12, May 2011). Reverse complement of the filtered sequence was generated using FASTX Toolkit. A customized script was used to identify the sequence with both forward primer "GTGCTCCTCG" (SEQ ID NO 462) and reverse primer "CACGGGCAGT" (SEQ ID NO 463) in the 5' to 3' direction and remove any adapter sequences before or after these two primers. These trimmed sequences were counted and clustered (with Hamming Edit Distance<=15) with FASTAptamer to identify the enriched aptamer. Alignment was generated using MUSCLE (v3.8.31; Alam K K, Chang J L, Burke D H. FASTAptamer: A Bioinformatic Toolkit for High-throughput Sequence Analysis of Combinatorial Selections. Mol. Ther. Nucleic Acids. 2015 Mar. 3; 4:e230. doi: 10.1038/mtna.2015.4; Edgar, R. C. MUSCLE: multiple sequence alignment with high accuracy and high throughput. Nucleic Acids Res 32(5), 1792-97).

Eighteen aptamer samples were sequenced, and a total of 256662255 reads were generated (Table 3). Aptamers with a minimum of five reads in a sample were analyzed and clustered. Each cluster shares 85% sequence identify with the cluster center sequences, which are listed in Tables 4, 5, 6, 7, 8 and 9.

TABLE 3

DNA reads in aptamer samples.

| LPS Target | REV Primer Length | filename | Number of reads |
|---|---|---|---|
| *E. coli* K12 commercial LPS | 20 | O1.q30.m85M125.fastq | 20005629 |
| *P. gingivalis* commercial LPS | 20 | O2.q30.m85M125.fastq | 12536966 |
| *P. pallens* commercial LPS | 20 | O3.q30.m85M125.fastq | 19539513 |
| *E. coli* K12 commercial LPS | 25 | O4.q30.m85M125.fastq | 22019078 |
| *P. gingivalis* commercial LPS | 25 | O5.q30.m85M125.fastq | 16893936 |
| *P. pallens* commercial LPS | 25 | O6.q30.m85M125.fastq | 14700108 |
| *E. coli* K12 commercial LPS | 30 | O7.q30.m85M125.fastq | 14136757 |
| *P. gingivalis* commercial LPS | 30 | O8.q30.m85M125.fastq | 20400990 |
| *P. pallens* commercial LPS | 30 | O9.q30.m85M125.fastq | 14107302 |
| *E. coli* K12 commercial LPS | 30 | O10.q30.m85M125.fastq | 10358693 |
| *P. gingivalis* LPS of Cellufine ETclean isolate | 30 | O11.q30.m85M125.fastq | 14427337 |
| *P. pallens* LPS of Cellufine ETclean isolate | 30 | O12.q30.m85M125.fastq | 14486056 |
| *P. gingivalis*: OMV Cellufine ETclean/TFF | 30 | O13.q30.m85M125.fastq | 12606784 |
| *P. pallens*: OMV Cellufine ETclean/TFF | 30 | O14.q30.m85M125.fastq | 13788734 |
| *P. gingivalis*: OMV Total | 30 | O15.q30.m85M125.fastq | 5321713 |
| LPS Cross reactive (*E. coli*, *P. gingivalis*, *P. pallens*) | 30 | O16.q30.m85M125.fastq | 17577128 |
| LPS Cross reactive (*E. coli*, *P. gingivalis*, *P. pallens*) | 30 | O17.q30.m85M125.fastq | 7046197 |
| LPS Cross reactive (*E. coli*, *P. gingivalis*, *P. pallens*) | 30 | O18.q30.m85M125.fastq | 6709334 |
| | | total | 256662255 |

Cellufine ™ ETclean-L, JNC Corporation, Japan.

In Table 4, the 250 aptamer sequences are selected from 250 clusters. Each sequence represents the cluster center sequence. The cluster center sequence is derived from the aptamer which has the highest copy number in the particular cluster in a sample. For example, the sequence with SEQ ID NO 32 is derived from a cluster with 7 unique aptamers that were sequenced in the same sample. The sequence with SEQ ID NO 32 is the cluster center sequence, accounting for 69.24 reads in a million of sequences. If the sequences of any aptamer share 85% nucleotide identity with the cluster center sequences, it will belong to the same cluster.

Table 4 lists the aptamers of 1 to 250 that target the outer membrane vesicles and LPS. As discussed in EXAMPLE 2, almost all secreted endotoxin activities are associated with outer membrane vesicles in *P. pallens*. It is advantageous to detect outer membrane vesicle directly. First, the aptamers that target *P. pallens* endotoxins are selected. And then, outer membrane vesicles are applied to the mixture of aptamers selected against *P. pallens* endotoxins. The aptamers are enriched to against outer membrane vesicles. So this class of aptamers target endotoxins only existing on outer membrane surfaces.

TABLE 4 lists aptamers of 1 to 250, that target endotoxins and outer membrane vesicles of *E. coli*, *P. gingivalis* and *P. pallens*.

| SEQ ID NO | Sequence |
|---|---|
| 1 | TGTTGAAGTGGTGTAACTGAGAAAGTGAGATACATCACTCAGTTGATTGGACTAAGCAATCCTGGCACGGGCAGTG |
| 2 | AAGTGGGTGTTTACATGGTATCCGTCGAGAGTAACCTTTATCGCCATCCAGTAATACGTACCTGGCACGGGCAGTG |
| 3 | TGACGTGAAGTGGCTATGCTATTCTCTAGTTGAAGGAGGATTGTTACCTGGCACGGGCAGTG |
| 4 | AAGTGGAAAGGATACAGTTTGCACATCTAGGGGTAACCGAGAGTTACTTAATGTCACCTGGCACGGGCAGTG |
| 5 | TGAAGTGGCTTACACTCACATCCTCGTTCAACACGTGACCTTAGTATCTTATTTGATCAACCTGGCACGGGCAGTG |
| 6 | AAGTGGCGATTAACTGCAATGTTTGTGTTTACCTGGTTTTAGGGTTTGATTTCATTCTCACCTGGCACGGGCAGTG |
| 7 | AAGTGGCTATGGATGTAGTTCGCTTTACCTCTGTCTATCTCGTTGGATGGTTAGTAATATCCTGGCACGGGCAGTG |
| 8 | TGGACAGTTTATAACCAGGACTTGGATCTGTTGTTTCTACACCTTTCATGCTCCACTTCTCCTGGCACGGGCAGTG |
| 9 | TGGGAAGTGGCTTCTTTTTCACTCGGCAACAATAGCCTAGGAGATATGTATCCAAGGAAACCTGGCACGGGCAGTG |
| 10 | TTAAATAATATAACCACATTTATTTCTACTTCTATTATTATACTGTAGTATTATTCAAATCCTGGCACGGGCAGTG |
| 11 | ATCTCTAAGAATCTCAGTGCATTATGTGATGCATTGAGAATGATTAGAGATGTTATGGAGCCTGGCACGGGCAGTG |
| 12 | GAGACAGACACGATAAAATGACGTAATTTAGACGATATAATCTGTAATTGAATATTGCCTGGCACGGGCAGTG |
| 13 | TGGTTGATAAGATCACATTCAATGAGGGTGTAGAAGAGGAGATCAAGACCTTGAATGGAGCCTGGCACGGGCAGTG |
| 14 | ACGTCATATCACTTTACTGTGATTATGTAACGTCAGAGGAATACAATAGCCCTTAATGCACCTGGCACGGGCAGTG |
| 15 | TGTATACACGTACAAGACAGTTCTGGGCTAAGTATTGGTACTTACCCATTATCTTATGCACCTGGCACGGGCAGTG |
| 16 | GGTTGCACAAATATAGACAGCTTCAACGATTTCATTCTCTGTGAGAGATGTAATGGAGCCTGGCACGGGCAGTG |
| 17 | ACCCTTGTATGTATTGATTTACCGATATCGATACTAGGATAGTGCACATGGAAGATGGAGCCTGGCACGGGCAGTG |
| 18 | TCTTACATACTTATACACCTGGATAAACACGGGAAGTTATTCGTAGTATGAGGAATGGAGCCTGGCACGGGCAGTG |
| 19 | ACACAAAATCCACGCTAAGTTTCAACAAATCGAATTAGTTACCAATAGACTATTTCTTCGCCTGGCACGGGCAGTG |
| 20 | TGAGTAAAGACTAACTTCCAGGATGTATGTGATGCATAGTACACTAGGCAACAAAATCCGCCTGGCACGGGCAGTG |
| 21 | CCATTATGTTGGTCTGGATATTTAACATTGGGAGGAGGATAGACACGGTAAAGGATCACACCTGGCACGGGCAGTG |
| 22 | GATGTTCGTCGAAGATCGAACATCATTTGACACGATATATTATATCGGAGGTAAATGGAGCCTGGCACGGGCAGTG |
| 23 | AAGATATTTACCTAAGCACATAGACACGTCATTCTGTCCTTGATGAACAATTTGTTGCATCCTGGCACGGGCAGTG |
| 24 | AGATGCACTAGATCAGTTCTAGATTTATGTCGGCTATGACTAATGTAAGGTGAATGACATCCTGGCACGGGCAGTG |
| 25 | CTGATCTTAAGTAGGTAGGTACAAGTACACGCAGATCGATTGTTCTGAATTATAATTTCGCCTGGCACGGGCAGTG |

TABLE 4-continued lists aptamers of 1 to 250, that target endotoxins and outer membrane vesicles of *E. coli*, *P. gingivalis* and *P. pallens*.

| SEQ ID NO | Sequence |
|---|---|
| 26 | AGCATGAGACGATTCCAATGTTCAACGTATTATACGTTGCGGCATTTTTCATT ATTGGAGCCTGGCACGGGCAGTG |
| 27 | TCCTAATTATGGCAATAGGTAAGTTCATCATTACCGATGTCAATAATTTTAAT GATGGAGCCTGGCACGGGCAGTG |
| 28 | GTGGTCCGATGAATGAAATCGTATACCACGATTGAAATCATTTAGCACAGAG ACAATTCACCTGGCACGGGCAGTG |
| 29 | GAAACACAATAACGTCAGATTTGAGAGGTAATAGTGGGGATGGTATTCAGA TGGAGCCTGGCACGGGCAGTG |
| 30 | TACAAGTACACGAGAATTCTATGTAGAGACTCATACAAGTATTTGTTGACAC TTTGACATCCTGGCACGGGCAGTG |
| 31 | TGTGCACAAGATCACCAAAATTTACAAAATTAGACGTTCTTACGTGTAAATG TATTGGAGCCTGGCACGGGCAGTG |
| 32 | AATAATATATCTCTAGAACATTAAATATCATTTTCATATATTTAAAGTATATC ATAATAACCTGGCACGGGCAGTG |
| 33 | TACTATATATTTCTATCTGAATATCGTTATTAATAAAATTTAACTATCTTAATT AAATACCTGGCACGGGCAGTG |
| 34 | TAATAAGATAGTGAAACATATATTATTGTCATATACACATTTTTATTAAATTT TAATAATCCTGGCACGGGCAGTG |
| 35 | AAATAATAAGGATATTTAATAACAATCTTTATTTAAGTAGATATTAATGTCTT AAATAATCCTGGCACGGGCAGTG |
| 36 | TATATCTTCTCAATATAGTTATCTTTATTTCACTATTATTGAATATATTTCATA TATAACCTGGCACGGGCAGTG |
| 37 | AATATTTATCTATTAACCAATATATAATTGTAGATTCTAGATACTAATTATAT CTAATCCTGGCACGGGCAGTG |
| 38 | TAATTTTAAACTAATTATAATGAATTAACATAAATTTCAATTAAAATGATTTT AATAATTCCTGGCACGGGCAGTG |
| 39 | AAATCTAATTTAATTGAAATAGTATCTATCTATAATAGTTAATTAGATATTTC AATATTTCCTGGCACGGGCAGTG |
| 40 | TTGAATATTTCATAGAATTATTTGAAATTATCCTTAATAATTCTAAATTTAAA TTAGATTCCTGGCACGGGCAGTG |
| 41 | TATCATAATAGAAACAAATAAATCAGTCAAATATTATATTTTCTTCTAAGTAT ATTTATTCCTGGCACGGGCAGTG |
| 42 | ATAATAACATTCTGATAACATTATATCTTTAATAATGATTACATTCATAAATT TCTATATCCTGGCACGGGCAGTG |
| 43 | AATTATCAATATAATCTTTTTTTATTCTAATTCAATTAATAAATAAAGCTAAT AATTATCCTGGCACGGGCAGTG |
| 44 | TATGTGTGTCTAACACTGTGCGCATTCAGCCCGACAAGTTCCCCTCATTTGGA TTTCATTCCTGGCACGGGCAGTG |
| 45 | TATTTTATCTCATAACAAAATATTATGTATATCACTTTACAATAAATAATATA CTCTATTCCTGGCACGGGCAGTG |
| 46 | TTAAATAAAGATTAATAATTATGAAATTTACTGTTCTATTTTAACTATAATTT TATTTCACCTGGCACGGGCAGTG |
| 47 | ATAAAGTATATAATTAATAATGATAACTTATGTCTCATTAATATATTCCTAAA TATCTTCCTGGCACGGGCAGTG |
| 48 | TATTACCAATATATCTAATAAACACAGTTATTCTAATTATACTTTTTTAATAC ATTATATCCTGGCACGGGCAGTG |
| 49 | AACATACATAATTAATTTCTTAAGAATATATGTTCTAGATTCTTTAATTATTA TTTATCTCCTGGCACGGGCAGTG |

TABLE 4-continued lists aptamers of 1 to 250, that target endotoxins and outer membrane vesicles of *E. coli*, *P. gingivalis* and *P. pallens*.

| SEQ ID NO | Sequence |
|---|---|
| 50 | ATACTTATATGATCCTTTTTATATATGCATTATTTTATCATTATATATGTCATT ATTATTCCTGGCACGGGCAGTG |
| 51 | TATAATCTTATATCCAAATACTTCATATATTATACATCATTTCATGTTTAATA ATTAAATCCTGGCACGGGCAGTG |
| 52 | TCTAAATTTCCTAAAATAATGTATTTATTGTATACCTATATAATTGTTAGAAA TAATAAACCTGGCACGGGCAGTG |
| 53 | TAATAAATTATTTCTTGTTATTATTAATCATGTCTAAACCAAATTTATTAGTAT ATTAATCCTGGCACGGGCAGTG |
| 54 | ATTTTTTTCTATTCATATGTTTTTCATATACTTAAGAATTATTTTTTTATATGTT TAATTCCTGGCACGGGCAGTG |
| 55 | AATAATATATCTCTAGAACATTAAATATCATTTTCATATATTTAAAGTATATC ATAATAACCTGGCACGGGCAGTG |
| 56 | TAATAAGATAGTGAAACATATATTATTGTCATATACACATTTTTATTAAATTT TAATAATCCTGGCACGGGCAGTG |
| 57 | AAATAATAAGGATATTTAATAACAATCTTTATTTAAGTAGATATTAATGTCTT AAATAATCCTGGCACGGGCAGTG |
| 58 | TACTATATATTTCTATCTGAATATCGTTATTAATAAAATTTAACTATCTTAATT AAATACCTGGCACGGGCAGTG |
| 59 | TATATCTTCTCAATATAGTTATCTTTATTTCACTATTATTGAATATATTTCATA TATAACCTGGCACGGGCAGTG |
| 60 | TAATTTTAAACTAATTATAATGAATTAACATAAATTTCAATTAAAATGATTTT AATAATTCCTGGCACGGGCAGTG |
| 61 | ATAAAGTATATAATTAATAATGATAACTTATGTCTCATTAATATATTCCTAAA TATCTTCCTGGCACGGGCAGTG |
| 62 | AATATTTATCTATTAACCAATATATAATTGTAGATTCTAGATACTAATTATAT CTAATCCTGGCACGGGCAGTG |
| 63 | TATGTGTGTCTAACACTGTGCGCATTCAGCCCGACAAGTTCCCCTCATTTGGA TTTCATTCCTGGCACGGGCAGTG |
| 64 | ATAATAACATTCTGATAACATTATATCTTTAATAATGATTACATTCATAAATT TCTATATCCTGGCACGGGCAGTG |
| 65 | TATTACCAATATATCTAATAAACACAGTTATTCTAATTATACTTTTTTAATAC ATTATATCCTGGCACGGGCAGTG |
| 66 | TATCATAATAGAAACAAATAAATCAGTCAAATATTATATTTTCTTCTAAGTAT ATTTATTCCTGGCACGGGCAGTG |
| 67 | AAATCTAATTTAATTGAAATAGTATCTATCTATAATAGTTAATTAGATATTTC AATATTTCCTGGCACGGGCAGTG |
| 68 | ATACTTATATGATCCTTTTTATATATGCATTATTTTATCATTATATATGTCATT ATTATTCCTGGCACGGGCAGTG |
| 69 | TATAATCTTATATCCAAATACTTCATATATTATACATCATTTCATGTTTAATA ATTAAATCCTGGCACGGGCAGTG |
| 70 | TATTTTATCTCATAACAAAATATTATGTATATCACTTTACAATAAATAATATA CTCTATTCCTGGCACGGGCAGTG |
| 71 | TCTAAATTTCCTAAAATAATGTATTTATTGTATACCTATATAATTGTTAGAAA TAATAAACCTGGCACGGGCAGTG |
| 72 | TTGAATATTTCATAGAATTATTTGAAATTATCCTTAATAATTCTAAATTTAAA TTAGATTCCTGGCACGGGCAGTG |
| 73 | AACATACATAATTAATTTCTTAAGAATATATGTTCTAGATTCTTTAATTATTA TTTATCTCCTGGCACGGGCAGTG |
| 74 | ATAATAACAATATTACTATTGAATATTTAGATGATTATAAAAATCAGTATATT ATATAACCCTGGCACGGGCAGTG |

TABLE 4-continued lists aptamers of 1 to 250, that target endotoxins and outer membrane vesicles of *E. coli*, *P. gingivalis* and *P. pallens*.

| SEQ ID NO | Sequence |
|---|---|
| 75 | TTAAATAAAGATTAATAATTATGAAATTTACTGTTCTATTTTAACTATAATTT TATTTCACCTGGCACGGGCAGTG |
| 76 | GAGTTACGAAGCCATGGTTAACTAAAGTCGGGACGTTTTCTCAGACGGGTCT ATATTATGGCCTGGCACGGGCAGTG |
| 77 | AGAACCATAGCCCTACTTCTCCATGCGTCACGTGCAGTGTTTAATTCAGTTCT TTGATTTCCTGGCACGGGCAGTG |
| 78 | TCTTACATACTTATACACCTGGATAAACACGGGAAGTTATTCGTAGTATGAG GAATGGAGCCTGGCACGGGCAGTG |
| 79 | TCTCTGACTAGAGACGTATAGTCTCGTGTTGGTTGGCACATTGAGCCCTTCTT TTTGGAGCCTGGCACGGGCAGTG |
| 80 | TGGATCTCGTCGTAAGGGTTACCTTACGTATCCGAGGGCCTAGCCGCGTCTA GAATGGAGCCTGGCACGGGCAGTG |
| 81 | AGCATCTAGACACGCATTAGAATTAGCTAATATAGAGCTGTGTATCTGTAGA GTTTGTCACCTGGCACGGGCAGTG |
| 82 | GAGAAGACCTGTGGAGCAACTTTAAGCATGCTTAAATAGTCCACGTGAGAG AATTCAGCCCCTGGCACGGGCAGTG |
| 83 | TGGTGCATTCAGCCCTTCTATTGAATGGTATCCAAATGCATTCTGCTGAAATC ATTCTCACCTGGCACGGGCAGTG |
| 84 | AAGATATTTACCTAAGCACATAGACACGTCATTCTGTCCTTGATGAACAATTT GTTGCATCCTGGCACGGGCAGTG |
| 85 | CATTGCTAGATTCACTGAGATGCATCGGATGCACTAAGCCCGCCCCACAACT TGTTGTCACCTGGCACGGGCAGTG |
| 86 | TGTCAACACAACATGTGTGTTAGAGATCGCGGGGGAGTATAGTCACGAAAG ACTCCACAACCTGGCACGGGCAGTG |
| 87 | GAGACAGACACGATAAAATGACGTAATTTAGACGATATAATCTGTAATTGAA TATTGCCTGGCACGGGCAGTG |
| 88 | TGTGATGGAATTCTTTTCATCAGGGAGTAGGTGCAGAAGGCAGGGATGGGA AATTTGGCGCCTGGCACGGGCAGTG |
| 89 | CCAGAACATGTGTACGTCAGTGAGGGTAGAGTTTTGCTGTGTCTGTCGAGAA TGTGAGCACCTGGCACGGGCAGTG |
| 90 | AAAACCATGTCTCGAAATATTGGGTTAAACGTTCGTGAGCCTAGCCACGACA TTTGGATCCTGGCACGGGCAGTG |
| 91 | ATCCCATCGATGGTCTACAGTACGAAGTAGGAGTACAAATGCCCTTCAGTTT AGTAAGCACCTGGCACGGGCAGTG |
| 92 | AGCAATTGCCACGTTAATTGTGGAAATGGTTTCCAGCAATTTGTTAATGTCAC ATAACAACCTGGCACGGGCAGTG |
| 93 | AGCATTTGCCACGAGTTAATATGTGACTGGCACGGGTACAGTTACGTGGTTG ATTAGACTCCTGGCACGGGCAGTG |
| 94 | GATTTACAAAGTGAGACGATTTGTCCAAGACAAAACTCACTGGTAATCCATT TGGTGGAGCCTGGCACGGGCAGTG |
| 95 | TCATTATGCATGGACATAGCACTAAGTCACGTCATTCAATTATCAACCAAGA TTTAATCACCTGGCACGGGCAGTG |
| 96 | ATGGTCTTATCGGTGATTGAACATCGGACAGAACGCCACGACATTGGACGTA GATGGAGCCTGGCACGGGCAGTG |
| 97 | CCGGATTTTGATCAAACCAAATTTGAATATGGTAACGGGGAGCGCTAGTCA TTTCTCCGCCTGGCACGGGCAGTG |
| 98 | TGTTGAAGTGGTGTAACTGAGAAAGTGAGATACATCACTCAGTTGATTGGAC TAAGCAATCCTGGCACGGGCAGTG |

TABLE 4-continued lists aptamers of 1 to 250, that target endotoxins and outer membrane vesicles of *E. coli*, *P. gingivalis* and *P. pallens*.

| SEQ ID NO | Sequence |
|---|---|
| 99 | AAGTGGGTGTTTACATGGTATCCGTCGAGAGTAACCTTTATCGCCATCCAGT AATACGTACCTGGCACGGGCAGTG |
| 100 | TGGACAGTTTATAACCAGGACTTGGATCTGTTGTTTCTACACCTTTCATGCTC CACTTCTCCTGGCACGGGCAGTG |
| 101 | AAGTGGCTATGGATGTAGTTCGCTTTACCTCTGTCTATCTCGTTGGATGGTTA GTAATATCCTGGCACGGGCAGTG |
| 102 | TGATTGAAATGGATCTCTCGTAAGATCTGTAGACGGGTAACTTTCAACTTTG AGTGGTTTCCTGGCACGGGCAGTG |
| 103 | TGAAGTGGCTTACACTCACATCCTCGTTCAACACGTGACCTTAGTATCTTATT TGATCAACCTGGCACGGGCAGTG |
| 104 | AATCCAAGTTTATCACTGGGTAGACGCTCGAATTGTGGGTCTCTTATCCAGG AGATAGTTCCTGGCACGGGCAGTG |
| 105 | GATGTTCAGATTACTGTGCTCTCAGGAATTATACTCTTCACAGTCAACCTAGC TATGACACCTGGCACGGGCAGTG |
| 106 | GTGCTCCTCGGTGAAGTGGCTTGTGCTCCTCGGTGAAGTGGCTTGTGCTCCTC GGTGAAGTGTTTTTCAATCCTGGCACGGGCAGTG |
| 107 | GTGCTCCTCGAAGTGGCTTGTGCTCCTCGAAGTGGCTTGTGCTCCTCGAAGTG GCTTGTGCTCCTCGTCGTTCTTTAGTATTCCTGGCACGGGCAGTG |
| 108 | GTGCTCCTCGAAGTGGCTTGTGCTCCTCGAAGTGGCTTGTGCTCCTCGAGCAA GTTTATTTAATTGACACCTGGCACGGGCAGTG |
| 109 | GTGCTCCTCGTGAAGTGGCTTGTGCTCCTCGTGGTTGATACATGAACATTAAC CTGGCACGGGCAGTG |
| 110 | GTGCTCCTCGGTGAAGTGGCTTGTGCTCCTCGGTGAAGTGGCTTGTGCTCCTC GGTGAAGTGGCTTGTGCTCCTCGGTGAAGTGTTTTTCAATCCTGGCACGGGC AGTG |
| 111 | GTGCTCCTCGAAGTGGCTTTGCATGGCTGAATGTTACAACGAAGTGTATGGT CTAAACAATAGTTTGGTTCCTGGCACGGGCAGTG |
| 112 | GTGCTCCTCGAAGTGGCTTGTGCTCCTCGATAGAAGAGTGACACGTTCTAAG AAAGAACCTGGCACGGGCAGTG |
| 113 | GTGCTCCTCGTGACGTGAAGTGGCTTGTGCTCCTCGTGACGTGAAGTGGCTA TGCTATTCTCTAGTTGAAGGAGGATTGTTACCTGGCACGGGCAGTG |
| 114 | GTGCTCCTCGAAGTGGCTTGTGCTCCTCGGATCAAATACCAATATTGTTGTTC TCCTGGCACGGGCAGTG |
| 115 | GTGCTCCTCGAAGTGGCTTGTGCTCCTCGAAGTGGCATAATGTTGTTAAGTA GACTGGTCCTGGCACGGGCAGTG |
| 116 | GTGCTCCTCGTTCCTTTTACGCCCTGAAGTGGCTTGCACTCGTTATAGCTCAT GTTGTGAGGTTTAACTCCCTGGCACGGGCAGTG |
| 117 | GTGCTCCTCGTTTACATTGTTTTGAAGCACATCATAATCTTTGCCTCGATATTT TACTCATTTCTCTTCCCTGGCACGGGCAGTG |
| 118 | GTGCTCCTCGAAGTGGCTTGTTAATTTAGTGTTTTACGATGTTTGTGTGTTCTA GTGGTGTCACAGTTGTCCTGGCACGGGCAGTG |
| 119 | GTGCTCCTCGAAGTGGCTTGTGCTCCTCGAAGTGGCTTGTGCTCCTCGGTGAT GTTTCTATCAGACTGTTATGTTGTCCTGGCACGGGCAGTG |
| 120 | GTGCTCCTCGTTTGAAGTGGCTTTCTTCAACCAGTGCGTGTTGTGTTTTATTC AGTAATGAATCTTGTTCCCTGGCACGGGCAGTG |
| 121 | GTGCTCCTCGCTCGAAGTGGCTTGTGCTCCTCGCTCGAAGTGGCTTGTGCTCC TCGCTCGAAGTGGCTTGTGCTCCTCGTCATCGTTGATGGACCTGGCACGGGC AGTG |
| 122 | GTGCTCCTCGTCCACCTTGAAGTGTACCTTACACTGGTGTTCTAGGAGCTTAC CGGTTGGGTGCATCATACCTGGCACGGGCAGTG |

TABLE 4-continued lists aptamers of 1 to 250, that target endotoxins and outer membrane vesicles of *E. coli*, *P. gingivalis* and *P. pallens*.

| SEQ ID NO | Sequence |
|---|---|
| 123 | GTGCTCCTCGTTTCATGATTTTGTACTGTGTTAAAGATCCTAAATACTTCTTG GTGCAAGGCATGTAAACCCTGGCACGGGCAGTG |
| 124 | GTGCTCCTCGAAGTGGCTTGTGTTCCTCGTATATCTTCTCAATCTTCTGTACA ATGTCATATTCTTCCCCTGGCACGGGCAGTG |
| 125 | GTGCTCCTCGTGAAGTGGCTTGTCCTAGCTGTTTTCACTGTTCACCCTGTTATT CTCCTTATTACACAATCCTGGCACGGGCAGTG |
| 126 | GTGCTCCTCGTGAAGTGGCTTGTGCTCCTCGTGAAGTGGCTGACTTATCACTT GCTCCAAGGTATAATCCTGGCACGGGCAGTG |
| 127 | GTGCTCCTCGTACTCCCTAAGGACTAGGAAGAACATAATGCCATTTCCACAC TGTGTGTGATATAATCCACCTGGCACGGGCAGTG |
| 128 | GTGCTCCTCGTATGGTGTAAGTCTCTATAACCTCGTTATGAGAGATTGTACCA GAAGAGGATTTAAAGCACCTGGCACGGGCAGTG |
| 129 | GTGCTCCTCGTAGCACATAGACATGTCATTGAACTGTCCGAATCTTCTTGTGA GTGTTAGATATTCTCCGCCTGGCACGGGCAGTG |
| 130 | GTGCTCCTCGGTGAAGTGGCTTGTGCTCCTCGGTGAAGTGGCTTGTGCTCCTC GGTGAAGTGTTTTTCAATCCTGGCACGGGCAGTG |
| 131 | GTGCTCCTCGACGATTGAAGGATACAACGTAGAACTTTAGAACTATCGCTAA TCGTCGGGATAAATGGAGCCTGGCACGGGCAGTG |
| 132 | GTGCTCCTCGATTGAATTATGCTAATGATTAACAATCGTGGGGAGAAGCCTA CGAAAGAGGAATTCAGCACCTGGCACGGGCAGTG |
| 133 | GTGCTCCTCGTATATGTTTATAAATCTCTAAGTTATAATTAATCATATAAATC CTAAGATTTTATTTCCTCCTGGCACGGGCAGTG |
| 134 | GTGCTCCTCGTGATGCTCTCTAGCAGTCATATCACTGAGGATACCAAGCCTA ATTAGTGTAATATATGCGCCTGGCACGGGCAGTG |
| 135 | GTGCTCCTCGCTCAAGAGGAATTCACACGTATTTATGCGTGTTATTCCTGTAC CACTTATTTTTTGTCACCCTGGCACGGGCAGTG |
| 136 | GTGCTCCTCGGCAAGAACATACCGTTACGGATTTCCGAGTAGTCACTAGTAA CACTTCAGAATATTTCCGCCTGGCACGGGCAGTG |
| 137 | GTGCTCCTCGCAGCATCTGATAGGACCAATTCATTTTTTGAACGTGAGTTCGT TAATGATTTTTTGCTACCTGGCACGGGCAGTG |
| 138 | GTGCTCCTCGTCACTTGAGTAATAACTGTCCCTCTGAATGTGTATGAGGATGT ATCAAGTGTATGTGGAGCCTGGCACGGGCAGTG |
| 139 | GTGCTCCTCGCAACGTTCTCTATGAGATGGAGTTAAGCCTGGTTTTTGATATG ATAGAAATTGGTTGGAGCCTGGCACGGGCAGTG |
| 140 | GTGCTCCTCGTGTAGAAGAACAGAGGAGTACAAAAACGTTTACGATAGGCTT TAAGCCGATAATTTGTTGCCTGGCACGGGCAGTG |
| 141 | GTGCTCCTCGAAAATAATACTTTCATATTTAATCCTTTATGTATATCATTTGTA ATATACTACATAAATTCCTGGCACGGGCAGTG |
| 142 | GTGCTCCTCGTGCACATGTCCAAACTTCGTTTATTCTTACTTTCCATCGTGGTT AACATGGAAATGGATCCTGGCACGGGCAGTG |
| 143 | GTGCTCCTCGAGGTCACATCTATGCCAGTTCTAAAAATCGATTTATGTGATTT TTACAAGTAATAAGTCACCTGGCACGGGCAGTG |
| 144 | GTGCTCCTCGTGCAAATCAGATGATCTATTGACTGGTTATTTCCTGATTTGTA AGAAGAGTACCCACTTCCCTGGCACGGGCAGTG |
| 145 | GTGCTCCTCGCACAGATCACGTGAGTAATTTCAAAGGTACCTGACCTAGGGT ATTCTTTGAAATCATTCGCCTGGCACGGGCAGTG |
| 146 | GTGCTCCTCGTGTTAACCATTTACATAACACAGAGACATTAGGCACGTTTAG AATACAATTCTTATGGAGCCTGGCACGGGCAGTG |
| 147 | GTGCTCCTCGTATGAATTACTAATCTATATCAGAAAAATTAATTCTCTGTTTA ATTTAATTTTAATGTTTCCTGGCACGGGCAGTG |

TABLE 4-continued lists aptamers of 1 to 250, that target endotoxins and outer membrane vesicles of E. coli, P. gingivalis and P. pallens.

| SEQ ID NO | Sequence |
|---|---|
| 148 | GTGCTCCTCGCACTAATAGACAATTCAATAAATCCAACCCATTGGATTATCTT GAAGTTTTTCATTTTCCCCCTGGCACGGGCAGTG |
| 149 | GTGCTCCTCGATACTCCGAATTCTGGAACTGATTTATCGGTGCGTCAGAGAG GAAGTTAATATTGTGGAGCCTGGCACGGGCAGTG |
| 150 | GTGCTCCTCGGCATAAGTACACGTAGTTCTGTTTCAATTGTACTTTTGAGCAG AACCTAGATTATTTCCGCCTGGCACGGGCAGTG |
| 151 | GTGCTCCTCGTAAGAGTACAAAGACCTTCTCCCACAGACGTTTGGATCAACA TGGTAGATAAATTGTACGCCTGGCACGGGCAGTG |
| 152 | GTGCTCCTCGTGAGACAGCCATGACACAAATAATCAGTGGATACATTGAGTA TATGAGTCTTACTTTCTCCCTGGCACGGGCAGTG |
| 153 | GTGCTCCTCGCTGCAAGACCTTACGATACATGGATGTAATGTAATGATCATC TAGAATAGGTTAATGGAGCCTGGCACGGGCAGTG |
| 154 | GTGCTCCTCGCAGAGGGAGAATAAGCCTAAGATTTTTCGAATGAAAAACTTA AACTTGTCAGGAAGAATGCCTGGCACGGGCAGTG |
| 155 | GTGCTCCTCGTATTGGAATACTAATATATCTATAATAATGCAAATTAATCTAT ATCTTACTTTTTAATATCCTGGCACGGGCAGTG |
| 156 | GTGCTCCTCGAATATTAATAATATCATGTATGTATCATTAAGATTCTATTTTC ATTTATTACTTAATAATCCTGGCACGGGCAGTG |
| 157 | GTGCTCCTCGATACATATAATTACATGAAAGTATTAAATTATCTATGAAATTT ATCATTTATTATTTGTTCCTGGCACGGGCAGTG |
| 158 | GTGCTCCTCGTAATTTACATTTTAATCTTTACCTTAAATCTCATTATAAATATC ATATTAGTAAATAATACCTGGCACGGGCAGTG |
| 159 | GTGCTCCTCGTACAGTTTAAATAGATTATAACAATCATTATATTACAAATTAT GTGTTTTAATATTAATTCCTGGCACGGGCAGTG |
| 160 | GTGCTCCTCGAACTATTATTAATGTATTATGATTCTATTCTCTAATGTAATATT ATTTTTATTTTAACAACCTGGCACGGGCAGTG |
| 161 | GTGCTCCTCGTATTAATAACTTAAATATGATAGTTTAGACTTTATAATCATTT ATCTACTTATTTAATATCCTGGCACGGGCAGTG |
| 162 | GTGCTCCTCGAACAATTAAATCTAAATATCTCTAAATATTTTTTAACATTTTG AATTTAACATTAATATTCCTGGCACGGGCAGTG |
| 163 | GTGCTCCTCGAATTATTATTATACATTAACACAATCTATAATCAATTTATTTA TAACACAAATAAAGTATCCTGGCACGGGCAGTG |
| 164 | GTGCTCCTCGTTTATATTATGATAAAATGTTCAAGTATTATACTATAATTGAT AAGTAATAAGATTACATCCTGGCACGGGCAGTG |
| 165 | GTGCTCCTCGTTTATCAATATTAGCAGTAATATTTTATAGATATTTTTATCCCA TTAATATATCTATTTCCTGGCACGGGCAGTG |
| 166 | GTGCTCCTCGTAGTAAAAATTTAATGAAAATATGAATCAAATATTTTCACAA ATAATAATTATTTTAAAACCTGGCACGGGCAGTG |
| 167 | GTGCTCCTCGCTAGAATAATAATCACTATTCTTAGTTGATTTAATATTAATAT TTATGAAAAATATAATTCCTGGCACGGGCAGTG |
| 168 | GTGCTCCTCGAATTTTAAATGATATATTTTAATGTTATATCTATCAACTTCTTT AAATTAATTATTTTCTCCTGGCACGGGCAGTG |
| 169 | GTGCTCCTCGCAATAATAATTAAAAATTATGCAATATATTATTAATTAATTCA TATGCTATTATTTATTCCCTGGCACGGGCAGTG |
| 170 | GTGCTCCTCGAATATTATATATTCGTTCTTCTTTAGTATAGTTGTTACAATTAA TAAAAAATTATTATTCCTGGCACGGGCAGTG |
| 171 | GTGCTCCTCGTAATACAATTTTATTAAATTCATAGTTCTAATTAATAACACTA TTCTTCTTATTTAAATTCCTGGCACGGGCAGTG |

TABLE 4-continued lists aptamers of 1 to 250, that target endotoxins and outer membrane vesicles of *E. coli, P. gingivalis* and *P. pallens.*

| SEQ ID NO | Sequence |
|---|---|
| 172 | GTGCTCCTCGTTATAGTTATTTAATTCTCATATTTATATCACCTTTAAATCAAT AATTAATGTATATTCTCCTGGCACGGGCAGTG |
| 173 | GTGCTCCTCGTAAAAATACATTGATTTTTATTCTAATTTATTCTTTTAAATTGC TTATATAGTATTTAATTCCTGGCACGGGCAGTG |
| 174 | GTGCTCCTCGAAACATATTTTAGTATTCTATATGACATATTTTTTAAGAATAT AGATCTATTTTATATTTCCTGGCACGGGCAGTG |
| 175 | GTGCTCCTCGACATTAATTATTTTCTATTCAATTATCTAATTTAGTTCAAGTAT TAAAATGATTATAATTCCTGGCACGGGCAGTG |
| 176 | GTGCTCCTCGTTTTAAATAACTTTTTTATTCATTATCCATTTTAACTAGATTTA AAATAAAAATAATTCTCCTGGCACGGGCAGTG |
| 177 | GTGCTCCTCGAAAGAATATAATTCAATGTAGATTTATCAATATTTATTTATTT AATTAAGTATCATTATTCCTGGCACGGGCAGTG |
| 178 | GTGCTCCTCGAAAGTTTAATTAATAATCTATTCTTAAGATTACAGAAATATAT TTGTATTTAAATATTATCCTGGCACGGGCAGTG |
| 179 | GTGCTCCTCGTATTTATCATTCTTAGTTAATAATACTAACTGTATATATAATA CACATATATTTGATCTTCCTGGCACGGGCAGTG |
| 180 | GTGCTCCTCGAAATCTTCATTGTTATTAATAGATACAATATAAGTTTAAATAG AATATAGATGTAATAATCCTGGCACGGGCAGTG |
| 181 | GTGCTCCTCGTCTAAAATATAATCATTATGTTAGTTAGATAATCTTTTTGTAA TATTATCAATTATATTCCCTGGCACGGGCAGTG |
| 182 | GTGCTCCTCGAATATTAATAATATCATGTATGTATCATTAAGATTCTATTTTC ATTTATTACTTAATAATCCTGGCACGGGCAGTG |
| 183 | GTGCTCCTCGTACAGTTTAAATAGATTATAACAATCATTATATTACAAATTAT GTGTTTTAATATTAATTCCTGGCACGGGCAGTG |
| 184 | GTGCTCCTCGTATTGGAATACTAATATATCTATAATAATGCAAATTAATCTAT ATCTTACTTTTTAATATCCTGGCACGGGCAGTG |
| 185 | GTGCTCCTCGATACATATAATTACATGAAAGTATTAAATTATCTATGAAATTT ATCATTTATTATTTGTTCCTGGCACGGGCAGTG |
| 186 | GTGCTCCTCGTATTAATAACTTAAATATGATAGTTTAGACTTTATAATCATTT ATCTACTTATTTAATATCCTGGCACGGGCAGTG |
| 187 | GTGCTCCTCGTTAATATTTATATTATACTACTTGCTATATAAGTAATATAATC AATTCATTAATAAGATCCTGGCACGGGCAGTG |
| 188 | GTGCTCCTCGCAATAATAATTAAAAATTATGCAATATATTATTAATTAATTCA TATGCTATTATTTATTCCCTGGCACGGGCAGTG |
| 189 | GTGCTCCTCGTTTATATTATGATAAAATGTTCAAGTATTATACTATAATTGAT AAGTAATAAGATTACATCCTGGCACGGGCAGTG |
| 190 | GTGCTCCTCGTAGTATTTACATAGATTAGATATATCGATATATTCTTCTTGTA TATTTTAACTTAATATCCTGGCACGGGCAGTG |
| 191 | GTGCTCCTCGTTTATCAATATTAGCAGTAATATTTTATAGATATTTTTATCCCA TTAATATATCTATTTCCTGGCACGGGCAGTG |
| 192 | GTGCTCCTCGTATTTATCATTCTTAGTTAATAATACTAACTGTATATATAATA CACATATATTTGATCTTCCTGGCACGGGCAGTG |
| 193 | GTGCTCCTCGTAATTTACATTTTAATCTTTACCTTAAATCTCATTATAAATATC ATATTAGTAAATAATACCTGGCACGGGCAGTG |
| 194 | GTGCTCCTCGTAGAAGATAAAGATAAATTTCTAGTTATTATTTGACATCATAT TTATATAAATTATCATTCCTGGCACGGGCAGTG |
| 195 | GTGCTCCTCGAAACATATTTTAGTATTCTATATGACATATTTTTTAAGAATAT AGATCTATTTTATATTTCCTGGCACGGGCAGTG |
| 196 | GTGCTCCTCGTTGTATAAAATATATCTATCTAAATCGTAATGAGATATATTCT ATTTGAATTAATTATTCCTGGCACGGGCAGTG |

TABLE 4-continued lists aptamers of 1 to 250, that target endotoxins and outer membrane vesicles of *E. coli*, *P. gingivalis* and *P. pallens*.

| SEQ ID NO | Sequence |
|---|---|
| 197 | GTGCTCCTCGTTATAGTTATTTAATTCTCATATTTATATCACCTTTAAATCAAT AATTAATGTATATTCTCCTGGCACGGGCAGTG |
| 198 | GTGCTCCTCGAATTATTATTATACATTAACACAATCTATAATCAATTTATTTA TAACACAAATAAAGTATCCTGGCACGGGCAGTG |
| 199 | GTGCTCCTCGAATTTTAAATGATATATTTTAATGTTATATCTATCAACTTCTTT AAATTAATTATTTTCTCCTGGCACGGGCAGTG |
| 200 | GTGCTCCTCGTAAAAAATAATGTGTTATTCTTTATCATGTTATTAATTTAGTT AACATGTAAAATATATTCCTGGCACGGGCAGTG |
| 201 | GTGCTCCTCGTAATGTGATCATATTCTATGATTATTATACAGATATGTTTTCT ATTTATATAAATGTATTCCTGGCACGGGCAGTG |
| 202 | GTGCTCCTCGCTAGAATAATAATCACTATTCTTAGTTGATTTAATATTAATAT TTATGAAAAATATAATTCCTGGCACGGGCAGTG |
| 203 | GTGCTCCTCGAACTATTATTAATGTATTATGATTCTATTCTCTAATGTAATATT ATTTTTATTTTAACAACCTGGCACGGGCAGTG |
| 204 | GTGCTCCTCGTCTTATTAAATGTATTATAATTGAAAGATTCTATGATAAATAT TATTGGTATATTATCCTCCTGGCACGGGCAGTG |
| 205 | GTGCTCCTCGAGTATAATTTAATAGATTCTTTTATATAATATTACTCTCATATT CTGTAGATATATTAATCCTGGCACGGGCAGTG |
| 206 | GTGCTCCTCGTTTTATTTATTAGAGTTAATAATATATATCATTACTAAGGTAA TTAGAATTCTATATAATCCTGGCACGGGCAGTG |
| 207 | GTGCTCCTCGTAATACAATTTTATTAAATTCATAGTTCTAATTAATAACACTA TTCTTCTTATTTAAATTCCTGGCACGGGCAGTG |
| 208 | GTGCTCCTCGTAAAATATTTGTTTAATTGTTATTGTATAATACTCTTTAGTGTT CATACTATATTATATTCCTGGCACGGGCAGTG |
| 209 | GTGCTCCTCGAACAATTAAATCTAAATATCTCTAAATATTTTTTAACATTTTG AATTTAACATTAATATTCCTGGCACGGGCAGTG |
| 210 | GTGCTCCTCGGTAATAATTATAGAGATTAATTGTATAAATCGTAATCTATAAA TATTTAATAATAAACATCCTGGCACGGGCAGTG |
| 211 | GTGCTCCTCGTACTCCCTAAGGACTAGGAAGAACATAATGCCATTTCCACAC TGTGTGTGATATAATCCACCTGGCACGGGCAGTG |
| 212 | GTGCTCCTCGGAGCTGGTAGACACGATAAACGTACAGTTAGCTGGCACGACT GTTAAATTCTCTCGTTCCCTGGCACGGGCAGTG |
| 213 | GTGCTCCTCGAAATCCTACACATACGGATAAAGTCTTTGGGTGATCACGGGT ACAGTGTAATTTCGGGAGCCTGGCACGGGCAGTG |
| 214 | GTGCTCCTCGATTGAATTATGCTAATGATTAACAATCGTGGGGAGAAGCCTA CGAAAGAGGAATTCAGCACCTGGCACGGGCAGTG |
| 215 | GTGCTCCTCGTTGCGAGGCCAAGACACGACATTTAGTATGAGGTGGAGGGTG GATCAATTGTATGATGTGCCTGGCACGGGCAGTG |
| 216 | GTGCTCCTCGTGTAACATGCCCGATTCAATTTCATACCATCTATCACTATGAT ACTTTAATTTCAACACCTGGCACGGGCAGTG |
| 217 | GTGCTCCTCGAGAGATGAAGCCGTACTTCTGCAGGTGACGTAGATCCCGTAA CCTGGTAGAAATTTGTTCCCTGGCACGGGCAGTG |
| 218 | GTGCTCCTCGTAGATTCATTCCGTACTAGGTAATGATACTGTGCACATTGCCA CGCTGCTCTATTGCTCACCTGGCACGGGCAGTG |
| 219 | GTGCTCCTCGCCACGAAAATTATTCGTTTACTTGTGACTATCCACATCAGCTT AGTTTCATTATTTCCCACCTGGCACGGGCAGTG |
| 220 | GTGCTCCTCGTCAAGCCCATGTATTAACGTCAATCATTACTAATCATTGTCTA ATCCTCTAATTTCACCACCTGGCACGGGCAGTG |

TABLE 4-continued lists aptamers of 1 to 250, that target endotoxins and outer membrane vesicles of *E. coli*, *P. gingivalis* and *P. pallens*.

| SEQ ID NO | Sequence |
|---|---|
| 221 | GTGCTCCTCGCATTCTTCGATGATATCGTAGTTGTCTAGTAACGGGCCAAGCC<br>TACATCACTTCCAGCACCTGGCACGGGCAGTG |
| 222 | GTGCTCCTCGTATCCAAGCGGGGATTCCATAGATCAGCTATACGTACAAGCC<br>GCGCCACGTAAAGTATTCCCTGGCACGGGCAGTG |
| 223 | GTGCTCCTCGCATAACCAGTTCGTTTACTTTATATCCCATTTCAATTCCATAG<br>AAATGGTAATTTCTCTCCCTGGCACGGGCAGTG |
| 224 | GTGCTCCTCGCACTAATAGACAATTCAATAAATCCAACCCATTGGATTATCTT<br>GAAGTTTTTCATTTTCCCCCTGGCACGGGCAGTG |
| 225 | GTGCTCCTCGTACTAGACACGACATGCATATTTTCGTGATTTGGATAAGTTAC<br>AGTGTTTCTGTTATGACCTGGCACGGGCAGTG |
| 226 | GTGCTCCTCGCAAACGAGGAAGCATGCCACGCTCACTGTTTCTCGGTTGCAT<br>TCCAGACACTTGTTAGTTCCTGGCACGGGCAGTG |
| 227 | GTGCTCCTCGATACTTCTGCTACGCAGTGAGAGAAAGCACCAGGGCACGGAT<br>AAAGTGTAAATTCTGTCCCTGGCACGGGCAGTG |
| 228 | GTGCTCCTCGGCCAATGTAGCCAAGACACGACTATTAGGGGGGTTCAGGGTA<br>GAGTAAGAAGTAATTCAGCCTGGCACGGGCAGTG |
| 229 | GTGCTCCTCGGGGATAGAGGTTGTTGGCTGCAAATAACCTCTGGAACCGAGG<br>TATCCACTTCAATTGGAGCCTGGCACGGGCAGTG |
| 230 | GTGCTCCTCGTACACACAGGCACGTCTTGACTAGGTCTCCATACAGCAACCA<br>TTGAGATGTATTTGGTCACCTGGCACGGGCAGTG |
| 231 | GTGCTCCTCGACAGGAGTTTACAGGAGCCACGTACAGTCAGTTTCGCCATTT<br>CCGTAAAGGAATTAATCACCTGGCACGGGCAGTG |
| 232 | GTGCTCCTCGTATGCACTACAAGACCTTCCTTTTTCCCTATCATACACTCAAT<br>TTGTCAATTAAATGGATCCTGGCACGGGCAGTG |
| 233 | GTGCTCCTCGAAATGCTATGTACATAAGTAATTTATCCACAATTACTACGTTC<br>ATAGTCTTTTGGAGCACCTGGCACGGGCAGTG |
| 234 | GTGCTCCTCGCAACATTTATGTTGTGTGGATAAAGACCTTCTTCAAAGAATA<br>ACTAGTTTAATTTATGATCCTGGCACGGGCAGTG |
| 235 | GTGCTCCTCGTATATGTTTATAAATCTCTAAGTTATAATTAATCATATAAATC<br>CTAAGATTTTATTTCCTCCTGGCACGGGCAGTG |
| 236 | GTGCTCCTCGTGGTTTAAATACCACAGGGGGAATCAGCTACGATTTCTTCCTA<br>TTAGAGAAGAAAATCCTCCTGGCACGGGCAGTG |
| 237 | GTGCTCCTCGTATGGTGTAAGTCTCTATAACCTCGTTATGAGAGATTGTACCA<br>GAAGAGGATTTAAAGCACCTGGCACGGGCAGTG |
| 238 | GTGCTCCTCGAGCTCTATCTTACGTTATCAAGCCCTTCCACTAACCCTGATTT<br>TGTGTTCTTAATCTGCACCTGGCACGGGCAGTG |
| 239 | GTGCTCCTCGCTCGAAGTGGCTTGTGCTCCTCGCTTGAAGTGGCTTCTGCTCC<br>TCGTCATCGTTGATGGACCTGGCACGGGCAGTG |
| 240 | GTGCTCCTCGTTCCTTTTACGCCCTGAAGTGGCTTGCACTCGTTATAGCTCAT<br>GTTGTGAGGTTTAACTCCCTGGCACGGGCAGTG |
| 241 | GTGCTCCTCGAAGTGGCTTTGCATGGCTGAATGTTACAACGAAGTGTATGGT<br>CTAAACAATAGTTTGGTTCCTGGCACGGGCAGTG |
| 242 | GTGCTCCTCGTTTCATGATTTTGTACTGTGTTAAAGATCCTAAATACTTCTTG<br>GTGCAAGGCATGTAAACCCTGGCACGGGCAGTG |
| 243 | GTGCTCCTCGAAGTGATGACGACCAAAAGTCAATTATCCTCACTCAACACAA<br>CAAGTAACGGCAGCATCCCTGGCACGGGCAGTG |
| 244 | GTGCTCCTCGAAGTGGCTTGTTAATTTAGTGTTTTACGATGTTTGTGTGTTCTA<br>GTGGTGTCACAGTTGTCCTGGCACGGGCAGTG |
| 245 | GTGCTCCTCGTTTACATTGTTTTGAAGCACATCATAATCTTTGCCTCGATATTT<br>TACTCATTTCTCTTCCCTGGCACGGGCAGTG |

TABLE 4-continued lists aptamers of 1 to 250, that target endotoxins and outer
membrane vesicles of *E. coli*, *P. gingivalis* and *P. pallens*.

| SEQ ID NO | Sequence |
|---|---|
| 246 | GTGCTCCTCGTGAAGTGGCTTGTGCTCCTCGTGAAGTGGCTTGTGCTCCTCGTGGTTGATACATGAACATTAACCTGGCACGGGCAGTG |
| 247 | GTGCTCCTCGTCCACCTTGAAGTGTACCTTACACTGGTGTTCTAGGAGCTTACCGGTTGGGTGCATCATACCTGGCACGGGCAGTG |
| 248 | GTGCTCCTCGTGAAGTGGCTTGTGCTCCTCGTGAAGTGGCTTGTGCTCCTCGTGAAGTGGCTTGTGCTCCTCGACCCTGAAGTGAGCCTGGCACGGGCAGTG |
| 249 | GTGCTCCTCGTTATCTAGACGCACTTGTAAGAATCCCTGGATACATCAGCTTTTAGTGTATAAGTGACATCCTGGCACGGGCAGTG |
| 250 | GTGCTCCTCGAAGTGGCTTGTGCTCCTCGAAGTGGCTTGTGCTCCTCGAAGTGGTTGTGCCATCATGAGCATCCTGGCACGGGCAGTG |

TABLE 5 lists aptamers of 251 to 449, that were selected to target
outer membrane vesicles and endotoxins of
*E. coli*, *P. gingivalis* and *P. pallens*.
Table 5. Cross reactive aptamers targeting outer
membrane vesicles
and endotoxins of *E. coli*, *P. gingivalis* and *P. pallens*

| SEQ ID NO | Sequence |
|---|---|
| 251 | TAGGCGACTGAGTCGCGCGGCAGCGCCGATGGAGACGCCGCGGAGGGGCACGCCGAGCACCCTGGCACGGGCAGTGTAAA |
| 252 | GCGGTGGGCCCCGCAGGGGGCTAGGGGGCGTGGTGGGGACGAGCTGCGGGGAGGGGCAAGCCTGGCACGGGCAGTG |
| 253 | CGGGGCTGGGGGGGATGGGGTGGCACCCTCTACCGCGTGGGCCAGTCGGGGAGCCGCGCGCCTGGCACGGGCAGTG |
| 254 | CGGAAGGGGGTATGTGGGCGGCCGGCGGGAGGGTGGAGGGCGCGGGCGCGGCGTGTGGAGCCTGGCACGGGCAGTG |
| 255 | GGAGGCCGTCCGCCGATGAAAGTTCGGCGTGGGGGGGCGAGGCGCCGGGGCACGGCAGGACCTGGCACGGGCAGTGTAAA |
| 256 | ACTTTAAGCTTTACAGTGAATTATCTAGCAACCCCCTCTTCCTGGCACGGGCAGTGTAAA |
| 257 | TTGAGTCTAAGGATTTAACTCCCGATACTTATAACTAGAACCTGGCACGGGCAGTGTAAA |
| 258 | CTGGTGGCGCCGCGACCCGCGACCACACGGGCCGGCGGACGAGGCGTCGGGTAGCAGAAGACCTGGCACGGGCAGTGTAAA |
| 259 | TCACCTCGGTGTGAGGGGCAGGGCGGAGGGGAGGCGGAGGGCACGGTGCGGCGTCGCGGGCCTGGCACGGGCAGTG |
| 260 | TGGGGTGGGCTGGCAGGGAGGTGCCCCGGGGACCCGCGGGTGGAGGGCGGGTCGGATGTGCCTGGCACGGGCAGTG |
| 261 | CCGTGGGGCGTGCGGATGCTGCAGCTGGCCGGAGGGGCGGGGAGGAGGGCGGGGGCGCAGCCTGGCACGGGCAGTG |
| 262 | TGGGCGGGCAGAGGAGGGCCGGAGGCGTTCGACCGCGGGCTGGGCTGGGTTGGCGCGGTGCCTGGCACGGGCAGTG |
| 263 | GCGACGATGTGGCATTGCAGCGCGCGCTGCGGCGGGGGTGTGACGGGGGCCGGCGAGGCCTGGCACGGGCAGTG |
| 264 | AGTTGCTTTGGCCTTAATGGGATAAATGTTAGAGTTGTCACCTGGCACGGGCAGTG |

TABLE 5-continued lists aptamers of 251 to 449, that were selected to target outer membrane vesicles and endotoxins of *E. coli*, *P. gingivalis* and *P. pallens*.
Table 5. Cross reactive aptamers targeting outer membrane vesicles and endotoxins of *E. coli*, *P. gingivalis* and *P. pallens*

| SEQ ID NO | Sequence |
|---|---|
| 265 | AACCCATCATCAAAGAGAGGTGTATTGCTACTGTAATGCACCTGGCACGGGCAGTG |
| 266 | AGTTATCTATGTCCACATCTACCAAAAACGTATCCAACCCCCTGGCACGGGCAGTG |
| 267 | GAAGTGGCTTGTGTTCCTCGTCTTCTGACAATGGTCTTGTGCTCACAGGGATTACTTATGCCTGGCACGGGCAGTGTAAA |
| 268 | GTTTAGATGGTACGTTCTAATGGTTGTGAGCGAAGCAATACCTGGCACGGGCAGTG |
| 269 | CGTCTTTCTTCCCAGCGTTTGGACCCCAAATCTATCCTTGCCTGGCACGGGCAGTGTAAA |
| 270 | ATTTTTCACCGTCTGAAACTTTTGATGTTTTGGTCTTTATCCTGGCACGGGCAGTGTAAA |
| 271 | CGTTCTGCCTGGCATTTTTTTGCTGATTTCTTTCTTAGCACCTGGCACGGGCAGTG |
| 272 | CCATGGCTTGATTCTCGCTGGTAGGGCGGGGCGTAGATTACCTGGCACGGGCAGTG |
| 273 | CGTTCTGCCTGGCATTTTTTTGCTGATTTCTTTCTTAGCACCTGGCACGGGCAGTGTAAA |
| 274 | TTTCAAAGTGGGGTAGTGCATGTACTATGGGTTTGTGTACCTGGCACGGGCAGTGTAAA |
| 275 | GTTTAGATGGTACGTTCTAATGGTTGTGAGCGAAGCAATACCTGGCACGGGCAGTGTAAA |
| 276 | CCAGAATTCTCGTAAGACGGAGAGGAATGGATAGAGTGAACCTGGCACGGGCAGTGTAAA |
| 277 | CCAGAATTCTCGTAAGACGGAGAGGAATGGATAGAGTGAACCTGGCACGGGCAGTGTAAA |
| 278 | CACACGAATATGGCTCTCTTTCTCCCATTCACACTCCTCACCTGGCACGGGCAGTGTAAA |
| 279 | GAAGTGGCTTGTGTTCCTCGAACCCATCATCAAAGAGAGGTGTATTGCTACTGTAATGCACCTGGCACGGGCAGTGTAAA |
| 280 | AGTTATCTATGTCCACATCTACCAAAAACGTATCCAACCACCTGGCACGGGCAGTGTAAA |
| 281 | TCTTCTGACAATGGTCTTGTGCTCACAGGGATTACTTATACCTGGCACGGGCAGTGTAAA |
| 282 | CGTCTTTCTTCCCAGCGTTTGGACCCCAAATCTATCCTTACCTGGCACGGGCAGTGTAAA |
| 283 | CGCACGAATATGGCTCTCTTTCTCCCATTCACACTCCTCACCTGGCACGGGCAGTGTAAA |
| 284 | CTGCTTGTTGACGAAATTACGCTGCATTTGGGTGCTTCCACCTGGCACGGGCAGTGTAAA |
| 285 | GTGATAACGAATTTTAGACTGCCCAACGTCACAGCAAGTGCCTGGCACGGGCAGTGTAAA |
| 286 | TTGATGTTTGTCTACGAATTGTTGGCAGGTTACCGGGTAACCTGGCACGGGCAGTGTAAA |
| 287 | TCTACGTGGATGTCTTCACTACGGATTTATGCTGGCCTTACCTGGCACGGGCAGTGTAAA |
| 288 | ATGTCCACGAATTTTCACTCCCATAACGTTGCCACTGCAACCTGGCACGGGCAGTGTAAA |

TABLE 5-continued lists aptamers of 251 to 449, that were selected to target outer membrane vesicles and endotoxins of *E. coli*, *P. gingivalis* and *P. pallens*.
Table 5. Cross reactive aptamers targeting outer membrane vesicles and endotoxins of *E. coli*, *P. gingivalis* and *P. pallens*

| SEQ ID NO | Sequence |
|---|---|
| 289 | GTGATAACGAATTTTAGACTGCCCAACGTCACAACAAGTGCCTGGCACGGGCAGTGTAAA |
| 290 | GTGATAACGAATTTTAGACTGCCCAACGTCACAGTAAGTGCCTGGCACGGGCAGTGTAAA |
| 291 | TAGTTACTGCTAGTACGAATTTAGACAGTCCGTCTCTGACCCTGGCACGGGCAGTGTAAA |
| 292 | CTGCTTGTTGACGAAATTACGCTGCATTTGGGTGTTTCCACCTGGCACGGGCAGTGTAAA |
| 293 | GTGATAACGAATTTTAGACTGCCCAACGTCACAGCAAGTACCTGGCACGGGCAGTGTAAA |
| 294 | CTACTATGTACTGAAGCATGAACGAGTTTTCACGCCTGATCCTGGCACGGGCAGTGTAAA |
| 295 | GGTGGCGCGACGGACGTGCGAGAGGGGCGGAGCGCGGGGAAGGCGAGCGGTGTGAGGTGCCTGGCACGGGCAGTGTAAA |
| 296 | TCTACGTGGATGTCTTCACTACGGATTTATGCTGGCCTTACCTGGCACGGGCAGTGTAAA |
| 297 | AAGATATTTACCTAAGCACATAGACACGTCATTCTGTCCTTGATGAACAATTTGTTGCATCCTGGCACGGG |
| 298 | AATAATATATCTCTAGAACATTAAATATCATTTTCATATATTTAAAGTATATCATAATAACCTGGCACGGG |
| 299 | TGAAGTGGCTTACACTCACATCCTCGTTCAACACGTGACCTTAGTATCTTATTTGATCAACCTGGCACGGG |
| 300 | TAATAAGATAGTGAAACATATATTATTGTCATATACACATTTTTATTAAATTTTAATAATCCTGGCACGGG |
| 301 | TATGTGTGTCTAACACTGTGCGCATTCAGCCCGACAAGTTCCCCTCATTTGGATTTCATTCCTGGCACGGG |
| 302 | TATATCTTCTCAATATAGTTATCTTTATTTCACTATTATTGAATATATTTCATATATAACCTGGCACGGG |
| 303 | TGGACAGTTTATAACCAGGACTTGGATCTGTTGTTTCTACACCTTTCATGCTCCACTTCTCCTGGCACGGG |
| 304 | TGCACCGGGCGCAGGGCGAGAGCATACAAGGCACAGCGAGCCTGGCACGGG |
| 305 | AAGATATTTACCTAAGCACATAGACACGTCATTCTGTCCTTGATGAACAATTTGTTGCATCCTGGCACGGGCAGTGTAAA |
| 306 | AACATTAAATATCATTTTCATATATTTAAAGTATATCAATAACCTGGCACGGGCAGTGTAAA |
| 307 | AATAATATATCTCTAGAACATTAAATATCATTTTCATAACCTGGCACGGGCAGTGTAAA |
| 308 | ATTGACCTACGAAAGAGGAATTCAGCACCTGGCACGGGCAGTGTAAA |
| 309 | AATAATATATCTCTAGAACATTAAATATCATTTTCATATATTTAAAGTATATCATAATAACCTGGCACGGGCAGTGTAAA |
| 310 | AAGATATTTACCTAAGCACATAGACACGTCATTCTGTCCTTGATGAACAATTTGTTGCATCCTGGCACGGGCAGTGTAAA |
| 311 | ACACGTCATTCTGTCCTTGATGAACAATTTGTTGCATCCTGGCACGGGCAGTGTAA |
| 312 | ATTAACAATCGTGGGGAGAAGCCTACGAAAGAGGAATTCAGCACCTGGCACGGGCAGTGTAAA |

TABLE 5-continued lists aptamers of 251 to 449, that were selected to target outer membrane vesicles and endotoxins of *E. coli*, *P. gingivalis* and *P. pallens*.
Table 5. Cross reactive aptamers targeting outer membrane vesicles and endotoxins of *E. coli*, *P. gingivalis* and *P. pallens*

| SEQ ID NO | Sequence |
| --- | --- |
| 313 | AAGTGGCTTGTTAATTTAGTGTTTTACGATGTTTGTGTGTTGTCCTGGCACGGGCAGTGTAAA |
| 314 | GTCCAGTGCCTTGTATGGTAGGTCTATTATATCCCGACTTATATTGAGTGCAGTAAGCATCCTGGCACGGG |
| 315 | GTGGGGGTTTAGCTCTGGCGCATGGATAGACGATAGTGCGATGGGATAAAGAGGAGGTAGCCTGGCACGGG |
| 316 | TACTCTTTCACTCTGTGGTTCTGCTCTCAAACTGTCATGCTCTTTTCATTCACCTAGTTTCCTGGCACGGG |
| 317 | CTTGTCGTATGCTTATTTGTTTTCGCCTGTTTGTATTCTTGAGTGATATTGCAGCTCAAACCTGGCACGGG |
| 318 | TTTACGAACAAATCGATACGGTGGGGAATACATGGGATGCATCTAGTCGTTACTAAGCCACCTGGCACGGG |
| 319 | TAGTTTTTTAACGAGTTCGATCAACATGTGGATGTCTCTAATTCAATCCGGCAATTGATGCCTGGCACGGG |
| 320 | ACCGTGCCAGAGGGAACAGATTCGCGGGACGCATCGGTCGCGACCCGAAACATGGTTGGCTCCTGGCACGGG |
| 321 | AACCATCACAAATATAATGGATCGGACTTTGTTGTTTTGAAACACACACGTGTTGTTACCTGGCACGGG |
| 322 | AGTCATCGTTCGCGAATTAGTTTATTGTGCGCGGTAAATTGATTATGGCTAATGTATGGTCCTGGCACGGG |
| 323 | CAAATGGCCGTCTAAGGAGCATCCCAGGTGCAACACCACGATATTAGTATGCGGACGTCGCCTGGCACGGG |
| 324 | GAGGAGTTAATCGTAATGGCGCTTTAGCTATTGGGTGGAAGGGAGGCGGTAGGACTGCGCCCTGGCACGGG |
| 325 | CACTGTAGATGTGAGCATTCAATCCATAGGTTATATAGTTCCACGTCATGAAATTCACCCCCTGGCACGGG |
| 326 | GCGTTTACTACTACCATCCCCAATGTCTAAATTTCTGTCCTGTTTTGTTACATATGGATTCCTGGCACGGG |
| 327 | AGTAATCTATCGTGGAAGTCGGATTCTACTGGGCAGCATCTCACAGTGATTTACTGCACACCTGGCACGGG |
| 328 | CGACGGTGCAGACTTATATGTCTGTCAGACGGTGCCCTGGTACATTCCGTCAGTGACGGTCCTGGCACGGG |
| 329 | TCTATGTATTCAGGTCTCCTCGATTTGCATAGAGCAATTGGGCTGATGAGATCATTGAGTCCTGGCACGGG |
| 330 | GATGCATATTTTTACGTCTCACCGTAGACTGTCGTAGTTTCTAGGGTTTCCGAAGGTCGGCCTGGCACGGG |
| 331 | CACTACGTGGTGTCTACAACTTTTCAGCCGATTATCCTTGTTGTCTACGTCGTCGCCAACCCTGGCACGGG |
| 332 | CGTTAAATGTGAGCATCATTGGTGTGGAGTCCATAGCGTGGTTGTAGGTATTTTCCTTCTCCTGGCACGGG |
| 333 | TGCCAGGTACAATAACGGTGTTTATGGTCAGTTATATCTATCACTGGGACCCTCTTGCTTCCTGGCACGGG |
| 334 | TTGTTCCCGCTTTTGTGACTCAGGTCTACAGTGTCTGATGAACTCGATTTTAAAGCTCCACCTGGCACGGG |
| 335 | GCCTTTAGGCCCAGACTCCTTAAATAGCCTCGGCCGGCCATGTTAGATTATACCTTGTTTCCTGGCACGGG |

TABLE 5-continued lists aptamers of 251 to 449, that were selected to target outer membrane vesicles and endotoxins of *E. coli*, *P. gingivalis* and *P. pallens*.
Table 5. Cross reactive aptamers targeting outer membrane vesicles and endotoxins of *E. coli*, *P. gingivalis* and *P. pallens*

| SEQ ID NO | Sequence |
|---|---|
| 336 | TATTACTCCCGAGCACGTAGGTTAATTATTTAGAGGGGAAAAGGTGAGTAGAGTAGTTTTCCTGGCACGGG |
| 337 | TAGACATCCTACCCTTTAGATTTGATCTTATTTTACCAGACCTTCTATCATTGATTGCAGCCTGGCACGGG |
| 338 | TAGTGTATAAGTCATGCACCTTTTTAGTCGATCTTGACCAGAGTGTTTCGTGATAAGAGTCCTGGCACGGG |
| 339 | CCTACATTGGCAATAGCAAATCTGTTGACTGAGATGCACTCTAAAAGCAGTTCTCCTCCTCCTGGCACGGG |
| 340 | TGCGCAGGGCTAACATTAGTCATATTTTACTAAAGTATCCTCACCATCGCATTTGTTAGCCCTGGCACGGG |
| 341 | TTCGAGGGTTGCTTACTGAGATCTGTGTCAGACGCACAGCTCGTAGTTGGTTAGCTGTCCCCTGGCACGGG |
| 342 | AACTTGTTCGAAGTTTGGGAATTCCGGAAGAATTCTACGGATGGTTTGCTTATGTCGTTTCCTGGCACGGG |
| 343 | TTCTCCGAGTAAGTTCTAAATTCAATACCTCTTCCTAAAGGGTTGTGTGGGAGTATCTAACCTGGCACGGG |
| 344 | TAACACCGTACGTATTAGTCTCAGAGTTGGGCATATCTCACCTGGCACGGG |
| 345 | CCTTTCCTGTCGATTTGGAAACTCTTAGCAACAAATCATGCCAACTAATGTGCTGTTGATCCTGGCACGGG |
| 346 | AGGACGGTCTTCCCGGTTCGCGGGATGTGCAGGGTATGCATTAAAGATCTTTTAAGGATTGCCTGGCACGGG |
| 347 | CGTTTTCTTACTCATTCACTTAATCGTTATGTAATGATATCATGTAGGTGGTTATTGAAACCTGGCACGGG |
| 348 | GTTGCTTCTTTAATCTTAATTCGTGGCATAGAAGTTCAAGGTCACAAATATATTGGACATCCTGGCACGGG |
| 349 | TGACTCGATTTGGATGGGGTTATAACGTAGCTACGAAGGTTAACTTCTACACCTTGTTAGGCCTGGCACGGG |
| 350 | ATAGTGCGTGGGTGAACGGTATACAAAATTAACTGCGTGCATTCTTGGGTCTTGATCCACCCTGGCACGGG |
| 351 | TACTAGTGGTAAGGTACCTCGCGTGTTATGGCGGTACGTACTAACGACCGTAATTGTTCGCCTGGCACGGG |
| 352 | TTTAACGATTCGTGAGAGTGTGAATCACCTGGGATAATTTTTTAATGCTTGCAGCTTATGCCTGGCACGGG |
| 353 | ATCTTCTTTTTAGGTTTTAATGACCCAGGTTGTACCCTCACCTGGCACGGG |
| 354 | GTCGTCTAAAATATGTTAGCAGTGTCCCGACGTCAGTTTTTCAAGTTAGTTAGCATCGGACCTGGCACGGG |
| 355 | ATGGGTCATTACTCATGGCTGTTATTTCCGGCAGCGATGTTAGGATTCCATAAAGGTGCACCTGGCACGGG |
| 356 | GCCCGAACTACCGGTCTATGGCTCTCCCATGTCCCTGACGCCTGGCACGGG |
| 357 | CTACTAGTGGACCTTGCACGCACAAATCCACGGTATACGGACAGTAAATACTACCTGTCACCTGGCACGGG |
| 358 | CGGGGTCGAGATAGTGTCTGAAGTTGAGGGAAGGGCTGGGCCTGGCACGGG |
| 359 | GAAGTGGCTTGTGCTCCTCGAAGTGGCTTGTTAATTTAGTGTTTTACGATGTTTGTGTGTTCTAGTGGTGTCACAGTTGTCCTGGCACGGGCAGTGTAAA |
| 360 | GAAGTGGCTTGTGCTCCTCGATTGAATTATGCTAATGATTAACAATCGTGGGAGAAGCCTACGAAAGAGGAATTCAGCACCTGGCACGGGCAGTGTAAA |

TABLE 5-continued lists aptamers of 251 to 449, that were selected to target outer membrane vesicles and endotoxins of *E. coli*, *P. gingivalis* and *P. pallens*.
Table 5. Cross reactive aptamers targeting outer membrane vesicles and endotoxins of *E. coli*, *P. gingivalis* and *P. pallens*

| SEQ ID NO | Sequence |
| --- | --- |
| 361 | GAAGTGGCTTGTGCTCCTCGAAGTGGCTTGAAGTGGCTTGTGCTCCTCGCACCTGGCACGGGCAGTGTAAA |
| 362 | GAAGTGGCTTGTGCTCCTCGAAGATATTTACCTAAGCACATAGACACGTCATTCTGTTGCATCCTGGCACGGGCAGTGTAAA |
| 363 | GAAGTGGCTTGTGCTCCTCGAAGTGGCTTGAAGTGGCTTGTGCTCCTCGAAGTGGCTTGAAGTGGCTTGTGCTCCTCGCCTGGCACGGGCAGTGTAAA |
| 364 | GAAGTGGCTTGTGCTCCTCGATTGAATTATGCTAATGATTAACAATCGTGGGAATTCAGCACCTGGCACGGGCAGTGTAAA |
| 365 | GAAGTGGCTTGTGCTCCTCGAAGTGGCTTACGATGTTTGTGTGTTCTAGTGGTGTCACAGTTGTCCTGGCACGGGCAGTGTAAA |
| 366 | GAAGTGGCTTGTGCTCCTCGAAGTGGCTTGAAGTGGCTTGTGCTCCTCGAAGTGGCTTGAAGTGGCTTGTGCTCCTCGCCTGGCACGGGCAGTGTAAA |
| 367 | GAAGTGGCTTGTGCTCCTCGATTGAATTATGCTAATGATTAACAATCGTGGGAGAAGCCTACGAAAGAGGAATTCAGCACCTGGCACGGGCAGTGTAAA |
| 368 | GAAGTGGCTTGTGCTCCTCGTCGGCTGCGCGGTCCGGGCTGGCTAGCAGCCGCGTGGCACGGGGTGACGAGAGCGCGACACCTGGCACGGGCAGTGTAAA |
| 369 | GAAGTGGCTTGTGCTCCTCGCGGGCGAGGCTCGCGCGTGGCGCGCGGCCCCGTGAGAGGAAGCCGGGGGAGGGCAGTGGGCCTGGCACGGGCAGTG |
| 370 | GAAGTGGCTTGTGCTCCTCGGCCGCACCTGACAGTGGCGAGCCGGGGCTCGCGCGAAGGGCGGCAGCACGGGGTGGACAGCCTGGCACGGGCAGTG |
| 371 | GAAGTGGCTTGTGCTCCTCGCAGAGGGCGCGGCTCAGCGCGACCACGGCAGGATGCGGCTGGCGCGTCGGGTGGGTGCTACCTGGCACGGGCAGTGTAAA |
| 372 | GAAGTGGCTTGTGCTCCTCGGACCCACGGCTACGCCGTGCGGCGGGCGGAGAGGGAGCGGGGAGCCGCGGGCCGGCGGGACCTGGCACGGGCAGTGTAAA |
| 373 | GAAGTGGCTTGTGCTCCTCGCGACCTGTGCGCGGCAATGGCGCGCGGGACGGGGGCGTGGCGCTTGGCCGGGGAGAGGTGCCTGGCACGGGCAGTGTAAA |
| 374 | GAAGTGGCTTGTGCTCCTCGTCGTCCGGCGGCGCCCTCCCGGGTACGGAGGGCGGCAGCGCAGTCGCGGGTGAGGAAGGCCCTGGCACGGGCAGTGTAAA |
| 375 | GAAGTGGCTTGTGCTCCTCGTCAAGTCTAAGCATTAAGATTATTTCTCCTGCAACCCCACCCTGGCACGGGCAGTGTAAA |
| 376 | GAAGTGGCTTGTGCTCCTCGACTTTAAGCATACCTGTTAATCATAAGTGACTTCTAATAACCTGGCACGGGCAGTGTAAA |
| 377 | GAAGTGGCTTGTGCTCCTCGAACACTAAGCAGTTGAATGCTAATTGATTTTGCCCCTCTTCCTGGCACGGGCAGTGTAAA |
| 378 | GAAGTGGCTTGTGCTCCTCGTCCTTACTCTAAGCATTTACTCTGCCATTAACAAGCTTAGTTCTTTATGCTTGCCTGGCACGGGCAGTGTAAA |
| 379 | GAAGTGGCTTGTGCTCCTCGAGGGCAGGCCAGGGAAGGGGGGCGGGGGGCGGGGCTGGGCACGGGGAGAACGGCGAGCCCTGGCACGGGCAGTG |
| 380 | GAAGTGGCTTGTGCTCCTCACCAGAATTCTCGTAAGCGGAGAGGAATGGATAGAGTGAACCTGGCACGGGCAGTGTAAA |
| 381 | GAAGTGGCTTGTGCTCCTCGTTGTAGTATAGCCCGATACTTACCCCGTCTACCCAATAACCCTGGCACGGGCAGTG |
| 382 | GAAGTGGCTTGTGCTCCTCGCTCGACTGGAAGAATAGTTCTTTTAGTGTTGGGGATGATCCTGGCACGGGCAGTG |
| 383 | GTGCTCCTCGAAGTGGCTTGTGCTCCTCGCTCGACTGGAAGAATAGTTCTTTAGTGTTGGGGGATGATCCTGGCACGGGCAGTG |

TABLE 5-continued lists aptamers of 251 to 449, that were selected to target outer membrane vesicles and endotoxins of *E. coli*, *P. gingivalis* and *P. pallens*.
Table 5. Cross reactive aptamers targeting outer membrane vesicles and endotoxins of *E. coli*, *P. gingivalis* and *P. pallens*

| SEQ ID NO | Sequence |
|---|---|
| 384 | GTGCTCCTCGTTGATTGTTGTTTTTAAGTTACGATATTGCAACATTGACTCCTGGCACGGGCAGTG |
| 385 | GAAGTGGCTTGTGCTCCTCGTTGGATCGCGACATCTTCTGATTTGCTGACTGTTTGTTTACCTGGCACGGGCAGTGTAAA |
| 386 | GAAGTGGCTTGTGCTCCTCGTCCAGGACGAGGAGCACAAGCCACTTCCTGCCCGTGCCAGGAAGTGGCTTGTGCTCCTCGTCCTGGCACGGGCAGTGTAAA |
| 387 | GAAGTGGCTTGTACTCCTCGTTGTAGTATAGCCCGATACTTACCCCGTCTACCCAATAACCCTGGCACGGGCAGTGTAAA |
| 388 | GAAGTGGCTTGTGCTCCTCGTGTGGCCAAGCCTAAGGCTAGCTTGGGGGCAGTACGTGTCCCTGGCACGGGCAGTGTAAA |
| 389 | GAAGTGGCTTGTGCTCCTCGTGTGGCCAAGCCTAAGGCTAGCTTGGGGGCAGTATGTGTCCCTGGCACGGGCAGTGTAAA |
| 390 | GAAGTGGCTTGTGCTCCTCGCTCGACTGGAAGAATAGTTCTTTTAGTGTTGGGGGATGATCCTGGCACGGGCAGTGTAAA |
| 391 | GAAGTGGCTTGTGCTCCTCGACCTTTCTTATGTTTTCTTTTTACGATTTTACAGTGCTTTCCTGGCACGGGCAGTGTAAA |
| 392 | GAAGTGGCTTGTGCTCCTCGATGGATATTCACGTTAATGAGTAACGAGTTTTCACTGCTCCTCGTCATCGTTGATGGACCTGGCACGGGCAGTGTAAA |
| 393 | GAAGTGGCTTGTGCTCCTCGATGGATATTCACGTTAATGAGTAACGAGTTTTCACTGCTCCTGGCACGGGCAGTGTAAA |
| 394 | GAAGTGGCTTGTGCTCCTCGGTGATAACGAATTTTAGACTGCCCAACCTCACAGCAAGTGCCTGGCACGGGCAGTGTAAA |
| 395 | GAAGTGGCTTGTGCTCCTCGTACGGCGCGGGGGGTGCAGCGCACGCGTCCGTGTCGGCAGGGCATGTAGGCACGCGGGGGCCTGGCACGGGCAGTGTAAA |
| 396 | GAAGTGGCTTGTGCTCCTCGCGGAAATATATGTTTATTTGACTACGCATTTATACTGCAACCTGGCACGGGCAGTGTAAA |
| 397 | GAAGTGGCTTGTGCTCCTCGATGGATATTCACGTTAATGAGTAACGAGTTTTCACTGCTTCCTGGCACGGGCAGTGTAAA |
| 398 | GAAGTGGCTTGTGCTCCTCGATGGATATTCACGTTAATGAGTAACGAGTTTTCACTGCTACCTGGCACGGGCAGTGTAAA |
| 399 | GAAGTGGCTTGTGCTCCTCGTTCATACAGGGAGTGTGAGACACGCGGTATTTATGGGAGACCTGGCACGGGCAGTGTAAA |
| 400 | GAAGTGGCTTGTGCTCCTCGTCAATCTTTTGATACGACTTTACGCTGGCTCAGGTAATTACCTGGCACGGGCAGTGTAAA |
| 401 | GAAGTGGCTTGTGCTCCTCGTCCTGCCCGTGCCAGGACGAGGAGCACAAGCCACTTCCTGCCCGTGCTCCTCGTCCTGGCACGGGCAGTGTAAA |
| 402 | GAAGTGGCTTGTGCTCCTCGACCTTTCTTATGTTTTCTTTTTACGATTTTACAGTGCTCTCCTGGCACGGGCAGTGTAAA |
| 403 | GTGCTCCTCGAAGTGGCTTGTTAATTTAGTGTTTTACGATGTTTGTGTGTTCTAGTGGTGTCACAGTTGTCCTGGCACGGG |
| 404 | GTGCTCCTCGATTGAATTATGCTAATGATTAACAATCGTGGGGAGAAGCCTACGAAAGAGGAATTCAGCACCTGGCACGGG |
| 405 | GTGCTCCTCGCACTAATAGACAATTCAATAAATCCAACCCATTGGATTATCTTGAAGTTTTTCATTTTCCCCCTGGCACGGG |
| 406 | GTGCTCCTCGTACTCCCTAAGGACTAGGAAGAACATAATGCCATTTCCACACTGTGTGTGATATAATCCACCTGGCACGGG |

TABLE 5-continued lists aptamers of 251 to 449, that were selected to target outer membrane vesicles and endotoxins of *E. coli*, *P. gingivalis* and *P. pallens*.
Table 5. Cross reactive aptamers targeting outer membrane vesicles and endotoxins of *E. coli*, *P. gingivalis* and *P. pallens*

| SEQ ID NO | Sequence |
|---|---|
| 407 | GTGCTCCTCGGTGAAGTGGCTTGTGCTCCTCGGTGAAGTGGCTTGTGCTCCTCGGTGAAGTGTTTTTCAATCCTGGCACGGG |
| 408 | GTGCTCCTCGTAGCACATAGACATGTCATTGAACTGTCCGAATCTTCTTGTGAGTGTTAGATATTCTCCGCCTGGCACGGG |
| 409 | GTGCTCCTCGAAGTGGCTTTGCATGGCTGAATGTTACAACGAAGTGTATGGTCTAAACAATAGTTTGGTTCCTGGCACGGG |
| 410 | GTGCTCCTCGCGTGCGGCGCAGCACAGGAGAACAGAGGCGATGCAGCAGACCTGGCACGGG |
| 411 | GTGCTCCTCGTCTGGCACGGGCAGTGTAAACGAAGTGGCTTGTGCTCCTCGTCCTGGCACGGG |
| 412 | GTGCTCCTCGTACACTCATACTCAATCTATTTTATACGGCGATGATATTATTTGCGGGCGAGGTGGACGCCCTGGCACGGG |
| 413 | GTGCTCCTCGAAGTGGCTTGTGCTCCTCGTCCTGGCACGGG |
| 414 | GTGCTCCTCGGGTAGTGATCACCAATGATTGTCTCTTATCAGCAATTTTCCTATGGCACTTTGCTGCGGTCCTGGCACGGG |
| 415 | GTGCTCCTCGTCTTGTATACTCTCAGGGTTTAATCGAGTTTGAGGGTATGATTCTTTGAGACTGTGGGGACCTGGCACGGG |
| 416 | GTGCTCCTCGGAATTTCTAAAGGCTCTTCCTGTGGTTATCGTTTTTCGCTTGTATAAATTAAGTCATGTGCCTGGCACGGG |
| 417 | GTGCTCCTCGTTATGTCTTTGAGGTCTTGCAAGACCATCTAGCCCACACTCTGGCAGCGTTGTTGTTGGCCCTGGCACGGG |
| 418 | GTGCTCCTCGTCTTTCAGTAGGTTCATTTTGGAAAATGACAAGACAAGCCTTGGTGTTTCAATGTGTCGTCCTGGCACGGG |
| 419 | GTGCTCCTCGGATTTCTAGTCCAACTCCGTATATGCAATTCTTAAGTAGATTGTACCTGAAAGGTCAGATCCTGGCACGGG |
| 420 | GTGCTCCTCGTCAATCCCATTCTTCATCATGGTTTGGAGTAATAATCTCGACAGTTTTTGTCTTCAGTACCCTGGCACGGG |
| 421 | GTGCTCCTCGGAGCGCGCTAAGGTCAACCATTTCAATTCTTGCGTTTTTTGAATATCCTTTCCCAGCTCTCCTGGCACGGG |
| 422 | GTGCTCCTCGTTAGCGACAATACCTACAACTGATGAATAGTGTCAAATTGGTTCTTCATTTTTCTTCCTACCTGGCACGGG |
| 423 | GTGCTCCTCGTATGGGCATCTTGAAAACAGATTGTTATCTGAAATGTTTTAAATTTTGGTAGAATTATGTCCTGGCACGGG |
| 424 | GTGCTCCTCGGTTGATCGTTATCCAGCTCTCAGGCTATCTCATTAGACGCTTAAGTCGGGGGGCTCCGGCCTGGCACGGG |
| 425 | GTGCTCCTCGATCGACACTCCTATGTACTTGTATTTCGATCAGGTAGCCATACTCAAATTTTGTTGCCCCCTGGCACGGG |
| 426 | GTGCTCCTCGACGTATCGTTGGTATTAATCAGACCAGGTGTGTATTGTGTGTGGGGATTTCATATAAATTCCTGGCACGGG |
| 427 | GTGCTCCTCGCAATTGTGCTATTTTTGATTTGTAATCTCCCAGGAGGCAATACTAATAAGAGCAGTTCTGCCTGGCACGGG |
| 428 | GTGCTCCTCGTAGATTTGTTTGACCAGTTTGCTCTCTCATGTGAGCATTCACTTCATCTCAGCAATTTGGCCTGGCACGGG |
| 429 | GTGCTCCTCGACTAGTCCTTCCTGATTTTTATATGCAGCACTTATGCCAACCCTACTAATAGCACGCTTCCCTGGCACGGG |
| 430 | GTGCTCCTCGATACGACCCTCTTTTTGCGGCTTGCAACAATTATCGCCCGTCGTTTAGAGCATCCTAGCACCTGGCACGGG |

TABLE 5-continued lists aptamers of 251 to 449, that were selected to target
outer membrane vesicles and endotoxins of
E. coli, P. gingivalis and P. pallens.
Table 5. Cross reactive aptamers targeting outer
membrane vesicles
and endotoxins of E. coli, P. gingivalis and P. pallens

| SEQ ID NO | Sequence |
|---|---|
| 431 | GTGCTCCTCGTCTCAGACGTGAAGTGGTTTGTTATGCATACTGATGAATTTCCCTCATAATTACGGGTTGCCTGGCACGGG |
| 432 | GTGCTCCTCGTGGTTTTTATCTATTCTTCTTACTGAACCTCATAGTGTTATAGTTGAGCGGGGATGCGTTCCTGGCACGGG |
| 433 | GTGCTCCTCGTGCGGACTAGGAAGGACACCAGCGGTAAGATGCGTGGCACCACGTGGTAAGCAAGATGTGCCTGGCACGGG |
| 434 | GTGCTCCTCGTTCAAATATCATACTCTGATAATAGTTCGTTTTAGGTGGTACTTTCAATTCATTTCCGTACCTGGCACGGG |
| 435 | GTGCTCCTCGTTGATGTTTAGTCATTTCATGTTTTGAGTTTGCTTGGCTGTAGATTATAGAAGTTTGATCCCTGGCACGGG |
| 436 | GTGCTCCTCGTCCTCTTGCGCATTTTGATTGATATGTCTTATATAGCGATCAATCCCCTCACGATGTTTCCCTGGCACGGG |
| 437 | GTGCTCCTCGTATGGGACTTAGATTTGTTTGTGCTAATTGTGCATAAGCCAACAGGGTATCCTACATGATCCTGGCACGGG |
| 438 | GTGCTCCTCGTCTGATTGGTGCTGGACAATGCGCAACAAGTTTATCCAATTCATACTGATAATTTAATCCCCTGGCACGGG |
| 439 | GTGCTCCTCGTAGCATCCTCTTTGGACATATGATTCAACGCAGTATTAGGTAACATTCATCACATCCTATCCTGGCACGGG |
| 440 | GTGCTCCTCGGAATCATAATTACGGAGTTGGAACGGTATAGTCTGGCATCTTCTATTCTAGGCATTTCTTCCTGGCACGGG |
| 441 | GTGCTCCTCGAATACTGACTCATTCTATACATCCTCTGATGTGAACCCACTCTCTAAAGTATTTTCCATCCCTGGCACGGG |
| 442 | GTGCTCCTCGACATTAGTGAACCTGTCATTAACTGTGCGCTGGAAGCGCGGGTATTTGTCCAAATTGCTCCCTGGCACGGG |
| 443 | GTGCTCCTCGCTCAAAGTAGATCTTTCGACTATGGCACGCGACGGATCAGATGCTGAGGACCAGTAGGTGCCTGGCACGGG |
| 444 | GTGCTCCTCGCATGCTTGGCTATTGCAATCGAGTTTTAAATAGTATAAATAGGAAACCCAGGCATTTTCGCCTGGCACGGG |
| 445 | GTGCTCCTCGCACTGCGTAGCAATGTGCTATTTAAAAACCGCACTTGGAGCCTGGCACGGG |
| 446 | GTGCTCCTCGTTCATTTTATTGCGGATATCTTTCCTCCCGTTGGGGGCCTCCTGGCACGGG |
| 447 | GTGCTCCTCGATTGTCTCTTCCTTTTTGGGCCATAATGAGGCTTTGATGCTGAACGATCGTCTCGGATGGCCTGGCACGGG |
| 448 | GTGCTCCTCGGTACATTGGGTGAGAGCAGTGACTTGTGGGGCACAACAAACCCAGCATCTGGATGCTAACCCTGGCACGGG |
| 449 | GTGCTCCTCGCCGAGTTGCTTCTGGAATTTCACTGGGCGTTAACTGTGTCCTTGACTTTCTTAGCTGAAACCTGGCACGGG |

Example 6—Aptamer 2D Structure Prediction

Aptamer secondary structure was predicted using RNA Structure version 6.0.1 web service with default parameters (https://rna.urmc.rochester.edu/RNAstructureWeb/Servers/Predict1/Predict1.html, Reuter, J. S., & Mathews, D. H. RNA structure: software for RNA secondary structure prediction and analysis. BMC Bioinformatics. 2010; 11:129). RNA structure Fold Results predict Lowest free energy Structure. RNA structure MaxExpect Results generate structure composed of highly probable base pairs. This is an alternative method for structure prediction that may have higher fidelity in structure prediction. RNA structure ProbKnot Results predict a secondary structure of probable base pairs, which might include pseudoknots. The predicted 2D results were shown in FIG. 5A through FIG. 5J.

Figure 6A:
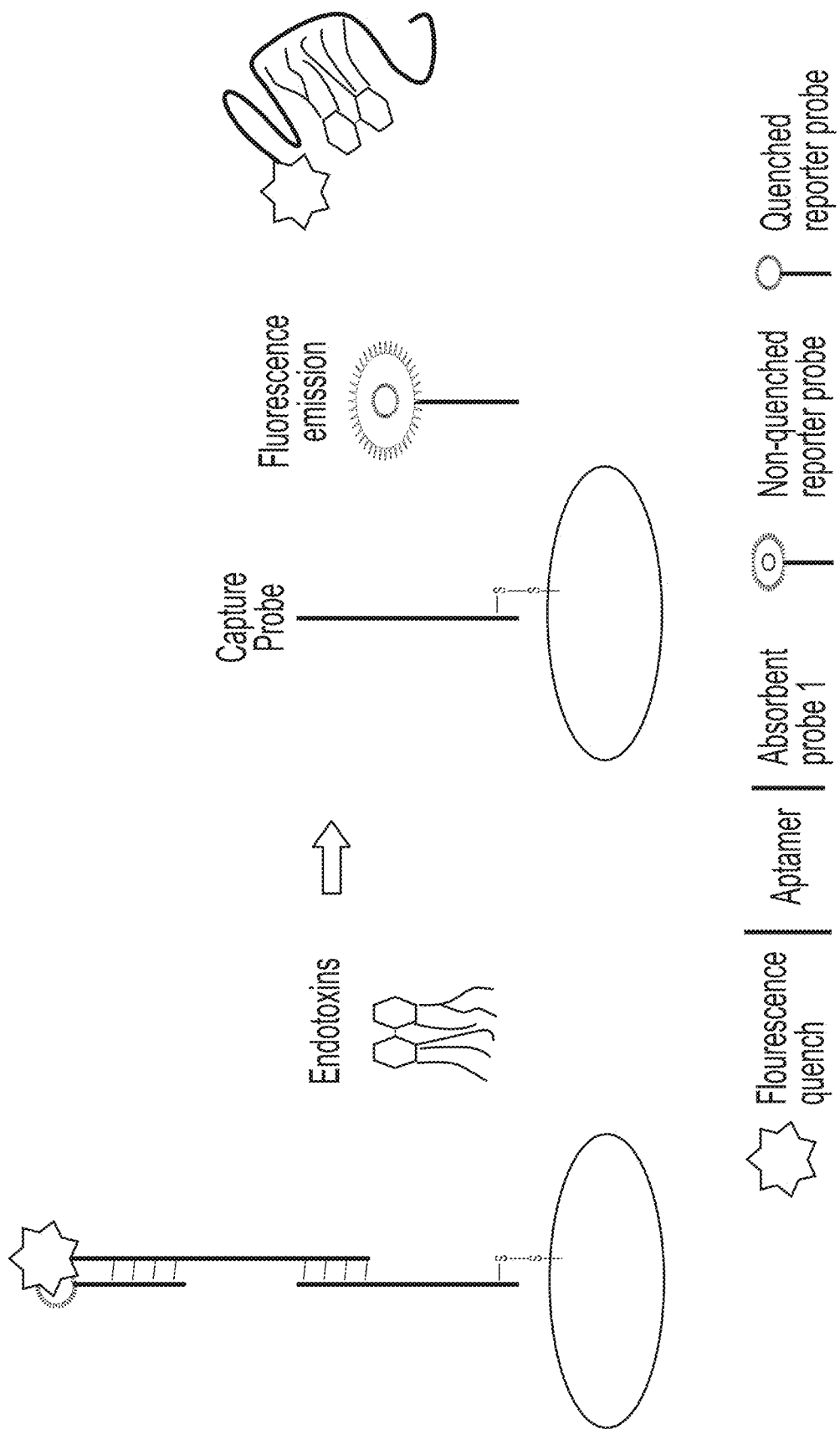
FIG. 6A shows an aptamer linked to a quencher that can reduce the intensity of a fluorescence molecule if the two are placed in proximity.

Example 7. Laboratory Tests to Measure the Abundance of Outer Membrane Vesicles and Lipopolysaccharides of *P. gingivalis* and *P. pallens* in Oral Samples Aptamers are conjugated to functional molecules to develop sensitive assays. As shown in FIG. 6A, an aptamer is linked to a quencher that can reduce the intensity of a fluorescence molecule if the two are placed in proximity. In this assay, a fluorescent molecule is conjugated to a reporter probe (fluorescence reporter probe, 5'-Fluorophore-GAAC-CACTCTAAGCATTTACACTGCCCGTGCCAGG-3' (SEQ ID NO 464); or 5' CGAGGAGCACAAGC-CACTTCTTTTTT-3' (SEQ ID NO 465)-fluorophore) which has a complementary sequence to the 3'-end of the target-binding aptamer, or the 5' end of the target-binding aptamer. A fluorescence reporter probe or fluorescence aptamer probe includes an oligonucleotide and a fluorescent dye or fluorophore molecule.

In the absence of targeted endotoxins, the fluorescence reporter probe is hybridized to the 3'-end of the target-binding aptamer, which contains a functional group that quenches fluorescence released by the fluorescence reporter probe. As a result, no fluorescence is detected. Upon binding to targeted endotoxins, the target-binding aptamer undergoes conformational changes, leading to dissociation from the fluorescence reporter probe, thus increasing the distance between the quenching group in the target-binding aptamer and the fluorescence molecule in the reporter probe. Without the interference of the quenching group, fluorescence is detectable upon absorbing electromagnetic radiation at a specific wavelength.

As used herein, quencher includes, but not limited to, Black Hole Quencher® 1, Black Hole Quencher® 2, Iowa Black® FQ, Iowa Black® RQ-Sp, Dabcyl, and mixtures thereof.

As used herein, fluorescence molecules, or fluorophores, include, but not limited to, 6-FAM™, Alexa Fluor® 488, Alexa Fluor® 532, Alexa Fluor® 594, Alexa Fluor® 647, Alexa Fluor® 660, Alexa Fluor® 750, Alexa Fluor® 546, ATTO™ 488, ATTO™ 532, ATTO™ 550, and mixtures thereof. Fluorophores typically contain several combined aromatic groups, or planar or cyclic molecules with several $\pi$ bonds. They emit light, or fluorescence, after absorbing light or electromagnetic radiation at a specific wavelength. Fluorophores can be directly conjugated to aptamers or other oligonucleotides.

As used herein, the term "fluorescence reporter probe" or "fluorescence reporter aptamer" is an oligonucleotide molecule or a protein or any chemical that is covalently or noncovalently linked to a fluorophore.

As used herein, the term "enzyme reporter probe" or "enzyme reporter aptamer" is an oligonucleotide molecule or a protein or any chemical that is covalently or noncovalently linked to an enzyme.

Figure 6B:
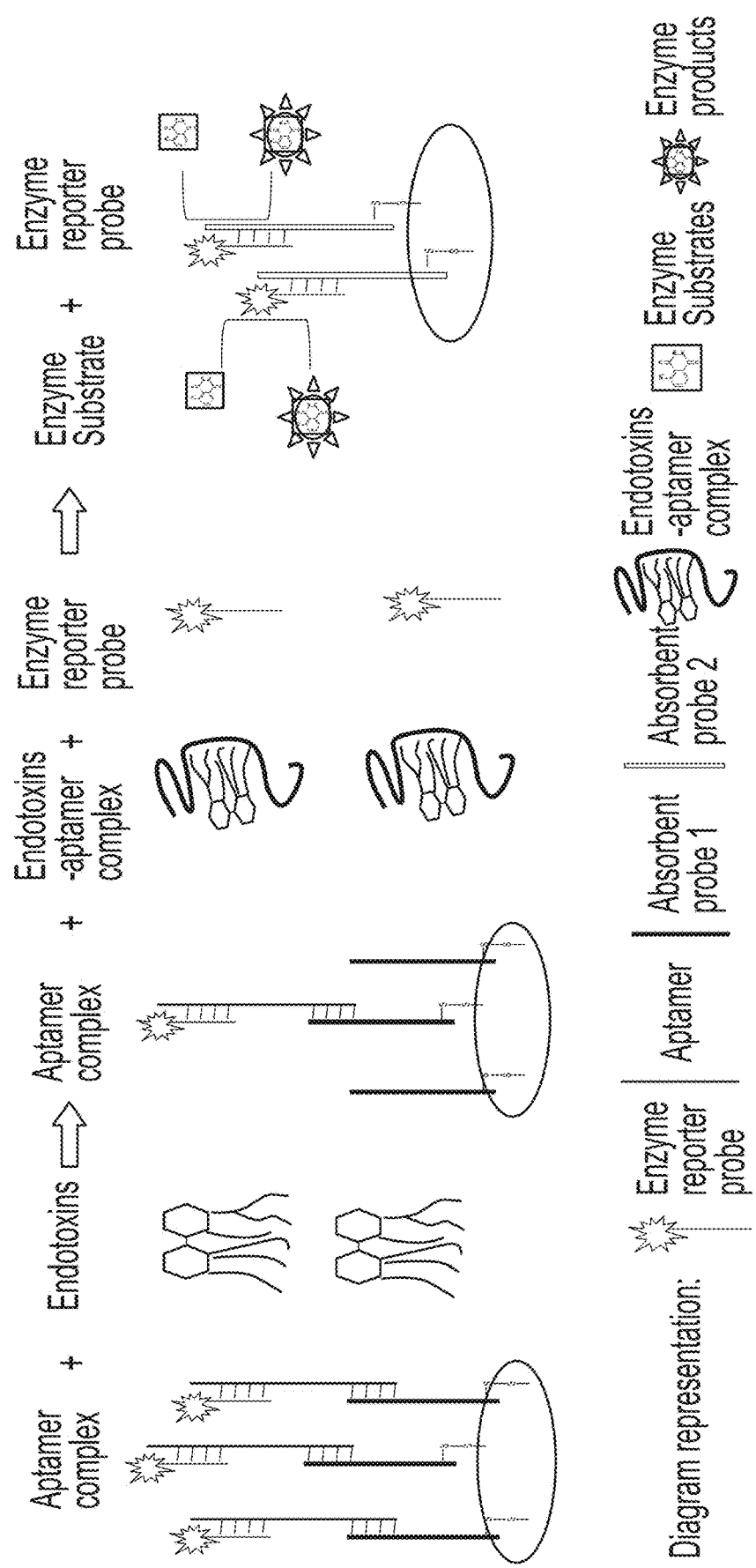
FIG. 6B shows how enzymes are employed to determine the abundance of endotoxins in oral samples.

Enzymes are also employed to determine the abundance of endotoxins in oral samples (FIG. 6B). An enzyme is conjugated to an oligonucleotide (enzyme reporter probe). In the assay system, a target-binding aptamer is first hybridized with the enzyme reporter probe at its 3' end, and with a capture probe at its 5' end, forming a complex containing a capture probe, a target-binding aptamer, and an enzyme reporter probe. The complex is anchored to the bottom of a 96-well plate through the capture probe by a biotin and Streptavidin binding. The enzyme reporter probe is dissociated from the target-binding aptamer upon binding to endotoxins due to conformation changes. Subsequently, the enzyme reporter probe is released from the complex of capture probe, aptamer and the enzyme reporter probe into the solution in the wells of a 96-well plate. The solution is transferred to a fresh 96-well plate. An enzyme substrate is added, and an enzyme product is generated and quantified in a spectrometer in a SpectraMax iD3 spectrometer reader (Molecular Device, Downingtown, Pa.).

As used herein, the enzyme includes, but is not limited to, horseradish peroxidase, alkaline phosphatase, luciferase, and mixtures thereof.

As used herein, enzyme substrates include, but are not limited to, colorimetric substrate, fluorescent substrate or chemiluminescent substrate.

Figure 7A:
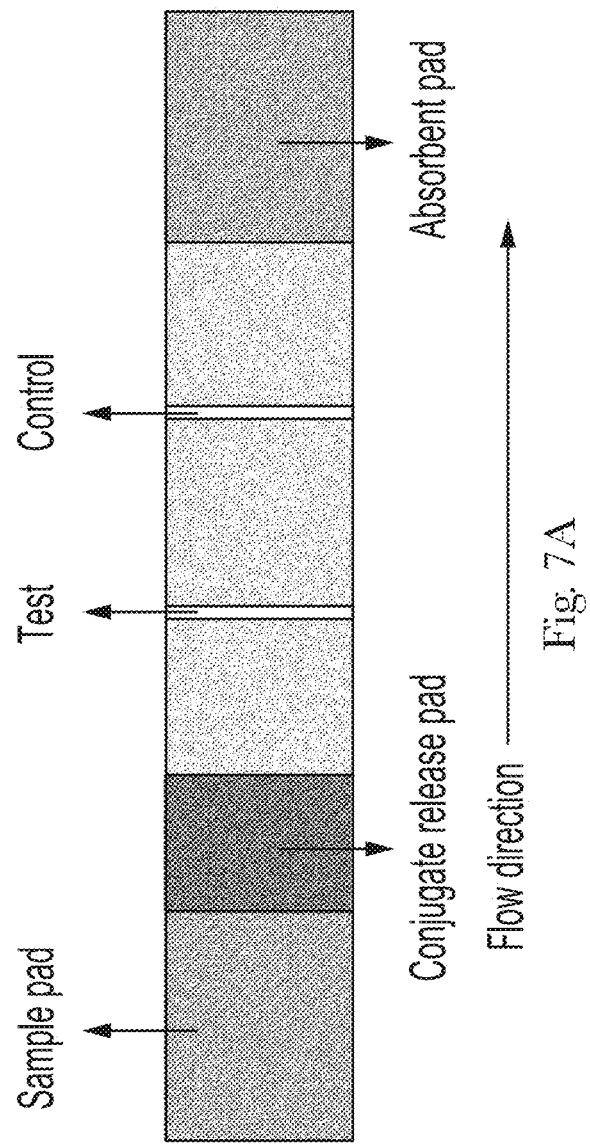
FIG. 7A shows lateral flow assays are typically composed of a nitrocellulose membrane, sample pad, conjugate pad, wicking or absorbent pad and backing pad.

Example 8—Point of Care Tests to Semi-Quantitate the Abundance of Outer Membrane Vesicles and Lipopolysaccharides of *P. gingivalis* and *P. pallens* in Oral Samples Multiple tests are being developed to detect and semi-quantitate the amount of outer membrane vesicles and lipopolysaccharides of *P. gingivalis, P. pallens* and other Gram negative bacteria in oral samples. Lateral flow assays are simple paper-based devices that can measure the presence (or absence) of a target analyte in liquid samples without the need for specialized and costly equipment and can be used directly by the consumers. Lateral flow assays are typically composed of a nitrocellulose membrane, sample pad, conjugate pad, wicking or absorbent pad and backing pad (FIG. 7A).

1. A sample pad: The sample pad acts as a sponge and holds an excess of sample fluid. Once applied, the fluid migrates to the conjugate pad. It is composed of cellulose and/or glass fiber (Cellulose Fiber Sample Pad Strips, Millipore-Sigma, St. Louis, Mo.).
2. A conjugate pad: This pad stores the reaction reagents. The fiber of conjugate pad releases labeled conjugates upon being resuspended in the moving liquid samples. Glass fiber, cellulose, polyesters and some other materials are used to make conjugate pad for lateral flow assays. For example, Glass Fiber Conjugate Pad Strips (Millipore Sigma, St. Louis, Mo.) is used for the lateral flow assay. This pad contains at least two reagents: A) an aptamer to endotoxins of *P. gingivalis, P. pallens* or any Gram-negative bacteria, that has been conjugated to a signal molecule or a reporter such as a color material or a fluorescence molecule or enzyme, B) reaction buffer components that contain everything to guarantee an optimized chemical reaction between the aptamer and endotoxins, such as 20 mM Tris-HCl pH 7.4, 140 mM NaCl, 5 mM KCl, 1 mM $MgCl_2$ and 1 mM $CaCl_2$), 1% fetal care serum. The color material can be a gold nanoparticle, or gold nanoparticle-modified nanomaterial for signal enhancement, carbon nanoparticles or colloidal selenium nanoparticles. In another embodiment, one more DNA oligonucleotide is included in the conjugation pad. This DNA oligonucleotide has a sequence that is complimentary to part of the aptamer sequence, such as 5'-ACGAATTTA-CACTGCCCGTGCCAGG-3' (SEQ ID NO 458), which is conjugated to a reporter molecule, including but not limited to, a color material or a fluorescence molecule or enzyme. In addition, this DNA oligonucleotide is also conjugated to a linker-molecule including, but not limited to, biotin, protein A, protein G, antibody, avidin, or streptavidin. In one more embodiment, the aptamer is conjugated to a reporter molecule and a linker molecule. The linker molecule includes, but is not limited to, biotin, protein A, protein G, antibody, avidin, or streptavidin. The reporter molecule is a color material or a fluorescence molecule or enzyme.

3. Nitrocellulose membrane: Nitrocellulose membranes are available from different vendors. Test and control lines are drawn over this piece of membrane; so, an ideal membrane should provide support and good binding to capture molecules including, but not limited to, aptamers, antibodies, biotin, streptavidin, avidin, protein A or protein G. GE Healthcare Life Sciences released a new version of the Whatman Fast Flow, High Performance (FF HP) nitrocellulose backed membranes, which is used in many lateral flow devices. Millipore-Sigma also sells Hi-Flow™ Plus Lateral Flow Membrane Cards. In the Cellulose membrane, two or multiple lines of capture molecules, or absorption molecules are prepared. The paper-based device has one or more areas or lines where capture molecules are immobilized. Depending upon the assay format (sandwich assay or competitive assay), different capture molecules are applied. In one embodiment of sandwich assay format, immobilized in the test line is another aptamer, (capture aptamer), that binds to target endotoxins, target outer membrane vesicles, or target bacteria in one site. The reporter aptamer, which is conjugated with a reporter molecule and is stored in the conjugate pad in the device, bind to another side of the target endotoxins, target outer membrane vesicles, and target bacteria. If target endotoxins, target outer membrane vesicles or target bacteria are present in the samples, the reporter aptamer will bind to those targets. As the target-reporter-aptamer complex migrates from the conjugation pad to the test line, it binds to the test capture aptamer. If the reporter molecule is gold nanoparticle, a red line will appear on the test line. If the target endotoxins, target outer membrane vesicles, or target bacteria are not in the samples, the reporter-aptamer will migrate past the test line, and bind to another capture molecules in the control line, called control capture molecules. The control capture molecules are DNA oligonucleotides, antibodies, protein A, protein G, avidin or streptavidin. The reporter aptamer contains another linker molecule, such as an antibody, or biotin. The control capture molecule can bind to any reporter aptamer that flow through the control line. In one embodiment of competitive assay, immobilized in the test line are target endotoxins, target endotoxins, or target bacteria. If they are present in the samples, the target endotoxins, target outer membrane vesicles will bind to the reporter aptamers. As a result, the reporter aptamer can't bind to the target endotoxins, target outer membrane vesicles, or target bacteria in the test time. If the targets are not in the samples, the reporter aptamer will bind to the target endotoxins, target outer membrane vesicles, or target bacteria. A red line will appear if the reporter molecule is gold nanoparticles.

4. A wick, or absorbent, pad: Absorbent pad: It works as sink at the end of the strip. It also helps in maintaining flow rate of the liquid over the membrane and stops back flow of the sample. Absorbent capacity to hold liquid can play an important role in results of assay. This pad simply acts as a waste container. After passing these reaction zones the fluid enters the final porous material, the wick pad.

The lateral flow assays are used to detect one or more targets. In FIG. 7B, only one type of endotoxin or outer membrane vesicle from one bacterial species is detected. For Example, one or two aptamers of P. gingivalis endotoxins are conjugated to the reporter molecule, such as gold nanoparticles. Another one or two aptamers of P. gingivalis endotoxins are immobilized to the nitrocellulose membrane at the target line. In the control, an additional oligonucleotide is immobilized onto the control region. This oligonucleotide can bind to the reporter conjugated aptamer. This type of device can detect only one biomarker.

Assay example 1: An example of a sandwich assay is given here with an antibody as the capture molecule.

In the conjugate pad: a DNA oligonucleotide with sequence of 5'-ACTCTAAGCATTTA-CACTGCCCGTGCCAGG-3' (SEQ ID NO 459) is conjugated with a gold nanoparticle. The gold nanoparticle contains biotin molecules that can bind to avidin or streptavidin. The reporter DNA oligonucleotide can hybridize with the aptamer at its 3'-end, such as the aptamer with SEQ ID NO 201 5'-AATAATATATCTCTAGAACATTAAATATCAT-TTTCATATATTTAAAGTATATCATAATAA CCTGGCACGGGCAGTG-3'. This aptamer is conjugated to a rabbit immunoglobulin G, which bind to Protein G with high affinity.

In the test line: Bacterial Protein G is immobilized on the test line. Protein G can bind to any immunoglobulin G.

In the control line: Streptavidin is immobilized in the control line. It can bind to biotin.

Before sample application, there is no red line in either test or control as shown in B-I of FIG. 7B. When a sample is applied, the target endotoxin will bind to the aptamers in the conjugate pad. Upon binding to endotoxins, the aptamer undergoes conformational changes, leading to dissociation from the DNA oligonucleotide that are linked to a gold nanoparticle. As the sample mix migrates to the test line, the aptamer will bind to the test line, where the immobilized Protein G will bind to the immunoglobulin G of the aptamer-immunoglobin G complex. The biotin-nanoparticle-oligonucleotide will continue to migrate to the control line where the immobilized streptavidin binds to the biotin in the biotin-gold nanoparticle-oligonucleotide. As shown in B-II of FIG. 7B, no red color appears in the test line if target endotoxins are in the samples. If the sample does not contain target endotoxins, the biotin-gold nanoparticle-oligonucleotide complex is still hybridized with the aptamer-immunoglobulin G. The Protein G in the test line bind to the immunoglobulin G, and a red color appears in the test line. In the lateral flow assay, excessive biotin-gold nanoparticle-oligonucleotide is applied, migrates past the control line and binds to the streptavidin in the control line. As shown in B-III of FIG. 7B, a red line appears in both test or control line.

Assay example 2: Another example of a sandwich assay is given here.

In the conjugate pad: a DNA oligonucleotide with sequence of 5'-ACTCTAAGCATTTA-CACTGCCCGTGCCAGG-3' (SEQ ID NO 459) is conjugated with a gold nanoparticle. The reporter DNA oligonucleotide can hybridize with the aptamer at its 3'-end, such as the aptamer with SEQ ID NO 201 5'-AATAATATATCTCTAGAACATTAAATATCATTTT-CATATATTTAAAGTATATCATAATAA CCTGGCACGGGCAGTG-3'. This aptamer is conjugated to a biotin molecule, which can bind to streptavidin in high affinity.

In the test line: A capture DNA oligonucleotide is immobilized in the test line. The capture DNA oligonucleotide has a sequence of 5'-CCTGGCACGGGCAGTGTAAATGCT- TAGAGTTTTTTT-3' (SEQ ID NO 466), complimentary to the sequence of the reporter oligonucleotide in the gold nanoparticle-oligonucleotide.

In the control line: Streptavidin is immobilized in the control line. It can bind to biotin in the aptamer-biotin complex.

Before sample application, there is no red line in either test or control as shown in C-I of FIG. 7C. When a sample is applied, the target endotoxin will bind to the aptamers in the conjugate pad. Upon binding to endotoxins, the aptamer undergoes conformational changes, leading to dissociation from the reporter gold nanoparticle-oligonucleotide. As the sample mix migrates to the test line, the reporter gold nanoparticle-oligonucleotide will hybridize with the capture oligonucleotide which is immobilized in the test line. A red line will appear in the test line, as shown in C-II of FIG. 7C. In the lateral flow assay, slightly excessive amount of gold nanoparticle-oligonucleotide and aptamer-biotin are applied and migrate past the test line and bind to the streptavidin in the control line. As shown in the C-II of FIG. 7C, a red line appears in both test or control lines.

If no target endotoxins are present in the sample, all complexes of gold nanoparticle-oligonucleotide and aptamer-biotin can't bind to the target endotoxins immobilized in the test line, thus migrates past the test line and binds to the streptavidin in the control line. As shown in C-III of FIG. 7C, a red line appears only in the control line.

An Assay Example 3: An example of a competitive assay is given here.

In the conjugate pad: A gold nanoparticle is conjugated to biotin molecules and an aptamer, such as the aptamer with SEQ ID NO 201 5'-AATAATATATCTCTAGAACAT-TAAATATCATTTTCATATATTTAAAGTATATCAT-AATAA CCTGGCACGGGCAGTG-3'. The biotin molecules in the gold nanoparticle-aptamer complex can bind to streptavidin in high affinity.

In the test line: Target endotoxins of bacteria, such as *P. gingivalis*, *P. pallens* or any Gram-negative bacteria, are immobilized at the test line. They can bind to the aptamer with high specificity.

In the control line: Streptavidin is immobilized in the control line. It can bind to biotin in the gold nanoparticle-aptamer-biotin complex.

Before sample application, there is no red line in either test or control as shown in D-I of FIG. 7D.

When a sample is applied, the target endotoxins will bind to the aptamers in the conjugate pad. The binding site in the aptamer is occupied. As the sample mix migrates to the test line, the gold nanoparticle-aptamer-endotoxin complex can't bind to the endotoxins that are immobilized to the test line. A red line will not appear in the test line, as shown in D-II of FIG. 7D. As the gold nanoparticle-aptamer-endotoxin complex migrates to the control line, the biotin in the gold nanoparticle-aptamer-endotoxin complex will bind to the streptavidin in the control line. As shown in D-II of FIG. 7D, a red line appears in the control line.

If no target endotoxins are present in the sample, some complexes of gold nanoparticle-aptamer-biotin will bind to the target endotoxins, a red line will appear in the test line. A slightly excessive amount of gold nanoparticle-aptamer-biotin migrates past the test line and binds to the streptavidin in the control line. As shown in D-III of FIG. 7D, a red line appears both in the test and control lines.

Figure 7E:
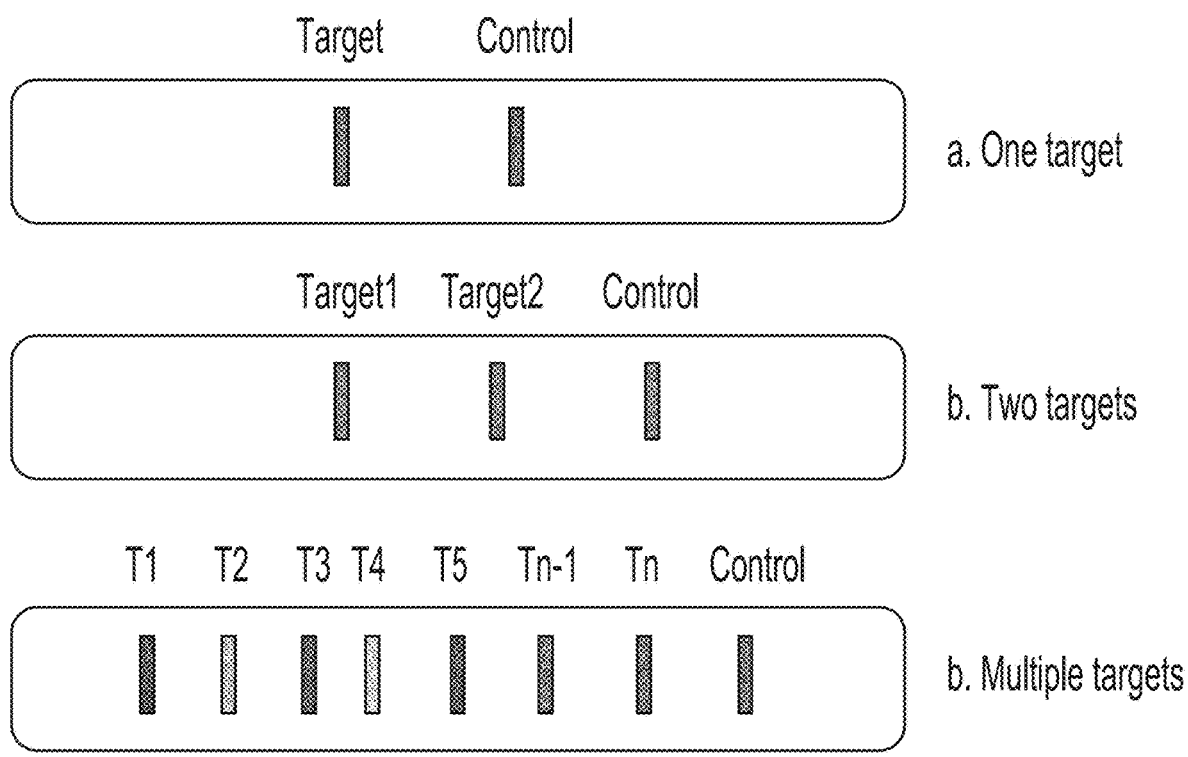
FIG. 7E shows in one device, one, two or more endotoxins, outer membrane vesicles or bacteria can be detected.

Multiplexing lateral flow assay or multiplexing point of care monitoring: In one device, one, two or more endotoxins, outer membrane vesicles or bacteria can be detected as illustrated in FIG. 7E.

A consumer diagnostic kit is being created.

A. A consumer diagnostic kit that can detect endotoxins of *P. gingivalis*, *P. pallens* and Gram-negative bacteria in oral samples.
B. A consumer diagnostic kit that can detect outer membrane vesicles of *P. gingivalis*, *P. pallens* and Gram-negative bacteria in oral samples.
C. The consumer diagnostic kit according to Paragraph A, wherein the consumer diagnostic kit is to determine the abundance of *P. gingivalis*, *P. pallens* and Gram-negative bacteria in oral samples.
D. The consumer diagnostic kit according to Paragraph A, B and C, wherein the Gram-negative bacteria include, but not limited to, Gram negative cocci, *Enterobacter, Fusobacterium, Haemophilus, Leptotrichia, Neisseria, Porphyromonas, Prevotella, Rothia, Serratia, Veillonella, Escherichia coli, Salmonella*, and *Shigella*.
E. The consumer diagnostic kit according to Paragraph A, B, C and D, wherein the consumer diagnostic kit is a diagnostic tool or instrument.
F. The consumer diagnostic kit according to Paragraph A through D, wherein endotoxins are detected using aptamer-based lateral flow assays.
G. The consumer diagnostic kit according to Paragraph A through D, wherein outer membrane vesicles are detected using aptamer-based lateral flow assays.
H. The consumer diagnostic kit according to Paragraph A through D, wherein the abundance of Gram-negative bacteria is detected using aptamer-based lateral flow assays.
I. The consumer diagnostic kit according to Paragraph F through H, wherein the aptamer-based lateral flow assays include one or more of the sequences in aptamers in SEQ ID NO 1 to SEQ ID NO 250 to SEQ ID NO 251 to SEQ ID NO 449.
J. The consumer diagnostic kit according to Paragraph F through H, wherein the aptamer-based lateral flow assays include one or more of the sequences that share 85% or higher sequence identities to the SEQ ID NO 1 to SEQ ID NO 250 to SEQ ID NO 251 to SEQ ID NO 449.
K. The consumer diagnostic kit according to Paragraph A through J, wherein the aptamer-based lateral flow assays include, but not limited to, a capillary flow layer, a nitrocellulose membrane, a sample application pad, a conjugate pad, a test line, a control line and absorbent pad.
L. The consumer diagnostic kit according to Paragraph A through J, wherein the aptamer-based lateral flow assays include, but not limited to, a readout reporter molecule, a mobile phase buffer, a biomolecule at the test line, and another biomolecule at the control line.
M. The consumer diagnostic kit according to Paragraph A through J, wherein the aptamer-based lateral flow assays include, but not limited to, aptamer functionalized gold nanoparticles, thiolated aptamers, a salt buffer, and streptavidin-biotinylated reagents.
N. The consumer diagnostic kit according to Paragraph A through J, wherein the aptamer-based assays include lateral flow assays, 96-well solution assay, and electrochemical assays.
O. The consumer diagnostic kit according to Paragraph A through J, wherein the aptamer-based lateral flow assays include, but not limited to, sandwich assays (Sandwich assays using a pair of aptamers, sandwich assays using a combination of aptamers and antibodies, and sandwich assays using split aptamers), competitive assays (competitive assays between target analytes in solution and the target analytes immobilized on the membrane, competitive assays between target analytes in solution a complementary DNA probe) and displacement assay.

P. The consumer diagnostic kit according to Paragraph L through O, wherein the readout reporters include, but not limited to, functionalized gold nanoparticles, functionalized silico nanoparticles with either color molecules or fluorescence molecules, horse radish peroxidase and alkaline phosphatase.

Q. The consumer diagnostic kit according to Paragraph L through O, wherein the assay signals are amplified through isothermal amplification techniques, including combination polymerase amplification, loop mediated amplification, exponential amplification reaction, strand displacement amplification, rolling circle amplification, nucleic acid sequence based amplification, and helicase dependent amplification.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aptamer composition comprising an oligonucleotide that is at least one of deoxyribonucleotides, ribonucleotides, derivatives of deoxyribonucleotides, derivatives of ribonucleotides, or mixtures thereof;
  wherein said aptamer composition has a binding affinity for one or more bacterial species from the genus *Prevotella* or the genus *Porphyromonas;*
  wherein the oligonucleotide has at least 50% nucleotide sequence identity to SEQ ID NO 1 to SEQ ID NO 105.

2. The aptamer composition of claim 1, wherein said one or more *Prevotella* species are at least one of: *Prevotella baroniae, Prevotella bivia, Prevotella buccae, Prevotella dentalis, Prevotella denticola, Prevotella disiens, Prevotella histicola, Prevotella intermedia, Prevotella loescheii, Prevotella maculosa, Prevotella marshii, Prevotella melaninogenica, Prevotella micans, Prevotella multiformis, Prevotella multisaccharivorax, Prevotella nanceiensis, Prevotella nigrescens, Prevotella oralis, Prevotella oris, Prevotella oulorum, Prevotella pallens, Prevotella pleuritidis, Prevotella saccharolytica, Prevotella salivae, Prevotella_sp_C561, Prevotella_sp_oral_taxon_306, Prevotella_sp_oral_taxon_317, Prevotella_sp_oral_taxon_473, Prevotella timonensis, Prevotella_veroralis*, or mixtures thereof.

3. The aptamer composition of claim 1, wherein said one or more *Prevotella* species are at least one of: *Prevotella denticola, Prevotella intermedia, Prevotella melaninogenica, Prevotella nigrescens, Prevotella pallens, Prevotella salivae*, or mixtures thereof.

4. The aptamer composition of claim 1, wherein said one or more *Porphyromonas* species are at least one of: *Porphyromonas asaccharolytica, Porphyromonas catoniae, Porphyromonas endodontalis, Porphyromonas gingivalis,*

*Porphyromonas*_sp_oral_taxon_278, *Porphyromonas*_sp_oral_taxon_279, *Porphyromonas_uenonis*, or mixtures thereof.

5. The aptamer composition of claim 1, wherein said one or more *Porphyromonas* species are at least one of: *Porphyromonas endodontalis, Porphyromonas gingivalis, Porphyromonas*_sp_oral_taxon_278, or mixtures thereof.

6. The aptamer composition of claim 1, wherein the oligonucleotide comprises at least one oligonucleotide of SEQ ID NO 1 to SEQ ID NO 105.

7. The aptamer composition of claim 1, wherein the oligonucleotide comprises one or more motifs of SEQ ID NO 1 to SEQ ID NO 105.

8. The aptamer composition of claim 1, wherein the oligonucleotide comprises natural or non-natural nucleobases.

9. The aptamer composition of claim 8, wherein said non-natural nucleobases are at least one of hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, or mixtures thereof.

10. The aptamer composition of claim 1, wherein the nucleosides of the oligonucleotide are linked by a chemical motif that is at least one of natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, or mixtures thereof.

11. The aptamer composition of claim 1, where said derivatives of ribonucleotides or said derivatives of deoxyribonucleotides are at least one of locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, or mixtures thereof.

12. The aptamer composition of claim 1, further comprising at least one polymeric material, wherein said at least one polymeric material is covalently linked to the oligonucleotide.

13. The aptamer composition of claim 12, wherein said at least one polymeric material is polyethylene glycol.

14. The aptamer composition of claim 1, wherein the nucleotides at the 5'- and 3'-ends of the oligonucleotide are inverted.

15. The aptamer composition of claim 1, wherein at least one nucleotide of the oligonucleotide is fluorinated at the 2' position of the pentose group.

16. The aptamer composition of claim 1, wherein the pyrimidine nucleotides of the oligonucleotide are fluorinated at the 2' position of the pentose group.

17. The aptamer composition of claim 1, wherein said at least one oligonucleotide is covalently or non-covalently attached to one or more reporter molecules; wherein said one or more reporter molecules are at least one of gold nanoparticles, fluorescent tags, horse radish peroxidase, alkaline phosphatase, green fluorescence proteins and latex, or mixtures thereof.

18. The aptamer composition of claim 17, wherein said one or more reporter molecules comprise gold nanoparticles.

* * * * *